US012492427B2

(12) United States Patent
Geipel et al.

(10) Patent No.: US 12,492,427 B2
(45) Date of Patent: Dec. 9, 2025

(54) MULTIPLEX METHOD FOR DETECTING DIFFERENT ANALYTES IN A SAMPLE

(71) Applicant: Resolve BioSciences GmbH, Monheim am Rhein (DE)

(72) Inventors: Andreas Geipel, Mettmann (DE); Frank Reinecke, Essen (DE); Christian Korfhage, Langenfeld (DE)

(73) Assignee: Resolve BioSciences GmbH, Monheim am Rhein (DE)

( * ) Notice: Subject to any disclaimer, the term of this patent is extended or adjusted under 35 U.S.C. 154(b) by 67 days.

(21) Appl. No.: 18/001,933

(22) PCT Filed: Jun. 18, 2021

(86) PCT No.: PCT/EP2021/066620

§ 371 (c)(1),
(2) Date: Dec. 15, 2022

(87) PCT Pub. No.: WO2021/255244

PCT Pub. Date: Dec. 23, 2021

(65) Prior Publication Data

US 2023/0227907 A1 Jul. 20, 2023

Related U.S. Application Data

(63) Continuation-in-part of application No. PCT/EP2020/067010, filed on Jun. 18, 2020.

(Continued)

(51) Int. Cl.

*C12Q 1/6841* (2018.01)
*C12Q 1/682* (2018.01)

(Continued)

(52) U.S. Cl.

CPC ........... *C12Q 1/6841* (2013.01); *C12Q 1/682* (2013.01); *C12Q 1/6876* (2013.01); *G01N 1/30* (2013.01);

(Continued)

(58) Field of Classification Search

CPC .................................................... C12Q 1/6841

See application file for complete search history.

(56) References Cited

U.S. PATENT DOCUMENTS 7,189,509 B2 3/2007 Shao et al.
10,227,639 B2 3/2019 Levner et al.

(Continued)

FOREIGN PATENT DOCUMENTS

EP 0611828 A1 8/1994
EP 2794928 A1 10/2014

(Continued)

OTHER PUBLICATIONS

Shah et al. In Situ Transcription Profiling of Single Cells Reveals Spatial Organization of Cells in the Mouse Hippocampus. Neuron. Oct. 19, 2016;92(2):342-357. doi: 10.1016/j.neuron.2016.10.001. PMID: 27764670; PMCID: PMC5087994 (Year: 2016).*

(Continued)

*Primary Examiner* — Aaron A Priest
*Assistant Examiner* — Tian Yu
(74) *Attorney, Agent, or Firm* — Garrett H. Anderson

(57) ABSTRACT

The technology provided herein relates to multiplex methods and kits for detecting different analytes in a sample in parallel by sequential signal-encoding of said analytes, as well as in vitro methods for screening, identifying and/or testing a substance and/or drug and in vitro methods for diagnosis of a disease, and an optical multiplexing system.

14 Claims, 35 Drawing Sheets

Specification includes a Sequence Listing.

Related U.S. Application Data

(60) Provisional application No. 63/127,910, filed on Dec. 18, 2020, provisional application No. 63/129,942, filed on Dec. 23, 2020.

(51) Int. Cl.
*C12Q 1/6876* (2018.01)
*G01N 1/30* (2006.01)
*G01N 33/569* (2006.01)

(52) U.S. Cl.
CPC ... *G01N 33/56961* (2013.01); *C12Q 2600/16* (2013.01)

(56) References Cited

U.S. PATENT DOCUMENTS

| | | | | |
|---|---|---|---|---|
| 10,457,980 | B2 | 10/2019 | Cai et al. | |
| 11,021,737 | B2 | 6/2021 | Church et al. | |
| 11,473,129 | B2 | 10/2022 | Cai et al. | |
| 2015/0105298 | A1 | 4/2015 | Czaplinski | |
| 2016/0369329 | A1 | 12/2016 | Cai et al. | |
| 2017/0212983 | A1* | 7/2017 | Cai | C12Q 1/6841 |
| 2018/0142286 | A1 | 5/2018 | Dunaway et al. | |
| 2019/0218608 | A1* | 7/2019 | Daugharthy | C12Q 1/6876 |

FOREIGN PATENT DOCUMENTS

| | | | | |
|---|---|---|---|---|
| EP | 2992115 | A2 | 3/2016 | |
| EP | 3626833 | A1 | 3/2020 | |
| EP | 3720972 | A1 | 10/2020 | |
| EP | 3891297 | A1 | 10/2021 | |
| WO | 2003083440 | A2 | 10/2003 | |
| WO | 2007001986 | A2 | 1/2007 | |
| WO | 2011038403 | A1 | 3/2011 | |
| WO | 2011048184 | A1 | 4/2011 | |
| WO | 2011112634 | A2 | 9/2011 | |
| WO | 2012003742 | A1 | 1/2012 | |
| WO | 2013096851 | A1 | 6/2013 | |
| WO | 2013157821 | A1 | 10/2013 | |
| WO | 2014182528 | | 11/2014 | |
| WO | 2016011429 | A1 | 1/2016 | |
| WO | 2016081740 | A1 | 5/2016 | |
| WO | 2016201142 | A1 | 12/2016 | |
| WO | 2017189525 | A1 | 11/2017 | |
| WO | 2017201073 | A1 | 11/2017 | |
| WO | 2018005336 | A1 | 1/2018 | |
| WO | WO-2018026873 | A1 * | 2/2018 | C12Q 1/6813 |
| WO | 2018044939 | A1 | 3/2018 | |
| WO | 2018094385 | A1 | 5/2018 | |
| WO | 2019113547 | A1 | 6/2019 | |
| WO | 2019222178 | A1 | 11/2019 | |
| WO | 2020093019 | A2 | 5/2020 | |
| WO | 2020117713 | A1 | 6/2020 | |
| WO | 2020123742 | A1 | 6/2020 | |
| WO | 2020163397 | A2 | 8/2020 | |
| WO | 2020240025 | A1 | 12/2020 | |
| WO | 2021021982 | A1 | 2/2021 | |
| WO | 2021067475 | A1 | 4/2021 | |
| WO | 2021108370 | A1 | 6/2021 | |
| WO | 2021108459 | A1 | 6/2021 | |
| WO | 2021119402 | A1 | 6/2021 | |
| WO | 2021247618 | A1 | 12/2021 | |
| WO | 2021258024 | A1 | 12/2021 | |

OTHER PUBLICATIONS

"Daphnis et al., Hum Reprod, Jan. 2005, vol. 20(1): pp. 129-137, Detailed FISH analysis of day 5 human embryos reveals the mechanisms leading to mosaic aneuploidy".

Almstrand et al., Appl Environ Microbiol, Oct. 2013, vol. 79(19): pp. 5978-5987, New methods for analysis of spatial distribution and coaggregation of microbial populations in complex biofilms.

Chen et al., Sci, Apr. 9, 2015: pp. 1-21 Spatially resolved, highly multiplexed RNA profiling in single cells; publishedApr. 24, 2015.

Choi et al., ACS NANO, May 27, 2014, vol. 8(5): pp. 4284-4294, Next-generation in situ hybridization chain reaction: Higher gain, lower cost, greater durability.

Choi et al., Development, Jun. 15, 2018, vol. 145(12): pp. 1-10 Third-generation in situ hybridization chain reaction: multiplexed, quantitative, sensitive, versatile, robust; published Jun. 15, 2018.

Choi et al., Nat Biotechnol, Nov. 2010, vol. 28(11): pp. 1208-1212 "Programmable in situ amplification for multiplexedimaging of mRNA expression"; available May 1, 2011.

Eng et al., Nature, Sep. 25, 2019, Transcriptome-scale super-resolved imaging in tissues by RNA seqFISH+.

Epstein et al., Cytometry, 1995, vol. 21: pp. 378-381 Reutilization of previously hybridized slides for fluorescence in situ hybridization.

Fields et al., eLife, 2019 ; 8:e42823 "A multiplexed DNA FISH strategy for assessing genome architecture inCaenorhabditis elegans"; published May 14, 2019.

Gasparini et al. Research Square (2006) doi.org/10.1038/nprot.2006.361 "Fluorescence in situ hybridization (FISH) for DNA replication origins" published Oct. 27, 2006.

Gerner et al. Immunity 37(2):364-376 August (2012) "Histo-Cytometry: in situ multiplex cell phenotyping, quantification, and spatial analysis applied to dendritic cell subset micro-anatomy in lymph nodes"; available onlineDec. 5, 2012.

Henegariu et al. Nature Genetics vol. 23, p. 263 (1999) Colour-changing karyotyping: an alternative to M-FISH/SKY; published Nov. 1999.

Kishi et al, Nature Methods vol. 16, pp. 533-544, Jun. 2019 "SABER amplifies FISH: enhanced multiplexed imagingof RNA and DNA in cells and tissues" published online May 20, 2019.

Kris et al. Plant Physiology vol. 144 pp. 1256-1266 (2007) "High-Throughput, High-Sensitivity Analysis of GeneExpression in *Arabidopsis*"; published May 11, 2007.

Lubeck et al., Nat Meth, Apr. 2014, vol. 11(4): pp. 360-361 "Single cell in situ RNA profiling by sequentialhybridization"; published Mar. 28, 2014.

Lubeck et al., Nat Meth, Jul. 31, 2012, vol. 9(7): pp. 743-748 Single-cell systems biology by super-resolution imaging and combinatorial labeling.

Mali et al Nature Methods vol. 10 No. 5 pp. 403 (2013) "Barcoding cells using cell-surface programmable DNA-binding domains" published online Mar. 17, 2013.

Mateo et al., Nature, Apr. 2019, vol. 568: pp. 49-54 "Visualizing DNA folding and RNA in embryos at single-cellresolution"; available Sep. 18, 2019.

Miner et al., Nucl Acid res, 2004, vol. 32(17): pp. e135, Mulecular barcodes detect redundancy and contamination in hairpin-bisulfite PCR.

Moffitt et al., PNAS, Sep. 27, 2016, vol. 113(39): pp. 11046-11051 "High-throughput single-cell gene-expressionprofiling with multiplexed error-robust fluorescence in situ hybridization"; published online Sep. 13, 2016.

Mokros et al., Genome, 2006, vol. 49: pp. 1036-1042 Identification of chromosomal fusion sites in *Arabidopsis* mutants using sequential bicolour BAC-FISH.

Mudiyanselage et al., Methods 2019, vol. 161, pp. 24-34 "Second generation fluorogenic RNA-based sensors" available online Jan. 17, 2019.

Muller et al., Chromosome Res, vol. 10(3): pp. 223-232 Towards unlimited colors for fluorescence in-situ hybridization (FISH).

https://www.molecularcatalog.abbott/int/en/Vysis-MultiVysion-PGT-Multi-color-Probe; 3 pages.

P.M. Nederlof et al., Cytometry 11:126-131 (1990), Multiple Fluorescence In Situ Hybridization.

Player et al., J Histochem Cytochem, 2001, vol. 49(5): pp. 603-611 "Single-copy gene detection using branchedDNA (bDNA) in situ hybridization"; published May 1, 2001.

Rimsza et al. Clinical Cancer Research 17(11) p. 3727 (2011) "Accurate Classification of Diffuse Large B-CellLymphoma into

(56) References Cited

OTHER PUBLICATIONS

GerminalCenter and Activated B-Cell Subtypes Using a Nuclease Protection Assay on Formalin-Fixed, Paraffin-EmbeddedTissues" published online Mar. 1, 2011.
Rouhanifard et al. Nature Biotech vol. 37 pp. 84-91 "ClampFISH detects individual nucleic acid molecules; usingclick chemistry-based amplification" published online Nov. 12, 2018.
Shah et al., Cell, Jul. 12, 2018, vol. 174(2): pp. 363-376 Dynamics and spatial genomics of the nascent transcriptomeby intron seqFISH; available Jul. 12, 2019.
Shah et al., Neuron, Oct. 19, 2016, vol. 92: pp. 342-357 "In situ transcription profiling of single cells reveals spatialorganization of cells in the mouse hippocampus"; published Oct. 19, 2017.
Sun et al., Nanomaterials (Basel) vol. 9 "Intracellular imaging with genetically encoded RNA-based molecularsensors" published Feb. 8, 2019.
Suppl. material: Almstrand et al., Appl Environ Microbiol, Oct. 2013, vol. 79(19): pp. 5978-5987 New methods for analysis of spatial distribution and coaggregation of microbial populations in complex biofilms.
Takei et al. BioRxiv preprint: doi.org/10.1101/2020.11.29.403055 "Global architecture of the nucleus in single cells byDNA seqFISH+ and multiplexed immunofluorescence" published online Nov. 30, 2020.
Takei, Nature, Jul. 27, 2021, Integrated spatial genomics reveals global architecture of single nuclei.
Uher et al., RBM, 2009, vol. 19(4): pp. 539-546, Non-informative results and monosomies in PGD: The importance of a third round of re-hybridization.
Wang et al., J Mol Diagn, Jan. 2012, vol. 14(1): pp. 22-29 "A novel in situ RNA analysis platform for formalin-fixed, paraffin-embedded tissues" published Jan. 2012.
Weremowicz et al, Prenatal Diagnosis 2006 vol. 26, pp. 1042-1050 "Validation of DNA probes forpreimplementation genetic diagnosis (PGD) by fluorescence in situ hybridization (FISH)" published online Sep. 4, 2006.
Xia et al. Sci Rep vol. 9, p. 7721 (2019) "Multiplexed detection of RNA using MERFISH and branched DNAamplification" published online May 22, 2019.
Zhen et al., Prenat Diagn, 1998, vol. 18: pp. 1181-1185, Poly-FISH: A technique of repeated hybridizations that improves cytogenetic analysis of fetal cells in maternal blood.
Zheng et al. PLoS Biology 17(12) e3000569. doi.org/10.1371/journal. pbio.3000569 (2019) "A new branchedproximity hybridization assay for the quantificationof nanoscale proteinprotein proximity." Published online Dec. 11, 2019.
A.P.K.K. Karunanayake Mudiyanselage et al., "Second-generation" fluorogenic RNA-based sensors, Elsevier Methods, 2019; 11 pages.
Hildyard, et al., Multiplex in situ hybridization within a single transcript: RNAscope reveals dystrophin mRNA dynamics, PLOS One | https://doi.org/10.1371/journal.pone.0239467 Sep. 24, 2020; 29 pages.

* cited by examiner

STEP 3

Round 8

| R1 | R2 | R3 | R4 | R5 | R6 | R7 | R8 |
|---|---|---|---|---|---|---|---|
| A | B | B | A | - | B | A | B |
| B | B | A | A | B | A | - | B |
| A | - | A | B | A | B | B | A |
| A | B | B | - | A | A | B | B |
| B | A | - | A | B | A | A | A |
| A | A | B | - | B | A | B | B |
| A | B | B | B | A | - | A | A |

STEP 3:

STEP 4:

SEQUENCE LISTING

<160> NUMBER OF SEQ ID NOS: 1400

<210> SEQ ID NO 1
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1
actactagag accggtagaa atgagtaacg attaccgact tatcc 45

<210> SEQ ID NO 2
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 2
tggcggggaa cgaagtatat agtaacgatt accgacttat cc 42

<210> SEQ ID NO 3
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 3
tggcgtcaat ggttgcggtg taacgattac cgacttatcc 40

<210> SEQ ID NO 4
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 4
tcggtcactc gaataacccg gtaacgatta ccgacttatc c 41

<210> SEQ ID NO 5
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 5
ctccaaatcg aggtgcacca gtaacgatta ccgacttatc c 41

<210> SEQ ID NO 6
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 6
ggccagttcc cgagttggtg taacgattac cgacttatcc 40

<210> SEQ ID NO 7
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 7
agacttcaag cgacatgctc tgtaacgatt accgacttat cc 42

<210> SEQ ID NO 8
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 8
ggagcaccac cgtagataca agtaacgatt accgacttat cc 42

<210> SEQ ID NO 9
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 9
ctctccaaat cacgtatttg tgggtaacga ttaccgactt atcc 44

<210> SEQ ID NO 10
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 10
agagtttgcc tatcaggtct tattgtaacg attaccgact tatcc 45

<210> SEQ ID NO 11
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 11
ggccaagtcg cactccacag taacgattac cgacttatcc 40

<210> SEQ ID NO 12
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 12
tccttttcta cgtcatgaca cagtaacgat taccgactta tcc 43

<210> SEQ ID NO 13
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 13
ttccattaga cgaataagtt tttcagtaac gattaccgac ttatcc 46

<210> SEQ ID NO 14
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 14
tttctggtaa gctcatcaca tctgtaacga ttaccgactt atcc 44

<210> SEQ ID NO 15
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 15
gagttagggt agtcataatt gatgagtaac gattaccgac ttatcc 46

<210> SEQ ID NO 16
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 16
ttcttccaat tcgatgaata taatccgtaa cgattaccga cttatcc 47

<210> SEQ ID NO 17
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 17
tgttattagg tgtaaagaaa gtgtatggta acgattaccg acttatcc 48

<210> SEQ ID NO 18
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 18
gagataaggt cgctcacttg cgtaacgatt accgacttat cc 42

<210> SEQ ID NO 19
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 19
acctctgtct tcgaccaact ggtaacgatt accgacttat cc 42

<210> SEQ ID NO 20
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 20
acccctggaa cgacctgaac gtaacgatta ccgacttatc c 41

<210> SEQ ID NO 21
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 21
agtatctgtc ccgacggtca gtaacgatta ccgacttatc c 41

<210> SEQ ID NO 22
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 22
accccttttg cccgcagagg taacgattac cgacttatcc 40

<210> SEQ ID NO 23
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 23
tttaagcagg ctagagtaac ctcgtaacga ttaccgactt atcc 44

<210> SEQ ID NO 24
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 24
gcattggata accaatcata ggtggtaacg attaccgact tatcc 45

<210> SEQ ID NO 25
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 25
tcccctagtc cgagttgctc gtaaccctaa ttatgggaat c 41

<210> SEQ ID NO 26
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 26
ccaatttgca cttggatgtg tagtaaccct aattatggga atc 43

<210> SEQ ID NO 27

<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 27
ttttgccagt agaacaagca tggtaaccct aattatggga atc 43

<210> SEQ ID NO 28
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 28
ggaggcaagg ttccgcaacg taaccctaat tatgggaatc 40

<210> SEQ ID NO 29
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 29
agaattccac gtaaatcaca tgcgtaaccc taattatggg aatc 44

<210> SEQ ID NO 30
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 30
tatgcatgta cagggaagta tccgtaaccc taattatggg aatc 44

<210> SEQ ID NO 31
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 31
gtgtgcatgc cttagaaaaa gcgtaaccct aattatggga atc 43

<210> SEQ ID NO 32
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 32
agcttttgtg cccttatcat gagtaaccct aattatggga atc 43

<210> SEQ ID NO 33
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 33
cttcattagt atcttgtcac ttggggtaac cctaattatg ggaatc 46

<210> SEQ ID NO 34
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 34
agatgatgac cctaccaaat ttgggtaacc ctaattatgg gaatc 45

<210> SEQ ID NO 35
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 35
aggcaagaga tagatatgtg ggcgtaaccc taattatggg aatc 44

<210> SEQ ID NO 36
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 36
cagctgccac tataatcatg tttgtaaccc taattatggg aatc 44

<210> SEQ ID NO 37
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 37
ggaacatgct aatttaaggt gagtgtaacc ctaattatgg gaatc 45

<210> SEQ ID NO 38
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 38
aggactttgc tatatcaagt agttcgtaac cctaattatg ggaatc 46

<210> SEQ ID NO 39
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 39
aaaggagata gtaacaatgg ttttcgtaac cctaattatg ggaatc 46

<210> SEQ ID NO 40
<211> LENGTH: 43
<212> TYPE: DNA

<213> ORGANISM: Artificial Sequence
<220> FEATURE:
<223> OTHER INFORMATION: Target Specific Oligonucleotide

<400> SEQUENCE: 40
aaatcagtgg ttcaccctgt tcgtaaccct aattatggga atc 43

<210> SEQ ID NO 41
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 41
cttgtcataa gataattagg caaattagta accctaatta tgggaatc 48

<210> SEQ ID NO 42
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 42
tcattaagtt aatgctaagg atctttgtaa ccctaattat gggaatc 47

<210> SEQ ID NO 43
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 43
tgtcactggt acaagtggac ttgtaaccct aattatggga atc 43

<210> SEQ ID NO 44
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 44
ttggtcacta tacaagtgac ttctgtaacc ctaattatgg gaatc 45

<210> SEQ ID NO 45
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 45
aggaaaatgg gcgtaaagga gggtaaccct aattatggga atc 43

<210> SEQ ID NO 46
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 46
ttcatctaca atagggacaa caaacgtaac cctaattatg ggaatc 46

<210> SEQ ID NO 47
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 47
gataagtcta cgtggaaaag catgtaaccc taattatggg aatc 44

<210> SEQ ID NO 48
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 48
caggactaca gttaagcatt tactgtaacc ctaattatgg gaatc 45

<210> SEQ ID NO 49
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 49
gtctaggaaa ttgccgtggt tggtaaccct aattatggga atc 43

<210> SEQ ID NO 50
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 50
aatcatcgtc tcgaaagcgg tgtaacccta attatgggaa tc 42

<210> SEQ ID NO 51
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 51
cttgaccaaa ttcgaaggtc cagtaaccct aattatggga atc 43

<210> SEQ ID NO 52
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 52
gatgactctg ttcgcatcct cggtaaccct aattatggga atc 43

<210> SEQ ID NO 53
<211> LENGTH: 42
<212> TYPE: DNA
<213> ORGANISM: Artificial Sequence
<220> FEATURE:

<223> OTHER INFORMATION: Target Specific Oligonucleotide

<400> SEQUENCE: 53
gatgctagtg tcaaacctgc cgtaacccta attatgggaa tc 42

<210> SEQ ID NO 54
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 54
tgatacaggg ctcgtactta tccgtaaccc taattatggg aatc 44

<210> SEQ ID NO 55
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 55
aggagtcaca cgagttgaaa aggtaaccct aattatggga atc 43

<210> SEQ ID NO 56
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 56
ctcattacac cgaggtatga agggtaaccc taattatggg aatc 44

<210> SEQ ID NO 57
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 57
ctctgtcacg gctcgggtgg taaccctaat tatgggaatc 40

<210> SEQ ID NO 58
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 58
ctaccatatg tacccgacct cagtaaccct aattatggga atc 43

<210> SEQ ID NO 59
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 59
aaccttaggt cgggtataga gaggtaaccc taattatggg aatc 44

<210> SEQ ID NO 60
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 60
gaagcactta gacactgtaa ggcgtaaccc taattatggg aatc 44

<210> SEQ ID NO 61
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 61
aataatcacc ggcagtaacg ggtaacccta attatgggaa tc 42

<210> SEQ ID NO 62
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 62
aggaagaaac ctatggcaga cagtaaccct aattatggga atc 43

<210> SEQ ID NO 63
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 63
catgtgttat tacgatgttc tttgtgtaac cctaattatg ggaatc 46

<210> SEQ ID NO 64
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 64
actactgttt ggtacttgta tctggtaacc ctaattatgg gaatc 45

<210> SEQ ID NO 65
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 65
aaatcagtgg cggacagtag cgtaacccta attatgggaa tc 42

<210> SEQ ID NO 66
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 66
caggcaatgc cgactggatt gtaaccctaa ttatgggaat c 41

<210> SEQ ID NO 67
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 67
tcttatctaa gaccaactat aggtatggta accctaatta tgggaatc 48

<210> SEQ ID NO 68
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 68
gggaactgtc tattgagcac tcgtaaccct aattatggga atc 43

<210> SEQ ID NO 69
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 69
attacaatct ttagtactca tggaaagtaa ccctaattat gggaatc 47

<210> SEQ ID NO 70
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 70
aaggtattct catgcctaga atattgtaac cctaattatg ggaatc 46

<210> SEQ ID NO 71
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 71
tggacagaca cgttgtcatt tggtaaccct aattatggga atc 43

<210> SEQ ID NO 72
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 72
ctctcattac aatgctatac atttaacgta accctaatta tgggaatc 48

<210> SEQ ID NO 73
<211> LENGTH: 41

<212> TYPE: DNA
<213> ORGANISM: Artificial Sequence
<220> FEATURE:
<223> OTHER INFORMATION: Target Specific Oligonucleotide

<400> SEQUENCE: 73
tgcagctcgc aacggaacaa gtaacggatt ttacaacttt a 41

<210> SEQ ID NO 74
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 74
gagtccatcc ggacattgac ctgtaacgga ttttacaact tta 43

<210> SEQ ID NO 75
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 75
cttgaacggc ctcgacgagg gtaacggatt ttacaacttt a 41

<210> SEQ ID NO 76
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 76
cctcctcggt tatattggcc ccgtaacgga ttttacaact tta 43

<210> SEQ ID NO 77
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 77
accgagactt cgaaaatgaa cgagtaacgg attttacaac ttta 44

<210> SEQ ID NO 78
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 78
cctctggctc gaaactgaaa gggtaacgga ttttacaact tta 43

<210> SEQ ID NO 79
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 79
tgctatggac tagatctcgg caagtaacgg attttacaac ttta 44

<210> SEQ ID NO 80
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 80
gccttgaccg gtcagaagac ggtaacggat tttacaactt ta 42

<210> SEQ ID NO 81
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 81
taccacagag atcgcagctg cgtaacggat tttacaactt ta 42

<210> SEQ ID NO 82
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 82
accagcccga acctcgcccg taacggattt tacaacttta 40

<210> SEQ ID NO 83
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 83
actgtatgct tgccggtaat tctgtaacgg attttacaac ttta 44

<210> SEQ ID NO 84
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 84
gaacatgaac cggccccgac gtaacggatt ttacaacttt a 41

<210> SEQ ID NO 85
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 85
caggaatccc gtcaagggtg ggtaacggat tttacaactt ta 42

<210> SEQ ID NO 86
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 86
tctcgattta cctcgtttaa gatctcgtaa cggattttac aacttta 47

<210> SEQ ID NO 87
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 87
agaaccatgg tcgaactgac ctgtaacgga ttttacaact tta 43

<210> SEQ ID NO 88
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 88
tctgaggggc tacgctgaga gtaacggatt ttacaacttt a 41

<210> SEQ ID NO 89
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 89
aagcctctgt tacgcccacg gtaacggatt ttacaacttt a 41

<210> SEQ ID NO 90
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 90
aatgattcaa ctcgtactgg atcccgtaac ggattttaca acttta 46

<210> SEQ ID NO 91
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 91
cctcggaaat cccgattctg atagtaacgg attttacaac ttta 44

<210> SEQ ID NO 92
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 92
ggcccctact cggttgtggg gtaacggatt ttacaacttt a 41

<210> SEQ ID NO 93
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 93
ggaaaatgga acgaaactcc tgttgtaacg gattttacaa cttta 45

<210> SEQ ID NO 94
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 94
ctgggtcgtg cgaggtcctg taacggattt tacaacttta 40

<210> SEQ ID NO 95
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 95
cacggggcta ggacggggtg taacggattt tacaacttta 40

<210> SEQ ID NO 96
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 96
ccgatggcgt actcgtcggg taacccttat tcggtacta 39

<210> SEQ ID NO 97
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 97
gatcagatca gaatccgagg tggtaaccct tattcggtac ta 42

<210> SEQ ID NO 98
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 98
ggttgtactc gcgacagttg gtaaccctta ttcggtacta 40

<210> SEQ ID NO 99
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 99
gacctgctca ttcgaggtga gtaaccctta ttcggtacta 40

<210> SEQ ID NO 100
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 100
tcacgtagta gcggcttcgg taacccttat tcggtacta 39

<210> SEQ ID NO 101
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 101
ccaaagatgg gcctacttgt cagtaaccct tattcggtac ta 42

<210> SEQ ID NO 102
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 102
gacagagctg cacgcttggg taacccttat tcggtacta 39

<210> SEQ ID NO 103
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 103
ctgggcctgt ttgcgctcag taacccttat tcggtacta 39

<210> SEQ ID NO 104
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 104
tccttaggca tgcgcggcgt aacccttatt cggtacta 38

<210> SEQ ID NO 105
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 105
cagcggcagt actcgctgtg taacccttat tcggtacta 39

<210> SEQ ID NO 106

<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 106
atgccaccga tgacccgcgt aacccttatt cggtacta 38

<210> SEQ ID NO 107
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 107
atcagcgtcg ctccctcggt aacccttatt cggtacta 38

<210> SEQ ID NO 108
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 108
ctttgagagc tcgaacatcg tgtaaccctt attcggtact a 41

<210> SEQ ID NO 109
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 109
ttccagtagt taaggcagag cagtaaccct tattcggtac ta 42

<210> SEQ ID NO 110
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 110
gagctgcagg atcgggtccg taacccttat tcggtacta 39

<210> SEQ ID NO 111
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 111
acatgagtgg tttcgtagcg ggtaaccctt attcggtact a 41

<210> SEQ ID NO 112
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 112
tgccgatgac atggaactcg gtaacccttta ttcggtacta 40

<210> SEQ ID NO 113
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 113
tggtgtaatt gaccttgtag gtagtaaccc ttattcggta cta 43

<210> SEQ ID NO 114
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 114
cattggccga aagcaggctg taacccttat tcggtacta 39

<210> SEQ ID NO 115
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 115
gagacctctg ccgaaactgg gtaacccttta ttcggtacta 40

<210> SEQ ID NO 116
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 116
agtcttgtgc ttcgggtcaa agtaaccctt attcggtact a 41

<210> SEQ ID NO 117
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 117
cctcttctcg cctggcatag ggtaaccctt attcggtact a 41

<210> SEQ ID NO 118
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 118
gtaacggtga aaatggaccg ggtaaccctt attcggtact a 41

<210> SEQ ID NO 119
<211> LENGTH: 42
<212> TYPE: DNA

<213> ORGANISM: Artificial Sequence
<220> FEATURE:
<223> OTHER INFORMATION: Target Specific Oligonucleotide

<400> SEQUENCE: 119
tccctctaag ggattaatgc cagtaaccct tattcggtac ta 42

<210> SEQ ID NO 120
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 120
agttcaagta tcccgcgact agtaacaatt agagtgaaat acc 43

<210> SEQ ID NO 121
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 121
gaacgcaggc tgtttactgt tgtaacaatt agagtgaaat acc 43

<210> SEQ ID NO 122
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 122
ggtccaggta aactaatggc tggtaacaat tagagtgaaa tacc 44

<210> SEQ ID NO 123
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 123
ctctgttgag tttacctcgc aagtaacaat tagagtgaaa tacc 44

<210> SEQ ID NO 124
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 124
tacttcaact aaccagtcca cggtaacaat tagagtgaaa tacc 44

<210> SEQ ID NO 125
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 125
ccatgagaca aggcttaaga ctgtaacaat tagagtgaaa tacc 44

<210> SEQ ID NO 126
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 126
cggccaaaga atagtcgtag cgtaacaatt agagtgaaat acc 43

<210> SEQ ID NO 127
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 127
ccatttccct aaggtatgtg tgagtaacaa ttagagtgaa atacc 45

<210> SEQ ID NO 128
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 128
ctctcatact gttagtgatg tctggtaaca attagagtga aatacc 46

<210> SEQ ID NO 129
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 129
cagctttgtc ccgtgactgt gtaacaatta gagtgaaata cc 42

<210> SEQ ID NO 130
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 130
tgctgcaatg ctagcagcgg taacaattag agtgaaatac c 41

<210> SEQ ID NO 131
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 131
aagacaggaa cctatcaatg tagtgtaaca attagagtga aatacc 46

<210> SEQ ID NO 132
<211> LENGTH: 46
<212> TYPE: DNA
<213> ORGANISM: Artificial Sequence
<220> FEATURE:

<223> OTHER INFORMATION: Target Specific Oligonucleotide

<400> SEQUENCE: 132
tagattagat tatgcccaag tcaggtaaca attagagtga aatacc 46

<210> SEQ ID NO 133
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 133
catgtaaccc actttaggtt tacagtaaca attagagtga aatacc 46

<210> SEQ ID NO 134
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 134
ccagtctttc gtattaatga ttcaggtaac aattagagtg aaatacc 47

<210> SEQ ID NO 135
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 135
tgcaacccgt ctcgtcttcg gtaacaatta gagtgaaata cc 42

<210> SEQ ID NO 136
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 136
gtgtaggtat catctgtaat gtacagtaac aattagagtg aaatacc 47

<210> SEQ ID NO 137
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 137
tcccggactt cagtaccgcg taacaattag agtgaaatac c 41

<210> SEQ ID NO 138
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 138
cgaggaggtt gcgaaaggcg taacaattag agtgaaatac c 41

<210> SEQ ID NO 139
<211> LENGTH: 49
<212> TYPE: DNA
<213> ORGANISM: Artificial Sequence
<220> FEATURE:
<223> OTHER INFORMATION: Target Specific Oligonucleotide

<400> SEQUENCE: 139
tatacatata ctcaacactt atagagggta acaattagag tgaaatacc 49

<210> SEQ ID NO 140
<211> LENGTH: 49
<212> TYPE: DNA
<213> ORGANISM: Artificial Sequence
<220> FEATURE:
<223> OTHER INFORMATION: Target Specific Oligonucleotide

<400> SEQUENCE: 140
gtaatagata ccataatttg tacttgggta acaattagag tgaaatacc 49

<210> SEQ ID NO 141
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 141
tgctgctgcg ctagacccgt aacaattaga gtgaaatacc 40

<210> SEQ ID NO 142
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 142
gcgtggcgag ccaaagacgt aacaattaga gtgaaatacc 40

<210> SEQ ID NO 143
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 143
tccgcggttg ttggacgggt aacaattaga gtgaaatacc 40

<210> SEQ ID NO 144
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 144
ctgtcacata cgcaaactgg tgtaacatcg ttatagctag a 41

<210> SEQ ID NO 145
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 145
tcgccatata ccggtcaaag agtaacatcg ttatagctag a 41

<210> SEQ ID NO 146
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 146
tggatggtgc aataatccga gggtaacatc gttatagcta ga 42

<210> SEQ ID NO 147
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 147
agtgctgatc ccttaagtat gtcgtaacat cgttatagct aga 43

<210> SEQ ID NO 148
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 148
acctccatta accaatccag aaggtaacat cgttatagct aga 43

<210> SEQ ID NO 149
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 149
tggtgtactt gacccactta tttgtaacat cgttatagct aga 43

<210> SEQ ID NO 150
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 150
cagaagagaa cgtggagcag ggtaacatcg ttatagctag a 41

<210> SEQ ID NO 151
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 151
tccctgtgaa gtttatagac ttcagtaaca tcgttatagc taga 44

<210> SEQ ID NO 152
<211> LENGTH: 40

<212> TYPE: DNA
<213> ORGANISM: Artificial Sequence
<220> FEATURE:
<223> OTHER INFORMATION: Target Specific Oligonucleotide

<400> SEQUENCE: 152
tgtaaaagca aacgcacgcc gtaacatcgt tatagctaga 40

<210> SEQ ID NO 153
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 153
attcagatga cgagaaatga tacagtaaca tcgttatagc taga 44

<210> SEQ ID NO 154
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 154
tggtcacgcc atttccggcg taacatcgtt atagctaga 39

<210> SEQ ID NO 155
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 155
agcaagtata ccataaggaa attcagtaac atcgttatag ctaga 45

<210> SEQ ID NO 156
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 156
ctcgccgtcc tgtcgatttt gtaacatcgt tatagctaga 40

<210> SEQ ID NO 157
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 157
agcgagccga gaactccggt aacatcgtta tagctaga 38

<210> SEQ ID NO 158
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 158
tattttgttc agacaacatg gctgtaacat cgttatagct aga 43

<210> SEQ ID NO 159
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 159
ccacttggta caacggagcc gtaacatcgt tatagctaga 40

<210> SEQ ID NO 160
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 160
cagaacacct gcgaggagag gtaacatcgt tatagctaga 40

<210> SEQ ID NO 161
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 161
ttcatcagcg acgcccctgg taacatcgtt atagctaga 39

<210> SEQ ID NO 162
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 162
cctgcaaaaa aacggtcacg tgtaacatcg ttatagctag a 41

<210> SEQ ID NO 163
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 163
tgtgggagtc ccttaggtca agtaacatcg ttatagctag a 41

<210> SEQ ID NO 164
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 164
gcatcgggag cacgcactgt aacatcgtta tagctaga 38

<210> SEQ ID NO 165
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 165
ggctctgcac aacgcttgcg taacatcgtt atagctaga 39

<210> SEQ ID NO 166
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 166
agccaggaca caatagtcag ggtaacatcg ttatagctag a 41

<210> SEQ ID NO 167
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 167
agccaggaca caatagtcag ggtaacatcg ttatagctag a 41

<210> SEQ ID NO 168
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 168
ttgcacatcc tacggtcttc tgtaacttac tacggagtta ac 42

<210> SEQ ID NO 169
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 169
gtagctcatt cgcaaatctt gggtaactta ctacggagtt aac 43

<210> SEQ ID NO 170
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 170
cctttaagcg cgtcgtgtcc gtaacttact acggagttaa c 41

<210> SEQ ID NO 171
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 171
cctcgacgca tgatgccggt aacttactac ggagttaac 39

<210> SEQ ID NO 172
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 172
gccccatggc tcgtgtaggg taacttacta cggagttaac 40

<210> SEQ ID NO 173
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 173
ccaattgtgt tccggcaagt tgtaacttac tacggagtta ac 42

<210> SEQ ID NO 174
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 174
gataggattt ggtcggaaac ctgtaactta ctacggagtt aac 43

<210> SEQ ID NO 175
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 175
tagttgccaa cggtgttgta gtaacttact acggagttaa c 41

<210> SEQ ID NO 176
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 176
cttggcctat gcggaagtaa cgtaacttac tacggagtta ac 42

<210> SEQ ID NO 177
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 177
ctcgcagcga taggaaccat gtaacttact acggagttaa c 41

<210> SEQ ID NO 178
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 178
tttgcattcg tccatatcaa ctggtaactt actacggagt taac 44

<210> SEQ ID NO 179
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 179
tcaatatcaa cgggtaaacc gggtaactta ctacggagtt aac 43

<210> SEQ ID NO 180
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 180
ttgttactga cgtgggaaat attggtaact tactacggag ttaac 45

<210> SEQ ID NO 181
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 181
tctccgctga tacccgggtg taacttacta cggagttaac 40

<210> SEQ ID NO 182
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 182
ggccagtcac cgaaatttca tgtaacttac tacggagtta ac 42

<210> SEQ ID NO 183
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 183
agttcgtagc ctatctcaca ctgtaactta ctacggagtt aac 43

<210> SEQ ID NO 184
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 184
cacattcccg tacgtttgct ggtaacttac tacggagtta ac 42

<210> SEQ ID NO 185

<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 185
agtgagtccc tatgtatcct ttctgtaact tactacggag ttaac 45

<210> SEQ ID NO 186
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 186
aagcattata acgtgatcca caggtaactt actacggagt taac 44

<210> SEQ ID NO 187
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 187
tgcgccctga agcgcacgta acttactacg gagttaac 38

<210> SEQ ID NO 188
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 188
taaaaaatag cacgattaca gtatacgtaa cttactacgg agttaac 47

<210> SEQ ID NO 189
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 189
catatcgacg gattgagcct aacgtaactt actacggagt taac 44

<210> SEQ ID NO 190
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 190
cggtttctcg cgagagaaat agtaacttac tacggagtta ac 42

<210> SEQ ID NO 191
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 191
cttcccatct cgtgtaacat gagtaactta ctacggagtt aac 43

<210> SEQ ID NO 192
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 192
gcatttcaca tcggactgta ccgtaacttc gaaacggaaa c 41

<210> SEQ ID NO 193
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 193
tggaattctc ggcggaccag taacttcgaa acggaaac 38

<210> SEQ ID NO 194
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 194
gaagtggaaa tacgaccttt gcgtaacttc gaaacggaaa c 41

<210> SEQ ID NO 195
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 195
gctggtccct tgcgtaacat gtaacttcga aacggaaac 39

<210> SEQ ID NO 196
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 196
ttttcatcta ttcgagatgc tcccgtaact tcgaaacgga aac 43

<210> SEQ ID NO 197
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 197
tattcatccc gtggggtagt agtaacttcg aaacggaaac 40

<210> SEQ ID NO 198
<211> LENGTH: 42
<212> TYPE: DNA

<213> ORGANISM: Artificial Sequence
<220> FEATURE:
<223> OTHER INFORMATION: Target Specific Oligonucleotide

<400> SEQUENCE: 198
taaaaatagg cccggatttg tctgtaactt cgaaacggaa ac 42

<210> SEQ ID NO 199
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 199
tccaaccttg acgacaagat agggtaactt cgaaacggaa ac 42

<210> SEQ ID NO 200
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 200
aggcaacagt cgaaccattc tgtaacttcg aaacggaaac 40

<210> SEQ ID NO 201
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 201
gcttcatttg cgactgctct tgtaacttcg aaacggaaac 40

<210> SEQ ID NO 202
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 202
catcaggacg cttgtattgg tggtaacttc gaaacggaaa c 41

<210> SEQ ID NO 203
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 203
atcttcaatc cgagaatcca gcgtaacttc gaaacggaaa c 41

<210> SEQ ID NO 204
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 204
ctgtagtgtg gtagtaagga agagtaactt cgaaacggaa ac 42

<210> SEQ ID NO 205
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 205
gaacacctta cttacaacac ctggtaactt cgaaacggaa ac 42

<210> SEQ ID NO 206
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 206
gtacattgta caccgttaca atgggtaact tcgaaacgga aac 43

<210> SEQ ID NO 207
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 207
tttcaagtcg tctatgttag ctggtaactt cgaaacggaa ac 42

<210> SEQ ID NO 208
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 208
caaagcaact atatgaagct tcattgtaac ttcgaaacgg aaac 44

<210> SEQ ID NO 209
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 209
catacttcta tcgagagctc agggtaactt cgaaacggaa ac 42

<210> SEQ ID NO 210
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 210
acgaagaaat cgagtaggtc tagggtaact tcgaaacgga aac 43

<210> SEQ ID NO 211
<211> LENGTH: 41
<212> TYPE: DNA
<213> ORGANISM: Artificial Sequence
<220> FEATURE:

<223> OTHER INFORMATION: Target Specific Oligonucleotide

<400> SEQUENCE: 211
gaatcattga gtcgaccctt cagtaacttc gaaacggaaa c 41

<210> SEQ ID NO 212
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 212
tgatgtgctt aagtagtgca gcgtaacttc gaaacggaaa c 41

<210> SEQ ID NO 213
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 213
tccacggcat gatacataca acgtaacttc gaaacggaaa c 41

<210> SEQ ID NO 214
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 214
tctcagagca tcccgaatcc agtaacttcg aaacggaaac 40

<210> SEQ ID NO 215
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 215
gtggaacgaa gagtaggtag tttgtaactt cgaaacggaa ac 42

<210> SEQ ID NO 216
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 216
gatcaatact ggacggagtc aggtaacctc gtcggatca 39

<210> SEQ ID NO 217
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 217
gagcttgtta ctcgtgcctt ggtaacctcg tcggatca 38

<210> SEQ ID NO 218
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 218
cttcttacac ttgcggacgc gtaacctcgt cggatca 37

<210> SEQ ID NO 219
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 219
caatacctat tccgttacac acttgtaacc tcgtcggatc a 41

<210> SEQ ID NO 220
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 220
gctccttcag tccggtttta ttgtaacctc gtcggatca 39

<210> SEQ ID NO 221
<211> LENGTH: 36
<212> TYPE: DNA
<213> ORGANISM: Artificial Sequence
<220> FEATURE:
<223> OTHER INFORMATION: Target Specific Oligonucleotide

<400> SEQUENCE: 221
gacgcacgag ccgtgatctg taacctcgtc ggatca 36

<210> SEQ ID NO 222
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 222
gactgctaag gcataggaat tttcgtaacc tcgtcggatc a 41

<210> SEQ ID NO 223
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 223
caccacataa ttacggggac acgtaacctc gtcggatca 39

<210> SEQ ID NO 224
<211> LENGTH: 34
<212> TYPE: DNA
<213> ORGANISM: Artificial Sequence
<220> FEATURE:
<223> OTHER INFORMATION: Target Specific Oligonucleotide

<400> SEQUENCE: 224
cggcaaggcc cttcgcagta acctcgtcgg atca 34

<210> SEQ ID NO 225
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 225
tccatctggt acgtggtggg gtaacctcgt cggatca 37

<210> SEQ ID NO 226
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 226
gtcctgccgc gtatgatttc tgtaacctcg tcggatca 38

<210> SEQ ID NO 227
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 227
tgttcaggct gacgactgca gtaacctcgt cggatca 37

<210> SEQ ID NO 228
<211> LENGTH: 36
<212> TYPE: DNA
<213> ORGANISM: Artificial Sequence
<220> FEATURE:
<223> OTHER INFORMATION: Target Specific Oligonucleotide

<400> SEQUENCE: 228
gcatggaggt ccgtcctgtg taacctcgtc ggatca 36

<210> SEQ ID NO 229
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 229
ttgagggagc gtaatcccaa ggtaacctcg tcggatca 38

<210> SEQ ID NO 230
<211> LENGTH: 36
<212> TYPE: DNA
<213> ORGANISM: Artificial Sequence
<220> FEATURE:
<223> OTHER INFORMATION: Target Specific Oligonucleotide

<400> SEQUENCE: 230
ccggcgtctg cgtacttccg taacctcgtc ggatca 36

<210> SEQ ID NO 231
<211> LENGTH: 39

<212> TYPE: DNA
<213> ORGANISM: Artificial Sequence
<220> FEATURE:
<223> OTHER INFORMATION: Target Specific Oligonucleotide

<400> SEQUENCE: 231
cgactatctg cgtctatcat ccgtaacctc gtcggatca 39

<210> SEQ ID NO 232
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 232
gagaattcga tgatcaactc acggtaacct cgtcggatca 40

<210> SEQ ID NO 233
<211> LENGTH: 35
<212> TYPE: DNA
<213> ORGANISM: Artificial Sequence
<220> FEATURE:
<223> OTHER INFORMATION: Target Specific Oligonucleotide

<400> SEQUENCE: 233
tggcctgtcg tccggtctgt aacctcgtcg gatca 35

<210> SEQ ID NO 234
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 234
cagggattcc gtcatatggc tgtaacctcg tcggatca 38

<210> SEQ ID NO 235
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 235
agacatcgat ggtacatatg ggtgtaacct cgtcggatca 40

<210> SEQ ID NO 236
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 236
tctgagctgt atcgctgcaa gtaacctcgt cggatca 37

<210> SEQ ID NO 237
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 237
tcttaggccc attcgttgga gtaacctcgt cggatca 37

<210> SEQ ID NO 238
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 238
ttatacaccg tgccgaacgc gtaacctcgt cggatca 37

<210> SEQ ID NO 239
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 239
atgccctttg cgatctgcac gtaacctcgt cggatca 37

<210> SEQ ID NO 240
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 240
ggcagaattc cgaagttcag cgtaacataa tcgtagtttc gg 42

<210> SEQ ID NO 241
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 241
gtttccttca cgacaggtgt ggtaacataa tcgtagtttc gg 42

<210> SEQ ID NO 242
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 242
ctggtagaaa tgcgactaaa gacgtaacat aatcgtagtt tcgg 44

<210> SEQ ID NO 243
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 243
tgaccagcat cgtttcatct aatgtaacat aatcgtagtt tcgg 44

<210> SEQ ID NO 244
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 244
ttcgaagttc aaccgagtga cgtaacataa tcgtagtttc gg 42

<210> SEQ ID NO 245
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 245
ccaccaatcc aatgcggaat tgtaacataa tcgtagtttc gg 42

<210> SEQ ID NO 246
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 246
agactcggtg ccattcgtat tgtaacataa tcgtagtttc gg 42

<210> SEQ ID NO 247
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 247
ataactgcta actgcgcaac cgtaacataa tcgtagtttc gg 42

<210> SEQ ID NO 248
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 248
gtagtgaggc cgcttataac cagtaacata atcgtagttt cgg 43

<210> SEQ ID NO 249
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 249
ggtgatgatt cgatggagtg aagtaacata atcgtagttt cgg 43

<210> SEQ ID NO 250
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 250
ctgctgcttt acgtttggtg cgtaacataa tcgtagtttc gg 42

<210> SEQ ID NO 251
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 251
tcatcaacca cgtctttgga tagtaacata atcgtagttt cgg 43

<210> SEQ ID NO 252
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 252
aggcagatct taaagtgttg gttgtaacat aatcgtagtt tcgg 44

<210> SEQ ID NO 253
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 253
tgagggctta tacgaaagca aggtaacata atcgtagttt cgg 43

<210> SEQ ID NO 254
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 254
gctcagtact gactttggta tgtgtaacat aatcgtagtt tcgg 44

<210> SEQ ID NO 255
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 255
cagtcaatca ttagatccac atctgtaaca taatcgtagt ttcgg 45

<210> SEQ ID NO 256
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 256
ggaagctgct cgtcgaagcg taacataatc gtagtttcgg 40

<210> SEQ ID NO 257
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 257
gagaagatac ttatagcttc ttgtctgtaa cataatcgta gtttcgg 47

<210> SEQ ID NO 258
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 258
tcaatgctat ctaactgatg aagagtaaca taatcgtagt ttcgg 45

<210> SEQ ID NO 259
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 259
atcttcccaa ttgatgtaag tacttgtaac ataatcgtag tttcgg 46

<210> SEQ ID NO 260
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 260
catcacagtc cgagacgccg taacataatc gtagtttcgg 40

<210> SEQ ID NO 261
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 261
cattccaccg gcctgtgcgg taacataatc gtagtttcgg 40

<210> SEQ ID NO 262
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 262
ggacagcact actctagagt aaggtaacat aatcgtagtt tcgg 44

<210> SEQ ID NO 263
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 263
tgccaagtaa cttagcacac ccgtaacata atcgtagttt cgg 43

<210> SEQ ID NO 264

<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 264
gtgccacctt tcaccgtgag taaccggtag aattacgg 38

<210> SEQ ID NO 265
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 265
ccgcaggtac gacttgcctg taaccggtag aattacgg 38

<210> SEQ ID NO 266
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 266
tgggcttcaa tcagatggtc agtaaccggt agaattacgg 40

<210> SEQ ID NO 267
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 267
agaacaccag ggtacgcata gtgtaaccgg tagaattacg g 41

<210> SEQ ID NO 268
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 268
tctccgagag tgtcagcggg taaccggtag aattacgg 38

<210> SEQ ID NO 269
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 269
gtcttcccgg ccggtcttgg taaccggtag aattacgg 38

<210> SEQ ID NO 270
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 270
catgttgcag attgtcgcca gtaaccggta gaattacgg 39

<210> SEQ ID NO 271
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 271
ggttcagtcg tttgcgaaca gtaaccggta gaattacgg 39

<210> SEQ ID NO 272
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 272
agctaccaat tagacccact cggtaaccgg tagaattacg g 41

<210> SEQ ID NO 273
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 273
cgtagttctc gtctccgatc agtaaccggt agaattacgg 40

<210> SEQ ID NO 274
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 274
ggagctgaac ttgacgccag gtaaccggta gaattacgg 39

<210> SEQ ID NO 275
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 275
taatggatgt actcgttggg cgtaaccggt agaattacgg 40

<210> SEQ ID NO 276
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 276
tctgtgcata gccgtcccgg taaccggtag aattacgg 38

<210> SEQ ID NO 277
<211> LENGTH: 38
<212> TYPE: DNA

<213> ORGANISM: Artificial Sequence
<220> FEATURE:
<223> OTHER INFORMATION: Target Specific Oligonucleotide

<400> SEQUENCE: 277
tggctggacg gatcggatcg taaccggtag aattacgg 38

<210> SEQ ID NO 278
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 278
ggtttgcgtc gttgcggcgt aaccggtaga attacgg 37

<210> SEQ ID NO 279
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 279
tctctgggga cgtgacaaag gtaaccggta gaattacgg 39

<210> SEQ ID NO 280
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 280
gaattcatca gctagattgg caagtaaccg gtagaattac gg 42

<210> SEQ ID NO 281
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 281
tcactccgtg ggctaagcgg taaccggtag aattacgg 38

<210> SEQ ID NO 282
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 282
tgtaagggaa cacggaagtg ggtaaccggt agaattacgg 40

<210> SEQ ID NO 283
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 283
ctcaatggtg gcgcggatcg taaccggtag aattacgg 38

<210> SEQ ID NO 284
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 284
aaccactcaa tctgcgtctc ggtaaccggt agaattacgg 40

<210> SEQ ID NO 285
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 285
gctgtagggc gccattttgt gtaaccggta gaattacgg 39

<210> SEQ ID NO 286
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 286
tgagtgacgg cattgcgcag taaccggtag aattacgg 38

<210> SEQ ID NO 287
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 287
caaagtggct catcgccacc gtaaccggta gaattacgg 39

<210> SEQ ID NO 288
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 288
tctatatgct aaatgtattg ccatggtaac gcttctcata acact 45

<210> SEQ ID NO 289
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 289
ctatgaaact tcgtggtcac tccgtaacgc ttctcataac act 43

<210> SEQ ID NO 290
<211> LENGTH: 43
<212> TYPE: DNA
<213> ORGANISM: Artificial Sequence
<220> FEATURE:

<223> OTHER INFORMATION: Target Specific Oligonucleotide

<400> SEQUENCE: 290
aactaactca tctgcagtac catgtaacgc ttctcataac act 43

<210> SEQ ID NO 291
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 291
aaaacctgct tgatccacat tctgtaacgc ttctcataac act 43

<210> SEQ ID NO 292
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 292
acattaacaa atcactcttg attcagtaac gcttctcata acact 45

<210> SEQ ID NO 293
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 293
ttttgcttag ctcatggtaa acagtaacgc ttctcataac act 43

<210> SEQ ID NO 294
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 294
gaggagctgt tggataaata attttgtaac gcttctcata acact 45

<210> SEQ ID NO 295
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 295
aagcaggcag gtattgtatg attgtaacgc ttctcataac act 43

<210> SEQ ID NO 296
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 296
gcaacttata tatcagtggt gaatggtaac gcttctcata acact 45

<210> SEQ ID NO 297
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 297
agattatgta tgcatgagaa ccaacgtaac gcttctcata acact 45

<210> SEQ ID NO 298
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 298
gatcatgact ctccttatgg ttaatgtaac gcttctcata acact 45

<210> SEQ ID NO 299
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 299
tgtgaaaccg gtttataaac ctagtaacgc ttctcataac act 43

<210> SEQ ID NO 300
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 300
aataagatta gctactgtct acagtggtaa cgcttctcat aacact 46

<210> SEQ ID NO 301
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 301
taaacaaata gtgatacatc cacacgtaac gcttctcata acact 45

<210> SEQ ID NO 302
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 302
ttcagtcatc taacaatgta ttcctgtaac gcttctcata acact 45

<210> SEQ ID NO 303
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 303
agctgtggga aagtctttaa ctcgtaacgc ttctcataac act 43

<210> SEQ ID NO 304
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 304
atagatgaac tattgatgta cacaacgtaa cgcttctcat aacact 46

<210> SEQ ID NO 305
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 305
tacagatgaa attgagacct aaaacgtaac gcttctcata acact 45

<210> SEQ ID NO 306
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 306
agcaatttgg gttaacagaa atagagtaac gcttctcata acact 45

<210> SEQ ID NO 307
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 307
aatccaatgg gataagtact attagtgtaa cgcttctcat aacact 46

<210> SEQ ID NO 308
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 308
aatgttattc cgtggaaaat tacatgtaac gcttctcata acact 45

<210> SEQ ID NO 309
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 309
ttacagaatt gtgtctgaaa aattatggta acgcttctca taacact 47

<210> SEQ ID NO 310
<211> LENGTH: 40

<212> TYPE: DNA
<213> ORGANISM: Artificial Sequence
<220> FEATURE:
<223> OTHER INFORMATION: Target Specific Oligonucleotide

<400> SEQUENCE: 310
atcagagagg cgctatgcct gtaacgcttc tcataacact 40

<210> SEQ ID NO 311
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 311
cggcgacacg atacagcggt aacgcttctc ataacact 38

<210> SEQ ID NO 312
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 312
cacttcaaat gcgcaacaag cgtaacgtcg ctgaaaaatc 40

<210> SEQ ID NO 313
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 313
gtaagcactg cgcaagacaa gtaacgtcgc tgaaaaatc 39

<210> SEQ ID NO 314
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 314
gtgatgagct cgacaggata ttgtaacgtc gctgaaaaat c 41

<210> SEQ ID NO 315
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 315
atggcgtcgt cggcacacgt aacgtcgctg aaaaatc 37

<210> SEQ ID NO 316
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 316
tttacaacag cgtggcaagt ggtaacgtcg ctgaaaaatc 40

<210> SEQ ID NO 317
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 317
aggcatgaag tgagacaatg cgtaacgtcg ctgaaaaatc 40

<210> SEQ ID NO 318
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 318
cctggctagt ggtatatgtc acgtaacgtc gctgaaaaat c 41

<210> SEQ ID NO 319
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 319
gctgatgatg ttcaagcgca gtaacgtcgc tgaaaaatc 39

<210> SEQ ID NO 320
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 320
ctgccagtta gttaggcaag ttgtaacgtc gctgaaaaat c 41

<210> SEQ ID NO 321
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 321
gcagctccgg gctacaagtg taacgtcgct gaaaaatc 38

<210> SEQ ID NO 322
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 322
tggcagctgt ctaactggag cgtaacgtcg ctgaaaaatc 40

<210> SEQ ID NO 323
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 323
acgcgtgtgc gagtagatgg taacgtcgct gaaaaatc 38

<210> SEQ ID NO 324
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 324
agctccacga aggatgccag taacgtcgct gaaaaatc 38

<210> SEQ ID NO 325
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 325
tgaggacggc atcgagatcc gtaacgtcgc tgaaaaatc 39

<210> SEQ ID NO 326
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 326
gtcttgagac ccggtcttgg gtaacgtcgc tgaaaaatc 39

<210> SEQ ID NO 327
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 327
agtggtctgg atcggtgcgg taacgtcgct gaaaaatc 38

<210> SEQ ID NO 328
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 328
tccattctgg gtcgagtgga gtaacgtcgc tgaaaaatc 39

<210> SEQ ID NO 329
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 329
ggaccccaag gtgttccaag gtaacgtcgc tgaaaaatc 39

<210> SEQ ID NO 330
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 330
agcagcttgg ctactccccg taacgtcgct gaaaaatc 38

<210> SEQ ID NO 331
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 331
tttgggtatg ggtactgtgt agagtaacgt cgctgaaaaa tc 42

<210> SEQ ID NO 332
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 332
gccgcaggga tagatccagg gtaacgtcgc tgaaaaatc 39

<210> SEQ ID NO 333
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 333
tgaagacagt cctatggact tccgtaacgt cgctgaaaaa tc 42

<210> SEQ ID NO 334
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 334
aagctgaagc gcgggtcagt aacgtcgctg aaaaatc 37

<210> SEQ ID NO 335
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 335
ccacgcagcc cttcgagagt aacgtcgctg aaaaatc 37

<210> SEQ ID NO 336
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 336
tagtaggtgt cgacaactag agcgtaactc ttcaagatta atacc 45

<210> SEQ ID NO 337
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 337
gatggtcctg atcgagaaac cagtaactct tcaagattaa tacc 44

<210> SEQ ID NO 338
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 338
aagaggactt cgctgaattg acgtaactct tcaagattaa tacc 44

<210> SEQ ID NO 339
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 339
gaacctccga ctgtatgtca gcgtaactct tcaagattaa tacc 44

<210> SEQ ID NO 340
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 340
tctgaattag agcgatgttg acagtaactc ttcaagatta atacc 45

<210> SEQ ID NO 341
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 341
gcattcctcc gatcgcacag taactcttca agattaatac c 41

<210> SEQ ID NO 342
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 342
ctctatattt agctcgctgt tcaagtaact cttcaagatt aatacc 46

<210> SEQ ID NO 343

<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 343
tattcatcac ggcgcgcttg taactcttca agattaatac c 41

<210> SEQ ID NO 344
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 344
cattggggac cgtgcataaa agtaactctt caagattaat acc 43

<210> SEQ ID NO 345
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 345
caaggggtgc actatttggg agtaactctt caagattaat acc 43

<210> SEQ ID NO 346
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 346
ggaccgtatt tcggcgaaat agtaactctt caagattaat acc 43

<210> SEQ ID NO 347
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 347
atactgcact tgtcggcatg agtaactctt caagattaat acc 43

<210> SEQ ID NO 348
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 348
atggcagatc gatccattgg tgtaactctt caagattaat acc 43

<210> SEQ ID NO 349
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 349
tccctttgga ccgtcaagaa ggtaactctt caagattaat acc 43

<210> SEQ ID NO 350
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 350
aggcttgctg acatacgcag gtaactcttc aagattaata cc 42

<210> SEQ ID NO 351
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 351
cttgctttgt gcgaacaccc gtaactcttc aagattaata cc 42

<210> SEQ ID NO 352
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 352
ctgatatcga atgcaatgga tgagtaactc ttcaagatta atacc 45

<210> SEQ ID NO 353
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 353
taggactggt ccgtcaaaaa cgtaactctt caagattaat acc 43

<210> SEQ ID NO 354
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 354
tgaccattct cgggacacta acgtaactct tcaagattaa tacc 44

<210> SEQ ID NO 355
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 355
atgattgggt ccgtaaaaat gcgtaactct tcaagattaa tacc 44

<210> SEQ ID NO 356
<211> LENGTH: 45
<212> TYPE: DNA

<213> ORGANISM: Artificial Sequence
<220> FEATURE:
<223> OTHER INFORMATION: Target Specific Oligonucleotide

<400> SEQUENCE: 356
gtttcatgta tggtaggacc accgtaactc ttcaagatta atacc 45

<210> SEQ ID NO 357
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 357
ctcttgcatc gtagcgaact agtaactctt caagattaat acc 43

<210> SEQ ID NO 358
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 358
atgatgattc cctcggtcag agtaactctt caagattaat acc 43

<210> SEQ ID NO 359
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 359
agtagagaag atcgctgata tccggtaact cttcaagatt aatacc 46

<210> SEQ ID NO 360
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 360
aacccttgac atcgccagtt tgtaacgtac cgtttgtata tg 42

<210> SEQ ID NO 361
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 361
gaaggttaaa cgagatttcc aaaggtaacg taccgtttgt atatg 45

<210> SEQ ID NO 362
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 362
gccactcgac atttctgccg gtaacgtacc gtttgtatat g 41

<210> SEQ ID NO 363
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 363
tcatactgtc cgcaacatcc ggtaacgtac cgtttgtata tg 42

<210> SEQ ID NO 364
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 364
gccactcgac atttctgccg gtaacgtacc gtttgtatat g 41

<210> SEQ ID NO 365
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 365
tcatactgtc cgcaacatcc ggtaacgtac cgtttgtata tg 42

<210> SEQ ID NO 366
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 366
tgaattttgc ccgaacttca ctgtaacgta ccgtttgtat atg 43

<210> SEQ ID NO 367
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 367
acacactcgg agcgcgcgta acgtaccgtt tgtatatg 38

<210> SEQ ID NO 368
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 368
caaacctata tgcccgttga ctgtaacgta ccgtttgtat atg 43

<210> SEQ ID NO 369
<211> LENGTH: 44
<212> TYPE: DNA
<213> ORGANISM: Artificial Sequence
<220> FEATURE:

<223> OTHER INFORMATION: Target Specific Oligonucleotide

<400> SEQUENCE: 369
caggaacctt taccatgttc atggtaacgt accgtttgta tatg 44

<210> SEQ ID NO 370
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 370
gaaaatctct acggatgaat ttcttgtaac gtaccgtttg tatatg 46

<210> SEQ ID NO 371
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 371
gctgctaaga tagccttgtg aggtaacgta ccgtttgtat atg 43

<210> SEQ ID NO 372
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 372
tggcactaaa aaccggagaa cgtaacgtac cgtttgtata tg 42

<210> SEQ ID NO 373
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 373
tgcgggaccg ccgatacagt aacgtaccgt ttgtatatg 39

<210> SEQ ID NO 374
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 374
ggaaattaaa cggagtctta caacgtaacg taccgtttgt atatg 45

<210> SEQ ID NO 375
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 375
agccagagag cggtatgccg taacgtaccg tttgtatatg 40

<210> SEQ ID NO 376
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 376
ccaccaagtg gggatgtgac gtaacgtacc gtttgtatat g 41

<210> SEQ ID NO 377
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 377
cacacatgac ctttaagcgc tgtaacgtac cgtttgtata tg 42

<210> SEQ ID NO 378
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 378
tccacagatt gcgctgtcta gtaacgtacc gtttgtatat g 41

<210> SEQ ID NO 379
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 379
ctccacggac aggttactgc gtaacgtacc gtttgtatat g 41

<210> SEQ ID NO 380
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 380
gcgtcatggc gtcagcacgt aacgtaccgt ttgtatatg 39

<210> SEQ ID NO 381
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 381
tcctggccgg caacacacgt aacgtaccgt ttgtatatg 39

<210> SEQ ID NO 382
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 382
agccattttg tcgaggtttg ggtaacgtac cgtttgtata tg 42

<210> SEQ ID NO 383
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 383
catccgaagc atgatagttg atggtaacgt accgtttgta tatg 44

<210> SEQ ID NO 384
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 384
tagtgtgttg cgtatcaagt atctagacga tgcgaattaa cac 43

<210> SEQ ID NO 385
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 385
ttattgtgaa ctctagacat gagagtagac gatgcgaatt aacac 45

<210> SEQ ID NO 386
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 386
acagtgaata ctaagactgt aaaaactaga cgatgcgaat taacac 46

<210> SEQ ID NO 387
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 387
acacaaggca cgtagaaaca gtagacgatg cgaattaaca c 41

<210> SEQ ID NO 388
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 388
caatggacag cggttgtgaa atagacgatg cgaattaaca c 41

<210> SEQ ID NO 389
<211> LENGTH: 42

<212> TYPE: DNA
<213> ORGANISM: Artificial Sequence
<220> FEATURE:
<223> OTHER INFORMATION: Target Specific Oligonucleotide

<400> SEQUENCE: 389
caccatcacc tatcgacaga gttagacgat gcgaattaac ac 42

<210> SEQ ID NO 390
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 390
cattgcatta cgttccacat ggtagacgat gcgaattaac ac 42

<210> SEQ ID NO 391
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 391
acacagagtg tccgataccc atagacgatg cgaattaaca c 41

<210> SEQ ID NO 392
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 392
ggtgattaca ttgagtgcta ggatagacga tgcgaattaa cac 43

<210> SEQ ID NO 393
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 393
tccacataag cgttcaaggt atagacgatg cgaattaaca c 41

<210> SEQ ID NO 394
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 394
cagaataatc gctattccta gctgtagacg atgcgaatta acac 44

<210> SEQ ID NO 395
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 395
ttacactcat acgtcgccgg tagacgatgc gaattaacac 40

<210> SEQ ID NO 396
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 396
tggccataaa ggctacttac aattagacga tgcgaattaa cac 43

<210> SEQ ID NO 397
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 397
tttcaagtta ttcgatctgc taacctagac gatgcgaatt aacac 45

<210> SEQ ID NO 398
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 398
agttagtcaa ggactttact aaggttagac gatgcgaatt aacac 45

<210> SEQ ID NO 399
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 399
ttacctcaaa tacgggctac catagacgat gcgaattaac ac 42

<210> SEQ ID NO 400
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 400
gagttatatt actctaacta aagccagtag acgatgcgaa ttaacac 47

<210> SEQ ID NO 401
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 401
ttgtcaacac gcataaaatc tgctagacga tgcgaattaa cac 43

<210> SEQ ID NO 402
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 402
tcatatacaa tcggggatct gagtagacga tgcgaattaa cac 43

<210> SEQ ID NO 403
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 403
cccacaaaaa tacccgtaag ttatagacga tgcgaattaa cac 43

<210> SEQ ID NO 404
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 404
cactaaatta ttacgaattt tgcaaagtag acgatgcgaa ttaacac 47

<210> SEQ ID NO 405
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 405
tcaaataaaa accgtcaaaa gtttatagac gatgcgaatt aacac 45

<210> SEQ ID NO 406
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 406
agtgcaatgg tatcacgtac tgtagacgat gcgaattaac ac 42

<210> SEQ ID NO 407
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 407
atgtgtcttg caattggatt ccctagacga tgcgaattaa cac 43

<210> SEQ ID NO 408
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 408
ggtgtgcgcg tcgtacacta gacccgttat aagtgttg 38

<210> SEQ ID NO 409
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 409
gtgtttaggg tcgcggttga tagacccgtt ataagtgttg 40

<210> SEQ ID NO 410
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 410
gagaatggcg aagtaaatgc cctagacccg ttataagtgt tg 42

<210> SEQ ID NO 411
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 411
gtagatggaa tagacacggc tgtagacccg ttataagtgt tg 42

<210> SEQ ID NO 412
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 412
gctcttaatg catggtacaa ctgtagaccc gttataagtg ttg 43

<210> SEQ ID NO 413
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 413
aaaccagtat ttcgtcacag tgatagaccc gttataagtg ttg 43

<210> SEQ ID NO 414
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 414
gatgggaacg gtgtagagat gttagacccg ttataagtgt tg 42

<210> SEQ ID NO 415
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 415
ttccaaatgc cgtcaaaact gttagacccg ttataagtgt tg 42

<210> SEQ ID NO 416
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 416
tgggtcacag acggtgtggt agacccgtta taagtgttg 39

<210> SEQ ID NO 417
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 417
aatcaggtat acttctatcc ttgaaataga cccgttataa gtgttg 46

<210> SEQ ID NO 418
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 418
tgctgtatta gcaacttgga acttagaccc gttataagtg ttg 43

<210> SEQ ID NO 419
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 419
gccaataaag cgatggttga tctagacccg ttataagtgt tg 42

<210> SEQ ID NO 420
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 420
gtaaggatca ctggatccta ctgtagaccc gttataagtg ttg 43

<210> SEQ ID NO 421
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 421
gacctcattc agttgatgag aggtagaccc gttataagtg ttg 43

<210> SEQ ID NO 422

<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 422
gcataacaga cggttgcaag ttagacccgt tataagtgtt g 41

<210> SEQ ID NO 423
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 423
acctaaagcg agttgctgag ttagacccgt tataagtgtt g 41

<210> SEQ ID NO 424
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 424
gagtcagaaa cacgcatgga atagacccgt tataagtgtt g 41

<210> SEQ ID NO 425
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 425
agcaactctg ataggctcac actagacccg ttataagtgt tg 42

<210> SEQ ID NO 426
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 426
ccatacccac tacggataaa gatgtagacc cgttataagt gttg 44

<210> SEQ ID NO 427
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 427
gctttctgta cgactcaggt tttagacccg ttataagtgt tg 42

<210> SEQ ID NO 428
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 428
caatgttgag ccactaaacc actagacccg ttataagtgt tg 42

<210> SEQ ID NO 429
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 429
atgcttggat taggtccaaa gctagacccg ttataagtgt tg 42

<210> SEQ ID NO 430
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 430
cccggtgatg gattagtttg gtagacccgt tataagtgtt g 41

<210> SEQ ID NO 431
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 431
ccatggccat accctggaat ttagacccgt tataagtgtt g 41

<210> SEQ ID NO 432
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 432
attatactgt ccagcgtagg tggtagacaa ccgtcgttaa g 41

<210> SEQ ID NO 433
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 433
tcctggtaag gataggtacc atgtagacaa ccgtcgttaa g 41

<210> SEQ ID NO 434
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 434
cactgaaata ggacggaatc tgctagacaa ccgtcgttaa g 41

<210> SEQ ID NO 435
<211> LENGTH: 39
<212> TYPE: DNA

<213> ORGANISM: Artificial Sequence
<220> FEATURE:
<223> OTHER INFORMATION: Target Specific Oligonucleotide

<400> SEQUENCE: 435
aaagtttatt ggcgcttgcc gtagacaacc gtcgttaag 39

<210> SEQ ID NO 436
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 436
gcaatgccat tagcgatacg atagacaacc gtcgttaag 39

<210> SEQ ID NO 437
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 437
tgattgaaca ccacgcgaca tagacaaccg tcgttaag 38

<210> SEQ ID NO 438
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 438
agtcttcgaa gcactattgc catagacaac cgtcgttaag 40

<210> SEQ ID NO 439
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 439
tcaatggttg atcggcctct ctagacaacc gtcgttaag 39

<210> SEQ ID NO 440
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 440
tggcatgatg tctaatagga gtctagacaa ccgtcgttaa g 41

<210> SEQ ID NO 441
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 441
ctgcggttta gccttgacgt tagacaaccg tcgttaag 38

<210> SEQ ID NO 442
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 442
cccagaggac gccatcattt tagacaaccg tcgttaag 38

<210> SEQ ID NO 443
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 443
tttcttgaaa gacgacagca gttagacaac cgtcgttaag 40

<210> SEQ ID NO 444
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 444
attaaatgtt cggaaggatg acctagacaa ccgtcgttaa g 41

<210> SEQ ID NO 445
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 445
tcttttgtca gcacggttgc tagacaaccg tcgttaag 38

<210> SEQ ID NO 446
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 446
ctggatcagc tcgaccagga tagacaaccg tcgttaag 38

<210> SEQ ID NO 447
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 447
accatggtcc gacttctgcc tagacaaccg tcgttaag 38

<210> SEQ ID NO 448
<211> LENGTH: 40
<212> TYPE: DNA
<213> ORGANISM: Artificial Sequence
<220> FEATURE:

<223> OTHER INFORMATION: Target Specific Oligonucleotide

<400> SEQUENCE: 448
ctggatattc ggttatctgg gctagacaac cgtcgttaag 40

<210> SEQ ID NO 449
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 449 atcccctta cgatactctt cagtagacaa ccgtcgttaa g 41

<210> SEQ ID NO 450
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 450
tccagagcgg gaacagtatg tagacaaccg tcgttaag 38

<210> SEQ ID NO 451
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 451
gttgcctgca taagatgggc tagacaaccg tcgttaag 38

<210> SEQ ID NO 452
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 452
ccttttgtgc cgatgacccg tagacaaccg tcgttaag 38

<210> SEQ ID NO 453
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 453
gcttccgtgg actgggacgt agacaaccgt cgttaag 37

<210> SEQ ID NO 454
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 454
ccatagaagg acgaggtatt tcctagacaa ccgtcgttaa g 41

<210> SEQ ID NO 455
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 455
agaatgagtc gctgctcgat atagacaacc gtcgttaag 39

<210> SEQ ID NO 456
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 456
gcttcgacaa acgcaaagcg tagactcaat gatgataaag a 41

<210> SEQ ID NO 457
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 457
gctagttcac agaaagacca ttttagactc aatgatgata aaga 44

<210> SEQ ID NO 458
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 458
cagctcatcg aaagcgaccc tagactcaat gatgataaag a 41

<210> SEQ ID NO 459
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 459
cggctgctac aaacctcggt agactcaatg atgataaaga 40

<210> SEQ ID NO 460
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 460
aacaatttga aggccccaca atagactcaa tgatgataaa ga 42

<210> SEQ ID NO 461
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 461
gcgtctgcac cggagactta gactcaatga tgataaaga 39

<210> SEQ ID NO 462
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 462
gcgctgctca ggcattggta gactcaatga tgataaaga 39

<210> SEQ ID NO 463
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 463
ttgttgtgta acaacataat ttcaagtaga ctcaatgatg ataaaga 47

<210> SEQ ID NO 464
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 464
ctccacgtcg gcgtgcatag actcaatgat gataaaga 38

<210> SEQ ID NO 465
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 465
ctgcggggat tgtagccggt agactcaatg atgataaaga 40

<210> SEQ ID NO 466
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 466
atcttagcta ctgaccggct atagactcaa tgatgataaa ga 42

<210> SEQ ID NO 467
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 467
aagagattat acgcctcacg gatagactca atgatgataa aga 43

<210> SEQ ID NO 468
<211> LENGTH: 44

<212> TYPE: DNA
<213> ORGANISM: Artificial Sequence
<220> FEATURE:
<223> OTHER INFORMATION: Target Specific Oligonucleotide

<400> SEQUENCE: 468
tttcgagtaa cgaaattagc tcctagactc aatgatgata aaga 44

<210> SEQ ID NO 469
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 469
gacccgcaga ttggcacgta gactcaatga tgataaaga 39

<210> SEQ ID NO 470
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 470
atggccccaa tctcgtttgg tagactcaat gatgataaag a 41

<210> SEQ ID NO 471
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 471
ccagtagcta taacgaagtc ctctagactc aatgatgata aaga 44

<210> SEQ ID NO 472
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 472
acaaattccc ggacactatg gatagactca atgatgataa aga 43

<210> SEQ ID NO 473
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 473
ttcacagagt tgataaggcc actagactca atgatgataa aga 43

<210> SEQ ID NO 474
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 474
aactttgccg gtctctttac attagactca atgatgataa aga 43

<210> SEQ ID NO 475
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 475
ttccaatgtg caagaatgat ttcttagact caatgatgat aaaga 45

<210> SEQ ID NO 476
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 476
ctccttctgg ggtatttcct gctagactca atgatgataa aga 43

<210> SEQ ID NO 477
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 477
ccacttcagt tggccggtat agactcaatg atgataaaga 40

<210> SEQ ID NO 478
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 478
tccgtcaacg tccgcagtta gactcaatga tgataaaga 39

<210> SEQ ID NO 479
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 479
agtgagatcg ccatagtgca atagactcaa tgatgataaa ga 42

<210> SEQ ID NO 480
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 480
gaaggtgacc ctataaggag tcatagacta caacaaaaga tcg 43

<210> SEQ ID NO 481
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 481
aacaccgctt gcatagttgt gtagactaca acaaaagatc g 41

<210> SEQ ID NO 482
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 482
tacagacgcg gaatcattct ctagactaca acaaaagatc g 41

<210> SEQ ID NO 483
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 483
tggaggaaat gagcatgacc ttagactaca acaaaagatc g 41

<210> SEQ ID NO 484
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 484
atggtgtaca ctcgaggctg atagactaca acaaaagatc g 41

<210> SEQ ID NO 485
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 485
ccttgtggta gacgttcagc ttagactaca acaaaagatc g 41

<210> SEQ ID NO 486
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 486
ggatcaggtt taatggtcac tatgtagact acaacaaaag atcg 44

<210> SEQ ID NO 487
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 487
cacacggtca acgctgtaca tagactacaa caaaagatcg 40

<210> SEQ ID NO 488
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 488
caggtgtttg cggaagttcc tagactacaa caaaagatcg 40

<210> SEQ ID NO 489
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 489
gtgctcatgg tcgtagagga tagactacaa caaaagatcg 40

<210> SEQ ID NO 490
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 490
aagtcaaagt acgtctcgat cattagacta caacaaaaga tcg 43

<210> SEQ ID NO 491
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 491
tcgtagcagc cgttggagat agactacaac aaaagatcg 39

<210> SEQ ID NO 492
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 492
tcgtggccag agtaggcatt agactacaac aaaagatcg 39

<210> SEQ ID NO 493
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 493
ggtactctcc aaacgctcgg tagactacaa caaaagatcg 40

<210> SEQ ID NO 494
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 494
aggtacgaat agggatgtcg tctagactac aacaaaagat cg 42

<210> SEQ ID NO 495
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 495
agggtatcgt acatcgttcc aatagactac aacaaaagat cg 42

<210> SEQ ID NO 496
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 496
caggtgatct gcgccgttgt agactacaac aaaagatcg 39

<210> SEQ ID NO 497
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 497
ccacaggcga tacaaccggt agactacaac aaaagatcg 39

<210> SEQ ID NO 498
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 498
cagcagcttc gagtgctggt agactacaac aaaagatcg 39

<210> SEQ ID NO 499
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 499
ccctcacagg acgtcgtcat agactacaac aaaagatcg 39

<210> SEQ ID NO 500
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 500
gcacgaagcc ttcggtgtct agactacaac aaaagatcg 39

<210> SEQ ID NO 501

<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 501
tgggaagtgt cggctttcat gtagactaca acaaaagatc g 41

<210> SEQ ID NO 502
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 502
tgggaagtgt cggctttcat gtagactaca acaaaagatc g 41

<210> SEQ ID NO 503
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 503
tgctcgcact ttggccgcta gactacaaca aaagatcg 38

<210> SEQ ID NO 504
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 504
gtcttttggc acggtttctg ttagactgta ttcaacgtcc 40

<210> SEQ ID NO 505
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 505
tacttcttca acgcgaagag ctagactgta ttcaacgtcc 40

<210> SEQ ID NO 506
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 506
tttgaggttg tatccgctgc ttagactgta ttcaacgtcc 40

<210> SEQ ID NO 507
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 507
caagttgact aaatctcgta ctttctagac tgtattcaac gtcc 44

<210> SEQ ID NO 508
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 508
gccttattaa cggtatcttc agaatagact gtattcaacg tcc 43

<210> SEQ ID NO 509
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 509
tgttctggat ttcgcaggtc ctagactgta ttcaacgtcc 40

<210> SEQ ID NO 510
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 510
gctttatcag gttatgttgc atgtagactg tattcaacgt cc 42

<210> SEQ ID NO 511
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 511
gattctggct tatagggtat tcactagact gtattcaacg tcc 43

<210> SEQ ID NO 512
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 512
ttttcctccc gcaattccta gatagactgt attcaacgtc c 41

<210> SEQ ID NO 513
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 513
tgtttccgtc aaatcgtgtg gtagactgta ttcaacgtcc 40

<210> SEQ ID NO 514
<211> LENGTH: 41
<212> TYPE: DNA

<213> ORGANISM: Artificial Sequence
<220> FEATURE:
<223> OTHER INFORMATION: Target Specific Oligonucleotide

<400> SEQUENCE: 514
ggttccctct agatcttgcc tttagactgt attcaacgtc c 41

<210> SEQ ID NO 515
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 515
gcatgtacca cctatcatct aatgtagact gtattcaacg tcc 43

<210> SEQ ID NO 516
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 516
gttgccaaca cgagctgact tagactgtat tcaacgtcc 39

<210> SEQ ID NO 517
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 517
actgactact agttcaagcg catagactgt attcaacgtc c 41

<210> SEQ ID NO 518
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 518
tctcttgctc gctttggacc tagactgtat tcaacgtcc 39

<210> SEQ ID NO 519
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 519
cactgctaga acaactatca atttgtagac tgtattcaac gtcc 44

<210> SEQ ID NO 520
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 520
ttacatggct taagttgggg agtagactgt attcaacgtc c 41

<210> SEQ ID NO 521
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 521
gtgaggggac gctcttgtat ttagactgta ttcaacgtcc 40

<210> SEQ ID NO 522
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 522
aacggtgcta tgcctagtag atagactgta ttcaacgtcc 40

<210> SEQ ID NO 523
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 523
tttgccttcc ctagagtgct atagactgta ttcaacgtcc 40

<210> SEQ ID NO 524
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 524
atgtcccaat ggatacttaa agcctagact gtattcaacg tcc 43

<210> SEQ ID NO 525
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 525
cttccagtaa cgagatactt tccttagact gtattcaacg tcc 43

<210> SEQ ID NO 526
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 526
caaccatgaa ttagtccctt gggtagactg tattcaacgt cc 42

<210> SEQ ID NO 527
<211> LENGTH: 44
<212> TYPE: DNA
<213> ORGANISM: Artificial Sequence
<220> FEATURE:

<223> OTHER INFORMATION: Target Specific Oligonucleotide

<400> SEQUENCE: 527
cagcattatt agacacttta actgttagac tgtattcaac gtcc 44

<210> SEQ ID NO 528
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 528
tgcacatatg attgacgctc agtagactct tatattgagt ggt 43

<210> SEQ ID NO 529
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 529
ttcaccgcct gcaacaagat agactcttat attgagtggt 40

<210> SEQ ID NO 530
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 530
ttcacttaca ggtaacacca agttagactc ttatattgag tggt 44

<210> SEQ ID NO 531
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 531
aagcaataga tcgtccataa gttatagact cttatattga gtggt 45

<210> SEQ ID NO 532
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 532
tacaagaacc ctaattgtaa taatagatag actcttatat tgagtggt 48

<210> SEQ ID NO 533
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 533
gaataggacc aaagtgtccc ttgtagactc ttatattgag tggt 44

<210> SEQ ID NO 534
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 534
tccatcagga ctaaatctca cactagactc ttatattgag tggt 44

<210> SEQ ID NO 535
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 535
aaaggccata cgtttttcct acctagactc ttatattgag tggt 44

<210> SEQ ID NO 536
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 536
gcagtgtaca atgaacgaga aattagactc ttatattgag tggt 44

<210> SEQ ID NO 537
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 537
ggcattctgc tttaagatca gaatagactc ttatattgag tggt 44

<210> SEQ ID NO 538
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 538
ggccagccac gattcacagt agactcttat attgagtggt 40

<210> SEQ ID NO 539
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 539
gaagccagcg accggactta gactcttata ttgagtggt 39

<210> SEQ ID NO 540
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 540
ctgagggtcg tcgttgtctt tagactctta tattgagtgg t 41

<210> SEQ ID NO 541
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 541
ctgaaccact ggcatagagt tctagactct tatattgagt ggt 43

<210> SEQ ID NO 542
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 542
aaatcaacca cgggtcgcgt agactcttat attgagtggt 40

<210> SEQ ID NO 543
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 543
agcaacagtc gacgagggat agactcttat attgagtggt 40

<210> SEQ ID NO 544
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 544
atatattcca tactactaac agacatatag actcttatat tgagtggt 48

<210> SEQ ID NO 545
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 545
tccacaccgg catcggctag actcttatat tgagtggt 38

<210> SEQ ID NO 546
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 546
agaagggcaa tccggtggct agactcttat attgagtggt 40

<210> SEQ ID NO 547
<211> LENGTH: 40

<212> TYPE: DNA
<213> ORGANISM: Artificial Sequence
<220> FEATURE:
<223> OTHER INFORMATION: Target Specific Oligonucleotide

<400> SEQUENCE: 547
tcagggagtc tgcgaccagt agactcttat attgagtggt 40

<210> SEQ ID NO 548
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 548
gctttgccag ctcaccactt agactcttat attgagtggt 40

<210> SEQ ID NO 549
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 549 aaataccat aaggcgtgat gctagactct tatattgagt ggt 43

<210> SEQ ID NO 550
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 550
attactatcc tgcgtgaaat ccatagactc ttatattgag tggt 44

<210> SEQ ID NO 551
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 551
cccaaagtcg aacagttttg tctagactct tatattgagt ggt 43

<210> SEQ ID NO 552
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 552
tcctcaaatg tccgaggatg atagacctat tctatgcttc g 41

<210> SEQ ID NO 553
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 553
gtgaacacaa cgtaagaaca ggtagaccta ttctatgctt cg 42

<210> SEQ ID NO 554
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 554
actcctctgg ttacgcttca tttagaccta ttctatgctt cg 42

<210> SEQ ID NO 555
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 555
acctaacata accgtgctgc ctagacctat tctatgcttc g 41

<210> SEQ ID NO 556
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 556
ttcagttgac cgtctggaca ctagacctat tctatgcttc g 41

<210> SEQ ID NO 557
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 557
ctctgacaca cgtaacaata acatagacct attctatgct tcg 43

<210> SEQ ID NO 558
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 558
agtaatgtga ggtacaactg cattagacct attctatgct tcg 43

<210> SEQ ID NO 559
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 559
gcttctttcc cgcccaaaat atagacctat tctatgcttc g 41

<210> SEQ ID NO 560
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 560
aaagaaaagc ggtctactag attatagacc tattctatgc ttcg 44

<210> SEQ ID NO 561
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 561
tgacgtgcgg cgaaatttat gtagacctat tctatgcttc g 41

<210> SEQ ID NO 562
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 562
gcttattgca gcgatggatg atagacctat tctatgcttc g 41

<210> SEQ ID NO 563
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 563
tgtcagtaga cgatagagga ggtagaccta ttctatgctt cg 42

<210> SEQ ID NO 564
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 564
ttggttccga ctacccaaca gtagacctat tctatgcttc g 41

<210> SEQ ID NO 565
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 565
ctcttaagta cgcaataatt ctctctagac ctattctatg cttcg 45

<210> SEQ ID NO 566
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 566
gttccgtata tgtcggatct ctctagacct attctatgct tcg 43

<210> SEQ ID NO 567
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 567
aaattcaccg gacggagtgt ttagacctat tctatgcttc g 41

<210> SEQ ID NO 568
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 568
tttgtgaaac cgtagtggct cttagaccta ttctatgctt cg 42

<210> SEQ ID NO 569
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 569
acctctttaa cgaaggtgtc agtagaccta ttctatgctt cg 42

<210> SEQ ID NO 570
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 570
ggactccggt tctaacttgg ttagacctat tctatgcttc g 41

<210> SEQ ID NO 571
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 571
atctctatat gacgtgctgt tggtagacct attctatgct tcg 43

<210> SEQ ID NO 572
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 572
gttggaatta ttcggagact gagtagacct attctatgct tcg 43

<210> SEQ ID NO 573
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 573
gcacatttga cgacggcttc tagacctatt ctatgcttcg 40

<210> SEQ ID NO 574
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 574
actccgtgta aacgcagtgg tagacctatt ctatgcttcg 40

<210> SEQ ID NO 575
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 575
acacataact cgttaacacg ttctagacct attctatgct tcg 43

<210> SEQ ID NO 576
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 576
cagatctgtt gagctaacag ggtagacatg ttataccatg cg 42

<210> SEQ ID NO 577
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 577
ttctagacta tgcaaccctc taggtagaca tgttatacca tgcg 44

<210> SEQ ID NO 578
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 578
cacccatgtg agtaatacac tgctagacat gttataccat gcg 43

<210> SEQ ID NO 579
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 579
agtcccatat tgccgttcat gctagacatg ttataccatg cg 42

<210> SEQ ID NO 580

<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 580
atttcctcat aacggtcatg gctagacatg ttataccatg cg 42

<210> SEQ ID NO 581
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 581
ttactgccta gctagcaggt tatagacatg ttataccatg cg 42

<210> SEQ ID NO 582
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 582
acgtgccctt ggtactatga ctagacatgt tataccatgc g 41

<210> SEQ ID NO 583
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 583
cttgccaaac cctagcttgg atagacatgt tataccatgc g 41

<210> SEQ ID NO 584
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 584
attatcactt aacgaaggtc ctttgtagac atgttatacc atgcg 45

<210> SEQ ID NO 585
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 585
atatacagcc taagcaccaa ttatgtagac atgttatacc atgcg 45

<210> SEQ ID NO 586
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 586
ggcaacaaaa cgtcatggca tagacatgtt ataccatgcg 40

<210> SEQ ID NO 587
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 587
gtctgaggac taaccctaaa gggtagacat gttataccat gcg 43

<210> SEQ ID NO 588
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 588
cttaaaatag atcgaaactc tgtctctaga catgttatac catgcg 46

<210> SEQ ID NO 589
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 589
tgatctgtac aagctacgat tttatagaca tgttatacca tgcg 44

<210> SEQ ID NO 590
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 590
aaatcagtta taccaagggg agatagacat gttataccat gcg 43

<210> SEQ ID NO 591
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 591
taggaaaaca tacgtatact gaatatagac atgttatacc atgcg 45

<210> SEQ ID NO 592
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 592
agttggcctc acgttgcatt tagacatgtt ataccatgcg 40

<210> SEQ ID NO 593
<211> LENGTH: 40
<212> TYPE: DNA

<213> ORGANISM: Artificial Sequence
<220> FEATURE:
<223> OTHER INFORMATION: Target Specific Oligonucleotide

<400> SEQUENCE: 593
tttggtctcg gcttgcgaat tagacatgtt ataccatgcg 40

<210> SEQ ID NO 594
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 594
cagtagtcaa cgcagcactc atagacatgt tataccatgc g 41

<210> SEQ ID NO 595
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 595
caacaggatc acctaatatt cccatagaca tgttatacca tgcg 44

<210> SEQ ID NO 596
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 596
tttggacaga tatctcctcg aaatagacat gttataccat gcg 43

<210> SEQ ID NO 597
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 597
aaaggctatc tacactttgg caatagacat gttataccat gcg 43

<210> SEQ ID NO 598
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 598
tgcctggatc ctatcccgac tagacatgtt ataccatgcg 40

<210> SEQ ID NO 599
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 599
tgtggtcacc tacacgctgc tagacatgtt ataccatgcg 40

<210> SEQ ID NO 600
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 600
ggtgagctgg taatctgacc ttagacaatc tatttaccct acg 43

<210> SEQ ID NO 601
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 601
gttgcaggca tgacgcaagt agacaatcta tttaccctac g 41

<210> SEQ ID NO 602
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 602
aaaacgccta cgcatcatgt ctagacaatc tatttaccct acg 43

<210> SEQ ID NO 603
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 603
tggtcctgcg cggatgtcta gacaatctat ttaccctacg 40

<210> SEQ ID NO 604
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 604
ggtgagcttc tccgtggcgt agacaatcta tttaccctac g 41

<210> SEQ ID NO 605
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 605
agcgcagggc caattgactt agacaatcta tttaccctac g 41

<210> SEQ ID NO 606
<211> LENGTH: 43
<212> TYPE: DNA
<213> ORGANISM: Artificial Sequence
<220> FEATURE:

<223> OTHER INFORMATION: Target Specific Oligonucleotide

<400> SEQUENCE: 606
ccgggtacac ggttttgatc ttagacaatc tatttaccct acg 43

<210> SEQ ID NO 607
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 607
ccggctcgat gtcgggtata gacaatctat ttaccctacg 40

<210> SEQ ID NO 608
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 608
ggcgccttct cgccacatta gacaatctat ttaccctacg 40

<210> SEQ ID NO 609
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 609
cacgttgaag cgcgggtgta gacaatctat ttaccctacg 40

<210> SEQ ID NO 610
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 610
gcccacagaa accggtttaa tgtagacaat ctatttaccc tacg 44

<210> SEQ ID NO 611
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 611
tcagaatgag cgcaatccag gtagacaatc tatttaccct acg 43

<210> SEQ ID NO 612
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 612
ttcggacaca aagacgctcc tagacaatct atttacccta cg 42

<210> SEQ ID NO 613
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 613
agcttgacgt aggtgtcggt tagacaatct atttacccta cg 42

<210> SEQ ID NO 614
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 614
ggttcccgcc aaatttcccg tagacaatct atttacccta cg 42

<210> SEQ ID NO 615
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 615
cagggctcat gatagtacaa cagtagacaa tctatttacc ctacg 45

<210> SEQ ID NO 616
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 616
ggactttagc gcggtctcct agacaatcta tttaccctac g 41

<210> SEQ ID NO 617
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 617
gcagccgttc taagcgctgt agacaatcta tttaccctac g 41

<210> SEQ ID NO 618
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 618
gctggtaaag gcgcttccct agacaatcta tttaccctac g 41

<210> SEQ ID NO 619
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 619
gaagaagtcg gtgacgcggt agacaatcta tttaccctac g 41

<210> SEQ ID NO 620
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 620
ggctggaaac ctcgtccact agacaatcta tttaccctac g 41

<210> SEQ ID NO 621
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 621
tttattagag tttaggaggt cagaaataga caatctattt accctacg 48

<210> SEQ ID NO 622
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 622
tgggaggtcc catattcaga ggtagacaat ctatttaccc tacg 44

<210> SEQ ID NO 623
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 623
tccagggatg tcctacttgt cctagacaat ctatttaccc tacg 44

<210> SEQ ID NO 624
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 624
ccaggtttcc ggcacagtgg gtaactgaat tgtcacttta 40

<210> SEQ ID NO 625
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 625
tgttatactt tgtcgctctt agtagagtaa ctgaattgtc acttta 46

<210> SEQ ID NO 626
<211> LENGTH: 44

<212> TYPE: DNA
<213> ORGANISM: Artificial Sequence
<220> FEATURE:
<223> OTHER INFORMATION: Target Specific Oligonucleotide

<400> SEQUENCE: 626
agcttttaac caggtttcga cttcgtaact gaattgtcac ttta 44

<210> SEQ ID NO 627
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 627
gtatgagaat cccgataaaa ctggtgtaac tgaattgtca cttta 45

<210> SEQ ID NO 628
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 628
aagaggacat cgaccaatcc tcagtaactg aattgtcact tta 43

<210> SEQ ID NO 629
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 629
ggtttgtgca agggtcgaaa acgtaactga attgtcactt ta 42

<210> SEQ ID NO 630
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 630
acacctctcg tagctataga tgtggtaact gaattgtcac ttta 44

<210> SEQ ID NO 631
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 631
atgagagggc aaccgaggtg agtaactgaa ttgtcacttt a 41

<210> SEQ ID NO 632
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 632
ccgctgtcag ggtctatcat tccgtaactg aattgtcact tta 43

<210> SEQ ID NO 633
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 633
gcaatgagca tatcctcggg cgtaactgaa ttgtcacttt a 41

<210> SEQ ID NO 634
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 634
ggcttgagtg ggttcaccca ggtaactgaa ttgtcacttt a 41

<210> SEQ ID NO 635
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 635
gcaaggtatg gcaatagctg agtgtaactg aattgtcact tta 43

<210> SEQ ID NO 636
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 636
cagtaatagt agagacgcca ctacagtaac tgaattgtca cttta 45

<210> SEQ ID NO 637
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 637
cttccaaagt gtcgcttcag agggtaactg aattgtcact tta 43

<210> SEQ ID NO 638
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 638
aggcaatttt cccgatactt tttattgtaa ctgaattgtc acttta 46

<210> SEQ ID NO 639
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 639
tgttagcttc tatagtcact attcgagtaa ctgaattgtc acttta 46

<210> SEQ ID NO 640
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 640
tcaacaagta atgtatcccg ttcatgtaac tgaattgtca cttta 45

<210> SEQ ID NO 641
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 641
tttccttggc cgtaagttgt tttcgtaact gaattgtcac ttta 44

<210> SEQ ID NO 642
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 642
gggtcaaccc agtctgttac ctgtaactga attgtcactt ta 42

<210> SEQ ID NO 643
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 643
tctgagactg atagggaaac atatgggtaa ctgaattgtc acttta 46

<210> SEQ ID NO 644
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 644
tctttgccac caatagcttg gagtaactga attgtcactt ta 42

<210> SEQ ID NO 645
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 645
ctcattggaa tggttagtag agcaagtaac tgaattgtca cttta 45

<210> SEQ ID NO 646
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 646
ctgagtaaag agcgtgtatt ccaggtaact gaattgtcac ttta 44

<210> SEQ ID NO 647
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 647
tggaggcata aagctggtag gcgtaactga attgtcactt ta 42

<210> SEQ ID NO 648
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 648
ggatctcaag cgttgcaggc gtaacgatag atttatacga cg 42

<210> SEQ ID NO 649
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 649
gcaccgcgag cggactagta acgatagatt tatacgacg 39

<210> SEQ ID NO 650
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 650
tgctgaggtc gctcacgaag taacgataga tttatacgac g 41

<210> SEQ ID NO 651
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 651
ccggaccacg tagttaaatc ttgtaacgat agatttatac gacg 44

<210> SEQ ID NO 652
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 652
aagttctttt gggcgatgcc agtaacgata gatttatacg acg 43

<210> SEQ ID NO 653
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 653
gttcccttat tagtctaatg ttttgcgtaa cgatagattt atacgacg 48

<210> SEQ ID NO 654
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 654
ttggaccagt gtacataagg atggtaacga tagatttata cgacg 45

<210> SEQ ID NO 655
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 655
tggcagtgca cggatggtcg taacgataga tttatacgac g 41

<210> SEQ ID NO 656
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 656
ataccaattc tagtgagaag ttcacgtaac gatagattta tacgacg 47

<210> SEQ ID NO 657
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 657
tctctgtagg gtaaggctct gtgtaacgat agatttatac gacg 44

<210> SEQ ID NO 658
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 658
tttagaggta gaccattgtg tgggtaacga tagatttata cgacg 45

<210> SEQ ID NO 659

<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 659
agagagggca ctctacgctt gtaacgatag atttatacga cg 42

<210> SEQ ID NO 660
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 660
caaaaagccc tagctcagat gggtaacgat agatttatac gacg 44

<210> SEQ ID NO 661
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 661
cctctcctcc ctatttggct ggtaacgata gatttatacg acg 43

<210> SEQ ID NO 662
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 662
ttttacaacg aactcattag gtccgtaacg atagatttat acgacg 46

<210> SEQ ID NO 663
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 663
ggagtagatc ccccatctat tccgtaacga tagatttata cgacg 45

<210> SEQ ID NO 664
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 664
gtctcttgcc tcgtttctct ccgtaacgat agatttatac gacg 44

<210> SEQ ID NO 665
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 665
aattctggcg tagcacaaac agtaacgata gatttatacg acg 43

<210> SEQ ID NO 666
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 666
ggccatgaac ccctaaatct aaagtaacga tagatttata cgacg 45

<210> SEQ ID NO 667
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 667
gcccactggt accatcttgg gtaacgatag atttatacga cg 42

<210> SEQ ID NO 668
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 668
taccacgtgg cactaacaca gtaacgatag atttatacga cg 42

<210> SEQ ID NO 669
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 669
ttctagcttt tagaccagca gttgtaacga tagatttata cgacg 45

<210> SEQ ID NO 670
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 670
cccaagtgct agtagaacct gcgtaacgat agatttatac gacg 44

<210> SEQ ID NO 671
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 671
aaacacatct atactcaaag acagagtaac gatagattta tacgacg 47

<210> SEQ ID NO 672
<211> LENGTH: 43
<212> TYPE: DNA

<213> ORGANISM: Artificial Sequence
<220> FEATURE:
<223> OTHER INFORMATION: Target Specific Oligonucleotide

<400> SEQUENCE: 672
cacagacttg ccgactcttt ggtaacgata gatttatacg acg 43

<210> SEQ ID NO 673
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 673
cacatgttaa tgttcccgac cagtaacgat agatttatac gacg 44

<210> SEQ ID NO 674
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 674
attaatcgtt tgcggatctg ccgtaacgat agatttatac gacg 44

<210> SEQ ID NO 675
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 675
tgggtaacat cggacaagtt tggtaacgat agatttatac gacg 44

<210> SEQ ID NO 676
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 676
tctgaagttt cgagccaatg ttgtaacgat agatttatac gacg 44

<210> SEQ ID NO 677
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 677
ccattttcac cgctgaaata gagtaacgat agatttatac gacg 44

<210> SEQ ID NO 678
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 678
ctggatcaca tgcgttgtca ggtaacgata gatttatacg acg 43

<210> SEQ ID NO 679
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 679
atatttgcct cgtaagatcc cctgtaacga tagatttata cgacg 45

<210> SEQ ID NO 680
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 680
ctgaagcggt gttgtatcat agcgtaacga tagatttata cgacg 45

<210> SEQ ID NO 681
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 681
tagaataatg gttcgtgacc ttcgtaacga tagatttata cgacg 45

<210> SEQ ID NO 682
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 682
acctgaaggc gacgaggagg taacgataga tttatacgac g 41

<210> SEQ ID NO 683
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 683
gcctggagtc tatcgtacaa tcgtaacgat agatttatac gacg 44

<210> SEQ ID NO 684
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 684
acatttaatt agaccgtaac ccttcgtaac gatagattta tacgacg 47

<210> SEQ ID NO 685
<211> LENGTH: 45
<212> TYPE: DNA
<213> ORGANISM: Artificial Sequence
<220> FEATURE:

<223> OTHER INFORMATION: Target Specific Oligonucleotide

<400> SEQUENCE: 685
gctctggcca tacttaacag atagtaacga tagatttata cgacg 45

<210> SEQ ID NO 686
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 686
cagcattgag tgataatgca atctgtaacg atagatttat acgacg 46

<210> SEQ ID NO 687
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 687
atacacaccc gctaccttac tggtaacgat agatttatac gacg 44

<210> SEQ ID NO 688
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 688
acaaagacga gaactatggc aagtaacgat agatttatac gacg 44

<210> SEQ ID NO 689
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 689
aggcagacgc tctaagtcta aagtaacgat agatttatac gacg 44

<210> SEQ ID NO 690
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 690
tctcttactc atcgtgaaag gcgtaacgat agatttatac gacg 44

<210> SEQ ID NO 691
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 691
gcctcaagtt cgcattcagc gtaacgatag atttatacga cg 42

<210> SEQ ID NO 692
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 692
gaaatggaaa cgttaacagc cagtaacgat agatttatac gacg 44

<210> SEQ ID NO 693
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 693
cacctgcttc ggaatctcag tgtaacgata gatttatacg acg 43

<210> SEQ ID NO 694
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 694
gacttgtgct tcgttaatta aacagtaacg atagatttat acgacg 46

<210> SEQ ID NO 695
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 695
gctgtaatat acgcccactt tagcgtaacg atagatttat acgacg 46

<210> SEQ ID NO 696
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 696
ttccattgtg cggttgggat tgtaacttat aaaggataga catc 44

<210> SEQ ID NO 697
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 697
ctccagtaat cgcttatggt ccgtaactta taaaggatag acatc 45

<210> SEQ ID NO 698
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 698
cctcttctcc gtcaagaagt tcgtaactta taaaggatag acatc 45

<210> SEQ ID NO 699
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 699
tgattgagat ggcggtattt gagtaactta taaaggatag acatc 45

<210> SEQ ID NO 700
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 700
gccaattata agtactcggg ctgtaactta taaaggatag acatc 45

<210> SEQ ID NO 701
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 701
ccaggccagc gtatgttccg taacttataa aggatagaca tc 42

<210> SEQ ID NO 702
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 702
ctggggcaac caacacttgt gtaacttata aaggatagac atc 43

<210> SEQ ID NO 703
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 703
ggctggacaa taggctccca gtaacttata aaggatagac atc 43

<210> SEQ ID NO 704
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 704
aaagctatgg cacgaaagcc ggtaacttat aaaggataga catc 44

<210> SEQ ID NO 705
<211> LENGTH: 44

<212> TYPE: DNA
<213> ORGANISM: Artificial Sequence
<220> FEATURE:
<223> OTHER INFORMATION: Target Specific Oligonucleotide

<400> SEQUENCE: 705
gcagtccatc taaggtggac tgtaacttat aaaggataga catc 44

<210> SEQ ID NO 706
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 706
tgtatatgga gtaccctctt gctgtaactt ataaaggata gacatc 46

<210> SEQ ID NO 707
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 707
ctggatcacc aaaacggcaa tgtaacttat aaaggataga catc 44

<210> SEQ ID NO 708
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 708
ccaggataac ctttacttgc cagtaactta taaaggatag acatc 45

<210> SEQ ID NO 709
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 709
atttccagct gcgatatcta ctcgtaactt ataaaggata gacatc 46

<210> SEQ ID NO 710
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 710
tttatagcag ctagtccttt cttggtaact tataaaggat agacatc 47

<210> SEQ ID NO 711
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 711
tgatatgaga ttttcccgga tgggtaactt ataaaggata gacatc 46

<210> SEQ ID NO 712
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 712
tgacaacagt tagggcggtg gtaacttata aaggatagac atc 43

<210> SEQ ID NO 713
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 713
ttggttcccg agtactgtct agtaacttat aaaggataga catc 44

<210> SEQ ID NO 714
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 714
gtttagttcc aacgccatct gtgtaactta taaaggatag acatc 45

<210> SEQ ID NO 715
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 715
aagagttgcg acagtatcac ccgtaactta taaaggatag acatc 45

<210> SEQ ID NO 716
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 716
gctgctggat atccctcaga agtaacttat aaaggataga catc 44

<210> SEQ ID NO 717
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 717
tgcaagacag actatgtcta tgggtaactt ataaaggata gacatc 46

<210> SEQ ID NO 718
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 718
cttcaaggac taggtcaatt gcagtaactt ataaaggata gacatc 46

<210> SEQ ID NO 719
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 719
gatatgctgc actaactagt cttggtaact tataaaggat agacatc 47

<210> SEQ ID NO 720
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 720
atctcgagca agacgttcag tgtaacggtt atcgtggaaa 40

<210> SEQ ID NO 721
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 721
ctgtccataa ttagtccatg aggagtaacg gttatcgtgg aaa 43

<210> SEQ ID NO 722
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 722
atctttggat tatactgcct gaccgtaacg gttatcgtgg aaa 43

<210> SEQ ID NO 723
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 723
cagcaagctt gcgaccttga gtaacggtta tcgtggaaa 39

<210> SEQ ID NO 724
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 724
agttaaagtt gagagatcat ctccagtaac ggttatcgtg gaaa 44

<210> SEQ ID NO 725
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 725
aggaatggat ctatcactat ttctagtaac ggttatcgtg gaaa 44

<210> SEQ ID NO 726
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 726
cagcataatg attaggtatg caaaagtaac ggttatcgtg gaaa 44

<210> SEQ ID NO 727
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 727
ttcagtctga taaaatctac agtcagtaac ggttatcgtg gaaa 44

<210> SEQ ID NO 728
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 728
tccaacactt cgtggggtcc gtaacggtta tcgtggaaa 39

<210> SEQ ID NO 729
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 729
agggctacaa tgtgatggcc gtaacggtta tcgtggaaa 39

<210> SEQ ID NO 730
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 730
tcaaggtcat aacctggttc atcgtaacgg ttatcgtgga aa 42

<210> SEQ ID NO 731
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 731
cctacaacaa acttgtctgg aatgtaacgg ttatcgtgga aa 42

<210> SEQ ID NO 732
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 732
aaacaacaat ccgcccaaag ggtaacggtt atcgtggaaa 40

<210> SEQ ID NO 733
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 733
aaagctctac taagcagatg gcgtaacggt tatcgtggaa a 41

<210> SEQ ID NO 734
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 734
actgctgaca aagattcact gggtaacggt tatcgtggaa a 41

<210> SEQ ID NO 735
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 735
ctgatagtct ataggctcat agtgcgtaac ggttatcgtg gaaa 44

<210> SEQ ID NO 736
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 736
atcactaatc acgacgccag ggtaacggtt atcgtggaaa 40

<210> SEQ ID NO 737
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 737
tggcgatgtc aataggactc cgtaacggtt atcgtggaaa 40

<210> SEQ ID NO 738

<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 738
gaactctcat cttaggcttt gtagtaacgg ttatcgtgga aa 42

<210> SEQ ID NO 739
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 739
tcaacattac tgaaacacta ctaaagtaac ggttatcgtg gaaa 44

<210> SEQ ID NO 740
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 740
ggtcgccata acggagccgg taacggttat cgtggaaa 38

<210> SEQ ID NO 741
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 741
ttcttacaga tatgagttca atgtttgtaa cggttatcgt ggaaa 45

<210> SEQ ID NO 742
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 742
aggacagaac aaaacttctt agatggtaac ggttatcgtg gaaa 44

<210> SEQ ID NO 743
<211> LENGTH: 36
<212> TYPE: DNA
<213> ORGANISM: Artificial Sequence
<220> FEATURE:
<223> OTHER INFORMATION: Target Specific Oligonucleotide

<400> SEQUENCE: 743
tcgcagccgc ctgaagcgta acggttatcg tggaaa 36

<210> SEQ ID NO 744
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 744
ggaatttgga accggcttgc gtaacggtac tttatctagc t 41

<210> SEQ ID NO 745
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 745
agagtcttga gtataatctt ggtaggtaac ggtactttat ctagct 46

<210> SEQ ID NO 746
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 746
attcaggaag catacactaa ttcttgtaac ggtactttat ctagct 46

<210> SEQ ID NO 747
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 747
tccagaaata agcgaaaata gcagtaacgg tactttatct agct 44

<210> SEQ ID NO 748
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 748
atcttttgaa ctactagcta caaaatgtaa cggtacttta tctagct 47

<210> SEQ ID NO 749
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 749
taacaagctc gtaatggccc agtaacggta ctttatctag ct 42

<210> SEQ ID NO 750
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 750
catccaaacc gtgtgaaagc tgtaacggta ctttatctag ct 42

<210> SEQ ID NO 751
<211> LENGTH: 41
<212> TYPE: DNA

<213> ORGANISM: Artificial Sequence
<220> FEATURE:
<223> OTHER INFORMATION: Target Specific Oligonucleotide

<400> SEQUENCE: 751
acaacgccat gtgcgatttg gtaacggtac tttatctagc t 41

<210> SEQ ID NO 752
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 752
ctacctacca ctaggtacct atcagtaacg gtactttatc tagct 45

<210> SEQ ID NO 753
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 753
aggacattta cgtgtacagc acgtaacggt actttatcta gct 43

<210> SEQ ID NO 754
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 754
cgcctgaata caacgagtta acgtaacggt actttatcta gct 43

<210> SEQ ID NO 755
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 755
cttccagatt gtcgccgtta attgtaacgg tactttatct agct 44

<210> SEQ ID NO 756
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 756
cagatttacc taaaccacca ccagtaacgg tactttatct agct 44

<210> SEQ ID NO 757
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 757
tttgagctga tctagtaggt cttcgtaacg gtactttatc tagct 45

<210> SEQ ID NO 758
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 758
tctgtagctc gatccctgga gtaacggtac tttatctagc t 41

<210> SEQ ID NO 759
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 759
caactgtcat tcggttaaac tgagtaacgg tactttatct agct 44

<210> SEQ ID NO 760
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 760
tttgcttccg ttcatcatta gtcgtaacgg tactttatct agct 44

<210> SEQ ID NO 761
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 761
acttccaata gtctggaaat cacagtaacg gtactttatc tagct 45

<210> SEQ ID NO 762
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 762
tcatctgctg gattaagcta atacgtaacg gtactttatc tagct 45

<210> SEQ ID NO 763
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 763
agataggctc ccgtatgccc gtaacggtac tttatctagc t 41

<210> SEQ ID NO 764
<211> LENGTH: 41
<212> TYPE: DNA
<213> ORGANISM: Artificial Sequence
<220> FEATURE:

<223> OTHER INFORMATION: Target Specific Oligonucleotide

<400> SEQUENCE: 764
gcttctcggc taccacagac gtaacggtac tttatctagc t 41

<210> SEQ ID NO 765
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 765
agacttactc ttaagaccat acttcgtaac ggtactttat ctagct 46

<210> SEQ ID NO 766
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 766
gttgagaggt ggcgtttttg agtaacggta ctttatctag ct 42

<210> SEQ ID NO 767
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 767
tcaatacgtt tctgcaagag tttgtaacgg tactttatct agct 44

<210> SEQ ID NO 768
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 768
ttatggcctc tatagcatct cccgtaactc catctagacc g 41

<210> SEQ ID NO 769
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 769
cagtccgggc aactatctta ttgtaactcc atctagaccg 40

<210> SEQ ID NO 770
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 770
ttcaagatac gaataatcct ccgagtaact ccatctagac cg 42

<210> SEQ ID NO 771
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 771
gtaggcgctt agcttgattt tcgtaactcc atctagaccg 40

<210> SEQ ID NO 772
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 772
cttcaagtcg ggctcttgca gtaactccat ctagaccg 38

<210> SEQ ID NO 773
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 773
agaatgaggc acgcaaagct gtaactccat ctagaccg 38

<210> SEQ ID NO 774
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 774
ctcagcatcc gataggactt tcgtaactcc atctagaccg 40

<210> SEQ ID NO 775
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 775
aagtcactat aacacccgtc ctgtaactcc atctagaccg 40

<210> SEQ ID NO 776
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 776
ttggcatggt agatcgtcca ggtaactcca tctagaccg 39

<210> SEQ ID NO 777
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 777
caccttccaa cgactcaatc cgtaactcca tctagaccg 39

<210> SEQ ID NO 778
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 778
acaacctgta agtgtagttc tctggtaact ccatctagac cg 42

<210> SEQ ID NO 779
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 779
aaatcagata ctcgtctaca gaatggtaac tccatctaga ccg 43

<210> SEQ ID NO 780
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 780
agcagcaagt cgcattttcc gtaactccat ctagaccg 38

<210> SEQ ID NO 781
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 781
actggcatgg cggataaaaa ggtaactcca tctagaccg 39

<210> SEQ ID NO 782
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 782
cgggtgctct cgtgaacaaa gtaactccat ctagaccg 38

<210> SEQ ID NO 783
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 783
gatcgaagag tcgagataag gatgtaactc catctagacc g 41

<210> SEQ ID NO 784
<211> LENGTH: 41

<212> TYPE: DNA
<213> ORGANISM: Artificial Sequence
<220> FEATURE:
<223> OTHER INFORMATION: Target Specific Oligonucleotide

<400> SEQUENCE: 784
ttgttgaaga cgcttccata agtgtaactc catctagacc g 41

<210> SEQ ID NO 785
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 785
gtggtgacgc agaatcccgg taactccatc tagaccg 37

<210> SEQ ID NO 786
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 786
cattataaag acgtaataat ttagggtgta actccatcta gaccg 45

<210> SEQ ID NO 787
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 787
gctcccactc ctagacatgt tgtaactcca tctagaccg 39

<210> SEQ ID NO 788
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 788
tttgttacac ggttaaacag ccgtaactcc atctagaccg 40

<210> SEQ ID NO 789
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 789
gaggtaaata aacgtcgata ggaagtaact ccatctagac cg 42

<210> SEQ ID NO 790
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 790
ttaatgtgga gtgcaagttg gggtaactcc atctagaccg 40

<210> SEQ ID NO 791
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 791
ccttgtatct tagcttggga tgtgtaactc catctagacc g 41

<210> SEQ ID NO 792
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 792
tcaatgatca gcggatacct attgtaactc agtagatata gcg 43

<210> SEQ ID NO 793
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 793
cgtgtgatct tacgatcctt atagtaactc agtagatata gcg 43

<210> SEQ ID NO 794
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 794
tcatcctcta cgagtctatc ttggtaactc agtagatata gcg 43

<210> SEQ ID NO 795
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 795
tcaaagtaac ccgcgtaggc gtaactcagt agatatagcg 40

<210> SEQ ID NO 796
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 796
ataggacgca tactgtcgca agtaactcag tagatatagc g 41

<210> SEQ ID NO 797
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 797
ttatgtccgt cgaccttgca tgtaactcag tagatatagc g 41

<210> SEQ ID NO 798
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 798
ttccaaggaa cggacttcta gggtaactca gtagatatag cg 42

<210> SEQ ID NO 799
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 799
ataggtacga acgctctcga tcgtaactca gtagatatag cg 42

<210> SEQ ID NO 800
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 800
tcttggatga tcgcatgaaa ccgtaactca gtagatatag cg 42

<210> SEQ ID NO 801
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 801
acaacccaat taacgtgaag ccgtaactca gtagatatag cg 42

<210> SEQ ID NO 802
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 802
atgcggtata acgcacgttc cgtaactcag tagatatagc g 41

<210> SEQ ID NO 803
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 803
ctcaagtcac gacgcagttc tgtaactcag tagatatagc g 41

<210> SEQ ID NO 804
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 804
gcaagtcacg aacgtgactc gtaactcagt agatatagcg 40

<210> SEQ ID NO 805
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 805
ttggcgttat actgcgccac gtaactcagt agatatagcg 40

<210> SEQ ID NO 806
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 806
agtggtgcgt atcgtaagcg gtaactcagt agatatagcg 40

<210> SEQ ID NO 807
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 807
atccaggcga cgaaacgaga gtaactcagt agatatagcg 40

<210> SEQ ID NO 808
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 808
ttggatgaat cggcaggctg gtaactcagt agatatagcg 40

<210> SEQ ID NO 809
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 809
tcagtcaatt cgtaatgtac accgtaactc agtagatata gcg 43

<210> SEQ ID NO 810
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 810
catcgaagac gatccactgg cgtaactcag tagatatagc g 41

<210> SEQ ID NO 811
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 811
cacggatcaa gcggcacttg taactcagta gatatagcg 39

<210> SEQ ID NO 812
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 812
tccaccgtat cgcaagctgg taactcagta gatatagcg 39

<210> SEQ ID NO 813
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 813
atgcaaagtt tcgtagggcg agtaactcag tagatatagc g 41

<210> SEQ ID NO 814
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 814
gcgttggcac gacgacatgt aactcagtag atatagcg 38

<210> SEQ ID NO 815
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 815
ttgcagacgg acgcccaagt aactcagtag atatagcg 38

<210> SEQ ID NO 816
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 816
agctgtatcg tcaaggcact cgtaaccttt tgaaacgcta 40

<210> SEQ ID NO 817

<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 817
ctcgctccca gtccgaaatg gtaacctttt gaaacgcta 39

<210> SEQ ID NO 818
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 818
acttgtacta gtatgcctta agaaagtaac cttttgaaac gcta 44

<210> SEQ ID NO 819
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 819
gtgaccatga ctaatagcag tgggtaacct tttgaaacgc ta 42

<210> SEQ ID NO 820
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 820
gctgtgtcga gaatatccaa gagtaacctt ttgaaacgct a 41

<210> SEQ ID NO 821
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 821
cctactgtcg ctaatggatt gggtaacctt ttgaaacgct a 41

<210> SEQ ID NO 822
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 822
acactagcac tacctaagga ccgtaacctt ttgaaacgct a 41

<210> SEQ ID NO 823
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 823
gtctgtgaac tagttcaggc acgtaacctt ttgaaacgct a 41

<210> SEQ ID NO 824
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 824
ctaggtcagc gcaaccaaat ggtaaccttt tgaaacgcta 40

<210> SEQ ID NO 825
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 825
cctaataagc tataactggc ccagtaacct tttgaaacgc ta 42

<210> SEQ ID NO 826
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 826
ctaaattcct atgcagtgtg actcgtaacc ttttgaaacg cta 43

<210> SEQ ID NO 827
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 827
atcttgttga gctatccaaa ctggtaacct tttgaaacgc ta 42

<210> SEQ ID NO 828
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 828
aaatacgcat cgtgttatct ctggtaacct tttgaaacgc ta 42

<210> SEQ ID NO 829
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 829
tgttaagaga actagccaaa cctgtaacct tttgaaacgc ta 42

<210> SEQ ID NO 830
<211> LENGTH: 43
<212> TYPE: DNA

<213> ORGANISM: Artificial Sequence
<220> FEATURE:
<223> OTHER INFORMATION: Target Specific Oligonucleotide

<400> SEQUENCE: 830
cataaagtag cttgatcgaa gagtgtaacc ttttgaaacg cta 43

<210> SEQ ID NO 831
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 831
taagcaaaca cgcctttaca tagtaacctt ttgaaacgct a 41

<210> SEQ ID NO 832
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 832
aaggccttag taagatatta cagacgtaac cttttgaaac gcta 44

<210> SEQ ID NO 833
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 833
acaatatacg tctgctatat tcttccgtaa ccttttgaaa cgcta 45

<210> SEQ ID NO 834
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 834
tccactggat agggttctgt ctgtaacctt ttgaaacgct a 41

<210> SEQ ID NO 835
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 835
aagttatact atgaaagagc agtctgtaac cttttgaaac gcta 44

<210> SEQ ID NO 836
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 836
acatgttaat gcctaagtct atgtagtaac cttttgaaac gcta 44

<210> SEQ ID NO 837
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 837
gcctagaatg cctacttggg agtaaccttt tgaaacgcta 40

<210> SEQ ID NO 838
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 838
tcagtggaat cgtagcaaaa cagtaacctt ttgaaacgct a 41

<210> SEQ ID NO 839
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 839
acaataatta ggagtagtac agttcagtaa ccttttgaaa cgcta 45

<210> SEQ ID NO 840
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 840
ttccactcgg ataagatgct gagtaactca gacatgtaga tt 42

<210> SEQ ID NO 841
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 841
aatactccac acgcaaattt ccgtaactca gacatgtaga tt 42

<210> SEQ ID NO 842
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 842
ggccagacca tcgctatctg gtaactcaga catgtagatt 40

<210> SEQ ID NO 843
<211> LENGTH: 42
<212> TYPE: DNA
<213> ORGANISM: Artificial Sequence
<220> FEATURE:

<223> OTHER INFORMATION: Target Specific Oligonucleotide

<400> SEQUENCE: 843
caccacacta tgtcgaaaag tggtaactca gacatgtaga tt 42

<210> SEQ ID NO 844
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 844
ccctttcttg cggagattct ctgtaactca gacatgtaga tt 42

<210> SEQ ID NO 845
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 845
acaaacacgc acctcaaagc gtaactcaga catgtagatt 40

<210> SEQ ID NO 846
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 846
cccagtagat taccactgga gtgtaactca gacatgtaga tt 42

<210> SEQ ID NO 847
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 847
gcagtgctcg cttagtgctg taactcagac atgtagatt 39

<210> SEQ ID NO 848
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 848
ggctcgacgc taggatctga gtaactcaga catgtagatt 40

<210> SEQ ID NO 849
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 849
aggatgggcc tccggttcag taactcagac atgtagatt 39

<210> SEQ ID NO 850
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 850
ggaacatctc gaagcgctca gtaactcaga catgtagatt 40

<210> SEQ ID NO 851
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 851
agacggaaac cgtagctgcc gtaactcaga catgtagatt 40

<210> SEQ ID NO 852
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 852
tgttcaatat cgtccgggga cgtaactcag acatgtagat t 41

<210> SEQ ID NO 853
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 853
cattgcttgg gacggcaagg gtaactcaga catgtagatt 40

<210> SEQ ID NO 854
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 854
agtggagaat gtcagtctga gtgtaactca gacatgtaga tt 42

<210> SEQ ID NO 855
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 855 agtttttat ggcgggaggt agagtaactc agacatgtag att 43

<210> SEQ ID NO 856
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 856
tagaaactac caacccaccg agtaactcag acatgtagat t 41

<210> SEQ ID NO 857
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 857
ttccctggtt agtacggtga aggtaactca gacatgtaga tt 42

<210> SEQ ID NO 858
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 858
taagctggta tgtcctactc ccgtaactca gacatgtaga tt 42

<210> SEQ ID NO 859
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 859
ctgacgcaca cctattgcaa ggtaactcag acatgtagat t 41

<210> SEQ ID NO 860
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 860
tcaccgtcgt ggaaagcacg taactcagac atgtagatt 39

<210> SEQ ID NO 861
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 861
gtaaactaac ccttaactgc aagagtaact cagacatgta gatt 44

<210> SEQ ID NO 862
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 862
tttaggtact aaggttcacc aagagtaact cagacatgta gatt 44

<210> SEQ ID NO 863
<211> LENGTH: 46

<212> TYPE: DNA
<213> ORGANISM: Artificial Sequence
<220> FEATURE:
<223> OTHER INFORMATION: Target Specific Oligonucleotide

<400> SEQUENCE: 863
tcatcatata caagagatga aatcctgtaa ctcagacatg tagatt 46

<210> SEQ ID NO 864
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 864
ccatggtgac gatcctcacg gtaactaaca taaattcgat g 41

<210> SEQ ID NO 865
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 865
gtgaacgtct tgggttgctt cgtaactaac ataaattcga tg 42

<210> SEQ ID NO 866
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 866
ggcctggacg gcgtaagagt aactaacata aattcgatg 39

<210> SEQ ID NO 867
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 867
gaagctcatg cgggaagcgg taactaacat aaattcgatg 40

<210> SEQ ID NO 868
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 868
tgtcactgta cgagatgttt cggtaactaa cataaattcg atg 43

<210> SEQ ID NO 869
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 869
ttgaagcttg gtatgtcagg aggtaactaa cataaattcg atg 43

<210> SEQ ID NO 870
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 870
ggttcccgat acatagctgg agtaactaac ataaattcga tg 42

<210> SEQ ID NO 871
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 871
atctttgaag tcgaaagaca ggcgtaacta acataaattc gatg 44

<210> SEQ ID NO 872
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 872
gcttattaac acgaagcttt gaggtaacta acataaattc gatg 44

<210> SEQ ID NO 873
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 873
tttcattcca cgggaaggag agtaactaac ataaattcga tg 42

<210> SEQ ID NO 874
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 874
tcagtgcttc gttggccatt gtaactaaca taaattcgat g 41

<210> SEQ ID NO 875
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 875
ctctgcgtac caagcagtaa ttgtaactaa cataaattcg atg 43

<210> SEQ ID NO 876
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 876
tttcaaggcc tcgatttctg tcgtaactaa cataaattcg atg 43

<210> SEQ ID NO 877
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 877
tagttcacac cgtacatctc cagtaactaa cataaattcg atg 43

<210> SEQ ID NO 878
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 878
cccacatttc cggagtcatc tgtaactaac ataaattcga tg 42

<210> SEQ ID NO 879
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 879
ggtcctgagc tatcttcaga tattgtaact aacataaatt cgatg 45

<210> SEQ ID NO 880
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 880
tcctccgtgc gaatcgctgt aactaacata aattcgatg 39

<210> SEQ ID NO 881
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 881
gcccttttta ttccggattg cagtaactaa cataaattcg atg 43

<210> SEQ ID NO 882
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 882
gctgtctcct cagaccgcag taactaacat aaattcgatg 40

<210> SEQ ID NO 883
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 883 caccccctgtc ggagttctca gtaactaaca taaattcgat g 41

<210> SEQ ID NO 884
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 884
cagatttatt acccttttttg gaagcgtaac taacataaat tcgatg 46

<210> SEQ ID NO 885
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 885
tcatgggcgg gtacgtgggt aactaacata aattcgatg 39

<210> SEQ ID NO 886
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 886
caaaaatccc cgcttgtgaa cgtaactaac ataaattcga tg 42

<210> SEQ ID NO 887
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 887
ctggggtcgt agtcaccata cgtaactaac ataaattcga tg 42

<210> SEQ ID NO 888
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 888
cacacgatac cggcaaagaa ggtaacgtga cgattaccc 39

<210> SEQ ID NO 889
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 889
ggtgtcagtc tccgacgtga gtaacgtgac gattaccc 38

<210> SEQ ID NO 890
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 890
gtgatggtga tcatctgggc cgtaacgtga cgattaccc 39

<210> SEQ ID NO 891
<211> LENGTH: 36
<212> TYPE: DNA
<213> ORGANISM: Artificial Sequence
<220> FEATURE:
<223> OTHER INFORMATION: Target Specific Oligonucleotide

<400> SEQUENCE: 891
ttggcctcgg gaccaagcgt aacgtgacga ttaccc 36

<210> SEQ ID NO 892
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 892
ctgtcatctt ggtcaggtgg tgtaacgtga cgattaccc 39

<210> SEQ ID NO 893
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 893
atcaccttgc cgaaagtgcc gtaacgtgac gattaccc 38

<210> SEQ ID NO 894
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 894
actgcacggc cgtagtcatg taacgtgacg attaccc 37

<210> SEQ ID NO 895
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 895
aggtactcag gtgtgccgcg taacgtgacg attaccc 37

<210> SEQ ID NO 896

<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 896
gaaggtgcgt tcgatgacag gtaacgtgac gattaccc 38

<210> SEQ ID NO 897
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 897
ctcctcagga gtctccacat ggtaacgtga cgattaccc 39

<210> SEQ ID NO 898
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 898
gtctggaaag agtacttcag ggtaacgtg acgattaccc 40

<210> SEQ ID NO 899
<211> LENGTH: 36
<212> TYPE: DNA
<213> ORGANISM: Artificial Sequence
<220> FEATURE:
<223> OTHER INFORMATION: Target Specific Oligonucleotide

<400> SEQUENCE: 899
caggacgcgg ttctcggtgt aacgtgacga ttaccc 36

<210> SEQ ID NO 900
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 900
atctcagcgc catagaagcg gtaacgtgac gattaccc 38

<210> SEQ ID NO 901
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 901
tcgttcatgg tcacgcggtg taacgtgacg attaccc 37

<210> SEQ ID NO 902
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 902
cagcccgaag tctgtgatct tgtaacgtga cgattaccc 39

<210> SEQ ID NO 903
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 903
tcatggtggc accgtccttg taacgtgacg attaccc 37

<210> SEQ ID NO 904
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 904
ggtagtccag ggctgacaca gtaacgtgac gattaccc 38

<210> SEQ ID NO 905
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 905
ccatcattct tgaggaggaa gtagtaacgt gacgattacc c 41

<210> SEQ ID NO 906
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 906
acaaagcaga ggcggtcgtg taacgtgacg attaccc 37

<210> SEQ ID NO 907
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 907
cggtcctcgg agaacacacg gtaacgtgac gattaccc 38

<210> SEQ ID NO 908
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 908
gagcctcacg ttggtccacg taacgtgacg attaccc 37

<210> SEQ ID NO 909
<211> LENGTH: 40
<212> TYPE: DNA

<213> ORGANISM: Artificial Sequence
<220> FEATURE:
<223> OTHER INFORMATION: Target Specific Oligonucleotide

<400> SEQUENCE: 909
ctccttgtag ccaatgaagg tggtaacgtg acgattaccc 40

<210> SEQ ID NO 910
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 910
ttcacaatag ccacgtcgct gtaacgtgac gattaccc 38

<210> SEQ ID NO 911
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 911
ccctcgtttg tgcagccaag taacgtgacg attaccc 37

<210> SEQ ID NO 912
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 912
agctatgtcc gctatcttca tcggtaactc tcttctattg cag 43

<210> SEQ ID NO 913
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 913
ttggcacatc gagacatggt tgtaactctc ttctattgca g 41

<210> SEQ ID NO 914
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 914
ccatcttggt cgtactttgt gagtaactct cttctattgc ag 42

<210> SEQ ID NO 915
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 915
ccaactgagc atacgctagg agtaactctc ttctattgca g 41

<210> SEQ ID NO 916
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 916
tcacgtacta gccgttccat cgtaactctc ttctattgca g 41

<210> SEQ ID NO 917
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 917
tttctccaag tcgtctctca tctgtaactc tcttctattg cag 43

<210> SEQ ID NO 918
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 918
tcgtaagaaa cgccactaga aagtaactct cttctattgc ag 42

<210> SEQ ID NO 919
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 919
cactggcgtg cctaaaccag taactctctt ctattgcag 39

<210> SEQ ID NO 920
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 920
acatatcata cgtggacatt agaacgtaac tctcttctat tgcag 45

<210> SEQ ID NO 921
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 921
gccgatggaa tgctccatcc gtaactctct tctattgcag 40

<210> SEQ ID NO 922
<211> LENGTH: 43
<212> TYPE: DNA
<213> ORGANISM: Artificial Sequence
<220> FEATURE:

<223> OTHER INFORMATION: Target Specific Oligonucleotide

<400> SEQUENCE: 922
gattagcaat cggtcacaaa gacgtaactc tcttctattg cag 43

<210> SEQ ID NO 923
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 923
ggtgtagtag tacacattgg agcgtaactc tcttctattg cag 43

<210> SEQ ID NO 924
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 924
gatgaaactt cggttgtcag ctgtaactct cttctattgc ag 42

<210> SEQ ID NO 925
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 925
ttcttgaggc tagcaacttg tggtaactct cttctattgc ag 42

<210> SEQ ID NO 926
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 926
gtcccaaaac tcgattagct tccgtaactc tcttctattg cag 43

<210> SEQ ID NO 927
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 927
tattcgtgga acccctaaca gcgtaactct cttctattgc ag 42

<210> SEQ ID NO 928
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 928
caaagttgat atcgcccaaa atggtaactc tcttctattg cag 43

<210> SEQ ID NO 929
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 929
tagatccaag cggttccatt tcgtaactct cttctattgc ag 42

<210> SEQ ID NO 930
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 930
tgaccagttc ccgtaaaaca ctgtaactct cttctattgc ag 42

<210> SEQ ID NO 931
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 931
tggcacatgg tcgatacaca tgtaactctc ttctattgca g 41

<210> SEQ ID NO 932
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 932
tgacagcaca acgatcacaa cgtaactctc ttctattgca g 41

<210> SEQ ID NO 933
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 933
aagctcatga actatgccag aggtaactct cttctattgc ag 42

<210> SEQ ID NO 934
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 934
cgtcatacct gaccgagtac tgtaactctc ttctattgca g 41

<210> SEQ ID NO 935
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 935
tcttgattgt cgagaaagac ttggtaactc tcttctattg cag 43

<210> SEQ ID NO 936
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 936
tactgagccc tatcggaaag tgtaactgat cttcatatta cg 42

<210> SEQ ID NO 937
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 937
ccaaatccct tcgcagcaat tgtaactgat cttcatatta cg 42

<210> SEQ ID NO 938
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 938
gccatgatca atcgcatcac tgtaactgat cttcatatta cg 42

<210> SEQ ID NO 939
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 939
atcatccaga ttcgaaccgt ccgtaactga tcttcatatt acg 43

<210> SEQ ID NO 940
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 940
ggactacatt cgtgaagaag ctgtaactga tcttcatatt acg 43

<210> SEQ ID NO 941
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 941
ggagaggatc cgtccaagaa agtaactgat cttcatatta cg 42

<210> SEQ ID NO 942
<211> LENGTH: 42

<212> TYPE: DNA
<213> ORGANISM: Artificial Sequence
<220> FEATURE:
<223> OTHER INFORMATION: Target Specific Oligonucleotide

<400> SEQUENCE: 942
gtcccagcat tagaacctgt ggtaactgat cttcatatta cg 42

<210> SEQ ID NO 943
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 943
actctcagcc agacctttag cgtaactgat cttcatatta cg 42

<210> SEQ ID NO 944
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 944
catagtgtca tgtgcatgta gtcgtaactg atcttcatat tacg 44

<210> SEQ ID NO 945
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 945
ccctgaccag catattatct acagtaactg atcttcatat tacg 44

<210> SEQ ID NO 946
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 946
cagcgcctgt tacaagctct gtaactgatc ttcatattac g 41

<210> SEQ ID NO 947
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 947
cgccagtctt aactgccatg gtaactgatc ttcatattac g 41

<210> SEQ ID NO 948
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 948
tcttcccaac accgtaatct ttgtaactga tcttcatatt acg 43

<210> SEQ ID NO 949
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 949
gtgacttatg ttcgggtctc tcgtaactga tcttcatatt acg 43

<210> SEQ ID NO 950
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 950
tgttaggttc tagggccata gcgtaactga tcttcatatt acg 43

<210> SEQ ID NO 951
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 951
ctggatagct ttgggcaact cgtaactgat cttcatatta cg 42

<210> SEQ ID NO 952
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 952
tgcagacagg gtatgtatat ttgggtaact gatcttcata ttacg 45

<210> SEQ ID NO 953
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 953
aagaaaatat agctgagctc cctgtaactg atcttcatat tacg 44

<210> SEQ ID NO 954
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 954
gagaccggag aaacccggcg taactgatct tcatattacg 40

<210> SEQ ID NO 955
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 955
ccgcaggaga ccgaggtctg taactgatct tcatattacg 40

<210> SEQ ID NO 956
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 956
aggctagggc tcaagacaag ggtaactgat cttcatatta cg 42

<210> SEQ ID NO 957
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 957
gcgtccggtg tcgccatgta actgatcttc atattacg 38

<210> SEQ ID NO 958
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 958
actctgggtc ggcttgatcc gtaactgatc ttcatattac g 41

<210> SEQ ID NO 959
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 959
catgggagga tcgagcctgg gtaactgatc ttcatattac g 41

<210> SEQ ID NO 960
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 960
ggcactggaa acgattgact tgtaacggca atacatcgt 39

<210> SEQ ID NO 961
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 961
tcaggcattc gttcacctgt gtaacggcaa tacatcgt 38

<210> SEQ ID NO 962
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 962
actgtagcga ttaatgccat ccgtaacggc aatacatcgt 40

<210> SEQ ID NO 963
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 963
atagcctcca ttgcggttgg gtaacggcaa tacatcgt 38

<210> SEQ ID NO 964
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 964
cattcgggtg atcgatacac ttgtaacggc aatacatcgt 40

<210> SEQ ID NO 965
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 965
gcacactcat cgagttgctc cgtaacggca atacatcgt 39

<210> SEQ ID NO 966
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 966
tcccgcttaa tgcgcaggtg taacggcaat acatcgt 37

<210> SEQ ID NO 967
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 967
ggtcccctgt atggcgtgag taacggcaat acatcgt 37

<210> SEQ ID NO 968
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 968
aacacactgg cggttgtcaa gtaacggcaa tacatcgt 38

<210> SEQ ID NO 969
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 969
cacacatcga cgaaggtttc agtaacggca atacatcgt 39

<210> SEQ ID NO 970
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 970
ggctcttgca cgagttaact tgtaacggca atacatcgt 39

<210> SEQ ID NO 971
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 971
atgtcaatgg tacaccgctg agtaacggca atacatcgt 39

<210> SEQ ID NO 972
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 972
gccatgctta cgctttcgtt gtaacggcaa tacatcgt 38

<210> SEQ ID NO 973
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 973
ggtataccag taacacggac cagtaacggc aatacatcgt 40

<210> SEQ ID NO 974
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 974
gactctctca cgcataaacc tggtaacggc aatacatcgt 40

<210> SEQ ID NO 975

<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 975
aggagatgcg taggtcaatt cagtaacggc aatacatcgt 40

<210> SEQ ID NO 976
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 976
ccaacaggac gctagtgtag agtaacggca atacatcgt 39

<210> SEQ ID NO 977
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 977
cagtaccaat taggttagct tctggtaacg gcaatacatc gt 42

<210> SEQ ID NO 978
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 978
tccatggccg tcgatcaatg gtaacggcaa tacatcgt 38

<210> SEQ ID NO 979
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 979
tagtcaggaa tatgcggtca ttgtaacggc aatacatcgt 40

<210> SEQ ID NO 980
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 980
tatagcaact acttcgcatt tccgtaacgg caatacatcg t 41

<210> SEQ ID NO 981
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 981
cgatggtgtc ctacggatgt cgtaacggca atacatcgt 39

<210> SEQ ID NO 982
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 982
gtaaccatag taccacttat tagtgggtaa cggcaataca tcgt 44

<210> SEQ ID NO 983
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 983
cagcatcagc ccgtgagtag taacggcaat acatcgt 37

<210> SEQ ID NO 984
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 984
tcagatgcta ctggccgctt agacaagtta agatcggaa 39

<210> SEQ ID NO 985
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 985
cttgatcaag gcgctgaaca atagacaagt taagatcgga a 41

<210> SEQ ID NO 986
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 986
tcccttcgta tctcagcgag atagacaagt taagatcgga a 41

<210> SEQ ID NO 987
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 987
agactgttga ctggcgtgat gtagacaagt taagatcgga a 41

<210> SEQ ID NO 988
<211> LENGTH: 41
<212> TYPE: DNA

<213> ORGANISM: Artificial Sequence
<220> FEATURE:
<223> OTHER INFORMATION: Target Specific Oligonucleotide

<400> SEQUENCE: 988
ccaacatgct cgcatgagtt ctagacaagt taagatcgga a 41

<210> SEQ ID NO 989
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 989
ttccttcacc gaactgagga gtagacaagt taagatcgga a 41

<210> SEQ ID NO 990
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 990
agttccaacg agcggcttca tagacaagtt aagatcggaa 40

<210> SEQ ID NO 991
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 991
ccatggctga cgagatctga tagacaagtt aagatcggaa 40

<210> SEQ ID NO 992
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 992
tagcctaaga cccggagctt tagacaagtt aagatcggaa 40

<210> SEQ ID NO 993
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 993
gcagatactc agcggcattg tagacaagtt aagatcggaa 40

<210> SEQ ID NO 994
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 994
catagctcac gcagaacgtg tagacaagtt aagatcggaa 40

<210> SEQ ID NO 995
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 995
gtcggccacc gttgaatgat agacaagtta agatcggaa 39

<210> SEQ ID NO 996
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 996
agaacggtca gcgagcgtat agacaagtta agatcggaa 39

<210> SEQ ID NO 997
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 997
gttatgctta gagtgttatc tccatagaca agttaagatc ggaa 44

<210> SEQ ID NO 998
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 998
tggtgatgtc cgtgcgttcc tagacaagtt aagatcggaa 40

<210> SEQ ID NO 999
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 999
ggtccagagg atcgctctct tagacaagtt aagatcggaa 40

<210> SEQ ID NO 1000
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1000
cgtggactgc aagtcccgat agacaagtta agatcggaa 39

<210> SEQ ID NO 1001
<211> LENGTH: 41
<212> TYPE: DNA
<213> ORGANISM: Artificial Sequence
<220> FEATURE:

<223> OTHER INFORMATION: Target Specific Oligonucleotide

<400> SEQUENCE: 1001
acaggtcaat tcccgggtaa gtagacaagt taagatcgga a 41

<210> SEQ ID NO 1002
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1002
ctgcaccagg ttagggtgtt ttagacaagt taagatcgga a 41

<210> SEQ ID NO 1003
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1003
ggaaatggca tatacgtggg atttagacaa gttaagatcg gaa 43

<210> SEQ ID NO 1004
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1004
cttttgtctt tgcgcccagg tagacaagtt aagatcggaa 40

<210> SEQ ID NO 1005
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1005
tcctgccggt tgcactccta gacaagttaa gatcggaa 38

<210> SEQ ID NO 1006
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1006
atcatacagt gcaacgaaaa ggttagacaa gttaagatcg gaa 43

<210> SEQ ID NO 1007
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1007
tcccacttgt cgtagttggg tagacaagtt aagatcggaa 40

<210> SEQ ID NO 1008
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1008
aggtggtgtt ccgaacgagc tagacagccc aattaaacg 39

<210> SEQ ID NO 1009
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1009
agatccgtga gcggaatgta tagacagccc aattaaacg 39

<210> SEQ ID NO 1010
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1010
ctcactcgct ttagtggact cctagacagc ccaattaaac g 41

<210> SEQ ID NO 1011
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 1011
gccaaagacc gtggcgagta gacagcccaa ttaaacg 37

<210> SEQ ID NO 1012
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1012
agagttcttg gtcgttggat cctagacagc ccaattaaac g 41

<210> SEQ ID NO 1013
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1013
ctcctttgca accgggtctg tagacagccc aattaaacg 39

<210> SEQ ID NO 1014
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1014
cttgttattg acgtcgaagg cttagacagc ccaattaaac g 41

<210> SEQ ID NO 1015
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1015
caggaacgtg taactcttgc ctagacagcc caattaaacg 40

<210> SEQ ID NO 1016
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1016
ggagtttcac acacgagttg gtagacagcc caattaaacg 40

<210> SEQ ID NO 1017
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1017
aggttcccgc tctacggatg tagacagccc aattaaacg 39

<210> SEQ ID NO 1018
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1018
accgtcatgg actgccgtct agacagccca attaaacg 38

<210> SEQ ID NO 1019
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1019
tgggaccttt agacttcggt gtagacagcc caattaaacg 40

<210> SEQ ID NO 1020
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 1020
gtccctgtag acgcgcgtta gacagcccaa ttaaacg 37

<210> SEQ ID NO 1021
<211> LENGTH: 38

<212> TYPE: DNA
<213> ORGANISM: Artificial Sequence
<220> FEATURE:
<223> OTHER INFORMATION: Target Specific Oligonucleotide

<400> SEQUENCE: 1021
ccagagaggg cgcatcttgt agacagccca attaaacg 38

<210> SEQ ID NO 1022
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1022
tccactctgc acgctcatag ttagacagcc caattaaacg 40

<210> SEQ ID NO 1023
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1023
gtgaaactcg acgttcacgt atagacagcc caattaaacg 40

<210> SEQ ID NO 1024
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1024
acacctcttt gtcgttgacc ttagacagcc caattaaacg 40

<210> SEQ ID NO 1025
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1025
actgttgcga gttctgcgag tagacagccc aattaaacg 39

<210> SEQ ID NO 1026
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1026
tggcaactcc gtagttgtcc tagacagccc aattaaacg 39

<210> SEQ ID NO 1027
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1027
tcctcggacg ctaagctcat agacagccca attaaacg 38

<210> SEQ ID NO 1028
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1028
ttacccggag aaccctcgct agacagccca attaaacg 38

<210> SEQ ID NO 1029
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1029
tcccggaaca tgcggtaggt agacagccca attaaacg 38

<210> SEQ ID NO 1030
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1030
tgctcgatgt cgcccactgt agacagccca attaaacg 38

<210> SEQ ID NO 1031
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 1031
tgccggtgcc gcttatggta gacagcccaa ttaaacg 37

<210> SEQ ID NO 1032
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1032
ccaaagtctg ctagcttgat ggtagacggt ataatactta tttcc 45

<210> SEQ ID NO 1033
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 1033
tattaggatg gttaagctcc ttaagtagac ggtataatac ttatttcc 48

<210> SEQ ID NO 1034
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1034
catgggtgta agtacgaaca ggtagacggt ataatactta tttcc 45

<210> SEQ ID NO 1035
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1035
ggcagaaagc taggccctgg tagacggtat aatacttatt tcc 43

<210> SEQ ID NO 1036
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1036
gtacacaact ccgtacgtgc tagacggtat aatacttatt tcc 43

<210> SEQ ID NO 1037
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1037
atggaacgca gtatacctct cgtagacggt ataatactta tttcc 45

<210> SEQ ID NO 1038
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1038
cttggcttgt aatcaggcat agatagacgg tataatactt atttcc 46

<210> SEQ ID NO 1039
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1039
ctccatgaag cgccagcgta gacggtataa tacttatttc c 41

<210> SEQ ID NO 1040
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1040
ccgcttgtta gggtcgtagt tagacggtat aatacttatt tcc 43

<210> SEQ ID NO 1041
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1041
ctcggtggag gacccgatgt agacggtata atacttattt cc 42

<210> SEQ ID NO 1042
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1042
ttactaaaat cttgccgggc ctagacggta taatacttat ttcc 44

<210> SEQ ID NO 1043
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1043
gcagcatttg cgataacaag ctagacggta taatacttat ttcc 44

<210> SEQ ID NO 1044
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1044
agaaggctat cagagtcgaa gatagacggt ataatactta tttcc 45

<210> SEQ ID NO 1045
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1045
ttcaggagct cggtaccaca tagacggtat aatacttatt tcc 43

<210> SEQ ID NO 1046
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1046
ccccagagtc cgaaagatcc gtagacggta taatacttat ttcc 44

<210> SEQ ID NO 1047
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1047
acagggccca gtaccgtggt agacggtata atacttattt cc 42

<210> SEQ ID NO 1048
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1048
tcagcaataa ctaagagaag gggtagacgg tataatactt atttcc 46

<210> SEQ ID NO 1049
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1049
gtacggcaaa tctaacgtgt aggtagacgg tataatactt atttcc 46

<210> SEQ ID NO 1050
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1050
tgaaacaatg ttgccgcctc ctagacggta taatacttat ttcc 44

<210> SEQ ID NO 1051
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 1051
taataattat ggggcattca gagatagacg gtataatact tatttcc 47

<210> SEQ ID NO 1052
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1052
tctcacctgc ctcataaggc tagacggtat aatacttatt tcc 43

<210> SEQ ID NO 1053
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 1053
atggtgaagc aatagattgg aatgtagacg gtataatact tatttcc 47

<210> SEQ ID NO 1054

<211> LENGTH: 49
<212> TYPE: DNA
<213> ORGANISM: Artificial Sequence
<220> FEATURE:
<223> OTHER INFORMATION: Target Specific Oligonucleotide

<400> SEQUENCE: 1054
cactaactag ggtataaact gattggtaga cggtataata cttatttcc 49

<210> SEQ ID NO 1055
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1055
agaagggaca aacaagggga ctagacggta taatacttat ttcc 44

<210> SEQ ID NO 1056
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1056
agtccgatac tcaagcgcaa atagacaata aattctaacg agc 43

<210> SEQ ID NO 1057
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1057
cttgttgcgc tcacggtatg tagacaataa attctaacga gc 42

<210> SEQ ID NO 1058
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1058
ccagagttgt agacgagcag ctagacaata aattctaacg agc 43

<210> SEQ ID NO 1059
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1059
ttagcatggc aacacggcgt agacaataaa ttctaacgag c 41

<210> SEQ ID NO 1060
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1060
atgatgcgca cttcacgggt agacaataaa ttctaacgag c 41

<210> SEQ ID NO 1061
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1061
cccaccgcta ggagggtagc tagacaataa attctaacga gc 42

<210> SEQ ID NO 1062
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1062
gcagtgtggt taggccgatg tagacaataa attctaacga gc 42

<210> SEQ ID NO 1063
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1063
gacacggcgg tgcactatct agacaataaa ttctaacgag c 41

<210> SEQ ID NO 1064
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1064
gcccaaagcg gcttgcagta gacaataaat tctaacgagc 40

<210> SEQ ID NO 1065
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1065
atacacacac ggctaatact gctagacaat aaattctaac gagc 44

<210> SEQ ID NO 1066
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1066
gtgaccgtgt acaccaacaa ctagacaata aattctaacg agc 43

<210> SEQ ID NO 1067
<211> LENGTH: 46
<212> TYPE: DNA

<213> ORGANISM: Artificial Sequence
<220> FEATURE:
<223> OTHER INFORMATION: Target Specific Oligonucleotide

<400> SEQUENCE: 1067
ctcttcatac tagcatgact gtcatagaca ataaattcta acgagc 46

<210> SEQ ID NO 1068
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1068
agaaggcttt cgtcgttccc tagacaataa attctaacga gc 42

<210> SEQ ID NO 1069
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1069
tttgctccgt gcgttcaagg tagacaataa attctaacga gc 42

<210> SEQ ID NO 1070
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1070
tccagtgcat ccgtcacatc tagacaataa attctaacga gc 42

<210> SEQ ID NO 1071
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1071
gatgaacagc ggtgcgttgt agacaataaa ttctaacgag c 41

<210> SEQ ID NO 1072
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1072
cactgatacc ggctctccgt tagacaataa attctaacga gc 42

<210> SEQ ID NO 1073
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1073
gaacgcttgc gttccctagc tagacaataa attctaacga gc 42

<210> SEQ ID NO 1074
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1074
cagatagatt tccgggatac agctagacaa taaattctaa cgagc 45

<210> SEQ ID NO 1075
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1075
tctgctgcgg cgattgtgta gacaataaat tctaacgagc 40

<210> SEQ ID NO 1076
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1076
ctcggtgatc atgcgtccct agacaataaa ttctaacgag c 41

<210> SEQ ID NO 1077
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1077
tccaatttca gggcgttctc gtagacaata aattctaacg agc 43

<210> SEQ ID NO 1078
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1078
tgcgcaggtc gacgtcagta gacaataaat tctaacgagc 40

<210> SEQ ID NO 1079
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1079
gtccaggtag tatccggagg gtagacaata aattctaacg agc 43

<210> SEQ ID NO 1080
<211> LENGTH: 40
<212> TYPE: DNA
<213> ORGANISM: Artificial Sequence
<220> FEATURE:

<223> OTHER INFORMATION: Target Specific Oligonucleotide

<400> SEQUENCE: 1080
attcccgaca gactcatcgc tagacgataa attgcgaacg 40

<210> SEQ ID NO 1081
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1081
cagttacatg ttcgcgcacg tagacgataa attgcgaacg 40

<210> SEQ ID NO 1082
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1082
acgagcacta gggtcgtcgt agacgataaa ttgcgaacg 39

<210> SEQ ID NO 1083
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1083
ttttgataat cgaatgaaaa agtcactaga cgataaattg cgaacg 46

<210> SEQ ID NO 1084
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1084
ctgaatactg ctagacgaga agctagacga taaattgcga acg 43

<210> SEQ ID NO 1085
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1085
ctccttggaa cgaactaatc ctgtagacga taaattgcga acg 43

<210> SEQ ID NO 1086
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1086
ttcaggcggt taattggtac cctagacgat aaattgcgaa cg 42

<210> SEQ ID NO 1087
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1087
gttaggaatg gcgaacagac agtagacgat aaattgcgaa cg 42

<210> SEQ ID NO 1088
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1088
gatggtctta aagcgtgaag cctagacgat aaattgcgaa cg 42

<210> SEQ ID NO 1089
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1089
ctgtgcctag ccctaactta tatagacgat aaattgcgaa cg 42

<210> SEQ ID NO 1090
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1090
agagaccacc cataacaaga gttagacgat aaattgcgaa cg 42

<210> SEQ ID NO 1091
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1091
ttggagcacc gatatagata tggtagacga taaattgcga acg 43

<210> SEQ ID NO 1092
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1092
tcaaagacgc aaacgtccaa atagacgata aattgcgaac g 41

<210> SEQ ID NO 1093
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1093
gagagctgat taggtgctca ggtagacgat aaattgcgaa cg 42

<210> SEQ ID NO 1094
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1094
tgcttgtacg cggagaaggt tagacgataa attgcgaacg 40

<210> SEQ ID NO 1095
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1095
ctgcagacac gtgtatgtgc tagacgataa attgcgaacg 40

<210> SEQ ID NO 1096
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1096
catccaatgc aagtccggtg tagacgataa attgcgaacg 40

<210> SEQ ID NO 1097
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1097
accaagtgat aacgtgttca gatagacgat aaattgcgaa cg 42

<210> SEQ ID NO 1098
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1098
aatctgagct ttgcgaaatg gttagacgat aaattgcgaa cg 42

<210> SEQ ID NO 1099
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1099
caaagcccac ataacactat cttttagacg ataaattgcg aacg 44

<210> SEQ ID NO 1100
<211> LENGTH: 44

<212> TYPE: DNA
<213> ORGANISM: Artificial Sequence
<220> FEATURE:
<223> OTHER INFORMATION: Target Specific Oligonucleotide

<400> SEQUENCE: 1100
tgtactggac tatagacacc aatttagacg ataaattgcg aacg 44

<210> SEQ ID NO 1101
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1101
atcaatatac cacgttagta gtcactagac gataaattgc gaacg 45

<210> SEQ ID NO 1102
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1102
tgtattttaa cgccaagcag gctagacgat aaattgcgaa cg 42

<210> SEQ ID NO 1103
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1103
cactgaaaac acggttatgt cctagacgat aaattgcgaa cg 42

<210> SEQ ID NO 1104
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1104
cgagacagat cggagtagct gtagacgacc gaatttacgg 40

<210> SEQ ID NO 1105
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1105
tctctcaatg acgggacaaa gatagacgac cgaatttacg g 41

<210> SEQ ID NO 1106
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1106
cagatgtggt gtatggtcca catagacgac cgaatttacg g 41

<210> SEQ ID NO 1107
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1107
ttctcctcgg ttacttcgtg atagacgacc gaatttacgg 40

<210> SEQ ID NO 1108
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1108
tgtgctaagc cgaaggaggt tagacgaccg aatttacgg 39

<210> SEQ ID NO 1109
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1109
gtaaacatag aacgactcat agtcatagac gaccgaattt acgg 44

<210> SEQ ID NO 1110
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1110
ttccacttca attagctctt gaattagacg accgaattta cgg 43

<210> SEQ ID NO 1111
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1111
ctggggtaga gatagctcgc ttagacgacc gaatttacgg 40

<210> SEQ ID NO 1112
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1112
gctataagct cgcctaccat tctagacgac cgaatttacg g 41

<210> SEQ ID NO 1113
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1113
ttcttggggc gggtagagtg tagacgaccg aatttacgg 39

<210> SEQ ID NO 1114
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1114
aagacctcag accgtcagaa gtagacgacc gaatttacgg 40

<210> SEQ ID NO 1115
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1115
tcagatcctg acgacctgca tagacgaccg aatttacgg 39

<210> SEQ ID NO 1116
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1116
gcagaaatct cgagaggacg ctagacgacc gaatttacgg 40

<210> SEQ ID NO 1117
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1117
ctcgcagtct aggccgaaga tagacgaccg aatttacgg 39

<210> SEQ ID NO 1118
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1118
ccggtctccc tcgagaatca tagacgaccg aatttacgg 39

<210> SEQ ID NO 1119
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1119
tcctggtgag aacgtcctgc tagacgaccg aatttacgg 39

<210> SEQ ID NO 1120
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1120
tgccctttgg taaggcgcct agacgaccga atttacgg 38

<210> SEQ ID NO 1121
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1121
cacagacaca gccgaggact agacgaccga atttacgg 38

<210> SEQ ID NO 1122
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1122
tcccaaaagc taccgctgag tagacgaccg aatttacgg 39

<210> SEQ ID NO 1123
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1123
taaggtagag tcgggcgaag tagacgaccg aatttacgg 39

<210> SEQ ID NO 1124
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1124
gagtggccgg aaaaacccgt agacgaccga atttacgg 38

<210> SEQ ID NO 1125
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 1125
atgcggacat ggtcgcccta gacgaccgaa tttacgg 37

<210> SEQ ID NO 1126
<211> LENGTH: 37
<212> TYPE: DNA
<213> ORGANISM: Artificial Sequence
<220> FEATURE:
<223> OTHER INFORMATION: Target Specific Oligonucleotide

<400> SEQUENCE: 1126
ggctcccaaa cgccctgata gacgaccgaa tttacgg 37

<210> SEQ ID NO 1127
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1127
tccatttcac cgtcagaaag gtagacgacc gaatttacgg 40

<210> SEQ ID NO 1128
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1128
ttgcctagac agcaccgtaa tgtagacacg aatattccaa ttc 43

<210> SEQ ID NO 1129
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1129
ttcccagagc gtggttccat agacacgaat attccaattc 40

<210> SEQ ID NO 1130
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1130
taaggacatc gcttttccgg ttagacacga atattccaat tc 42

<210> SEQ ID NO 1131
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1131
ttctccacgt cgcggacact agacacgaat attccaattc 40

<210> SEQ ID NO 1132
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1132
gttctcatga tagaggttcc ttaagtagac acgaatattc caattc 46

<210> SEQ ID NO 1133

<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1133
ggccacgtcg gtgcagatag acacgaatat tccaattc 38

<210> SEQ ID NO 1134
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1134
gttgtggacg atcaacgggg tagacacgaa tattccaatt c 41

<210> SEQ ID NO 1135
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1135
tgtccccttc ggggtcatac ctagacacga atattccaat tc 42

<210> SEQ ID NO 1136
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1136
aatagaacct catccggtag tggtagacac gaatattcca attc 44

<210> SEQ ID NO 1137
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1137
cagtgcagcg tatgtggtat ttagacacga atattccaat tc 42

<210> SEQ ID NO 1138
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1138
aaagcttgtc cgattggatg gtagacacga atattccaat tc 42

<210> SEQ ID NO 1139
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1139
aacccttgta gatcggtggt atagacacga atattccaat tc 42

<210> SEQ ID NO 1140
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1140
agtagagaac gtttccaccg ttagacacga atattccaat tc 42

<210> SEQ ID NO 1141
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1141
actgctcatt gtcgttggtt ctagacacga atattccaat tc 42

<210> SEQ ID NO 1142
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1142
aacgtattgc cgagaaccca tagacacgaa tattccaatt c 41

<210> SEQ ID NO 1143
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1143
acaaagtgca tatagagtgg cctagacacg aatattccaa ttc 43

<210> SEQ ID NO 1144
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1144
agccatccct agacactcgt ttagacacga atattccaat tc 42

<210> SEQ ID NO 1145
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1145
gcgatttgga gcataccaga gtagacacga atattccaat tc 42

<210> SEQ ID NO 1146
<211> LENGTH: 42
<212> TYPE: DNA

<213> ORGANISM: Artificial Sequence
<220> FEATURE:
<223> OTHER INFORMATION: Target Specific Oligonucleotide

<400> SEQUENCE: 1146
aggatccgat cgaaactcag ctagacacga atattccaat tc 42

<210> SEQ ID NO 1147
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1147
ctggaatata tcgcttgtag ctgtagacac gaatattcca attc 44

<210> SEQ ID NO 1148
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1148
cttcaggtca tgcgtggaca tagacacgaa tattccaatt c 41

<210> SEQ ID NO 1149
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1149
agagaagcgc acttccgtgt tagacacgaa tattccaatt c 41

<210> SEQ ID NO 1150
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1150
tgatgttatc cgtgcgcagg tagacacgaa tattccaatt c 41

<210> SEQ ID NO 1151
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1151
aaagaccgta atcgttcaca ttgtagacac gaatattcca attc 44

<210> SEQ ID NO 1152
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1152
agagatttgt ctacgtagag ccgtagactc agaaatctca cg 42

<210> SEQ ID NO 1153
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1153
tcctttgcat acggtctctt cgtagactca gaaatctcac g 41

<210> SEQ ID NO 1154
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1154
aagtttgttt acatccgatg ttactagact cagaaatctc acg 43

<210> SEQ ID NO 1155
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1155
ttcccataca gaacgtggcc tagactcaga aatctcacg 39

<210> SEQ ID NO 1156
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1156
aacagatcaa cggcaaaagc ctagactcag aaatctcacg 40

<210> SEQ ID NO 1157
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1157
catccttggg tagtaggatg aactagactc agaaatctca cg 42

<210> SEQ ID NO 1158
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1158
gaatttgcta gttgcagggc atagactcag aaatctcacg 40

<210> SEQ ID NO 1159
<211> LENGTH: 45
<212> TYPE: DNA
<213> ORGANISM: Artificial Sequence
<220> FEATURE:

<223> OTHER INFORMATION: Target Specific Oligonucleotide

<400> SEQUENCE: 1159
tgatcttaca attgatactg tcaatgtaga ctcagaaatc tcacg 45

<210> SEQ ID NO 1160
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1160
tggatgtgga ggcgaccgtt agactcagaa atctcacg 38

<210> SEQ ID NO 1161
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1161
acttctggac ctatagtagc ctgtagactc agaaatctca cg 42

<210> SEQ ID NO 1162
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1162
caacacggat agcttatcca acctagactc agaaatctca cg 42

<210> SEQ ID NO 1163
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1163
tgtcaaggta acgtgagcac ttagactcag aaatctcacg 40

<210> SEQ ID NO 1164
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1164
tttacagaaa tcggcatcca catagactca gaaatctcac g 41

<210> SEQ ID NO 1165
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1165
cagctactag aggtctataa ttccttagac tcagaaatct cacg 44

<210> SEQ ID NO 1166
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1166
ctggcacctc tatggaatcc ctagactcag aaatctcacg 40

<210> SEQ ID NO 1167
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1167
attctgatat cggctattgt gagatagact cagaaatctc acg 43

<210> SEQ ID NO 1168
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1168
gccaccagtc tagtgccaac tagactcaga aatctcacg 39

<210> SEQ ID NO 1169
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1169
caactacccc ggacaatttg atagactcag aaatctcacg 40

<210> SEQ ID NO 1170
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1170
aggacttaac atgggctatg cctagactca gaaatctcac g 41

<210> SEQ ID NO 1171
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1171
ctctgcgaac gaagtgtttt tgtagactca gaaatctcac g 41

<210> SEQ ID NO 1172
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1172
tgcagcatat taaggtgttg attttagact cagaaatctc acg 43

<210> SEQ ID NO 1173
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1173
aagtaactaa acccatagac tgaaatagac tcagaaatct cacg 44

<210> SEQ ID NO 1174
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1174
ctgccagggc ttaacataag gtagactcag aaatctcacg 40

<210> SEQ ID NO 1175
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1175
ataacatttg atagggccac tcctagactc agaaatctca cg 42

<210> SEQ ID NO 1176
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1176
ctgaagataa tcgcagacac cctagacgtc tcccgtattt t 41

<210> SEQ ID NO 1177
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1177
tgactgaaca cgtgttctgt tctagacgtc tcccgtattt t 41

<210> SEQ ID NO 1178
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1178
tttcagccat acccggatgg tagacgtctc ccgtatttt 39

<210> SEQ ID NO 1179
<211> LENGTH: 41

<212> TYPE: DNA
<213> ORGANISM: Artificial Sequence
<220> FEATURE:
<223> OTHER INFORMATION: Target Specific Oligonucleotide

<400> SEQUENCE: 1179
tgagaagagt aaccgctgaa tatagacgtc tcccgtattt t 41

<210> SEQ ID NO 1180
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1180
acactgcaat tccgccgtct agacgtctcc cgtatttt 38

<210> SEQ ID NO 1181
<211> LENGTH: 38
<212> TYPE: DNA
<213> ORGANISM: Artificial Sequence
<220> FEATURE:
<223> OTHER INFORMATION: Target Specific Oligonucleotide

<400> SEQUENCE: 1181
ttgtcgtggc cggtactgat agacgtctcc cgtatttt 38

<210> SEQ ID NO 1182
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1182
ggcaggcgac actaccttca tagacgtctc ccgtatttt 39

<210> SEQ ID NO 1183
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1183
ctgggccagt attgaccact gtagacgtct cccgtatttt 40

<210> SEQ ID NO 1184
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1184
tctcagatca gtgcggagaa atagacgtct cccgtatttt 40

<210> SEQ ID NO 1185
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1185
gcccacaaat atccgtctgc tagacgtctc ccgtatttt 39

<210> SEQ ID NO 1186
<211> LENGTH: 36
<212> TYPE: DNA
<213> ORGANISM: Artificial Sequence
<220> FEATURE:
<223> OTHER INFORMATION: Target Specific Oligonucleotide

<400> SEQUENCE: 1186
ccatgttcgc gcggcgatag acgtctcccg tatttt 36

<210> SEQ ID NO 1187
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1187
atgaaaggtc gctagagaag tcctagacgt ctcccgtatt tt 42

<210> SEQ ID NO 1188
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1188
aatcacaaac ccggacttgg atagacgtct cccgtatttt 40

<210> SEQ ID NO 1189
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1189
actagcctgt cacgtttgtc ttagacgtct cccgtatttt 40

<210> SEQ ID NO 1190
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1190
atctttacaa tgcggtcggt cctagacgtc tcccgtattt t 41

<210> SEQ ID NO 1191
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1191
tgtcctggta tgatcccaac actagacgtc tcccgtattt t 41

<210> SEQ ID NO 1192
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1192
ctgatcattt cgcatcacag tgtagacgtc tcccgtattt t 41

<210> SEQ ID NO 1193
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1193
ctttccttac gtgtgtcaca catagacgtc tcccgtattt t 41

<210> SEQ ID NO 1194
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1194
tagtttgatc gcctccttaa acctagacgt ctcccgtatt tt 42

<210> SEQ ID NO 1195
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1195
aaatccctag gatagcacct ttgtagacgt ctcccgtatt tt 42

<210> SEQ ID NO 1196
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1196
cttacactta cgatgagcag atgtagacgt ctcccgtatt tt 42

<210> SEQ ID NO 1197
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1197
catttgctac ctagcatatg agagtagacg tctcccgtat ttt 43

<210> SEQ ID NO 1198
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1198
acagatgtca aacggtcaca tttagacgtc tcccgtattt t 41

<210> SEQ ID NO 1199
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1199
ttctaagata cgtcactcca attctagacg tctcccgtat ttt 43

<210> SEQ ID NO 1200
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1200
acagtccgtc gattctttac aatagactct ataaatcagc gt 42

<210> SEQ ID NO 1201
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1201
tctccacgta aatcccgatc ttagactcta taaatcagcg t 41

<210> SEQ ID NO 1202
<211> LENGTH: 40
<212> TYPE: DNA
<213> ORGANISM: Artificial Sequence
<220> FEATURE:
<223> OTHER INFORMATION: Target Specific Oligonucleotide

<400> SEQUENCE: 1202
cacgtgctga accaaccact tagactctat aaatcagcgt 40

<210> SEQ ID NO 1203
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1203
tcttgccgaa gttggccgtt agactctata aatcagcgt 39

<210> SEQ ID NO 1204
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1204
agcagcagtt ggatctacag ttagactcta taaatcagcg t 41

<210> SEQ ID NO 1205
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1205
gtctagcagt aaacctgtaa acctagactc tataaatcag cgt 43

<210> SEQ ID NO 1206
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1206
gtgcattatt ggacgaacat catagactct ataaatcagc gt 42

<210> SEQ ID NO 1207
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1207
gctgttgtta atggtctata atccatagac tctataaatc agcgt 45

<210> SEQ ID NO 1208
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1208
cacacatatc ctatgttcat caatatagac tctataaatc agcgt 45

<210> SEQ ID NO 1209
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1209
ttgagtggtc gttttcttac acatagactc tataaatcag cgt 43

<210> SEQ ID NO 1210
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1210
cataatcaaa acgaaatgtt tggtttagac tctataaatc agcgt 45

<210> SEQ ID NO 1211
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1211
tttgtagcat caacgtcctg gtagactcta taaatcagcg t 41

<210> SEQ ID NO 1212

<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1212
caacacattt gacctcccgt ttagactcta taaatcagcg t 41

<210> SEQ ID NO 1213
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1213
ctaaccaccg aatagattcc tggtagactc tataaatcag cgt 43

<210> SEQ ID NO 1214
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1214
gcagatgttt gaccggatgt ttagactcta taaatcagcg t 41

<210> SEQ ID NO 1215
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1215
tgcttgatgt attcggccat cgtagactct ataaatcagc gt 42

<210> SEQ ID NO 1216
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1216
tgagtttact tgcacggaaa ggtagactct ataaatcagc gt 42

<210> SEQ ID NO 1217
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1217
cactttatcc cgcagttcag tttagactct ataaatcagc gt 42

<210> SEQ ID NO 1218
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1218
gcaaagcatg tagccattcc ctagactcta taaatcagcg t 41

<210> SEQ ID NO 1219
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1219
aaagacatct cgagctgcta atgtagactc tataaatcag cgt 43

<210> SEQ ID NO 1220
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1220
gtcaccaccc atagtatgag ttttagactc tataaatcag cgt 43

<210> SEQ ID NO 1221
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1221
tttctaccta aggctctgat gcatagactc tataaatcag cgt 43

<210> SEQ ID NO 1222
<211> LENGTH: 41
<212> TYPE: DNA
<213> ORGANISM: Artificial Sequence
<220> FEATURE:
<223> OTHER INFORMATION: Target Specific Oligonucleotide

<400> SEQUENCE: 1222
tagagctgca cggaaagatt ttagactcta taaatcagcg t 41

<210> SEQ ID NO 1223
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1223
gtgtagcata tgaatcgaca tcatagactc tataaatcag cgt 43

<210> SEQ ID NO 1224
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1224
tagccttgta tggcagaatc gtagacctaa attactgtga atg 43

<210> SEQ ID NO 1225
<211> LENGTH: 45
<212> TYPE: DNA

<213> ORGANISM: Artificial Sequence
<220> FEATURE:
<223> OTHER INFORMATION: Target Specific Oligonucleotide

<400> SEQUENCE: 1225
tgaattgccc tgggtataac tcctagacct aaattactgt gaatg 45

<210> SEQ ID NO 1226
<211> LENGTH: 42
<212> TYPE: DNA
<213> ORGANISM: Artificial Sequence
<220> FEATURE:
<223> OTHER INFORMATION: Target Specific Oligonucleotide

<400> SEQUENCE: 1226
ttcctgttgc aacgtgaggg tagacctaaa ttactgtgaa tg 42

<210> SEQ ID NO 1227
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1227
atgaaagaca cgatcaaaat tgaatagacc taaattactg tgaatg 46

<210> SEQ ID NO 1228
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1228
gtcagcacga agtgagttca atagacctaa attactgtga atg 43

<210> SEQ ID NO 1229
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1229
cagtttgcag cgtagaatct cttagaccta aattactgtg aatg 44

<210> SEQ ID NO 1230
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1230
gtgcagataa tacgtgtctt tgctagacct aaattactgt gaatg 45

<210> SEQ ID NO 1231
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1231
tccaatgagt atgacaagtc cattagacct aaattactgt gaatg 45

<210> SEQ ID NO 1232
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1232
tgtaagaaag ctcggtcttc aaatagacct aaattactgt gaatg 45

<210> SEQ ID NO 1233
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1233
ccatgtaaga tacacgtaag agaatagacc taaattactg tgaatg 46

<210> SEQ ID NO 1234
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1234
gactcaagag catttcgtaa ttgttagacc taaattactg tgaatg 46

<210> SEQ ID NO 1235
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1235
atgtcattag tcacctcaag ttcttagacc taaattactg tgaatg 46

<210> SEQ ID NO 1236
<211> LENGTH: 39
<212> TYPE: DNA
<213> ORGANISM: Artificial Sequence
<220> FEATURE:
<223> OTHER INFORMATION: Target Specific Oligonucleotide

<400> SEQUENCE: 1236
ccgcactcgc acgcagatag acctaaatta ctgtgaatg 39

<210> SEQ ID NO 1237
<211> LENGTH: 47
<212> TYPE: DNA
<213> ORGANISM: Artificial Sequence
<220> FEATURE:
<223> OTHER INFORMATION: Target Specific Oligonucleotide

<400> SEQUENCE: 1237
tgttaacagt atcgtgaata tcacttagac ctaaattact gtgaatg 47

<210> SEQ ID NO 1238
<211> LENGTH: 45
<212> TYPE: DNA
<213> ORGANISM: Artificial Sequence
<220> FEATURE:

<223> OTHER INFORMATION: Target Specific Oligonucleotide

<400> SEQUENCE: 1238
actttgccat ctataaggga ggttagacct aaattactgt gaatg 45

<210> SEQ ID NO 1239
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 1239
cttgctatct cgataattta tgaaactaga cctaaattac tgtgaatg 48

<210> SEQ ID NO 1240
<211> LENGTH: 48
<212> TYPE: DNA
<213> ORGANISM: Artificial Sequence
<220> FEATURE:
<223> OTHER INFORMATION: Target Specific Oligonucleotide

<400> SEQUENCE: 1240
ttaatgtatc aagagtgtta ctgaaataga cctaaattac tgtgaatg 48

<210> SEQ ID NO 1241
<211> LENGTH: 46
<212> TYPE: DNA
<213> ORGANISM: Artificial Sequence
<220> FEATURE:
<223> OTHER INFORMATION: Target Specific Oligonucleotide

<400> SEQUENCE: 1241
tcaaatggga taccttaaca gatctagacc taaattactg tgaatg 46

<210> SEQ ID NO 1242
<211> LENGTH: 50
<212> TYPE: DNA
<213> ORGANISM: Artificial Sequence
<220> FEATURE:
<223> OTHER INFORMATION: Target Specific Oligonucleotide

<400> SEQUENCE: 1242
ataaataagc ttcgatttat attacagcta gacctaaatt actgtgaatg 50

<210> SEQ ID NO 1243
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1243
cttgtgtggt aggattaacc tggtagacct aaattactgt gaatg 45

<210> SEQ ID NO 1244
<211> LENGTH: 43
<212> TYPE: DNA
<213> ORGANISM: Artificial Sequence
<220> FEATURE:
<223> OTHER INFORMATION: Target Specific Oligonucleotide

<400> SEQUENCE: 1244
gttggtcaac tcgagcatct ttagacctaa attactgtga atg 43

<210> SEQ ID NO 1245
<211> LENGTH: 44
<212> TYPE: DNA
<213> ORGANISM: Artificial Sequence
<220> FEATURE:
<223> OTHER INFORMATION: Target Specific Oligonucleotide

<400> SEQUENCE: 1245
tttggtttgt aggcctgtag cttagaccta aattactgtg aatg 44

<210> SEQ ID NO 1246
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1246
cattaggcag taactcttgt tcctagacct aaattactgt gaatg 45

<210> SEQ ID NO 1247
<211> LENGTH: 45
<212> TYPE: DNA
<213> ORGANISM: Artificial Sequence
<220> FEATURE:
<223> OTHER INFORMATION: Target Specific Oligonucleotide

<400> SEQUENCE: 1247
cttctcagat acgcttcttc ttatagacct aaattactgt gaatg 45

<210> SEQ ID NO 1248
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1248
ggctaattta ttaccttcta gctataacga t 31

<210> SEQ ID NO 1249
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1249
accttaagaa tggaattcta gctataacga t 31

<210> SEQ ID NO 1250
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1250
acttaacttg agtggtctag ctataacgat 30

<210> SEQ ID NO 1251
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1251
ggctaattta ttacctcggt ctagatgga 29

<210> SEQ ID NO 1252
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1252
accttaagaa tggaatcggt ctagatgga 29

<210> SEQ ID NO 1253
<211> LENGTH: 28
<212> TYPE: DNA
<213> ORGANISM: Artificial Sequence
<220> FEATURE:
<223> OTHER INFORMATION: Decoding Oligonucleotide

<400> SEQUENCE: 1253
acttaacttg agtggcggtc tagatgga 28

<210> SEQ ID NO 1254
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1254
ggctaattta ttacctgtta actccgtagt aa 32

<210> SEQ ID NO 1255
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1255
accttaagaa tggaatgtta actccgtagt aa 32

<210> SEQ ID NO 1256
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1256
acttaacttg agtgggttaa ctccgtagta a 31

<210> SEQ ID NO 1257
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1257
ggctaattta ttacctcgct atatctactg a 31

<210> SEQ ID NO 1258
<211> LENGTH: 31

<212> TYPE: DNA
<213> ORGANISM: Artificial Sequence
<220> FEATURE:
<223> OTHER INFORMATION: Decoding Oligonucleotide

<400> SEQUENCE: 1258
accttaagaa tggaatcgct atatctactg a 31

<210> SEQ ID NO 1259
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1259
acttaacttg agtggcgcta tatctactga 30

<210> SEQ ID NO 1260
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1260
ggctaattta ttacctgttt ccgtttcgaa 30

<210> SEQ ID NO 1261
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1261
accttaagaa tggaatgttt ccgtttcgaa 30

<210> SEQ ID NO 1262
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1262
acttaacttg agtgggtttc cgtttcgaa 29

<210> SEQ ID NO 1263
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1263
ggctaattta ttaccttagc gtttcaaaag 30

<210> SEQ ID NO 1264
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1264
accttaagaa tggaattagc gtttcaaaag 30

<210> SEQ ID NO 1265
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1265
acttaacttg agtggtagcg tttcaaaag 29

<210> SEQ ID NO 1266
<211> LENGTH: 28
<212> TYPE: DNA
<213> ORGANISM: Artificial Sequence
<220> FEATURE:
<223> OTHER INFORMATION: Decoding Oligonucleotide

<400> SEQUENCE: 1266
ggctaattta ttaccttgat ccgacgag 28

<210> SEQ ID NO 1267
<211> LENGTH: 28
<212> TYPE: DNA
<213> ORGANISM: Artificial Sequence
<220> FEATURE:
<223> OTHER INFORMATION: Decoding Oligonucleotide

<400> SEQUENCE: 1267
accttaagaa tggaattgat ccgacgag 28

<210> SEQ ID NO 1268
<211> LENGTH: 27
<212> TYPE: DNA
<213> ORGANISM: Artificial Sequence
<220> FEATURE:
<223> OTHER INFORMATION: Decoding Oligonucleotide

<400> SEQUENCE: 1268
acttaacttg agtggtgatc cgacgag 27

<210> SEQ ID NO 1269
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1269
ggctaattta ttacctaatc tacatgtctg a 31

<210> SEQ ID NO 1270
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1270
accttaagaa tggaataatc tacatgtctg a 31

<210> SEQ ID NO 1271
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1271
acttaacttg agtggaatct acatgtctga 30

<210> SEQ ID NO 1272
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1272
ggctaattta ttacctggac gttgaataca 30

<210> SEQ ID NO 1273
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1273
accttaagaa tggaatggac gttgaataca 30

<210> SEQ ID NO 1274
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1274
acttaacttg agtggggacg ttgaataca 29

<210> SEQ ID NO 1275
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1275
ggctaattta ttaccttaaa gtgacaattc a 31

<210> SEQ ID NO 1276
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1276
accttaagaa tggaattaaa gtgacaattc a 31

<210> SEQ ID NO 1277
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1277
acttaacttg agtggtaaag tgacaattca 30

<210> SEQ ID NO 1278
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1278
ggctaattta ttacctgatt cccataatta gg 32

<210> SEQ ID NO 1279
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1279
accttaagaa tggaatgatt cccataatta gg 32

<210> SEQ ID NO 1280
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1280
acttaacttg agtgggattc ccataattag g 31

<210> SEQ ID NO 1281
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1281
ggctaattta ttacctcgtc gtataaatct atc 33

<210> SEQ ID NO 1282
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1282
accttaagaa tggaatcgtc gtataaatct atc 33

<210> SEQ ID NO 1283
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1283
acttaacttg agtggcgtcg tataaatcta tc 32

<210> SEQ ID NO 1284
<211> LENGTH: 34
<212> TYPE: DNA
<213> ORGANISM: Artificial Sequence
<220> FEATURE:
<223> OTHER INFORMATION: Decoding Oligonucleotide

<400> SEQUENCE: 1284
ggctaattta ttacctgatg tctatccttt ataa 34

<210> SEQ ID NO 1285
<211> LENGTH: 34
<212> TYPE: DNA
<213> ORGANISM: Artificial Sequence
<220> FEATURE:
<223> OTHER INFORMATION: Decoding Oligonucleotide

<400> SEQUENCE: 1285
accttaagaa tggaatgatg tctatccttt ataa 34

<210> SEQ ID NO 1286
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1286
acttaacttg agtgggatgt ctatccttta taa 33

<210> SEQ ID NO 1287
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1287
ggctaattta ttacctttc cacgataacc 30

<210> SEQ ID NO 1288
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1288
accttaagaa tggaattttc cacgataacc 30

<210> SEQ ID NO 1289
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1289
acttaacttg agtggtttcc acgataacc 29

<210> SEQ ID NO 1290
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1290
ggctaattta ttaccttagt accgaataag g 31

<210> SEQ ID NO 1291

<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1291
accttaagaa tggaattagt accgaataag g 31

<210> SEQ ID NO 1292
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1292
acttaacttg agtggtagta ccgaataagg 30

<210> SEQ ID NO 1293
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1293
ggctaattta ttaccttaaa gttgtaaaat cc 32

<210> SEQ ID NO 1294
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1294
accttaagaa tggaattaaa gttgtaaaat cc 32

<210> SEQ ID NO 1295
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1295
acttaacttg agtggtaaag ttgtaaaatc c 31

<210> SEQ ID NO 1296
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1296
ggctaattta ttacctggat aagtcggtaa tc 32

<210> SEQ ID NO 1297
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1297
accttaagaa tggaatggat aagtcggtaa tc 32

<210> SEQ ID NO 1298
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1298
acttaacttg agtggggata agtcggtaat c 31

<210> SEQ ID NO 1299
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1299
ggctaattta ttacctggta tttcactcta att 33

<210> SEQ ID NO 1300
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1300
accttaagaa tggaatggta tttcactcta att 33

<210> SEQ ID NO 1301
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1301
acttaacttg agtggggtat ttcactctaa tt 32

<210> SEQ ID NO 1302
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1302
ggctaattta ttacctagct agataaagta cc 32

<210> SEQ ID NO 1303
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1303
accttaagaa tggaatagct agataaagta cc 32

<210> SEQ ID NO 1304
<211> LENGTH: 31
<212> TYPE: DNA

<213> ORGANISM: Artificial Sequence
<220> FEATURE:
<223> OTHER INFORMATION: Decoding Oligonucleotide

<400> SEQUENCE: 1304
acttaacttg agtggagcta gataaagtac c 31

<210> SEQ ID NO 1305
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1305
ggctaattta ttacctccga aactacgatt at 32

<210> SEQ ID NO 1306
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1306
accttaagaa tggaatccga aactacgatt at 32

<210> SEQ ID NO 1307
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1307
acttaacttg agtggccgaa actacgatta t 31

<210> SEQ ID NO 1308
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1308
ggctaattta ttacctcatc gaatttatgt ta 32

<210> SEQ ID NO 1309
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1309
accttaagaa tggaatcatc gaatttatgt ta 32

<210> SEQ ID NO 1310
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1310
acttaacttg agtggcatcg aatttatgtt a 31

<210> SEQ ID NO 1311
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1311
ggctaattta ttacctccgt aattctaccg 30

<210> SEQ ID NO 1312
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1312
accttaagaa tggaatccgt aattctaccg 30

<210> SEQ ID NO 1313
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1313
acttaacttg agtggccgta attctaccg 29

<210> SEQ ID NO 1314
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1314
ggctaattta ttacctgggt aatcgtcac 29

<210> SEQ ID NO 1315
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1315
accttaagaa tggaatgggt aatcgtcac 29

<210> SEQ ID NO 1316
<211> LENGTH: 28
<212> TYPE: DNA
<213> ORGANISM: Artificial Sequence
<220> FEATURE:
<223> OTHER INFORMATION: Decoding Oligonucleotide

<400> SEQUENCE: 1316
acttaacttg agtgggggta atcgtcac 28

<210> SEQ ID NO 1317
<211> LENGTH: 31
<212> TYPE: DNA
<213> ORGANISM: Artificial Sequence
<220> FEATURE:

<223> OTHER INFORMATION: Decoding Oligonucleotide

<400> SEQUENCE: 1317
ggctaattta ttacctagtg ttatgagaag c 31

<210> SEQ ID NO 1318
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1318
accttaagaa tggaatagtg ttatgagaag c 31

<210> SEQ ID NO 1319
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1319
acttaacttg agtggagtgt tatgagaagc 30

<210> SEQ ID NO 1320
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1320
ggctaattta ttacctctgc aatagaagag a 31

<210> SEQ ID NO 1321
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1321
accttaagaa tggaatctgc aatagaagag a 31

<210> SEQ ID NO 1322
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1322
acttaacttg agtggctgca atagaagaga 30

<210> SEQ ID NO 1323
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1323
ggctaattta ttacctgatt tttcagcgac 30

<210> SEQ ID NO 1324
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1324
accttaagaa tggaatgatt tttcagcgac 30

<210> SEQ ID NO 1325
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1325
acttaacttg agtgggattt ttcagcgac 29

<210> SEQ ID NO 1326
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1326
ggctaattta ttacctcgta atatgaagat ca 32

<210> SEQ ID NO 1327
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1327
accttaagaa tggaatcgta atatgaagat ca 32

<210> SEQ ID NO 1328
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1328
acttaacttg agtggcgtaa tatgaagatc a 31

<210> SEQ ID NO 1329
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1329
ggctaattta ttacctgaat tggaatattc gt 32

<210> SEQ ID NO 1330
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1330
accttaagaa tggaatgaat tggaatattc gt 32

<210> SEQ ID NO 1331
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1331
acttaacttg agtgggaatt ggaatattcg t 31

<210> SEQ ID NO 1332
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1332
ggctaattta ttacctggta ttaatcttga aga 33

<210> SEQ ID NO 1333
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1333
accttaagaa tggaatggta ttaatcttga aga 33

<210> SEQ ID NO 1334
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1334
acttaacttg agtggggtat taatcttgaa ga 32

<210> SEQ ID NO 1335
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1335
ggctaattta ttacctacga tgtattgcc 29

<210> SEQ ID NO 1336
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1336
accttaagaa tggaatacga tgtattgcc 29

<210> SEQ ID NO 1337
<211> LENGTH: 28

<212> TYPE: DNA
<213> ORGANISM: Artificial Sequence
<220> FEATURE:
<223> OTHER INFORMATION: Decoding Oligonucleotide

<400> SEQUENCE: 1337
acttaacttg agtggacgat gtattgcc 28

<210> SEQ ID NO 1338
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1338
ggctaattta ttacctcata tacaaacggt ac 32

<210> SEQ ID NO 1339
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1339
accttaagaa tggaatcata tacaaacggt ac 32

<210> SEQ ID NO 1340
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1340
acttaacttg agtggcatat acaaacggta c 31

<210> SEQ ID NO 1341
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1341
ggctaattta ttacctttcc gatcttaact t 31

<210> SEQ ID NO 1342
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1342
accttaagaa tggaatttcc gatcttaact t 31

<210> SEQ ID NO 1343
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1343
acttaacttg agtggttccg atcttaactt 30

<210> SEQ ID NO 1344
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1344
ggctaattta ttacctgtgt taattcgcat c 31

<210> SEQ ID NO 1345
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1345
accttaagaa tggaatgtgt taattcgcat c 31

<210> SEQ ID NO 1346
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1346
acttaacttg agtgggtgtt aattcgcatc 30

<210> SEQ ID NO 1347
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1347
ggctaattta ttacctcgtt taattgggct 30

<210> SEQ ID NO 1348
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1348
accttaagaa tggaatcgtt taattgggct 30

<210> SEQ ID NO 1349
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1349
acttaacttg agtggcgttt aattgggct 29

<210> SEQ ID NO 1350
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1350
ggctaattta ttacctcaac acttataacg g 31

<210> SEQ ID NO 1351
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1351
accttaagaa tggaatcaac acttataacg g 31

<210> SEQ ID NO 1352
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1352
acttaacttg agtggcaaca cttataacgg 30

<210> SEQ ID NO 1353
<211> LENGTH: 34
<212> TYPE: DNA
<213> ORGANISM: Artificial Sequence
<220> FEATURE:
<223> OTHER INFORMATION: Decoding Oligonucleotide

<400> SEQUENCE: 1353
ggctaattta ttacctggaa ataagtatta tacc 34

<210> SEQ ID NO 1354
<211> LENGTH: 34
<212> TYPE: DNA
<213> ORGANISM: Artificial Sequence
<220> FEATURE:
<223> OTHER INFORMATION: Decoding Oligonucleotide

<400> SEQUENCE: 1354
accttaagaa tggaatggaa ataagtatta tacc 34

<210> SEQ ID NO 1355
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1355
acttaacttg agtggggaaa taagtattat acc 33

<210> SEQ ID NO 1356
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1356
ggctaattta ttacctctta acgacggtt 29

<210> SEQ ID NO 1357
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1357
accttaagaa tggaatctta acgacggtt 29

<210> SEQ ID NO 1358
<211> LENGTH: 28
<212> TYPE: DNA
<213> ORGANISM: Artificial Sequence
<220> FEATURE:
<223> OTHER INFORMATION: Decoding Oligonucleotide

<400> SEQUENCE: 1358
acttaacttg agtggcttaa cgacggtt 28

<210> SEQ ID NO 1359
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1359
ggctaattta ttacctgctc gttagaattt att 33

<210> SEQ ID NO 1360
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1360
accttaagaa tggaatgctc gttagaattt att 33

<210> SEQ ID NO 1361
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1361
acttaacttg agtgggctcg ttagaattta tt 32

<210> SEQ ID NO 1362
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1362
ggctaattta ttaccttctt tatcatcatt ga 32

<210> SEQ ID NO 1363
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1363
accttaagaa tggaattctt tatcatcatt ga 32

<210> SEQ ID NO 1364
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1364
acttaacttg agtggtcttt atcatcattg a 31

<210> SEQ ID NO 1365
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1365
ggctaattta ttacctcgtt cgcaatttat c 31

<210> SEQ ID NO 1366
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1366
accttaagaa tggaatcgtt cgcaatttat c 31

<210> SEQ ID NO 1367
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1367
acttaacttg agtggcgttc gcaatttatc 30

<210> SEQ ID NO 1368
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1368
ggctaattta ttacctcgat cttttgttgt a 31

<210> SEQ ID NO 1369
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1369
accttaagaa tggaatcgat cttttgttgt a 31

<210> SEQ ID NO 1370

<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1370
acttaacttg agtggcgatc ttttgttgta 30

<210> SEQ ID NO 1371
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1371
ggctaattta ttacctacca ctcaatataa ga 32

<210> SEQ ID NO 1372
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1372
accttaagaa tggaatacca ctcaatataa ga 32

<210> SEQ ID NO 1373
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1373
acttaacttg agtggaccac tcaatataag a 31

<210> SEQ ID NO 1374
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1374
ggctaattta ttacctccgt aaattcggtc 30

<210> SEQ ID NO 1375
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1375
accttaagaa tggaatccgt aaattcggtc 30

<210> SEQ ID NO 1376
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1376
acttaacttg agtggccgta aattcggtc 29

<210> SEQ ID NO 1377
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1377
ggctaattta ttacctcgtg agatttctga 30

<210> SEQ ID NO 1378
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1378
accttaagaa tggaatcgtg agatttctga 30

<210> SEQ ID NO 1379
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1379
acttaacttg agtggcgtga gatttctga 29

<210> SEQ ID NO 1380
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1380
ggctaattta ttacctcgaa gcatagaata g 31

<210> SEQ ID NO 1381
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1381
accttaagaa tggaatcgaa gcatagaata g 31

<210> SEQ ID NO 1382
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1382
acttaacttg agtggcgaag catagaatag 30

<210> SEQ ID NO 1383
<211> LENGTH: 30
<212> TYPE: DNA

<213> ORGANISM: Artificial Sequence
<220> FEATURE:
<223> OTHER INFORMATION: Decoding Oligonucleotide

<400> SEQUENCE: 1383
ggctaattta ttacctaaaa tacgggagac 30

<210> SEQ ID NO 1384
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1384
accttaagaa tggaataaaa tacgggagac 30

<210> SEQ ID NO 1385
<211> LENGTH: 29
<212> TYPE: DNA
<213> ORGANISM: Artificial Sequence
<220> FEATURE:
<223> OTHER INFORMATION: Decoding Oligonucleotide

<400> SEQUENCE: 1385
acttaacttg agtggaaaat acgggagac 29

<210> SEQ ID NO 1386
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1386
ggctaattta ttacctcgca tggtataaca t 31

<210> SEQ ID NO 1387
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1387
accttaagaa tggaatcgca tggtataaca t 31

<210> SEQ ID NO 1388
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1388
acttaacttg agtggcgcat ggtataacat 30

<210> SEQ ID NO 1389
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1389
ggctaattta ttacctacgc tgatttatag a 31

<210> SEQ ID NO 1390
<211> LENGTH: 31
<212> TYPE: DNA
<213> ORGANISM: Artificial Sequence
<220> FEATURE:
<223> OTHER INFORMATION: Decoding Oligonucleotide

<400> SEQUENCE: 1390
accttaagaa tggaatacgc tgatttatag a 31

<210> SEQ ID NO 1391
<211> LENGTH: 30
<212> TYPE: DNA
<213> ORGANISM: Artificial Sequence
<220> FEATURE:
<223> OTHER INFORMATION: Decoding Oligonucleotide

<400> SEQUENCE: 1391
acttaacttg agtggacgct gatttataga 30

<210> SEQ ID NO 1392
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1392
ggctaattta ttacctcgta gggtaaatag att 33

<210> SEQ ID NO 1393
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1393
accttaagaa tggaatcgta gggtaaatag att 33

<210> SEQ ID NO 1394
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1394
acttaacttg agtggcgtag ggtaaataga tt 32

<210> SEQ ID NO 1395
<211> LENGTH: 33
<212> TYPE: DNA
<213> ORGANISM: Artificial Sequence
<220> FEATURE:
<223> OTHER INFORMATION: Decoding Oligonucleotide

<400> SEQUENCE: 1395
ggctaattta ttacctcatt cacagtaatt tag 33

<210> SEQ ID NO 1396
<211> LENGTH: 33
<212> TYPE: DNA
<213> ORGANISM: Artificial Sequence
<220> FEATURE:

-continued

```
<223> OTHER INFORMATION: Decoding Oligonucleotide

<400> SEQUENCE: 1396

accttaagaa tggaatcatt cacagtaatt tag                                  33


<210> SEQ ID NO 1397
<211> LENGTH: 32
<212> TYPE: DNA
<213> ORGANISM: Artificial Sequence
<220> FEATURE:
<223> OTHER INFORMATION: Decoding Oligonucleotide

<400> SEQUENCE: 1397

acttaacttg agtggcattc acagtaattt ag                                   32


<210> SEQ ID NO 1398
<211> LENGTH: 15
<212> TYPE: DNA
<213> ORGANISM: Artificial Sequence
<220> FEATURE:
<223> OTHER INFORMATION: Signal Oligonucleotide

<400> SEQUENCE: 1398

ccactcaagt taagt                                                      15


<210> SEQ ID NO 1399
<211> LENGTH: 16
<212> TYPE: DNA
<213> ORGANISM: Artificial Sequence
<220> FEATURE:
<223> OTHER INFORMATION: Signal Oligonucleotide

<400> SEQUENCE: 1399

attccattct taaggt                                                     16


<210> SEQ ID NO 1400
<211> LENGTH: 16
<212> TYPE: DNA
<213> ORGANISM: Artificial Sequence
<220> FEATURE:
<223> OTHER INFORMATION: Signal Oligonucleotide

<400> SEQUENCE: 1400

aggtaataaa ttagcc                                                     16
```

MULTIPLEX METHOD FOR DETECTING DIFFERENT ANALYTES IN A SAMPLE

CROSS-REFERENCE TO RELATED APPLICATIONS

This document is a US National Phase entry of PCT Application No PCT/EP2021/066620, filed Jun. 18, 2021, and published Dec. 23, 2021 as PCT Publication No WO2021/255244, and claims priority to PCT Application No PCT/EP2020/067010, filed Jun. 18, 2020, and to U.S. Prov. Ser. No. 63/127,910, filed Dec. 18, 2020, and to U.S. Prov. Ser. No. 63/129,942, filed Dec. 23, 2020, the contents of each of which are hereby incorporated by reference in their entirety.

SEQUENCE LISTING

This document contains a sequence listing in computer readable format entitled Resolve. 014NP sequence listing.txt, created Dec. 23, 2021, having a size of about 275 kb. The computer readable form is hereby incorporated by reference in its entirety.

FIELD OF THE DISCLOSURE

The technology provided herein relates to multiplex methods and kits for detecting different analytes in a sample in parallel by sequential signal-encoding of said analytes, as well as in vitro methods for screening, identifying and/or testing a substance and/or drug and in vitro methods for diagnosis of a disease, and an optical multiplexing system.

BACKGROUND

The analysis and detection of small quantities of analytes in biological and non-biological samples has become a routine practice in the clinical and analytical environment. Numerous analytical methods have been established for this purpose. Some of them use encoding techniques assigning a particular readable code to a specific first analyte which differs from a code assigned to a specific second analyte.

One of the prior art techniques in this field is the so-called 'single molecule fluorescence in situ hybridization' (smFISH) essentially developed to detect mRNA molecules in a sample. In Lubeck et al. (2014), Single-cell in situ RNA profiling by sequential hybridization, Nat. Methods 11(4), p. 360-361, the mRNAs of interest are detected via specific directly labeled probe sets. After one round of hybridization and detection, the set of mRNA specific probes is eluted from the mRNAs and the same set of probes with other (or the same) fluorescent labels is used in the next round of hybridization and imaging to generate gene specific color-code schemes over several rounds. The technology needs several differently tagged probe sets per transcript and needs to denature these probe sets after every detection round.

A further development of this technology does not use directly labeled probe sets. Instead, the oligonucleotides of the probe sets provide nucleic acid sequences that serve as initiator for hybridization chain reactions (HCR), a technology that enables signal amplification; see Shah et al. (2016), In situ transcription profiling of single cells reveals spatial organization of cells in the mouse hippocampus, Neuron 92 (2), p. 342-357.

Another technique referred to as 'multiplexed error robust fluorescence in situ hybridization' (merFISH) is described by Chen et al. (2015), RNA imaging. Spatially resolved, highly multiplexed RNA profiling in single cells, Science 348 (6233): aaa6090. There, the mRNAs of interest are detected via specific probe sets that provide additional sequence elements for the subsequent specific hybridization of fluorescently labeled oligonucleotides. Each probe set provides four different sequence elements out of a total of 16 sequence elements. After hybridization of the specific probe sets to the mRNAs of interest, the so-called readout hybridizations are performed. In each readout hybridization, one out of the 16 fluorescently labeled oligonucleotides complementary to one of the sequence elements is hybridized. All readout oligonucleotides use the same fluorescent color. After imaging, the fluorescent signals are destroyed via illumination and the next round of readout hybridization takes place without a denaturing step. As a result, a binary code is generated for each mRNA species. A unique signal signature of 4 signals in 16 rounds is created using only a single hybridization round for binding of specific probe sets to the mRNAs of interest, followed by 16 rounds of hybridization of readout oligonucleotides labeled by a single fluorescence color.

A further development of this technology improves the throughput by using two different fluorescent colors, eliminating the signals via disulfide cleavage between the readout-oligonucleotides and the fluorescent label and an alternative hybridization buffer; see Moffitt et al. (2016), High-throughput single-cell gene-expression profiling with multiplexed error-robust fluorescence in situ hybridization, Proc. Natl. Acad. Sci. USA. 113 (39), p. 11046-11051.

A technology referred to as 'intron seqFISH' is described in Shah et al. (2018), Dynamics and spatial genomics of the nascent transcriptome by intron seqFISH, Cell 117 (2), p. 363-376. There, the mRNAs of interest are detected via specific probe sets that provide additional sequence elements for the subsequent specific hybridization of fluorescently labeled oligonucleotides. Each probe set provides one out of 12 possible sequence elements (representing the 12 'pseudo colors' used) per color-coding round. Each color-coding round consists of four serial hybridizations. In each of these serial hybridizations, three readout probes, each labeled with a different fluorophore, are hybridized to the corresponding elements of the mRNA-specific probe sets. After imaging, the readout probes are stripped off by a 55% formamide buffer and the next hybridization follows. After 5 color-coding rounds with 4 serial hybridizations each, the color-codes are completed.

EP 0 611 828 discloses the use of a bridging element to recruit a signal generating element to probes that specifically bind to an analyte. A more specific statement describes the detection of nucleic acids via specific probes that recruit a bridging nucleic acid molecule. This bridging nucleic acids eventually recruit signal-generating nucleic acids. This document also describes the use of a bridging element with more than one binding site for the signal generating element for signal amplification like branched DNA.

Player et al. (2001), Single-copy gene detection using branched DNA (bDNA) in situ hybridization, J. Histochem. Cytochem. 49 (5), p. 603-611, describe a method where the nucleic acids of interest are detected via specific probe sets providing an additional sequence element. In a second step, a preamplifier oligonucleotide is hybridized to this sequence element. This preamplifier oligonucleotide comprises multiple binding sites for amplifier oligonucleotides that are hybridized in a subsequent step. These amplifier oligonucleotides provide multiple sequence elements for the labeled oligonucleotides. This way a branched oligonucleotide tree is build up that leads to an amplification of the signal.

A further development of this method referred to as is described by Wang et al. (2012), RNAscope: a novel in situ RNA analysis platform for formalin-fixed, paraffin-embedded tissues, J. Mol. Diagn. 14 (1), p.22-29, which uses another design of the mRNA-specific probes. Here two of the mRNA-specific oligonucleotides have to hybridize in close proximity to provide a sequence that can recruit the preamplifier oligonucleotide. This way the specificity of the method is increased by reducing the number of false positive signals.

Choi et al. (2010), Programmable in situ amplification for multiplexed imaging of mRNA expression, Nat. Biotechnol. 28 (11), p. 1208-1212, disclose a method known as 'HCR-hybridization chain reaction'. The mRNAs of interest are detected via specific probe sets that provide an additional sequence element. The additional sequence element is an initiator sequence to start the hybridization chain reaction. Basically, the hybridization chain reaction is based on metastable oligonucleotide hairpins that self-assemble into polymers after a first hairpin is opened via the initiator sequence.

A further development of the technology uses so called split initiator probes that have to hybridize in close proximity to form the initiator sequence for HCR, similarly to the RNAscope technology, this reduces the number of false positive signals; see Choi et al. (2018), Third-generation in situ hybridization chain reaction: multiplexed, quantitative, sensitive, versatile, robust. Development 145 (12).

Mateo et al. (2019), Visualizing DNA folding and RNA in embryos at single-cell resolution, Nature Vol, 568, p. 49ff., disclose a method called 'optical reconstruction of chromatin structure (ORCA). This method is intended to make the chromosome line visible.

EP 2 992 115 B1 describes a method of sequential single molecule hybridization and provides technologies for detecting and/or quantifying nucleic acids in cells, tissues, organs or organisms through sequential barcoding.

The methods known in the art, however, have numerous disadvantages. In particular, they are inflexible, expensive, complex, time consuming and quite often provide non-accurate results. In particular, the encoding capacities of the existing methods are low and do not meet the requirements of modern molecular biology and medicine.

Against this background, it is an object underlying the present disclosure to provide a method by means of which the disadvantages of the prior art methods can be reduced or even avoided.

SUMMARY OF THE DISCLOSURE

The present disclosure pertains to novel multiplex methods and kits for detecting different analytes in a sample in parallel by sequential signal-encoding of said analytes.

In a first aspect, embodiments of the disclosure in particular to a multiplex method for detecting different analytes in a sample by sequential signal-encoding of said analytes, comprising:

(A) contacting the sample with at least twenty (20) different sets of analyte-specific probes for encoding of at least 20 different analytes, each set of analyte-specific probes interacting with a different analyte, wherein if the analyte is a nucleic acid each set of analyte-specific probes comprises at least five (5) analyte-specific probes which specifically interact with different sub-structures of the same analyte, each analyte-specific probe comprising (aa) a binding element(S) that specifically interacts with one of the different analytes to be encoded, and (bb) an identifier element (T) comprising a nucleotide sequence which is unique to the analyte to be encoded (unique identifier sequence), wherein the analyte-specific probes of a particular set of analyte-specific probes differ from the analyte-specific probes of another set of analyte-specific probes in the nucleotide sequence of the identifier element (T), wherein the analyte-specific probes in each set of analyte-specific probes binds to the same analyte and comprises the same nucleotide sequence of the identifier element (T) which is unique to said analyte; and (B) contacting the sample with at least one set of decoding oligonucleotides per analyte, wherein in each set of decoding oligonucleotides for an individual analyte each decoding oligonucleotide comprises:

(aa) an identifier connector element (t) comprising a nucleotide sequence which is essentially complementary to at least a section of the unique identifier sequence of the identifier element (T) of the corresponding analyte-specific probe set, and (bb) a translator element (c) comprising a nucleotide sequence allowing a specific hybridization of a signal oligonucleotide;

wherein the decoding oligonucleotides of a set for an individual analyte differ from the decoding oligonucleotides of another set for a different analyte in the first connect element (t); and (C) contacting the sample with at least a set of signal oligonucleotides, each signal oligonucleotide comprising:

(aa) a translator connector element (C) comprising a nucleotide sequence which is essentially complementary to at least a section of the nucleotide sequence of a translator element (c) comprised in a decoding oligonucleotide, and (bb) a signal element.

(D) Detecting the signal caused by the signal element;

(E) selectively removing the decoding oligonucleotides and signal oligonucleotides from the sample, thereby essentially maintaining the specific binding of the analyte-specific probes to the analytes to be encoded;

(F) Performing at least three (3) further cycles comprising steps B) to E) to generate an encoding scheme with a code word per analyte, wherein in particular the last cycle may stop with step (D).

In a second aspect, embodiments of this disclosure relate to kits for multiplex analyte encoding, comprising (A) at least twenty (20) different sets of analyte-specific probes for encoding of at least 20 different analytes, each set of analyte-specific probes interacting with a different analyte, wherein if the analyte is a nucleic acid each set of analyte-specific probes comprises at least five (5) analyte-specific probes which specifically interact with different sub-structures of the same analyte, each analyte-specific probe comprising (aa) a binding element(S) that specifically interacts with one of the different analytes to be encoded, and (bb) an identifier element (T) comprising a nucleotide sequence which is unique to the analyte to be encoded (unique identifier sequence), wherein the analyte-specific probes of a particular set of analyte-specific probes differ from the analyte-specific probes of another set of analyte-specific probes in the nucleotide sequence of the identifier element (T), wherein the analyte-specific probes in each set of analyte-specific probes binds to the same analyte and comprises the same nucleotide sequence of the identifier element (T) which is unique to said analyte; and (B) at least one set of decoding oligonucleotides per analyte, wherein in each set of decoding oligonucleotides for an individual analyte each decoding oligonucleotide comprises:

(aa) an identifier connector element (t) comprising a nucleotide sequence which is essentially complementary to at least a section of the unique identifier sequence of the identifier element (T) of the corresponding analyte-specific probe set, and (bb) a translator element (c) comprising a nucleotide sequence allowing a specific hybridization of a signal oligonucleotide;

wherein the decoding oligonucleotides of a set for an individual analyte differ from the decoding oligonucleotides of another set for a different analyte in the identifier connect element (t); and (C) a set of signal oligonucleotides, each signal oligonucleotide comprising:

(aa) a translator connector element (C) comprising a nucleotide sequence which is essentially complementary to at least a section of the nucleotide sequence of a translator element (c) comprised in a decoding oligonucleotide, and (bb) a signal element.

In a third aspect, embodiments of this disclosure relate to in vitro methods for diagnosis of a disease selected from the group comprising cancer, neuronal diseases, cardiovascular diseases, inflammatory diseases, autoimmune diseases, diseases due to a viral or bacterial infection, skin diseases, skeletal muscle diseases, dental diseases and prenatal diseases comprising the use of the multiplex method according to the present disclosure.

In a fourth aspect, embodiments of this disclosure provide in vitro methods for diagnosis of a disease in plants selected from the group comprising: diseases caused by biotic stress, preferably by infectious and/or parasitic origin, or diseases caused by abiotic stress, preferably caused by nutritional deficiencies and/or unfavorable environment, said method comprising the use of the multiplex method according to the present disclosure.

In a fifth aspect, some embodiments of this disclosure relate to optical multiplexing systems suitable for the method according to the present disclosure, comprising at least:

at least one reaction vessel for containing the kits or part of the kits;

a detection unit comprising a microscope, in particular a fluorescence microscope a camera a liquid handling device.

Further, some embodiments pertain to kits for multiplex analyte encoding, comprising (A) optionally at least twenty (20) different sets of analyte-specific probes for encoding of at least 20 different analytes, each set of analyte-specific probes interacting with a different analyte, wherein if the analyte is a nucleic acid each set of analyte-specific probes comprises at least five (5) analyte-specific probes which specifically interact with different sub-structures of the same analyte, each analyte-specific probe comprising (aa) a binding element(S) that specifically interacts with one of the different analytes to be encoded, and (bb) an identifier element (T) comprising a nucleotide sequence which is unique to the analyte to be encoded (unique identifier sequence), wherein the analyte-specific probes of a particular set of analyte-specific probes differ from the analyte-specific probes of another set of analyte-specific probes in the nucleotide sequence of the identifier element (T), wherein the analyte-specific probes in each set of analyte-specific probes binds to the same analyte and comprises the same nucleotide sequence of the identifier element (T) which is unique to said analyte; and (B) at least one set of decoding oligonucleotides per analyte, wherein in each set of decoding oligonucleotides for an individual analyte each decoding oligonucleotide comprises:

(aa) an identifier connector element (t) comprising a nucleotide sequence which is essentially complementary to at least a section of the unique identifier sequence of the identifier element (T) of the corresponding analyte-specific probe set, and (bb) a translator element (c) comprising a nucleotide sequence allowing a specific hybridization of a signal oligonucleotide;

wherein the decoding oligonucleotides of a set for an individual analyte differ from the decoding oligonucleotides of another set for a different analyte in the identifier connect element (t); and (C) a set of signal oligonucleotides, each signal oligonucleotide comprising:

(aa) a translator connector element (C) comprising a nucleotide sequence which is essentially complementary to at least a section of the nucleotide sequence of a translator element (c) comprised in a decoding oligonucleotide, and (bb) a signal element.

In a sixth aspect, some embodiments provide in vitro methods for screening, identifying and/or testing a substance and/or drug comprising:

(a) contacting a test sample comprising a sample with a substance and/or drug (b) detecting different analytes in a sample by sequential signal-encoding of said analytes with a method according to the present disclosure.

According to the present disclosure, unique tags (identifier) are used per target (e.g. mRNA of one single gene) or for a target group. Groups can be formed to be indicative for a certain identity, process, biological function or disease (examples: cell type, inflammation, signal processing, cancer).

Surprisingly, the methods and kits according to the present disclosure lead to the reduction of complexity. Many different probes with different binding sequences share the same (one per target) unique tag. These tags have reduced the sequence complexity (to one per target) and also have predetermined constant properties (e.g. thermodynamic stability).

Advantages of the methods and kits according to the present disclosure are:

a) Full flexibility of the process to determine the identity of the tag, e.g. use more or less signals and/or rounds, varying numbers of fluorophores, number of total signals per tag→lower numbers of targets (e.g. 20) can be identified with high confidence in less rounds (e.g. 4) than a large number of targets (e.g. 100, these need 8 rounds for the same level of confidence), even if in both cases the exact same unique tags are used.

b) All unique tags are used (recycled) in many consecutive rounds of hybridization and all primary probes contribute (provide information about their identity) in every round of identification.

c) As all tags share the same predefined properties (e.g. thermodynamic stability which allows for selective denaturing).

In some advantageous embodiments, the unique tags are design as follow:

No cross-hybridization between all oligonucleotides of the process (probes, decoders, readout), so that all tag sequences are usable together (compatible)

No cross-hybridization between connector elements (bridges) of different unique tags Stability of hybridization of the unique tags should be in a narrow range: as stable as possible (fast hybridization, i.e. short cycle times) but significantly different (in this case less stable) than the primary probe (for differential denaturation, without removing primary probes)

Therefore, the present description pertains in particular to the usage of a set of labeled and unlabeled nucleic acid sequences for specific quantitative and/or spatial detection of different analytes in parallel via specific hybridization. The technology allows the discrimination of more different analytes than different detection signals are available. The discrimination is realized via sequential signal-coding of the analytes achieved by several cycles of specific hybridization, detection of signals and selective elution of the hybridized nucleic acid sequences. In contrast to other state-of-the-art methods, the oligonucleotides providing the detectable signal are not directly interacting with sample-specific nucleic acid sequences but are mediated by so called “decoding-oligonucleotides”. This mechanism decouples the dependency between the analyte-specific oligonucleotides and the signal oligonucleotides. The use of decoding-oligonucleotides allows a much higher flexibility while dramatically decreasing the number of different signal oligonucleotides needed which in turn increases the coding capacity achieved with a certain number of detection rounds. The utilization of decoding-oligonucleotides leads to a sequential signal-coding technology that is e.g. more flexible, cheaper, simpler, faster and/or more accurate than other methods.

Furthermore, the present disclosure pertains to the use of improved decoding-oligonucleotides to increase the efficiency of the encoding scheme. The so called “multi-decoders” allows the recruiting of more than just one signal oligonucleotide and therefore can generate new signal types by utilizing the combination of two or more different signal-oligonucleotides without decreasing the brightness of the signals.

Before the disclosure is described in detail, it is to be understood that this disclosure is not limited to the particular component parts of the steps of the methods described. It is also to be understood that the terminology used herein is for purposes of describing particular embodiments only, and is not intended to be limiting. It must be noted that, as used in the specification and the appended claims, the singular forms “a,” “an” and “the” include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

1) With detectable label F: detectable during imaging
2) With detectable label F and quencher Q: not detectable during imaging
3) With quencher Q: not detectable during imaging
4) Without label F: not detectable during imaging
5) Without signaling oligonucleotide: not detectable during imaging
6) With a decoder oligonucleotide that cannot recruit a signaling oligonucleotide
7) Without decoder oligonucleotide: not detectable during imaging

DETAILED DESCRIPTION OF THE DISCLOSURE

Figure 1:
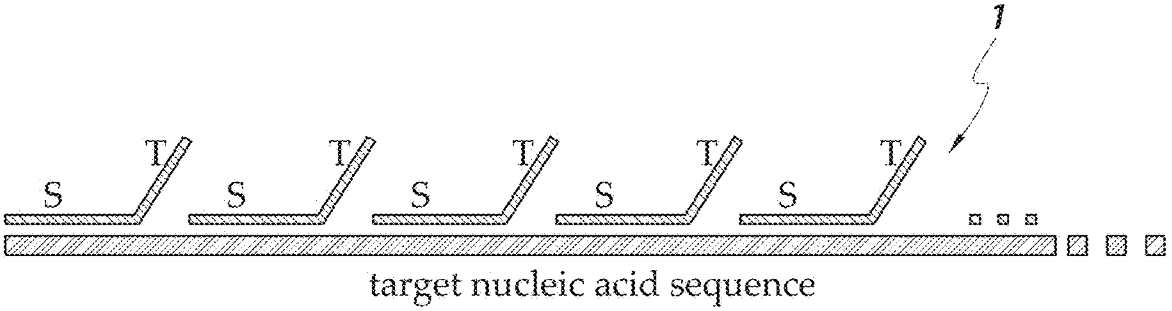
FIG. 1: Embodiment where the analyte is a nucleic acid and the probe set comprises oligonucleotides specifically binding to the analyte. The probes comprise a unique identifier sequence allowing hybridization of decoding oligonucleotides.

Disclosed herein are novel multiplex methods and kits for detecting different analytes in a sample by sequential signal-encoding of said analytes.

The present disclosure describes the usage of a set of labeled and unlabeled nucleic acid sequences for specific quantitative and/or spatial detection of different analytes in parallel via specific hybridization. The technology allows the discrimination of more different analytes than different detection signals are available. The discrimination may be realized via sequential signal-coding of the analytes achieved by several cycles of specific hybridization, detection of signals and selective elution of the hybridized nucleic acid sequences.

In contrast to other state-of-the-art methods, the oligonucleotides providing the detectable signal are not directly interacting with sample-specific nucleic acid sequences but are mediated by so called "decoding-oligonucleotides". This mechanism decouples the dependency between the analyte-specific oligonucleotides and the signal oligonucleotides. The use of decoding-oligonucleotides allows a much higher flexibility while dramatically decreasing the number of different signal oligonucleotides needed which in turn increases the coding capacity achieved with a certain number of detection rounds.

The utilization of decoding-oligonucleotides leads to a sequential signal-coding technology that is more flexible, cheaper, simpler, faster and/or more accurate than other methods.

A. Definitions

According to the present disclosure an "analyte" is the subject to be specifically detected as being present or absent in a sample and, in case of its presence, to encode it. It can be any kind of entity, including a protein, polypeptide, protein or a nucleic acid molecule (e.g. RNA, PNA or DNA) of interest. The analyte provides at least one site for specific binding with analyte-specific probes. Sometimes herein the term "analyte" is replaced by "target". An "analyte" according to the disclosure incudes a complex of subjects, e.g. at least two individual nucleic acid, protein or peptides molecules. In an embodiment of the disclosure an "analyte" excludes a chromosome. In another embodiment of the disclosure an "analyte" excludes DNA.

In some embodiments, an analyte may be a "coding sequence", "encoding sequence", "structural nucleotide sequence" or "structural nucleic acid molecule" which refers to a nucleotide sequence that is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, EST and recombinant nucleotide sequences.

A "sample" as referred to herein is a composition in liquid or solid form suspected of comprising the analytes to be encoded. In particular, the sample is a biological sample, preferably comprising biological tissue, further preferably comprising biological cells and/or extracts and/or part of cells. For example, the cell is a prokaryotic cells or a eukaryotic cell, in particular a mammalian cell, in particular a human cell. In some embodiments, the biological tissue, biological cells, extracts and/or part of cells are fixed. In particular, the analytes are fixed in a permeabilized sample, such as a cell-containing sample.

As used in the present disclosure, "cell", "cell line", and "cell culture" can be used interchangeably and all such designations include progeny. Thus, the words "transformants" or "transformed cells" include the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

An "encoding scheme" may describe a set of code words that are associated with the analytes to be detected. Each code word refers to one of the analytes and can be distinguished from all other code words. A code word hereby is a sequence of signs provided by the detection cycles of the method. A sign within a code word is a detectable signal or the absence of a signal. A code word does not need to comprise of all different signals used in the method. The number of signs in a code word is defined by the number of detection cycles.

An "oligonucleotide" as used herein, refers to s short nucleic acid molecule, such as DNA, PNA, LNA or RNA. The length of the oligonucleotides is within the range 4-200 nucleotides (nt), preferably 6-80 nt, more preferably 8-60 nt, more preferably 10-50 nt, more preferably 12 to 35 depending on the number of consecutive sequence elements. The nucleic acid molecule can be fully or partially single-stranded. The oligonucleotides may be linear or may comprise hairpin or loop structures. The oligonucleotides may comprise modifications such as biotin, labeling moieties, blocking moieties, or other modifications.

The "analyte-specific probe" consists of at least two elements, namely the so-called binding element(S) which specifically interacts with one of the analytes, and a so-called identifier element (T) comprising the 'unique identifier sequence'. The binding element(S) may be a nucleic acid such as a hybridization sequence or an aptamer, or a peptidic structure such as an antibody.

Also a "probe" consists of at least two elements, namely the so-called binding element(S) which specifically interacts with one of the analytes, and a so-called identifier element (T) comprising the 'unique identifier sequence'. The binding element(S) may be a nucleic acid such as a hybridization sequence or an aptamer, or a peptidic structure such as an antibody.

In particular, in some embodiments the binding element (S) comprises moieties which are affinity moieties from affinity substances or affinity substances in their entirety selected from the group consisting of antibodies, antibody fragments, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and their derivatives, mutants or combinations thereof. In further advantageous embodiments, the antibody fragment is a Fab, an scFv; a single domain, or a fragment thereof, a bis scFv, Fab2, Fab3, minibody, maxibody, diabody, triabody, tetrabody or tandab, in particular a single-chain variable fragment (scFv).

The "unique identifier sequence" as comprised by the analyte-specific probe is unique in its sequence compared to other unique identifiers. "Unique" in this context means that it specifically identifies only one analyte, such as Cyclin A, Cyclin D, Cyclin E etc., or, alternatively, it specifically identifies only a group of ana-lytes, independently whether the group of analytes comprises a gene family or not. Therefore, the analyte or a group of analytes to be encoded by this unique identifier can be distinguished from all other analytes or groups of analytes that are to be encoded based on the unique identifier sequence of the identifier element (T). Or, in other words, there is only one 'unique identifier sequence' for a particular analyte or a group of analytes, but not more than one, i.e. not even two. Due to the uniqueness of the unique identifier sequence the identifier element (T) hybridizes to exactly one type of decoding oligonucleotides. The length of the unique identifier sequence is within the range 8-60 nt, preferably 12-40 nt, more preferably 14-20 nt, depending on the number of analytes encoded in parallel and the stability of interaction needed. A unique identifier may be a sequence element of the analyte-specific probe, attached directly or by a linker, a covalent bond or high affinity binding modes, e.g. antibody-antigen interaction, streptavidin-biotin interaction etc. It is understood that the term "analyte specific probe" includes a plurality of probes which may differ in their binding elements(S) in a way that each probe binds to the same analyte but possibly to different parts thereof, for instance to different (e.g. neighboring) or overlapping sections of the nucleotide sequence comprised by the nucleic acid molecule to be encoded-ed. However, each of the plurality of the probes comprises the same identifier element (T).

A "bipartite labeling probe" comprises a binding sequence capable of hybridizing the analyte and a binding probe sequence capable of binding a detectable signal molecule like a fluorophore or a nucleic acid sequence comprising a fluorophore.

A "decoding oligonucleotide" or an "adapter" or a/adapter segment" consists of at least two sequence elements. One sequence element that can specifically bind to a unique identifier sequence, referred to as an "identifier connector element "(t) or "first connector element" (t), and a second sequence element specifically binding to a signal oligonucleotide, referred to as "translator element" (c). The length of the sequence elements is within the range 8-60 nt, preferably 12-40 nt, more preferably 14-20 nt, de-pending on the number of analytes to be encoded in parallel, the stability of interaction needed and the number of different signal oligonucleotides used. The length of the two sequence elements may or may not be the same.

In some advantageous embodiments, the decoding oligonucleotide in the kits and/or methods of the present disclosure may be a "multi-decoder". A "multi-decoder" is a decoding oligonucleotide that consists of at least three sequence elements. One sequence element (the identifier connector element (t)) can specifically bind to a unique identifier sequence (identifier element (T)) and at least two other sequence elements (translator elements (c)) specifically bind different signal oligonucleotides (each of these sequence elements specifically binds a signal oligonucleotide that differs to all other signal oligonucleotides recruited by other elements of the multi-decoder). The length of the sequence elements is within the range 8-60 nt, preferably 12-40 nt, more preferably 14-20 nt, depending on the number of analytes detected in parallel, the stability needed and the number of different signal oligonucleotides used. The length of the sequence elements may or may not be the same.

Therefore, in some advantageous embodiments, the decoding oligonucleotide is a multi-decoder comprising

- an identifier connector element (t) comprising a nucleotide sequence which is essentially complementary to at least a section of the unique identifier sequence of the identifier element (T) of the corresponding analyte-specific probe set, and
- at least two translator elements (c) comprising each a nucleotide sequence allowing a specific hybridization of a different signal oligonucleotide.

Therefore, the first translator element binds a different signal oligonucleotide as the second translator element. In particular, the signal oligonucleotides differ in the signal element comprised in the signal oligonucleotide, e.g. in the kind of the fluorophore.

A "signal oligonucleotide" or a "reporter" as used herein comprises at least two elements, a so-called "translator connector element" (C) or "second connector element" (C) having a nucleotide sequence specifically hybridizable to at least a section of the nucleotide sequence of the translator element (c) of the decoding oligonucleotide, and a "signal element" which provides a detectable signal. This element can either actively generate a detectable signal or provide such a signal via manipulation, e.g. fluorescent excitation. Typical signal elements are, for example, enzymes that catalyze a detectable reaction, fluorophores, radioactive elements or dyes.

A "set" refers to a plurality of moieties or subjects, e.g. analyte-specific probes or decoding oligonucleotides, whether the individual members of said plurality are identical or different from each other. In an analyte specific probe set, the analyte specific probes are identical in the identifier element (T) but may comprise a different binding element(S) for specifically interacting with the same analyte but for specifically interacting with different sub-structures of the same analyte to be encoded.

"Selective denaturation" may be the process of eliminating bound decoding oligonucleotides and signal oligonucleotides with highest efficiency while at the same time the target specific probes have to stay hybridized with the highest efficiency. The total efficiency of these two combined events may to be at least 0.22 for two detection cycles, 0.37 for three detection cycles, 0.47 for four detection cycles, 0.55 for five detection cycles, 0.61 for six detection cycles, 0.65 for seven detection cycles, 0.69 for eight detection cycles, 0.72 for nine detection cycles and 0.74 for 10 detection cycles, 0.76 for 11 detection cycles and 0.78 for 12 detection cycles.

In an embodiment of the disclosure a single set refers to a plurality of oligonucleotides.

An "analyte specific probe set" refers to a plurality of moieties or sub-jects, e.g. analyte-specific probes that are different from each other and bind to independent regions of the analyte. A single analyte specific probe set is further characterized by the same unique identifier.

A "decoding oligonucleotide set" refers to a plurality of decoding oligonucleotides specific for a certain unique identifier needed to realize the encoding independent of the length of the code word. Each and all of the decoding oligonucleotides included in a "decoding oligonucleotide set" bind to the same unique identifier element (T) of the analyte-specific probe.

Figure 13:
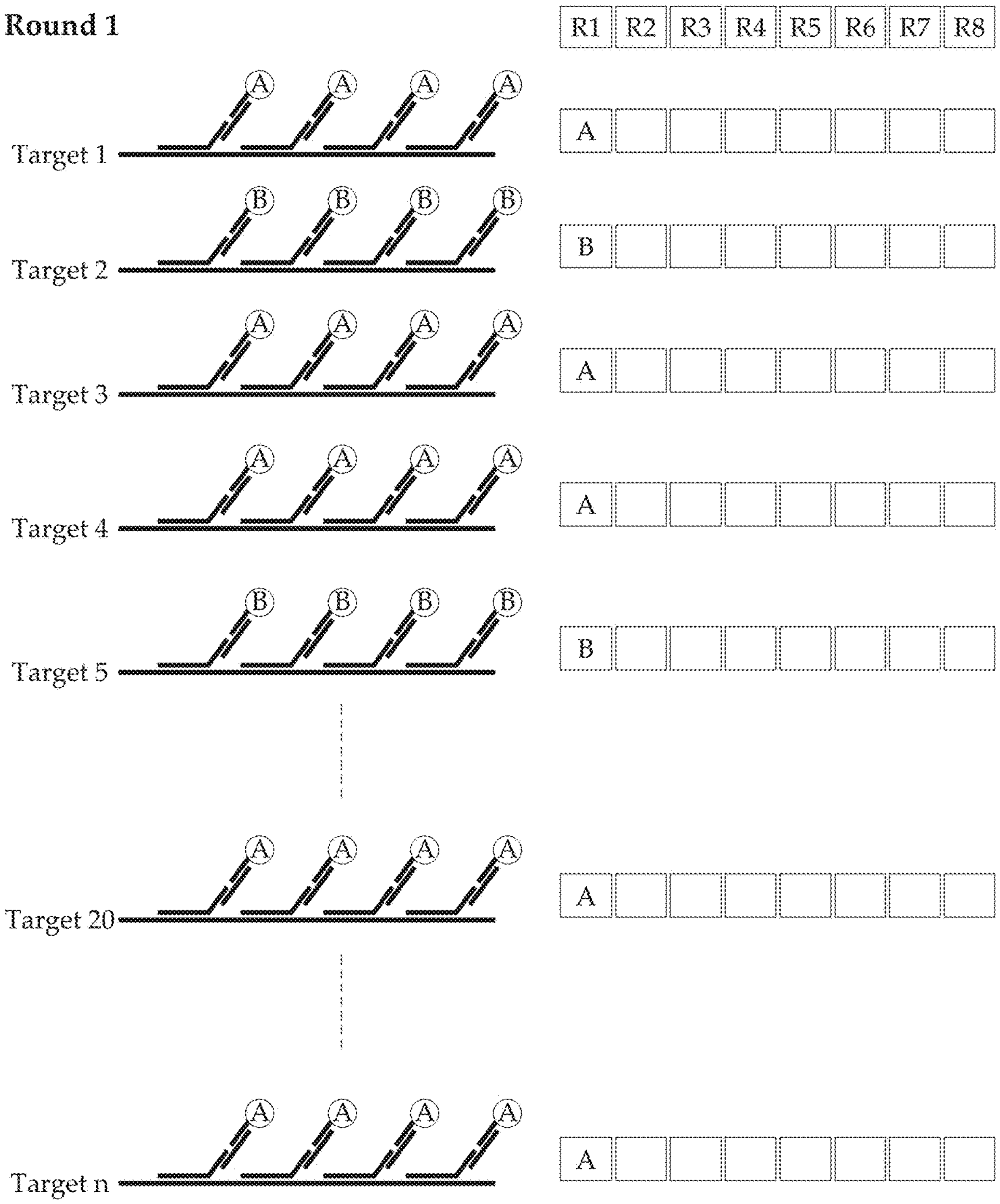
FIG. 13: Detection of multiple targets using a 8 round code with 2 labels (A and B) and no label (-). The targets 1, 2, 3, 4, 5, 20, and n are represented. The rounds 1, 2, 3, and 8 of the coding scheme are represented. Herein, the blank is part of the code.
Figure 13:
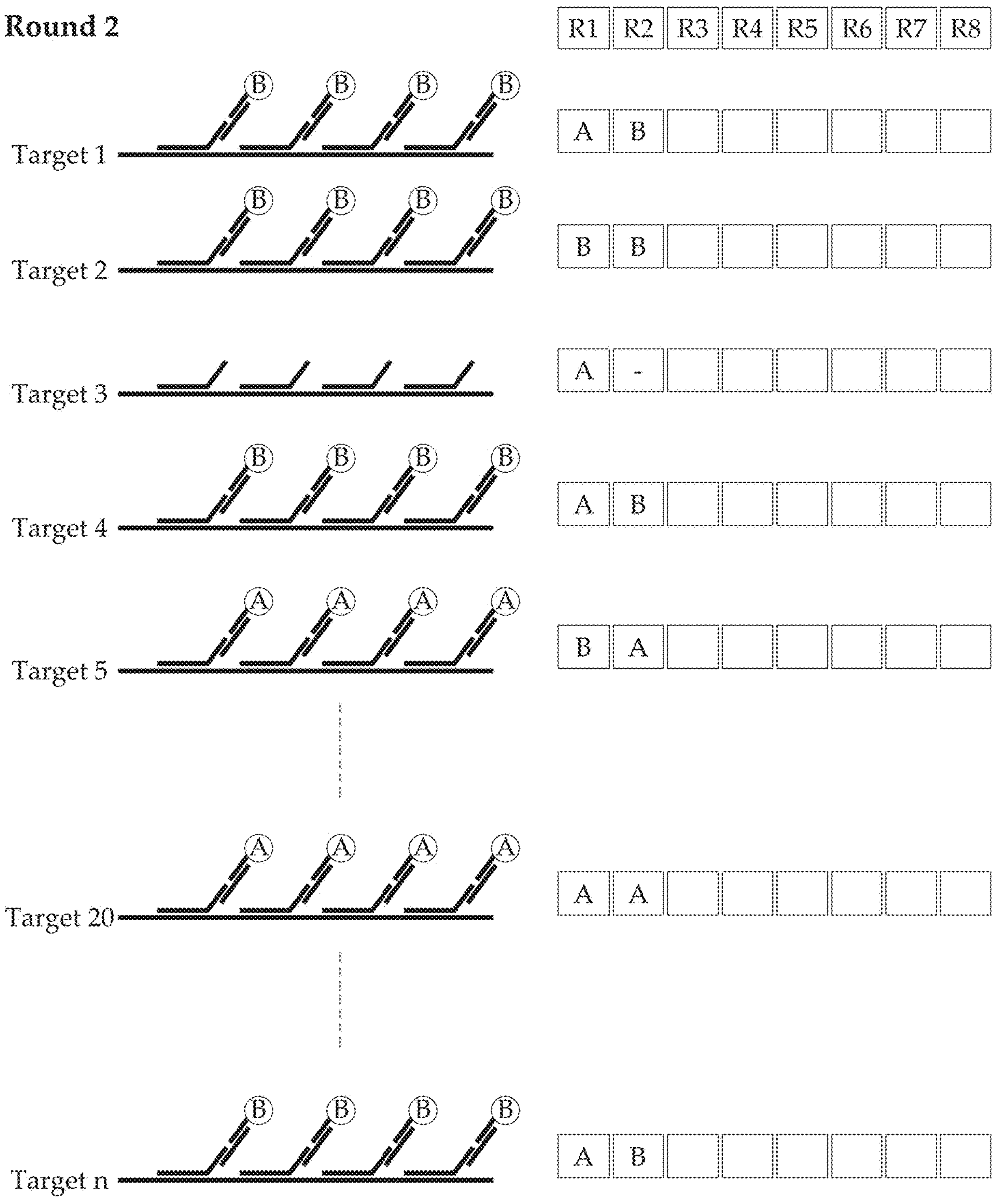
Figure 13:
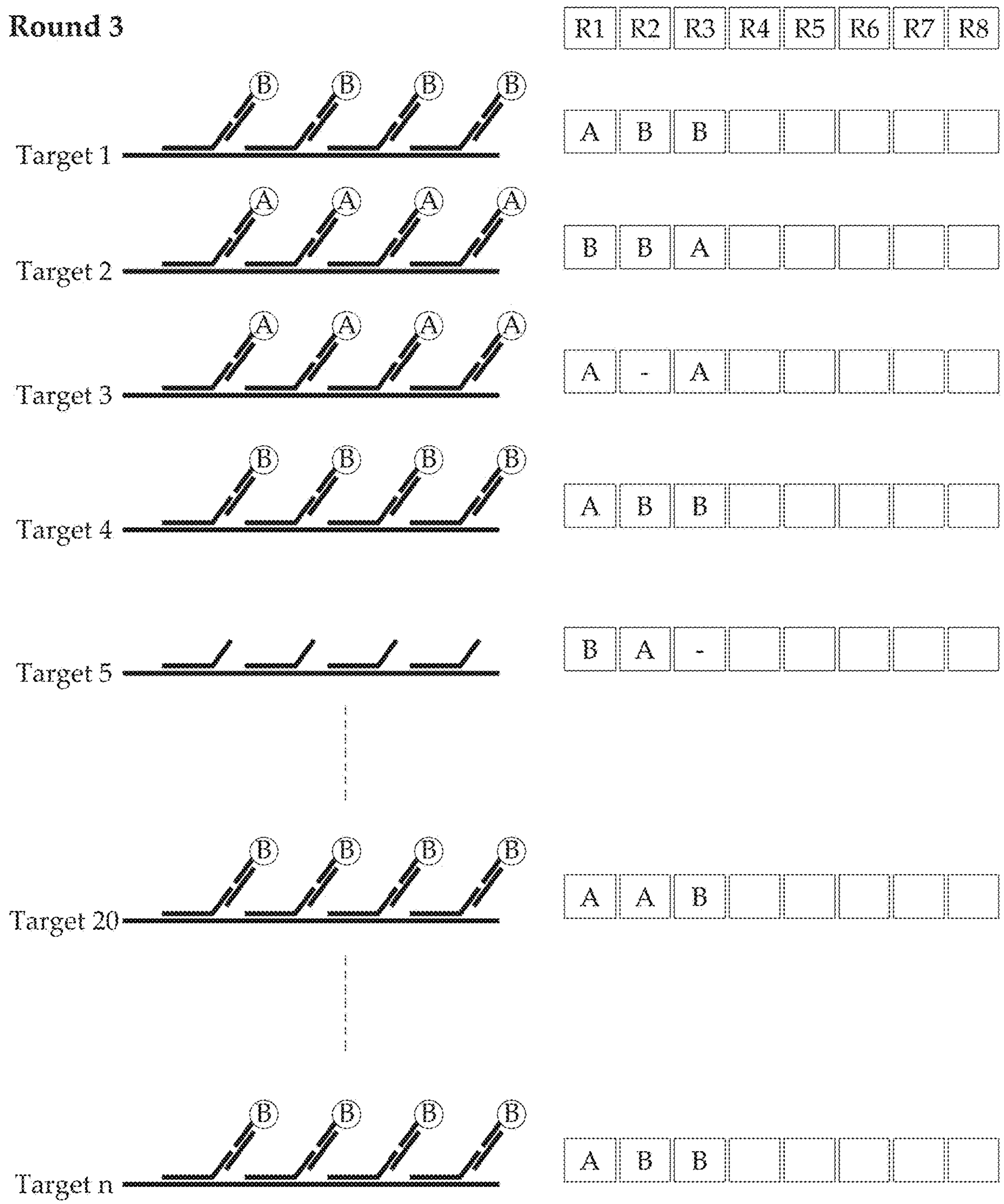
Figure 13:
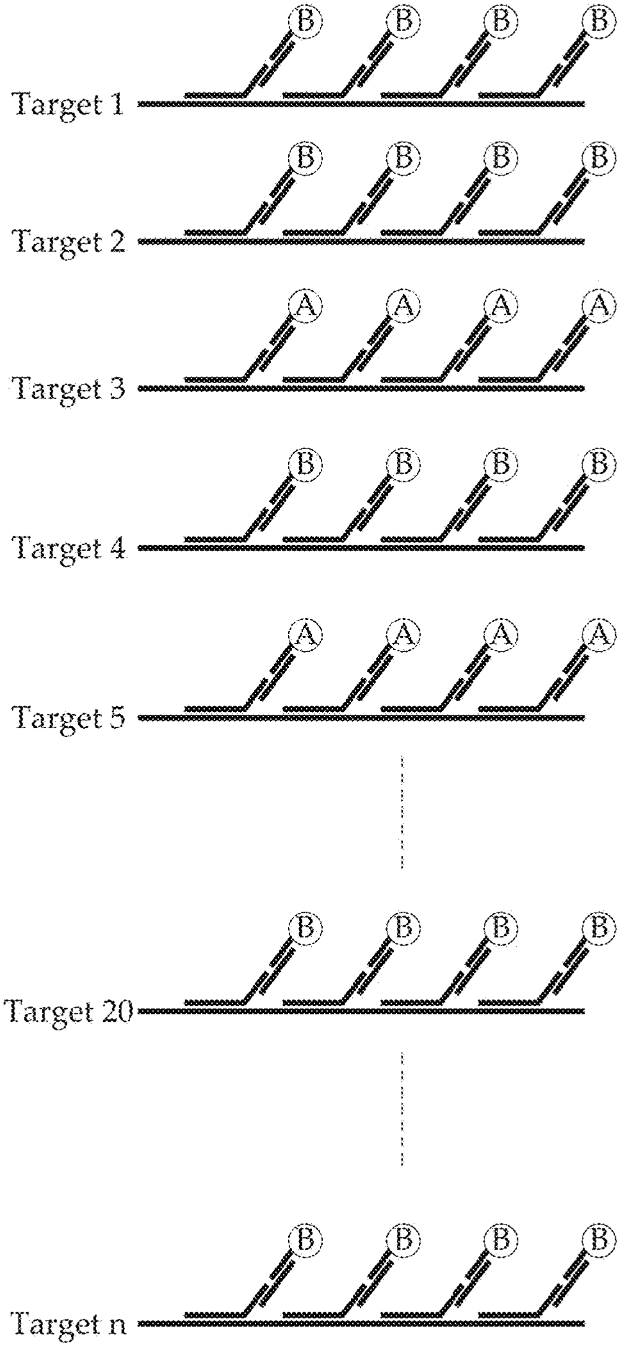

In certain embodiments, this pattern of binding or hybridization of the decoding oligonucleotides may be converted into a "code word." For example, the code words could be also "101" and "110" for an analyte, where a value of 1 represents binding and a value of 0 represents no binding. The code words may also have longer lengths in other embodiments (see FIG. 13). A code word can be directly related to a specific unique identifier sequence of a analyte-specific probe. Accordingly, different analyte-specific probe may match certain code words, which can then be used to identify the different analytes of the analyte-specific probe based on the binding patterns of the decoding oligonucleotide. However, if no binding is evident, then the code word would be "000" in this example.

The values in each code word can also be assigned in different fashions in some embodiments. For example, a value of 0 could represent binding while a value of 1 represents no binding. Similarly, a value of 1 could represent binding of a secondary nucleic acid probe with one type of signaling entity while a value of 0 could represent binding of a secondary nucleic acid probe with another type of distinguishable signaling entity. These signaling entities could be distinguished, for example, via different colors of fluorescence. In some cases, values in code words need not be confined to 0 and 1. The values could also be drawn from larger alphabets, such as ternary (e.g., 0, 1, and 2) or quaternary (e.g., 0, 1, 2, and 3) systems. Each different value could, for example, be represented by a different distinguishable signaling entity, including (in some cases) one value that may be represented by the absence of signal.

The code words for each analyte may be assigned sequentially, or may be assigned at random. For instance, a first analyte may be assigned to 101, while a second nucleic acid target may be assigned to 110. In addition, in some embodiments, the code words may be assigned using an error-detection system or an error-correcting system, such as a Hamming system, a Golay code, or an extended Hamming system (or a SECDED system, i.e., single error correction, double error detection). Generally speaking, such systems can be used to identify where errors have occurred, and in some cases, such systems can also be used to correct the errors and determine what the correct code word should have been. For example, a code word such as 001 may be detected as invalid and corrected using such a system to 101, e.g., if 001 is not previously assigned to a different target sequence. A variety of different error-correcting codes can be used, many of which have previously been developed for use within the computer industry; however, such error-correcting systems have not typically been used within biological systems. Additional examples of such error-correcting codes are discussed in more detail below.

"Essentially complementary" means, when referring to two nucleotide sequences, that both sequences can specifically hybridize to each other under stringent conditions, thereby forming a hybrid nucleic acid molecule with a sense and an antisense strand connected to each other via hydrogen bonds (Watson-and-Crick base pairs). "Essentially complementary" includes not only perfect base-pairing along the entire strands, i.e. perfect complementary sequences but also imperfect complementary sequences which, however, still have the capability to hybridize to each other under stringent conditions. Among experts it is well accepted that an "essentially complementary" sequence has at least 88% sequence identity to a fully or perfectly complementary sequence.

"Percent sequence identity" or "percent identity" in turn means that a sequence is compared to a claimed or described sequence after alignment of the sequence to be compared (the "Compared Sequence") with the described or claimed sequence (the "Reference Sequence"). The percent identity is then determined according to the following formula: percent identity=100 [1−(C/R)] wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

In the "incubation" steps as understood herein the respective moieties or subjects such as probes or oligonucleotide, are brought into contact with each other under conditions well known to the skilled person allowing a specific binding or hybridization reaction, e.g. pH, temperature, salt conditions etc.

Such steps may therefore, be preferably carried out in a liquid environment such as a buffer system which is well known in the art.

The "removing" steps according to the disclosure may include the washing away of the moieties or subjects to be removed such as the probes or oligonucleotides by certain conditions, e.g. pH, temperature, salt conditions etc., as known in the art.

It is understood that in an embodiment of the method according to the present disclosure a plurality of analytes can be encoded in parallel. This requires the use of different sets of analyte-specific probes in step (1). The analyte-specific probes of a particular set differ from the analyte-specific probes of another set. This means that the analyte-specific probes of set 1 bind to analyte 1, the analyte-specific probes of set 2 bind to analyte 2, the analyte-specific probes of set 3 bind to analyte 3, etc. In this embodiment also the use of different sets of decoding oligonucleotides is required in the methods according to the present disclosure.

The decoding oligonucleotides of a particular set differ from the decoding oligonucleotides of another set. This means, the decoding oligonucleotides of set 1 bind to the analyte-specific probes of above set 1 of analyte-specific probes, the decoding oligonucleotides of set 2 bind to the analyte-specific probes of above set 2 of analyte-specific probes, the decoding oligonucleotides of set 3 bind to the analyte-specific probes of above set 3 of analyte-specific probes, etc.

In this embodiment where a plurality of analytes is to be encoded in parallel the different sets of analyte-specific probes may be provided as a premixture of different sets of analyte-specific probes and/or the different sets of decoding oligonucleotides may be provided as a premixture of different sets of decoding oligonucleotides. Each mixture may be contained in a single vial. Alternatively, the different sets of analyte-specific probes and/or the different sets of decoding oligonucleotides may be provided in steps singularly.

A "kit" is a combination of individual elements useful for carrying out the use and/or method of the disclosure, wherein the elements are optimized for use together in the methods. The kits may also contain additional reagents, chemicals, buffers, reaction vials etc. which may be useful for carrying out the method according to the disclosure. Such kits unify all essential elements required to work the method according to the disclosure, thus minimizing the risk of errors. Therefore, such kits also allow semi-skilled laboratory staff to perform the method according to the present disclosure.

The term "quencher" or "quencher dye" or "quencher molecule" refers to a dye or an equivalent molecule, such as nucleoside guanosine (G) or 2'-deoxyguanosine (dG), which is capable of reducing the fluorescence of a fluorescent reporter dye or donor dye. A quencher dye may be a fluorescent dye or non-fluorescent dye. When the quencher is a fluorescent dye, its fluorescence wavelength is typically substantially different from that of the reporter dye and the quencher fluorescence is usually not monitored during an assay. Some embodiments of the present disclosure disclose signal oligonucleotides comprising a quencher and/or a quencher in combination with a signal element (see FIG. 14), and therefore the signal oligonucleotides is not detectable during imaging.

In an embodiment of the disclosure the sample is a biological sample, preferably comprising biological tissue, further preferably comprising biological cells. A biological sample may be derived from an organ, organoids, cell cultures, stem cells, cell suspensions, primary cells, samples infected by viruses, bacteria or fungi, eukaryotic or prokaryotic samples, smears, disease samples, a tissue section.

The method is particularly qualified to encode, identify, detect, count or quantify analytes or single analytes molecules in a biological sample, i.e. such as a sample which contains nucleic acids or proteins as said analytes. It is understood that the biological sample may be in a form as it is in its natural environment (i.e. liquid, semi-liquid, solid etc.), or processed, e.g. as a dried film on the surface of a device which may be re-liquefied before the method is carried out.

In another embodiment of the disclosure prior to step (2) the biological tissue and/or biological cells are fixed. For example, in some embodiments, the cell and/or the tissue is fixed prior to introducing the probes, e.g., to preserve the positions of the analytes like nucleic acids within the cell. Techniques for fixing cells are known to those of ordinary skill in the art. As non-limiting examples, a cell may be fixed using chemicals such as formaldehyde, paraformaldehyde, glutaraldehyde, ethanol, methanol, acetone, acetic acid, or the like. In one embodiment, a cell may be fixed using Hepes-glutamic acid buffer-mediated organic solvent (HOPE).

This measure has the advantage that the analytes to be encoded, e.g. the nuclei acids or proteins, are immobilized and cannot escape. In doing so, the analytes then prepared for a better detection or encoding by the method according to the disclosure.

In yet a further embodiment within the set of analyte-specific probes the individual analyte-specific probes comprise binding elements (S1, S2, S3, S4, S5) which specifically interact with different sub-structures of one of the analytes to be encoded.

By this measure the method becomes even more robust and reliable because the signal intensity obtained at the end of the method or a cycle, respectively, is increased. It is understood, that the individual probes of a set while binding to the same analyte differ in their binding position or binding site at or on the analyte. The binding elements S1, S2, S3, S4, S5 etc. of the first, second, third fourth, fifth etc. analyte-specific probes therefore bind to or at a different position which, however, may or may not overlap.

In an advantageous embodiment, the present disclosure pertains to kit for multiplex analyte encoding, comprising:

(A) at least twenty (20) different sets of analyte-specific probes for encoding of at least 20 different analytes, each set of analyte-specific probes interacting with a different analyte, wherein if the analyte is a nucleic acid each set of analyte-specific probes comprises at least five (5) analyte-specific probes which specifically interact with different sub-structures of the same analyte, each analyte-specific probe comprising (aa) a binding element(S) that specifically interacts with one of the different analytes to be encoded, and (bb) an identifier element (T) comprising a nucleotide sequence which is unique to the analyte to be encoded (unique identifier sequence), wherein the analyte-specific probes of a particular set of analyte-specific probes differ from the analyte-specific probes of another set of analyte-specific probes in the nucleotide sequence of the identifier element (T), wherein the analyte-specific probes in each set of analyte-specific probes binds to the same analyte and comprises the same nucleotide sequence of the identifier element (T) which is unique to said analyte; and (B) at least one set of decoding oligonucleotides per analyte, wherein in each set of decoding oligonucleotides for an individual analyte each decoding oligonucleotide comprises:

(aa) an identifier connector element (t) comprising a nucleotide sequence which is essentially complementary to at least a section of the unique identifier sequence of the identifier element (T) of the corresponding analyte-specific probe set, and (bb) a translator element (c) comprising a nucleotide sequence allowing a specific hybridization of a signal oligonucleotide;

wherein the decoding oligonucleotides of a set for an individual analyte differ from the decoding oligonucleotides of another set for a different analyte in the identifier connect element (t); and (C) a set of signal oligonucleotides, each signal oligonucleotide comprising:

(aa) a translator connector element (C) comprising a nucleotide sequence which is essentially complementary to at least a section of the nucleotide sequence of a translator element (c) comprised in a decoding oligonucleotide, and (bb) a signal element.

A multiplex method or assay allow the simultaneously measurement of multiple analytes According to the present disclosure it may be used to determine the presence or absence of a plurality of predetermined (known) analytes like nucleic acid target sequences in a sample. A analyte may be "predetermined" in that its sequence is known to design a probe that binds to the that target.

In some advantageous embodiments according to the present disclosure at least 20, in particular at least 25, in particular at least 30 different analytes are detected and/or quantified in a sample in parallel. For example, there may be at least 5, at least 10, at least 20, at least 50, at least 75, at least 100, at least 300, at least 1,000, at least 3,000, at least 10,000, or at least 30,000 distinguishable analyte-specific probes that are applied to a sample, e.g., simultaneously or sequentially.

In some advantageous embodiments for the multiplexing twenty (20) or more different sets of analyte-specific probes for encoding of at least 20 different analytes or more are required, in particular more than 50, more than 100 or more than 200. In the multiplexing methods of the present disclosure, in particular at least 20 different groups of analytes (e.g. mRNA molecules) i.e. tags are targeted.

In some advantageous embodiments, at least 4 rounds to collect information for identification of the analyte are carried out, wherein multiple readout increases the accuracy of identification and avoids false positives. The unique tag can be identified by various techniques, including hybridization, e.g. with labeled probes, directly or indirectly or by sequencing (by synthesis, ligation). In particular, the identity of the tag can be encoded with one single signal (binary code), two or more signals, wherein the signal can be a fluorescent label (e.g. attached to an oligonucleotide).

In some advantageous embodiments according to the present disclosure, the kit does not comprise sets of analyte-specific probes as defined under item A).

Preferably, if the analyte in the kits or methods according to the present disclosure is a nucleic acid, each set of analyte-specific probes comprises at least five (10) analyte-specific probes, in particular at least fifteen (15) analyte-specific probes, in particular at least twenty (20) analyte-specific probes which specifically interact with different sub-structures of the same analyte. Nucleic acid analyte includes specific DNA molecules, e.g. genomic DNA, nuclear DNA, mitochondrial DNA, viral DNA, bacterial DNA, extra- or intracellular DNA etc., and specific mRNA molecules, e.g. hnRNA, miRNA, viral RNA, bacterial RNA, extra- or intracellular RNA, etc.

Preferably, if the analyte in the kits or methods according to the present disclosure is a peptide, a polypeptide or a protein, each set of analyte-specific probes comprises at least two (2) analyte-specific probes, in particular at least three (3) analyte-specific probes, in particular at least four (4) analyte-specific probes which specifically interact with different sub-structures of the same analyte.

In some advantageous embodiments according to the present disclosure the kit comprises at least two different sets of signal oligonucleotides, wherein the signal oligonucleotides in each set comprise a different signal element and comprise a different connector element (C).

In particular, the kit may comprise at least two different sets of decoding oligonucleotides per analyte, wherein the decoding oligonucleotides comprised in these different sets comprise the same identifier connector element (t) comprising a nucleotide sequence which is essentially complementary to at least a section of the unique identifier sequence of the identifier element (T) of the corresponding analyte-specific probe set, and wherein the decoding oligonucleotides of the different sets per analyte differ in the translator element (c) comprising a nucleotide sequence allowing a specific hybridization of a signal oligonucleotide.

In some embodiments the kit comprises at least two different sets of decoding oligonucleotides per analyte, wherein the decoding oligonucleotides comprised in these different sets comprise the same identifier connector element (t) comprising a nucleotide sequence which is essentially complementary to at least a section of the unique identifier sequence of the identifier element (T) of the corresponding analyte-specific probe set, and wherein the decoding oligonucleotides of the different sets for at least one analyte differ in the translator element (c) comprising a nucleotide sequence allowing a specific hybridization of a signal oligonucleotide.

In some advantageous embodiments, the number of different sets of decoding oligonucleotides per analyte comprising different translator elements (c) corresponds to the number of different sets of signal oligonucleotides comprising different connector elements (C). However, the decoding oligonucleotides in a particular set of decoding oligonucleotides may interacts with identical identifier elements (T) which are unique to a particular analyte. In particular, all sets of decoding oligonucleotides for the different analytes may comprise the same type(s) of translator element(s) (c).

In another aspect, the present disclosure is generally directed to a methods including acts of exposing a sample to a plurality of analyte-specific probes; for each of the analyte-specific probes, determining binding of the analyte-specific probes within the sample; creating code words based on the binding of the analyte-specific probes, the decoding oligonucleotides and the signal oligonucleotides; and for at least some of the code words, matching the code word to a valid code word. In certain embodiments, this pattern of binding or hybridization of the analyte-specific probes, the decoding oligonucleotides and the signal oligonucleotides may be converted into a "code word." For example, for instance, the code words may be "101" and "110" for a first analyte and a second analyte, respectively, where a value of 1 represents binding and a value of 0 represents no binding of decoding oligonucleotides and/or the binding of signal oligonucleotides without and/or quenched signal element. The analyte in the detection round/cycle is therefore not detectable during imaging.

To create such a zero (0) in a code word for an individual analyte the kit may comprise:

(D) at least a set of non-signal decoding oligonucleotides for binding to a particular identifier element (T) of analyte-specific probes, wherein the decoding oligonucleotides in the same set of non-signal decoding oligonucleotides interacting with the same different identifier element (T), wherein each non-signal decoding oligonucleotide comprises an identifier connector element (t) comprising a nucleotide sequence which is essentially complementary to at least a section of a unique identifier sequence, and does not comprise a translator element (c) comprising a nucleotide sequence allowing a specific hybridization of a signal oligonucleotide.

To create such a zero (0) in a code word for an individual analyte the kit may comprise:

(D) at least a set of non-signal decoding oligonucleotides for binding to a particular identifier element (T) of analyte-specific probes, wherein the decoding oligonucleotides in the same set of non-signal decoding oligonucleotides interacting with the same different identifier element (T), wherein each non-signal decoding oligonucleotide comprises an identifier connector element (t) comprising a nucleotide sequence which is essentially complementary to at least a section of a unique identifier sequence, and comprise a translator element that does not interact/bind to a signal oligonucleotide due to an instable binding sequence and/or due to the translator element is to short (c) comprising a nucleotide sequence allowing a specific hybridization of a signal oligonucleotide.

In some advantageous embodiments, the kit comprises:

(D) at least two (2) different sets of non-signal decoding oligonucleotides for binding to at least two different identifier elements (T) of analyte-specific probes, each set of non-signal decoding oligonucleotides interacting with a different identifier element (T), wherein each non-signal decoding oligonucleotide comprises an identifier connector element (t) comprising a nucleotide sequence which is essentially complementary to at least a section of a unique identifier sequence, and does not comprise a translator element (c) comprising a nucleotide sequence allowing a specific hybridization of a signal oligonucleotide.

In some advantageous embodiments, the different sets of non-signal decoding oligonucleotides may be comprised in a pre-mixture of different sets of non-signal decoding oligonucleotides or exist separately.

Furthermore, in some advantageous embodiments the kit may comprise:

(E) a set of non-signal oligonucleotides, each non-signal oligonucleotide comprising:

(aa) a translator connector element (C) comprising a nucleotide sequence which is essentially complementary to at least a section of the nucleotide sequence of the translator element (c), and (bb) a quencher (Q), a signal element and a quencher (Q), or does not comprise a signal element. In some advantageous embodiments, the kit comprises:

(E) at least two sets of non-signal oligonucleotides, each non-signal oligonucleotide comprising:

(aa) a translator connector element (C) comprising a nucleotide sequence which is essentially complementary to at least a section of the nucleotide sequence of the translator element (c), and (bb) a quencher (Q), a signal element and a quencher (Q), or does not comprise a signal element.

In some advantageous embodiments, the different sets of non-signal oligonucleotides may be comprised in a pre-mixture of different sets of non-signal oligonucleotides or exist separately.

Further, in some embodiments the decoding oligonucleotides in a particular set of decoding oligonucleotides interacts with identical identifier elements (T) which are unique to a particular analyte.

In some advantageous embodiments, the different sets of decoding oligonucleotides may be comprised in a pre-mixture of different sets of decoding oligonucleotides or exist separately. In some advantageous embodiments, the different sets of analyte-specific probes may be comprised in a pre-mixture of different sets of analyte-specific probes or exist separately. In some advantageous embodiments, the different sets of signal oligonucleotides may be comprised in a pre-mixture of different sets of signal oligonucleotides or exist separately.

Figure 15:
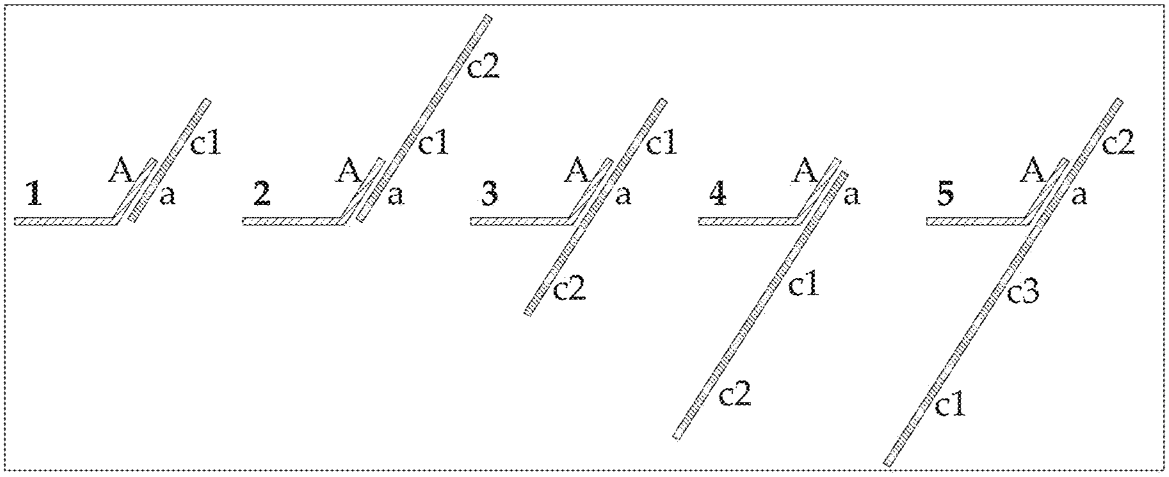
FIG. 15: Possible structures of a multi-decoder. The numbers depict the examples. (A) is the unique identifier sequence, (a) is the corresponding sequence of the decoding oligonucleotide or multi-decoder and (c1) to (c3) are different sequence elements, that specifically bind to different signal oligonucleotides. Examples 2 to 5 show different versions of multi decoders. The order of the different sequence elements as well as the number of signal oligonucleotide binding elements is not fixed. Example 1 shows a normal decoding oligonucleotide since there is only one signal oligonucleotide binding element (c1).

In some advantageous embodiments, a mixture of decoding oligonucleotides and/or multi-decoders is provided that specifically hybridize to the unique identifier sequences of the probe sets. In some embodiments, the decoding oligonucleotides comprise of at least two sequence elements, a first element that is complementary to the unique identifier sequences of the corresponding probe set and a second sequence element (translator element) that provides a sequence for the specific hybridization of a signal oligonucleotide, the translator element defines the type of signal that is recruited to the decoding oligonucleotide. In some embodiments multi-decoders comprising at least three sequence elements are used, a first element that is complementary to the unique identifier sequences of the corresponding probe set and at least to additional sequence elements (translator elements) that provide sequences for the specific hybridization of at least two different signal oligonucleotides. The translator elements define the type of signals that are recruited to the multi-decoder. Different possible structures of a multi-decoder can be seen in FIG. 15. Since a multi-decoder does recruit a full signal oligonucleotide per translator element, the brightness of the signals in each channel is not lower than the brightness of signals with decoding oligonucleotides.

Figure 16:
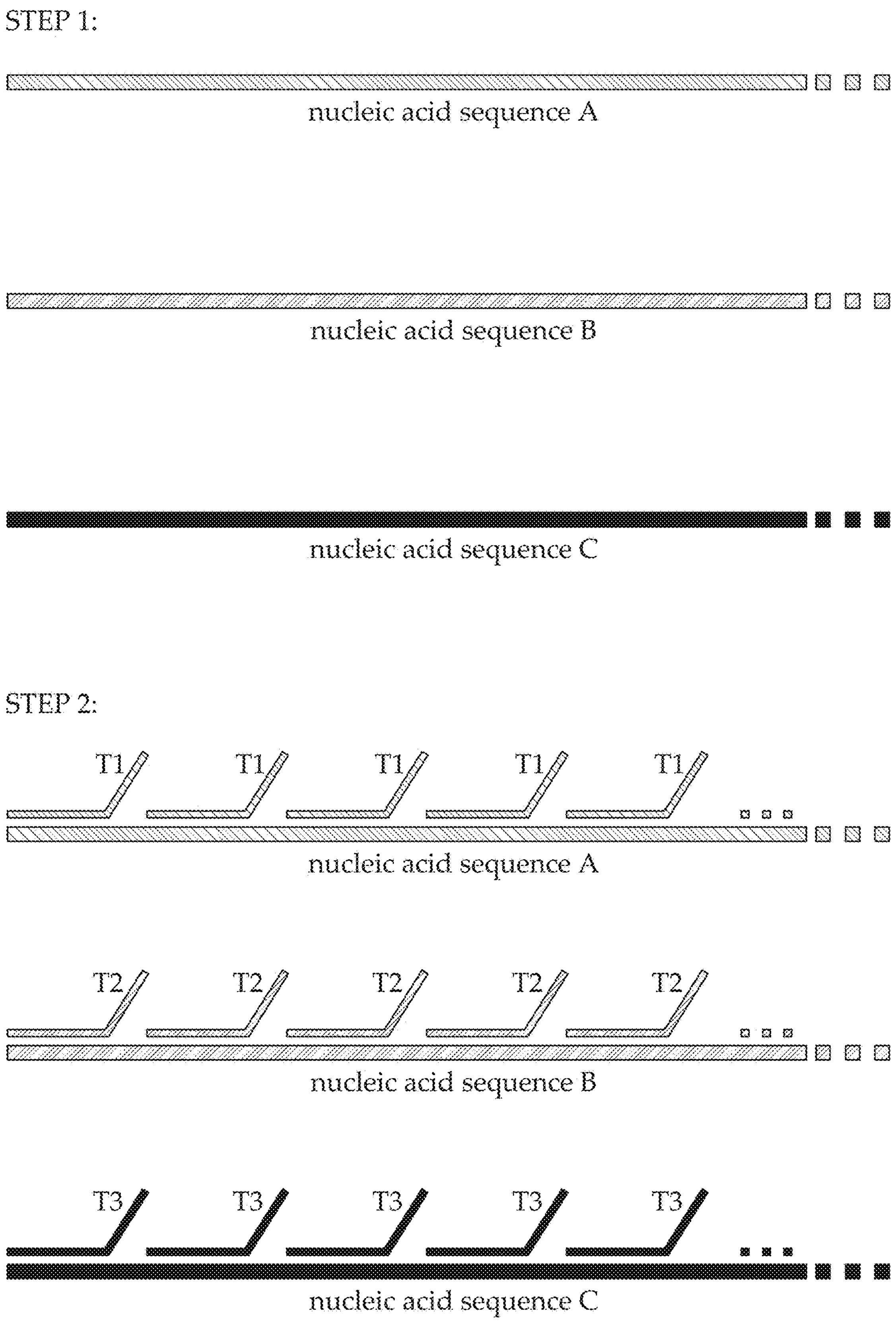
FIG. 16: Example for signal encoding of three different nucleic acid sequences by using multi-decoders and two different signal oligonucleotides creating three different signal types and three detection rounds. In this example, the encoding scheme includes error detection and correction.
Figure 16:
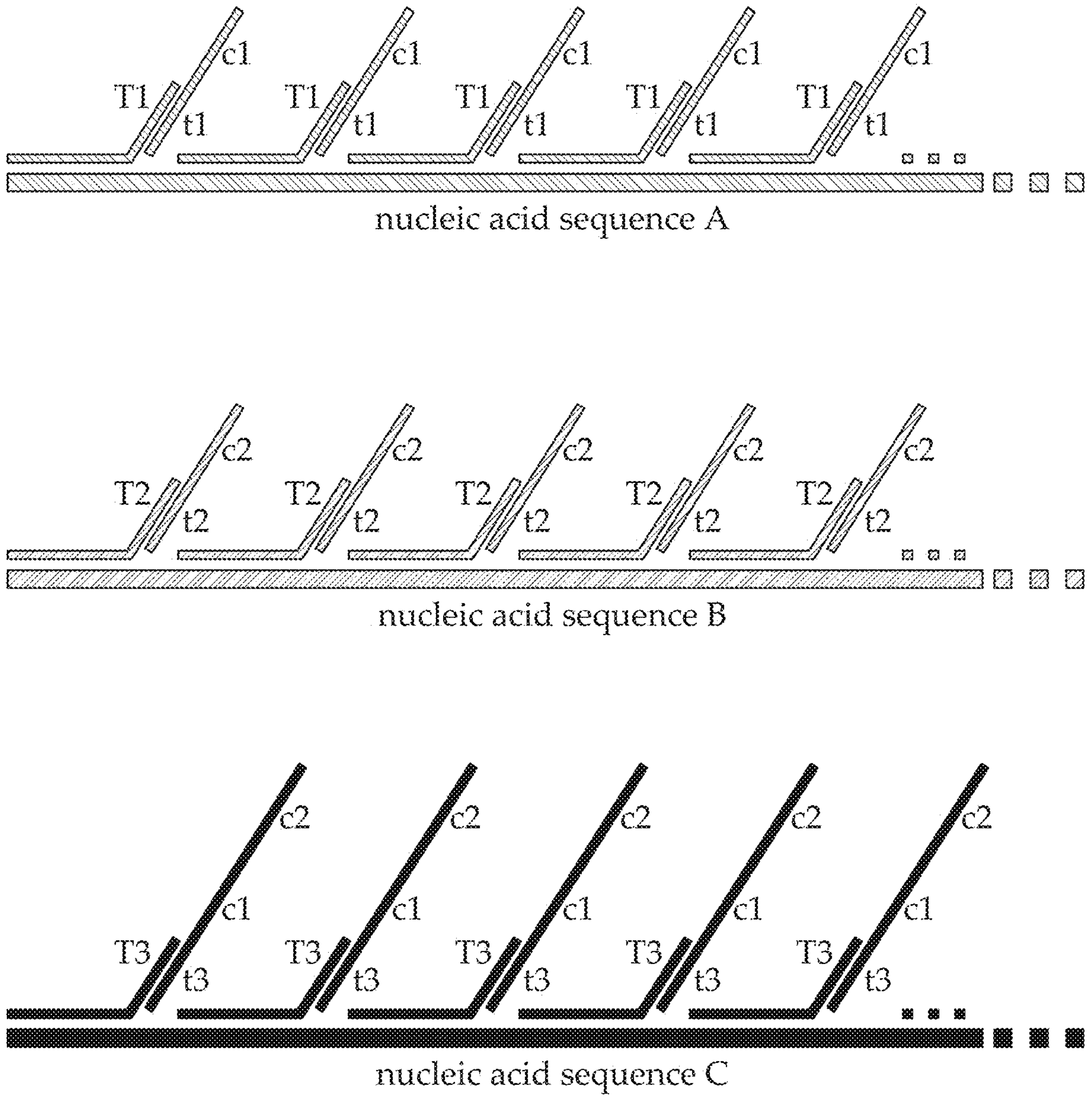
Figure 16:
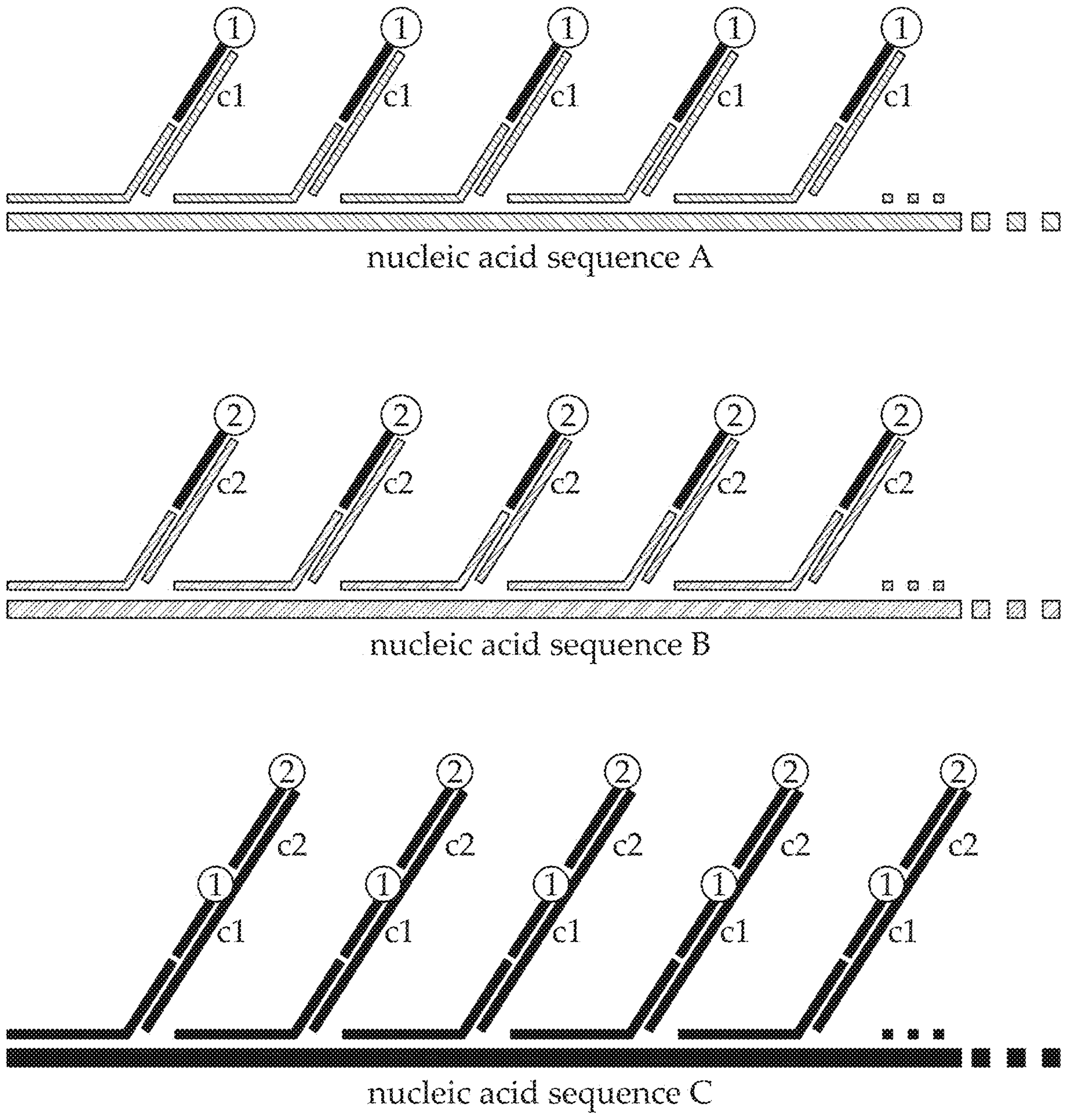
Figure 16:
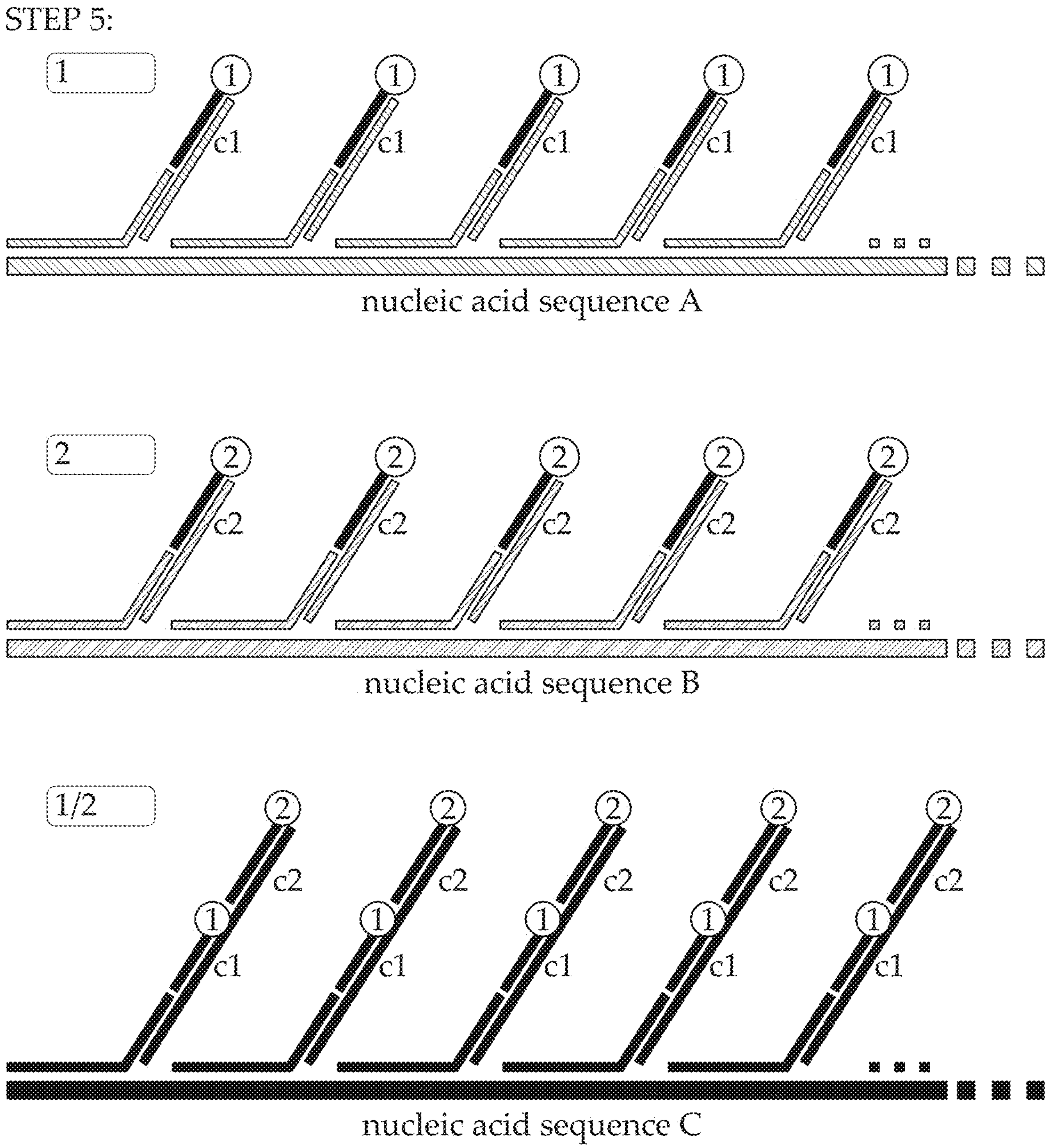
Figure 16:
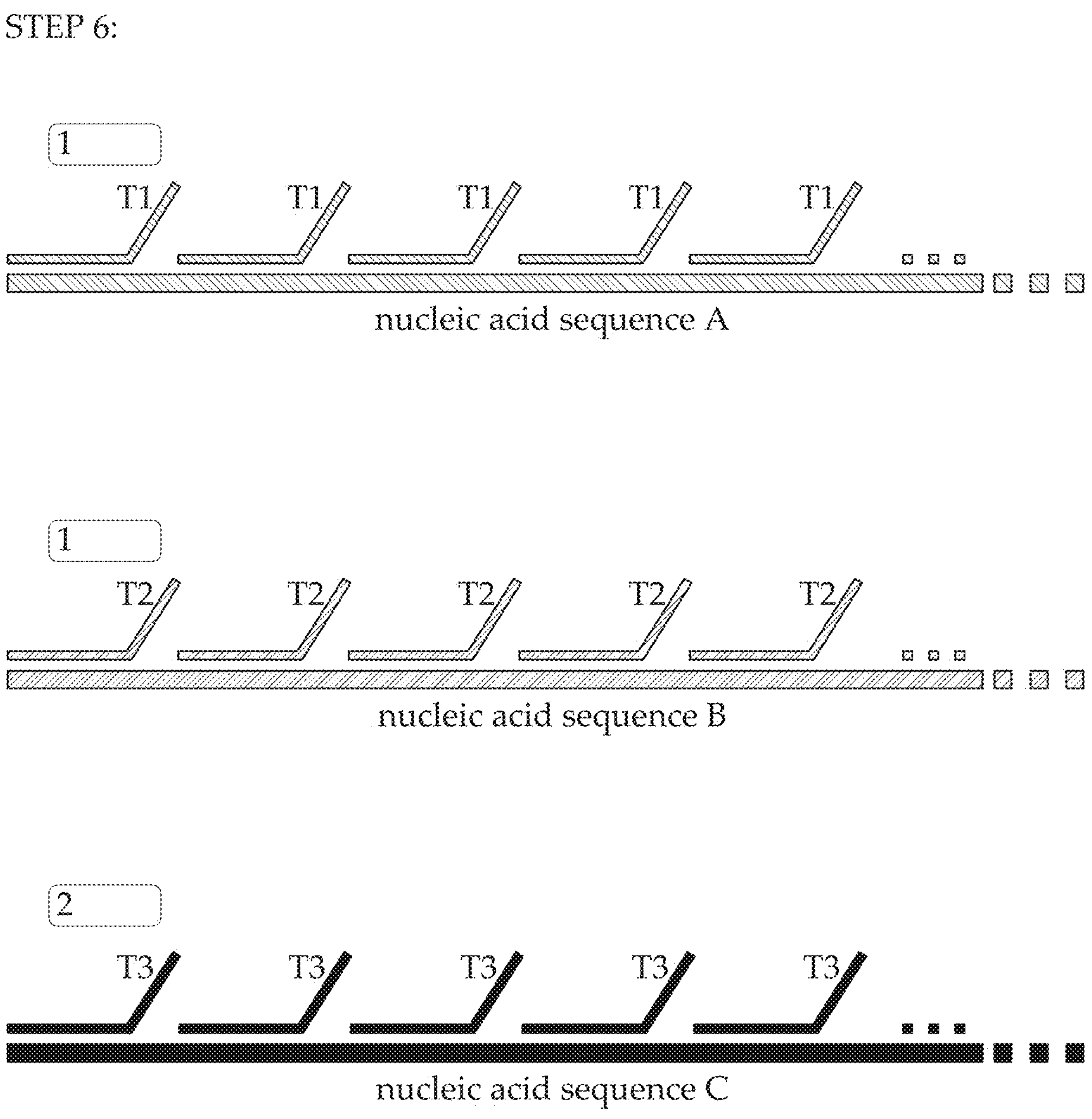
Figure 16:
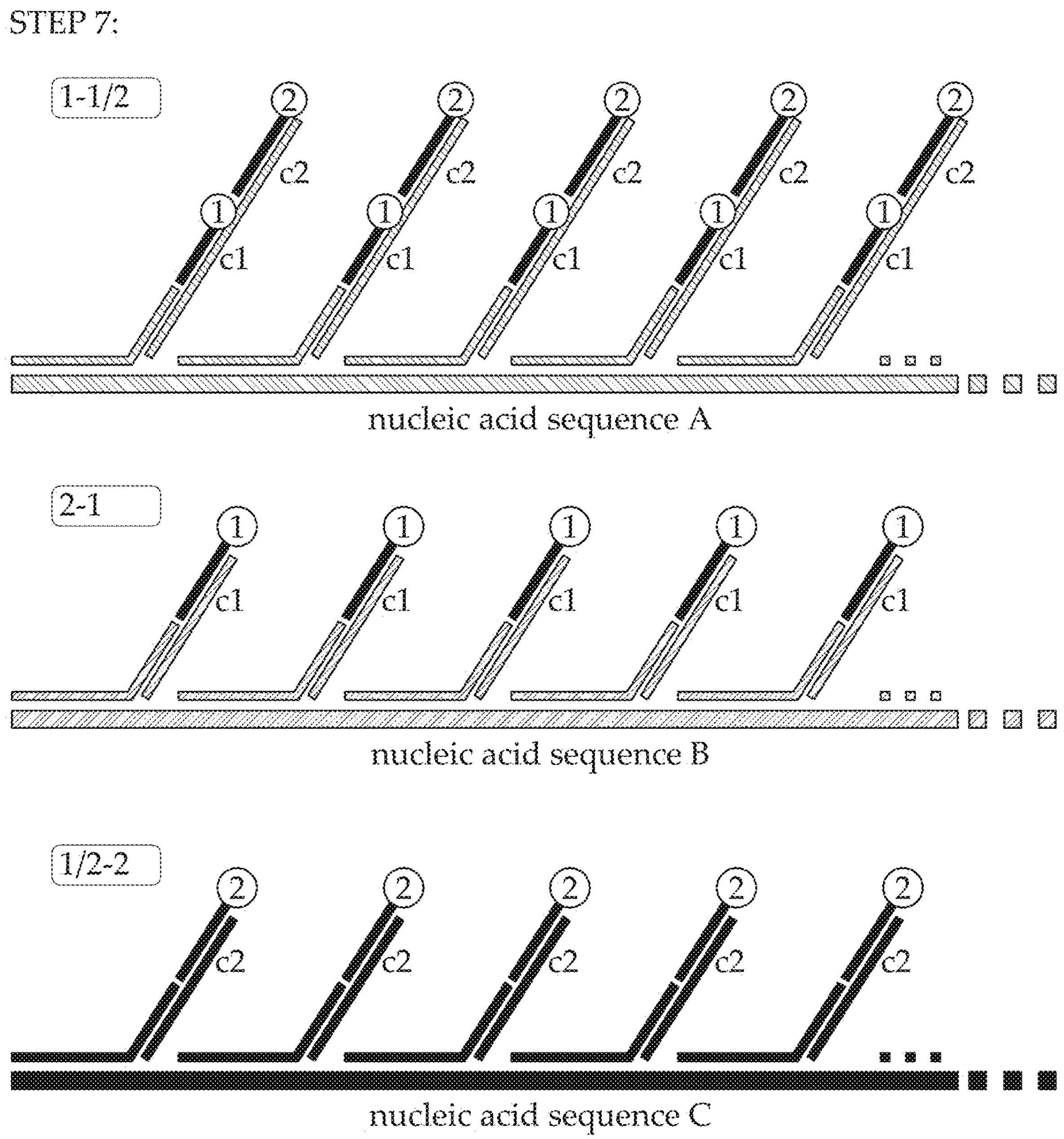
Figure 16:
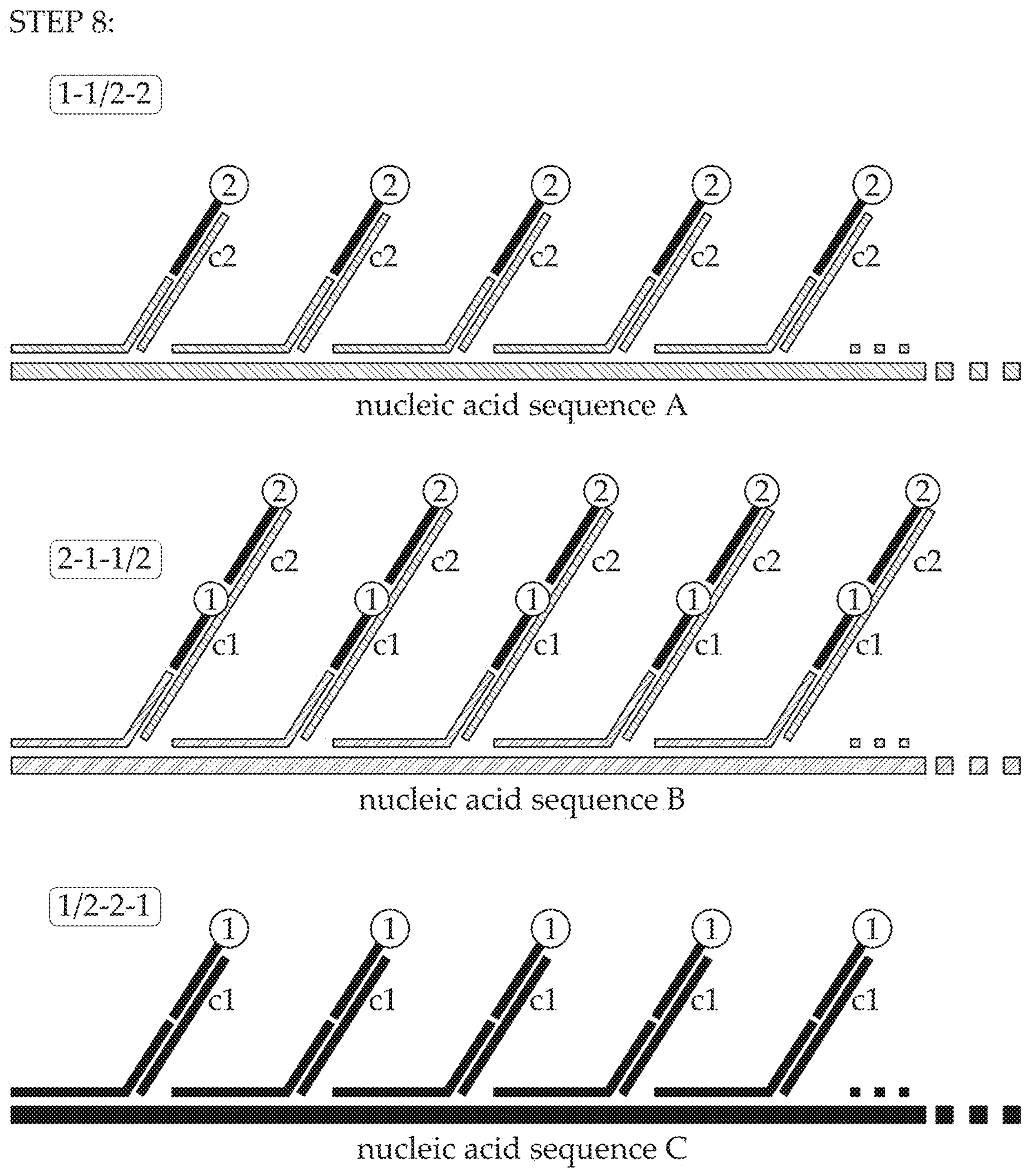

The usage of multi-decoders increases further the efficiency of the encoding scheme. FIG. 16 shows a possible encoding scheme using multi-decoders based upon the same conditions used for the examples with the decoding oligonucleotide with two sequence elements. One can clearly see that the multi-decoder based encoding scheme can create a higher hamming distance, with the same number of rounds and the same number of different signal oligonucleotides used in the example of FIG. 5.

As mentioned above the analyte to be encoded may be a nucleic acid, preferably DNA, PNA or RNA, in particular mRNA, a peptide, polypeptide, a protein, and/or mixtures thereof.

In some advantageous embodiments, the binding element (S) comprises an amino acid sequence allowing a specific binding to the analyte to be encoded. The binding element (S) may comprise moieties which are affinity moieties from affinity substances or affinity substances in their entirety selected from the group consisting of antibodies, antibody fragments, anticalin proteins, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and combinations thereof.

In some advantageous embodiments, the binding element (S) may comprise or is an antibody or an antibody fragment selected from the group consisting of Fab, scFv; single domain, or a fragment thereof, bis scFv, F (ab) 2, F (ab) 3, minibody, diabody, triabody, tetrabody and tandab.

The present disclosure pertains in particular to a multiplex method for detecting different analytes in a sample by sequential signal-encoding of said analytes, comprising the steps of:

(A) contacting the sample with at least twenty (20) different sets of analyte-specific probes for encoding of at least 20 different analytes, each set of analyte-specific probes interacting with a different analyte, wherein if the analyte is a nucleic acid each set of analyte-specific probes comprises at least five (5) analyte-specific probes which specifically interact with different sub-structures of the same analyte, each analyte-specific probe comprising (aa) a binding element(S) that specifically interacts with one of the different analytes to be encoded, and (bb) an identifier element (T) comprising a nucleotide sequence which is unique to the analyte to be encoded (unique identifier sequence), wherein the analyte-specific probes of a particular set of analyte-specific probes differ from the analyte-specific probes of another set of analyte-specific probes in the nucleotide sequence of the identifier element (T), wherein the analyte-specific probes in each set of analyte-specific probes binds to the same analyte and comprises the same nucleotide sequence of the identifier element (T) which is unique to said analyte; and (B) contacting the sample with at least one set of decoding oligonucleotides per analyte, wherein in each set of decoding oligonucleotides for an individual analyte each decoding oligonucleotide comprises:

(aa) an identifier connector element (t) comprising a nucleotide sequence which is essentially complementary to at least a section of the unique identifier sequence of the identifier element (T) of the corresponding analyte-specific probe set, and (bb) a translator element (c) comprising a nucleotide sequence allowing a specific hybridization of a signal oligonucleotide;

wherein the decoding oligonucleotides of a set for an individual analyte differ from the decoding oligonucleotides of another set for a different analyte in the first connect element (t); and (C) contacting the sample with at least a set of signal oligonucleotides, each signal oligonucleotide comprising:

(aa) a translator connector element (C) comprising a nucleotide sequence which is essentially complementary to at least a section of the nucleotide sequence of a translator element (c) comprised in a decoding oligonucleotide, and (bb) a signal element.

(D) Detecting the signal caused by the signal element;

(E) selectively removing the decoding oligonucleotides and signal oligonucleotides from the sample, thereby essentially maintaining the specific binding of the analyte-specific probes to the analytes to be encoded;

(F) Performing at least three (3) further cycles comprising steps B) to E) to generate an encoding scheme with a code word per analyte, wherein in particular the last cycle may stop with step (D).

As mentioned above, the method according to the present disclosure comprises selectively removing the decoding oligonucleotides and signal oligonucleotides from the sample, thereby essentially maintaining the specific binding of the analyte-specific probes to the analyte to be encoded. In particular all steps are performed sequentially. However some steps may be performed simultaneously, in particular the contacting steps A) to C), in particular B) and C).

By this measure the requirements for another round/cycle of binding further decoding oligonucleotides to the same analyte-specific probes are established, thus finally resulting in a code or encoding scheme comprising more than one signal. This step is realized by applying conditions and factors well known to the skilled person, e.g. pH, temperature, salt conditions, oligonucleotide concentration, polymers etc.

In another embodiment of the present disclosure, the method may comprise repeating steps (B)-(E) at least three times to generate an encoding scheme. With this measure a code of four signals in case of four cycles/rounds which are carried out by the user, where 'n' is an integer representing the number of rounds. The encoding capacity of the method according to the disclosure is herewith increased depending on the nature of the analyte and the needs of the operator. In an embodiment of the disclosure said encoding scheme is predetermined and allocated to the analyte to be encoded.

However, this measure enables a precise experimental set-up by providing the appropriate sequential order of the employed decoding and signal oligonucleotides and, therefore, allows the correct allocation of a specific analyte to a respective encoding scheme. The decoding oligonucleotides which are used in repeated steps (B)-(D2) may comprise a translator element (c2) which is identical with the translator element (c1) of the decoding oligonucleotides used in previous steps (B)-(E). In another embodiment of the disclosure decoding oligonucleotides are used in repeated steps (B)-(E) comprising a translator element (c2) which differs from the translator element (c1) of the decoding oligonucleotides used in previous steps (B)-(E). It is understood that the decoding elements may or may not be changed from round to round, i.e. in the second round (B)-(E) comprising the translator element c2, in the third round (B)-(E) comprising the translator element c3, in the fourth round (B)-(E) comprising the translator element c4 etc., wherein 'n' is an integer representing the number of rounds.

The signal oligonucleotides which are used in repeated steps (B)-(E) may comprise a signal element which is identical with the signal element of the decoding oligonucleotides used in previous steps (B)-(E). In a further embodiment of the disclosure signal oligonucleotides are used in repeated steps (B)-(E) comprising a signal element which differs from the signal element of the decoding oligonucleotides used in previous steps (B)-(E). In some embodiments no-signal oligonucleotides and/or no-signal decoding oligonucleotides for an individual analyte are used, resulting to the value 0 in the code word for this cycle/position. In some embodiments in a repeated cycle no decoding oligonucleotides for an individual analyte is contacted with the sample resulting also to the value 0 in the code word for this cycle/position.

By this measure each round the same or a different signal is provided resulting in an encoding scheme characterized by a signal sequence consisting of numerous different signals. This measure allows the creation of a unique code or code word which differs from all other code words of the encoding scheme. In another embodiment of the disclosure, the binding element(S) of the analyte-specific probe comprises a nucleic acid comprising a nucleotide sequence allowing a specific binding to the analyte to be encoded, preferably a specific hybridization to the analyte to be encoded.

In some advantageous embodiments, all steps are automated, in particular wherein steps B) to F) are automated, in particular by using a robotic system and/or an optical multiplexing system according to the present disclosure. In some examples, the steps may be performed in a fluidic system.

As mentioned above, with the methods according to the present disclosure an encoding scheme with a code word per analyte is generated. Therefore, each analyte may be associated with a specific code word, wherein said code word comprise a number of positions, and wherein each position corresponds to one cycle resulting in a plurality of distinguishable encoding schemes with the plurality of code words. In particular, said encoding scheme may be predetermined and allocated to the analyte to be encoded.

Figure 14:
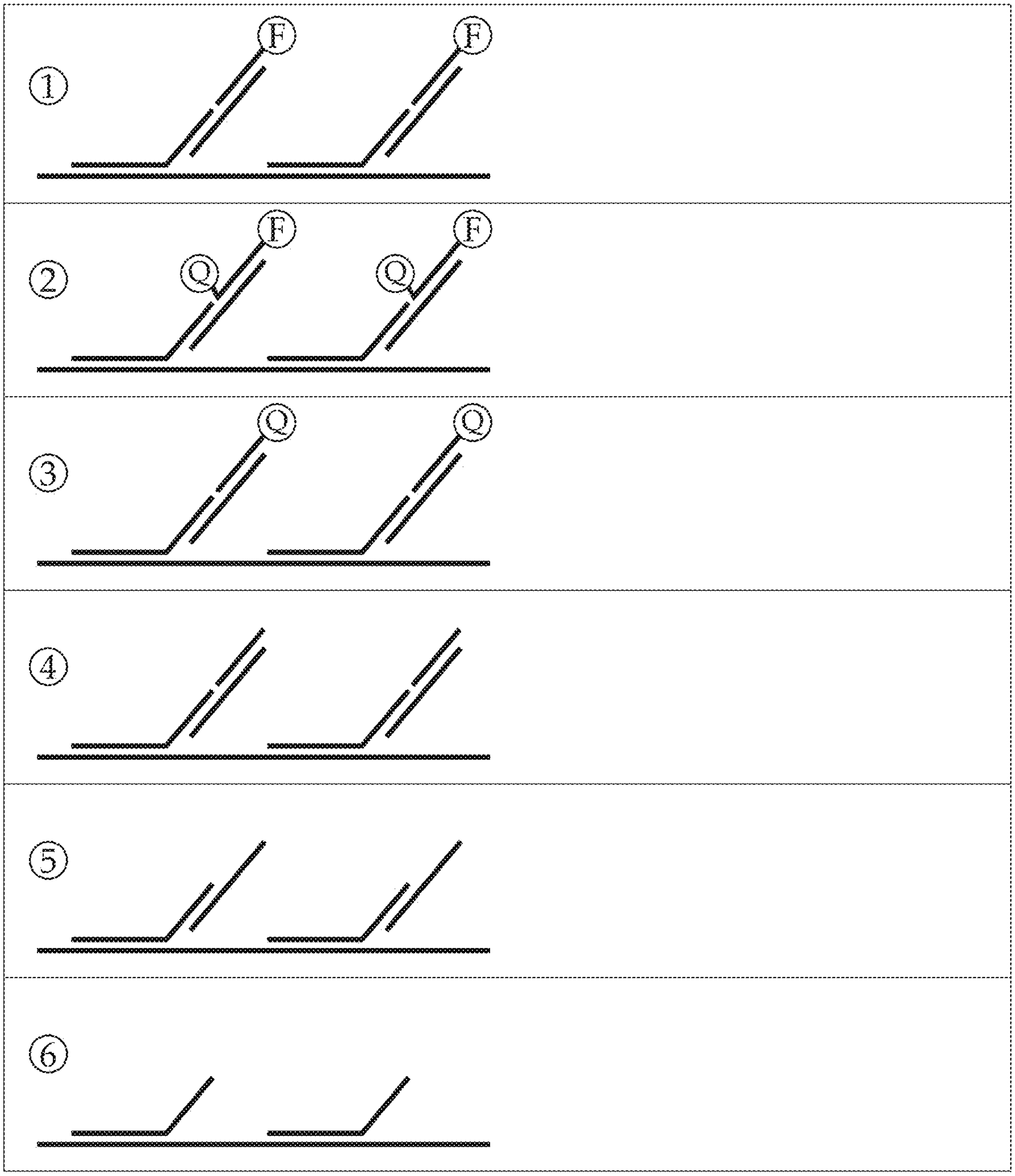
FIG. 14: Detection of multiple targets can be performed by an encoding scheme using a detectable marker. The ending scheme may comprise also the “0” as a marker. That means that at a specific position the transcript is not detected. Consequently, the encoding scheme may be represented by the following constructs using only two gene specific probes.

In some advantageous embodiments, the code words obtained for the individual analytes in the performed cycles comprise the detected signals and additionally at least one element corresponding to no detected signal like 0,1 or 0,1,2 etc. (see also FIG. 13 and FIG. 14). In particular, no signal is detected for at least one analyte within at least one cycle if using the a non-signal probe according to FIG. 14, No. 2 to 4, or a non-signal decoding oligonucleotide as shown in FIG. 14 No. 5, or if in one cycle no decoding oligonucleotide is contacted with the corresponding identifier sequence comprised on analyte-specific probe interacting with the corresponding analyte in the sample. In this cycle the position has the value zero (0).

In some advantageous embodiments, at least for one individual analyte a position of the code word is zero (0). In particular, the code word zero (0) is generated by using no decoding oligonucleotides having an identifier connector element (t) comprising a nucleotide sequence which is essentially complementary to at least a section of the unique identifier sequence of the identifier element (T) of a corresponding analyte-specific probe for an individual analyte. As mentioned above, in some embodiments, if at least for one individual analyte a position of the code word is zero (0) in this cycle no corresponding decoding oligonucleotides having an identifier connector element (t) comprising a nucleotide sequence which is essentially complementary to at least a section of the unique identifier sequence of the identifier element (T) of a corresponding analyte-specific probe for an individual analyte are used.

Furthermore, in some advantageous embodiments the sample is contacted with at least two different sets of signal oligonucleotides, wherein the signal oligonucleotides in each set comprise a different signal element and comprise a different connector element (C).

In more particular embodiments, the sample is contacted with at least two different sets of decoding oligonucleotides per analyte, wherein the decoding oligonucleotides comprised in these different sets comprise the same identifier connector element (t) comprising a nucleotide sequence which is essentially complementary to at least a section of the unique identifier sequence of the identifier element (T) of the corresponding analyte-specific probe set, and wherein the decoding oligonucleotides of the different sets per analyte differ in the translator element (c) comprising a nucleotide sequence allowing a specific hybridization of a signal oligonucleotide.

In more particular embodiments, the sample is contacted with at least two different sets of decoding oligonucleotides per analyte, wherein the decoding oligonucleotides comprised in these different sets comprise the same identifier connector element (t) comprising a nucleotide sequence which is essentially complementary to at least a section of the unique identifier sequence of the identifier element (T) of the corresponding analyte-specific probe set, and wherein the decoding oligonucleotides of the different sets per analyte differ in the translator element (c) comprising a nucleotide sequence allowing a specific hybridization of a signal oligonucleotide;

wherein only one set of decoding oligonucleotides per analyte is used per cycle, and/or wherein different sets of decoding oligonucleotides are used in different cycles in combination with the corresponding set of signal oligonucleotides in the same cycle.

In some advantageous embodiments, the number of different sets of decoding oligonucleotides per analyte comprising different translator elements (c) corresponds to the number of different sets of signal oligonucleotides comprising different connector elements (C). All sets of decoding oligonucleotides for the different analytes may comprise the same type(s) of translator element(s) (c).

In some advantageous embodiments of the method according to the present disclosure, the sample is contacted with at least a set of non-signal decoding oligonucleotides for binding to a particular identifier element (T) of analyte-specific probes, wherein the decoding oligonucleotides in the same set of non-signal decoding oligonucleotides interacting with the same different identifier element (T), wherein each non-signal decoding oligonucleotide comprises an identifier connector element (t) comprising a nucleotide sequence which is essentially complementary to at least a section of a unique identifier sequence, and does not comprise a translator element (c) comprising a nucleotide sequence allowing a specific hybridization of a signal oligonucleotide.

As mentioned above, the sample may be contacted with at least two (2) different sets of non-signal decoding oligonucleotides for binding to at least two different identifier elements (T) of analyte-specific probes, each set of non-signal decoding oligonucleotides interacting with a different identifier element (T), wherein each non-signal decoding oligonucleotide comprises an identifier connector element (t) comprising a nucleotide sequence which is essentially complementary to at least a section of a unique identifier sequence, and does not comprise a translator element (c) comprising a nucleotide sequence allowing a specific hybridization of a signal oligonucleotide.

In some advantageous embodiments of the method according to the present disclosure, the different sets of non-signal decoding oligonucleotides may be comprised in a pre-mixture of different sets of non-signal decoding oligonucleotides or exist separately.

Furthermore, in some advantageous embodiments of the method according to the present disclosure, the sample is contacted with a set of non-signal oligonucleotides, each non-signal oligonucleotide comprising:

(aa) a translator connector element (C) comprising a nucleotide sequence which is essentially complementary to at least a section of the nucleotide sequence of the translator element (c), and (bb) a quencher (Q), a signal element and a quencher (Q), or does not comprise a signal element.

In further embodiments, the sample may be contacted with:

at least two sets of non-signal oligonucleotides, each non-signal oligonucleotide comprising:

(aa) a translator connector element (C) comprising a nucleotide sequence which is essentially complementary to at least a section of the nucleotide sequence of the translator element (c), and (bb) a quencher (Q), a signal element and a quencher (Q), or does not comprise a signal element.

As mentioned above, the different sets of non-signal oligonucleotides may be comprised in a pre-mixture of different sets of non-signal oligonucleotides or exist separately.

In further embodiments, the decoding oligonucleotides in a particular set of decoding oligonucleotides interacts with identical identifier elements (T) which are unique to a particular analyte.

As mentioned above, the different sets of decoding oligonucleotides may be comprised in a pre-mixture of different sets of decoding oligonucleotides or exist separately as well as the different sets of analyte-specific probes may be comprised in a pre-mixture of different sets of analyte-specific probes or exist separately as well the different sets of signal oligonucleotides may be comprised in a pre-mixture of different sets of signal oligonucleotides or exist separately.

In some advantageous embodiments of the method according to the present disclosure, the binding element(S) comprise a nucleic acid comprising a nucleotide sequence allowing a specific binding to the analyte to be encoded, preferably a specific hybridization to the analyte to be encoded.

In some advantageous embodiments of the method according to the present disclosure, after step A) and before step B) the non-bound analyte-specific probes may be removed, in particular by washing, further after step B) and before step C) the non-bound decoding oligonucleotides may be removed, in particular by washing further, after step C) and before step D) the non-bound signal oligonucleotides may be removed, in particular by washing.

In some advantageous embodiments of the method according to the present disclosure, the analyte specific probes may be incubated with the sample, thereby allowing a specific binding of the analyte specific probes to the analytes to be encoded, further the decoding oligonucleotides may be incubated with the sample, thereby allowing a specific hybridization of the decoding oligonucleotides to identifier elements (T) of the respective analyte-specific probes, further the signal oligonucleotides may be incubated with the sample, thereby allowing a specific hybridization of the signal oligonucleotides to translator elements (T) of the respective decoding oligonucleotides.

As mentioned above, the analyte to be encoded may be a nucleic acid, preferably DNA, PNA, RNA, in particular mRNA, a peptide, polypeptide, a protein or combinations thereof. Therefore, the binding element(S) may comprise an amino acid sequence allowing a specific binding to the analyte to be encoded. Examples for a binding element(S) are moieties which are affinity moieties from affinity substances or affinity substances in their entirety selected from the group consisting of antibodies, antibody fragments, anticalin proteins, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and combinations thereof. In particular, the binding element(S) is an antibody or an antibody fragment selected from the group consisting of Fab, scFv; single domain, or a fragment thereof, bis scFv, Fab 2, Fab 3, minibody, diabody, triabody, tetrabody and tandab.

By this measure the method is further developed to such an extent that the encoded analytes can be detected by any means which is adapted to visualize the signal element. Examples of detectable physical features include e.g. light, chemical reactions, molecular mass, radioactivity, etc.

In some advantageous embodiments, the signal caused by the signal element, therefore in particular the binding of the signal oligonucleotides to the decoding oligonucleotides, interacting with the corresponding analyte probes, bound to the respective analyte is determined by:

(a) Imaging at least a portion of the sample; and/or
(b) Using an optical imaging technique; and/or
(c) Using a fluorescence imaging technique; and/or
(d) Multi-color fluorescence imaging technique; and/or
(e) Super-resolution fluorescence imaging technique.

The kits and method according to the present disclosure may be used ideally for in vitro methods for diagnosis of a disease selected from the group comprising cancer, neuronal diseases, cardiovascular diseases, inflammatory diseases, autoimmune diseases, diseases due to a viral or bacterial infection, skin diseases, skeletal muscle diseases, dental diseases and prenatal diseases.

Further, the kits and method according to the present disclosure may be used also ideally for in vitro methods for diagnosis of a disease in plants selected from the group comprising: diseases caused by biotic stress, preferably by infectious and/or parasitic origin, or diseases caused by abiotic stress, preferably caused by nutritional deficiencies and/or unfavorable environment.

Further, the kits and method according to the present disclosure may be used also ideally for in vitro methods for screening, identifying and/or testing a substance and/or drug comprising:

(a) contacting a test sample comprising a sample with a substance and/or drug
(b) detecting different analytes in a sample by sequential signal-encoding of said analytes with a method according to the present disclosure.

An optical multiplexing system suitable for the method according to the present disclosure, comprising at least:

a reaction vessel for containing the kits or part of the kits according to the present disclosure;
a detection unit comprising a microscope, in particular a fluorescence microscope;
a camera;
a liquid handling device.

In some embodiments, optical multiplexing system may comprises further a heat and cooling device and/or a robotic system.

In some embodiments, the method according to the present disclosure encodes a nucleic acid analyte, such as an mRNA, e.g. such an mRNA coding for a particular protein.

In some advantageous embodiments, the method described herein is used for specific detection of many different analytes in parallel. The technology allows to distinguish a higher number of analytes than different signals are available. The process includes at least four consecutive rounds of specific binding, signal detection and selective denaturation (if a next round is required), eventually producing a signal code. To decouple the dependency between the analyte specific binding and the oligonucleotides providing the detectable signal, a so called "decoding"-oligonucleotide is introduced. The decoding oligonucleotide transcribes the information of the analyte specific probe set to the signal oligonucleotides.

In a specific embodiment, the method may comprise the steps of 1. providing one or more analyte specific probe sets, the set of analyte specific probes consist of one or more different probes, each differing in the binding moiety that specifically interacts with the analyte, all probes of a single probe set are tethered to a sequence element (unique identifier), that is unique to a single probe set and allows the specific hybridization of a decoding oligonucleotide, 2. specific binding of the probe sets to their target binding sites of the analyte, 3. eliminating non-bound probes (e.g. by a wash step), 4. providing a mixture of decoding oligonucleotides that specifically hybridize to the unique identifier sequences of the probe sets, the decoding oligonucleotides comprise of at least two sequence elements, a first element that is complementary to the unique identifier sequences of the corresponding probe set and a second sequence element (translator element) that provides a sequence for the specific hybridization of a signal oligonucleotide, the translator element defines the type of signal that is recruited to the decoding oligonucleotide, 5. specific hybridization of the decoding oligonucleotides to the unique identifier sequences provided by the bound probe sets, 6. eliminating non-bound decoding oligonucleotides (e.g. by washing step), 7. providing a mixture of signal oligonucleotides, comprising of a signal that can be detected and a nucleic acid sequence that specifically hybridizes to the translator element of one of the decoding oligonucleotides used in the former hybridization step, 8. specific hybridization of the signal oligonucleotides, 9. eliminating non-bound signal oligonucleotides, 10. detection of the signals, 11. selective release of decoding oligonucleotides and signal oligonucleotides while the binding of specific probe sets to the analyte is almost or completely unaffected, 12. eliminating released decoding oligonucleotide and signal oligonucleotides (e.g. by a washing step) while the binding of specific probes sets to the analytes is almost or completely unaffected, repeating the steps 4 to 12 at least three times until the detection of a sufficient number of signals to generate an encoding scheme for each different analyte of interest.

It is to be understood that the before-mentioned features and those to be mentioned in the following cannot only be used in the combination indicated in the respective case, but also in other combinations or in an isolated manner without departing from the scope of the disclosure.

The disclosure is now further explained by means of embodiments resulting in additional features, characteristics and advantages of the disclosure. The embodiments are of pure illustrative nature and do not limit the scope or range of the disclosure. The features mentioned in the specific embodiments are general features of the disclosure which are not only applicable in the specific embodiment but also in an isolated manner in the context of any embodiment of the disclosure.

The method disclosed herein is used for specific detection of many different analytes in parallel. The technology allows distinguishing a higher number of analytes than different signals are available. The process preferably includes at least two consecutive rounds of specific binding, signal detection and selective denaturation (if a next round is required), eventually producing a signal code. To decouple the dependency between the analyte specific binding and the oligonucleotides providing the detectable signal, a so called "decoding" oligonucleotide is introduced. The decoding oligonucleotide transcribes the information of the analyte specific probe set to the signal oligonucleotides.

The present disclosure pertains further to methods of detecting an analyte, comprising:

attaching a plurality of analyte-specific probes to the analyte, wherein the analyte-specific probes independently attach to the analyte and wherein the analyte-specific probes share a common identifier segment (T);

annealing a plurality of first decoding oligonucleotides to the analyte-specific probes, wherein the first decoding oligonucleotides share a first common region that is reverse complementary to the common identifier segment and a second common region;

annealing a first signal oligonucleotide to at least one of the plurality of first decoding oligonucleotides such that an oligo tethered to the first signal oligonucleotide is reverse complementary to the second common region;

detecting the first signal oligonucleotide;

removing the plurality of first decoding oligonucleotides;

annealing a plurality of second decoding oligonucleotides to the analyte-specific probes, wherein the second decoding oligonucleotides share a first common region that is reverse complementary to the common identifier segment and a second decoding oligonucleotides second common region that differs from the second common region of the first decoding;

annealing a second signal oligonucleotide to at least one of the plurality of second decoding oligonucleotides such that an oligo tethered to the signal oligonucleotide is reverse complementary to the second decoding oligonucleotide second common region; and detecting the second signal oligonucleotide.

In particular, in the above mentioned embodiment a second aliquot of a plurality of first decoding oligonucleotides is annealed to the analyte-specific probes. Furthermore, a first aliquot of a plurality of first decoding oligonucleotides is annealed to the analyte-specific probes.

In some embodiments, no second signal oligonucleotide to the at least one of the plurality of first decoding oligonucleotides is annealed. In particular, no third signal oligonucleotide to the at least one of the plurality of first decoding oligonucleotides is annealed.

In some further advantageous embodiments, the present disclosure pertains to a method of assigning an analyte to a position in an image, comprising assigning a fluorescence pattern to the analyte, observing the fluorescence pattern at the position in the image, and assigning the analyte to the position, in particular wherein observing the fluorescence pattern comprises repeating steps of labeling the position using a fluorophore tagged oligo drawn from a re-accessible pool, performing a single excitation at the position in the image, and contacting the analyte to a denaturant, in particular wherein observing the fluorescence pattern comprises repeating steps of labeling the position using a fluorophore tag-recruiting bridging oligo drawn from a re-accessible pool, performing a single excitation at the position in the image, and contacting the analyte to a denaturant.

In some further advantageous embodiments, the present disclosure pertains to a composition comprising a cell having nucleic acids distributed therein, wherein a first nucleic acid is tagged by a first plurality of probes that target adjacent segments of the first nucleic acid and that share a common first tether segment; a second nucleic acid is tagged by a second plurality of probes that target adjacent segments of the second nucleic acid and that share a common second tether segment; and a third nucleic acid is tagged by a third plurality of probes that target adjacent segments of the third nucleic acid and that share a common third tether segment; a first adapter population comprising molecules having a first tether reverse complementary region and a first fluorophore adapter tether; a second adapter population comprising molecules having a second tether reverse complementary region and a second fluorophore adapter tether; a third adapter population comprising molecules having a third tether reverse complementary region and a first fluorophore adapter tether; a population of first fluorophores having a first tether reverse complementary region; and a population of second fluorophores having a second tether reverse complementary region.

In some further advantageous embodiments, the present disclosure pertains to a method of assigning coded fluorescence patterns to a plurality of target analytes in a cell, comprising: subjecting the cell to a plurality of detection rounds, each detection round comprising: contacting the cell to representatives of the same at least two populations of tagged fluorescence moieties, and removing the fluorescent moieties after a single excitation event, in particular wherein the number of patterns detectable increases exponentially with the number of detection rounds, wherein the fluorescence moieties are not tagged with nucleic acid tags that are specific to the target nucleic acids, and wherein separate aliquots of common tagged fluorescence moieties are used across multiple detection rounds.

In particular, with the above notified method a total decoding efficiency of at least 30% may be achieved.

In some further advantageous embodiments, the present disclosure pertains to a method of assigning coded fluorescence patterns to a plurality of target analytes in a cell, comprising: contacting a target to a bipartite labeling probe, the bipartite labeling probe comprising a target-specific moiety and a fluorophore-specifying moiety; contacting the bipartite labeling probe to a first aliquot of a fluorophore reservoir comprising no more than two populations of fluorophores; replacing the fluorophore specifying moiety in the bipartite probe, and contacting the bipartite labeling probe to a second aliquot of the fluorophore reservoir comprising the same no more than two populations.

In some embodiments of the above notified method, replacing the fluorophore specifying moiety in the bipartite probe comprises denaturing a binding between a target-specific moiety and a fluorophore-specifying moiety after subjecting the bipartite labeling probe bound to a fluorophore of the fluorophore to excitation energy. In particular, replacing the fluorophore specifying moiety in the bipartite probe comprises drawing from one of no more than two fluorophore specifying moiety reservoirs.

In some further advantageous embodiments, the present disclosure pertains to a method of detecting an analyte, comprising:

attaching a plurality of probes to the analyte, in particular a nucleic acid, wherein the probes independently attach/anneal to the analyte and wherein the probes share a common identifier segment;

annealing a plurality of first adapter segments to the probes, wherein the first adapter segments share a first common region that is reverse complementary to the common identifier segment and a second common region, in particular configured to accommodate a single reporter/selected from no more than two reporter categories;

annealing a first reporter to at least one of the plurality of first adapter segments such that an oligo tethered to the first reporter is reverse complementary to the second common region; detecting the first reporter;

removing the plurality of first adapter segments, in particular without annealing a second reporter to the at least one of the plurality of first adapter segments;

annealing a plurality of second adapter segments to the probes, wherein the second adapter segments share a first common region that is reverse complementary to the common identifier segment and a second adapter second common region that differs from the second common region of the first adapter segments, in particular configured to accommodate a single reporter/selected from no more than two reporter categories;

annealing a second reporter to at least one of the plurality of second adapter segments such that an oligo tethered to the second reporter is reverse complementary to the second adapter second common region; and detecting the second reporter, in particular without annealing a third reporter to the at least one of the plurality of first adapter segments.

Methods and Examples

In an application variant, the analyte or target is nucleic acid, e.g. DNA or RNA, and the probe set comprises oligonucleotides that are partially or completely complementary to the whole sequence or a subsequence of the nucleic acid sequence to be detected (FIG. 1). The nucleic acid sequence specific oligonucleotide probe sets comprising analyte-specific probes (1) including a binding element (S) that specifically hybridizes to the target nucleic acid sequence to be detected, and an identifier element (T) comprising a nucleotide sequence which is unique to said set of analyte-specific probes (unique identifier sequence)

Figure 2:
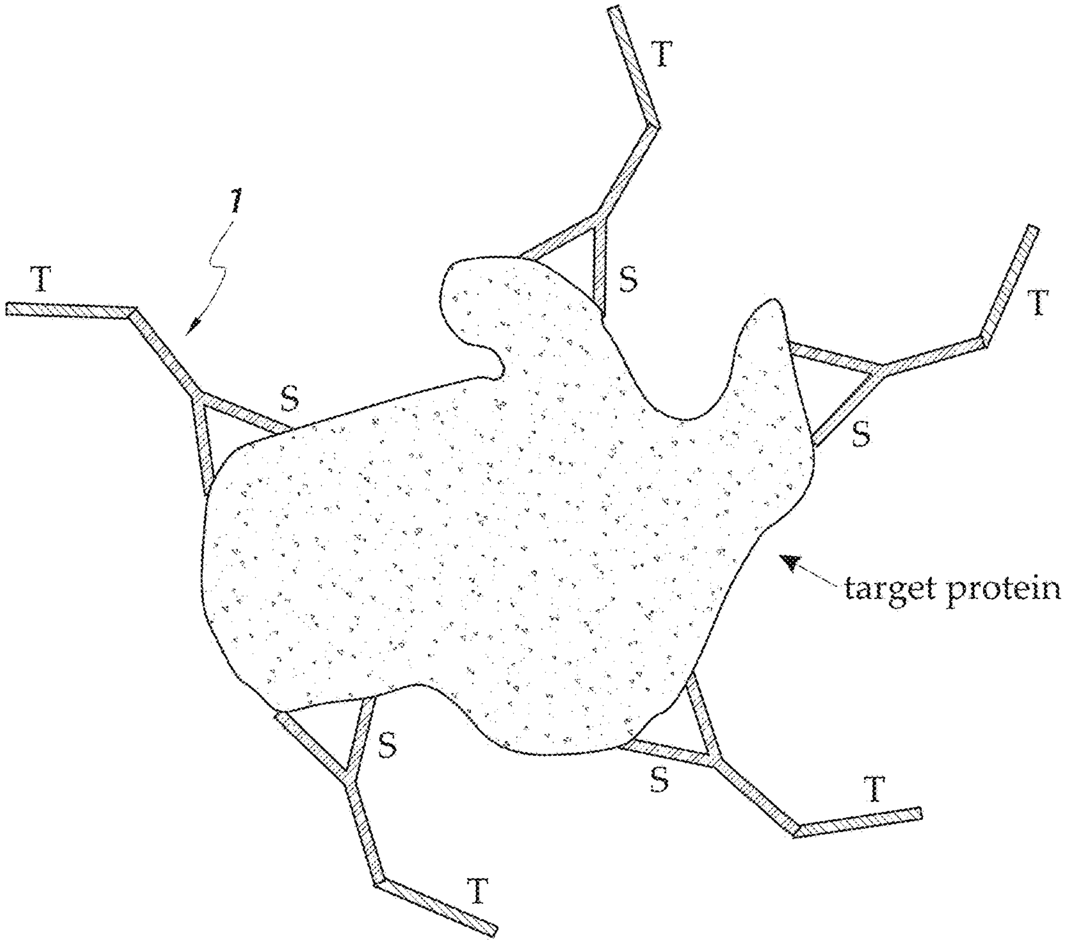
FIG. 2: Embodiment where the analyte is a protein and the probe set comprises proteins (here: antibodies) specifically binding to the analyte. The probes comprise a unique identifier sequence allowing hybridization of decoding oligonucleotides.

In a further application variant, the analyte or target is a protein and the probe set comprises one or more proteins, e.g. antibodies (FIG. 2). The protein specific probe set comprising analyte-specific probes (1) including a binding element (T) such as the (hyper-) variable region of an antibody, that specifically interacts with the target protein to be detected, and the identifier element (T).

In a further application variant, at least one analyte is a nucleic acid and at least a second analyte is a protein and at least the first probe set binds to the nucleic acid sequence and at least the second probe set binds specifically to the protein analyte. Other combinations are possible as well.

An Embodiments of the general method of the present disclosure may be:

Step 1: Applying the at least 20 analyte- or target-specific probe sets. The target nucleic acid sequence is incubated with a probe set consisting of oligonucleotides with sequences complementary to the target nucleic acid. In this example, a probe set of 5 different probes is shown, each comprising a sequence element complementary to an individual subsequence of the target nucleic acid sequence (S1 to S5). In this example, the regions do not overlap. Each of the oligonucleotides targeting the same nucleic acid sequence comprises the identifier element or unique identifier sequence (T), respectively.

Step 2: Hybridization of the probe set. The probe set is hybridized to the target nucleic acid sequence under conditions allowing a specific hybridization. After the incubation, the probes are hybridized to their corresponding target sequences and provide the identifier element (T) for the next steps.

Step 3: Eliminating non-bound probes. After hybridization, the unbound oligonucleotides are eliminated, e.g. by washing steps.

Step 4: Applying the decoding oligonucleotides. The decoding oligonucleotides consisting of at least two sequence elements (t) and (c) are applied. While sequence element (t) is complementary to the unique identifier sequence (T), the sequence element (c) provides a region for the subsequent hybridization of signal oligonucleotides (translator element).

Step 5: Hybridization of decoding oligonucleotides. The decoding oligonucleotides are hybridized with the unique identifier sequences of the probes (T) via their complementary first sequence elements (t). After incubation, the decoding oligonucleotides provide the translator sequence element (c) for a subsequent hybridization step.

Step 6: Eliminating the excess of decoding oligonucleotides. After hybridization, the unbound decoding oligonucleotides are eliminated, e.g. by washing steps.

Step 7: Applying the signal oligonucleotide. The signal oligonucleotides are applied. The signal oligonucleotides comprise at least one second connector element (C) that is essentially complementary to the translator sequence element (c) and at least one signal element that provides a detectable signal (F).

Step 8: Hybridization of the signal oligonucleotides. The signal oligonucleotides are hybridized via the complementary sequence connector element (C) to the translator element (c) of decoding oligonucleotide. After incubation, the signal oligonucleotides are hybridized to their corresponding decoding oligonucleotides and provide a signal (F) that can be detected.

Step 9: Eliminating the excess of signal oligonucleotides. After hybridization, the unbound signal oligonucleotides are eliminated, e.g. by washing steps.

Step 10: Signal detection. The signals provided by the signal oligonucleotides are detected.

The following steps (steps 11 and 12) are unnecessary for the last detection round.

Step 11: Selective denaturation. The hybridization between the unique identifier sequence (T) and the first sequence element (t) of the decoding oligonucleotides is dissolved. The destabilization can be achieved via different mechanisms well known to the trained person like for example: increased temperature, denaturing agents, etc. The target- or analyte-specific probes are not affected by this step.

Step 12: Eliminating the denatured decoding oligonucleotides. The denatured decoding oligonucleotides and signal oligonucleotides are eliminated (e.g. by washing steps) leaving the specific probe sets with free unique identifier sequences, reusable in a next round of hybridization and detection (steps 4 to 10). This detection cycle (steps 4 to 12) is repeated at least four times until the planed encoding scheme is completed.

Another Embodiment of the general method of the present disclosure using multi-decoders may be (FIG. 16):

Step 1: Target nucleic acids: In this example three different target nucleic acids (A), (B) and (C) have to be detected and differentiated by using only two different types of signal oligonucleotides. Before starting the experiment, a certain encoding scheme is set. In this example, the three different nucleic acid sequences are encoded by three rounds of detection with three different signal types (1), (2) and (½) and a resulting hamming distance of 3 to allow for error detection. The planed code words are:

sequence A: (1)-(1)-(2)

sequence B: (2)-(2)-(½)

sequence C: (½)-(½)-(1)

Step 2: Hybridization of the probe sets: For each target nucleic acid, an own probe set is applied, specifically hybridizing to the corresponding nucleic acid sequence of interest. Each probe set provides a unique identifier sequence (T1), (T2) or (T3). This way each different target nucleic acid is uniquely labeled. In this example sequence (A) is labeled with (T1), sequence (B) with (T2) and sequence (C) with (T3). The illustration in FIG. 16 summarizes Steps 1 to 3 of FIG. 3.

Step 3: Hybridization of the decoding oligonucleotides and multi-decoders: For each unique identifier present, a certain decoding oligonucleotide or multi-decoder is applied specifically hybridizing to the corresponding unique identifier sequence by its first sequence element (here (t1) to (T1), (t2) to (T2) and (t3) to (T3)). Each of the decoding oligonucleotides or multi-decoders provides a translator or two translator elements that define the signals that will be generated after hybridization of signal oligonucleotides. Here nucleic acid sequence (A) is labeled with (c1), (B) is labeled with (c2) and (C) is labeled with both translator elements (c1) and (c2) resulting in the signal (½). The illustration in FIG. 16 summarizes steps 4 to 6 of FIG. 3.

Step 4: Hybridization of signal oligonucleotides: For each type of translator element, a signal oligonucleotide with a certain signal, differentiable from signals of other signal oligonucleotides, is applied. This signal oligonucleotide can specifically hybridize to the corresponding translator element. The illustration in FIG. 16 summarizes steps 7 to 9 of FIG. 3.

Step 5: Signal detection for the encoding scheme: The different signals are detected. Note that in this example the nucleic acids (A), (B) and (C) can already be distinguished after the first round of detection. This is in contrast to the step 5 of FIG. 5 explained by the additional signal type (½) that can be realized due to multi-decoders. Although nucleic acid sequences can already be distinguished, the additional rounds contribute to the planned hamming distance of 3. The illustration in FIG. 16 corresponds to step 10 of FIG. 3.

Step 6: Selective denaturation: The decoding (and signal) oligonucleotides and/or multi-decoders of all nucleic acid sequences to be detected are selectively denatured and eliminated as described in steps 11 and 12 of FIG. 3. Afterwards the unique identifier sequences of the different probe sets can be used for the next round of hybridization and detection.

Step 7: Second round of detection: A next round of hybridization and detection is done as described in steps 3 to 5. Note that in this new round the mix of different decoding oligonucleotides and multi-decoders is changed. For example, decoding oligonucleotide of nucleic acid sequence (A) used in the first round comprised of sequence elements (t1) and (c1) while the new multi decoder of round 2 comprises of the sequence elements (t1), (c1) and (c2). Note that now a hamming distance of 2 is already given after 2 rounds, which is the final result of the example in FIG. 3 after 3 rounds.

Step 8: Third round of detection: Again, a new combination of decoding oligonucleotides and/or multi-decoders is used leading to new signal combinations. After signal detection, the resulting code words for the three different nucleic acid sequences are not only unique and therefore distinguishable but comprise a hamming distance of 3 to other code words. Due to the hamming distance, an error in the detection of the signals (signal exchange) would not result in a valid code word and therefore could be detected and because of hamming distance 3 also corrected, in contrast to the encoding scheme of FIG. 3. This way three different nucleic acids can be distinguished in three detection rounds with two different signals, allowing an error detection and correction.

Note that in every round of detection, the type of signal provided by a certain unique identifier is controlled by the use of a certain decoding oligonucleotide. As a result, the sequence of decoding oligonucleotides applied in the detection cycles transcribes the binding specificity of the probe set into a unique signal sequence.

Figure 4:
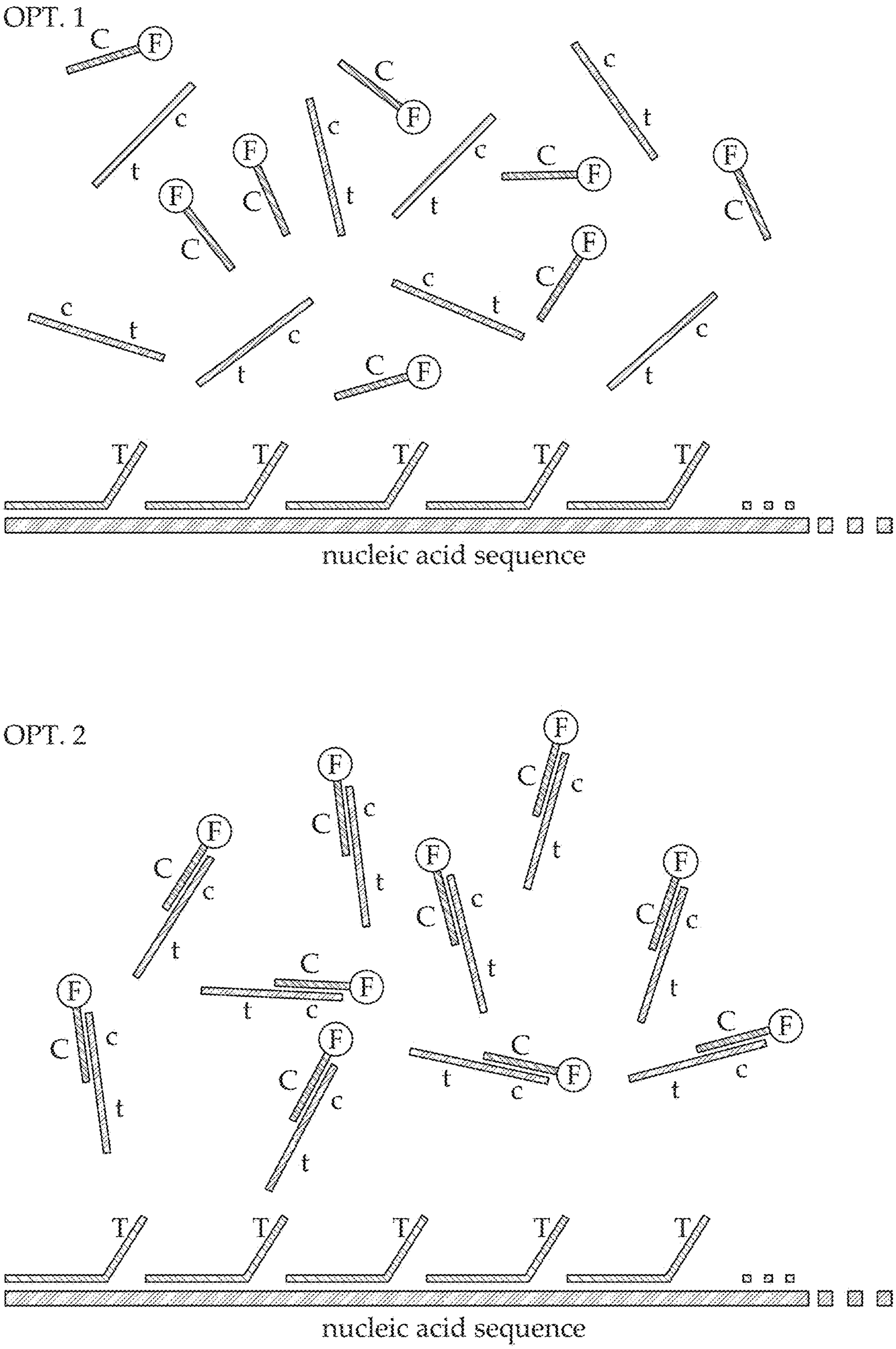
FIG. 4: Alternative options for the application of decoding and signal oligonucleotides.

The steps of decoding oligonucleotide hybridization (steps 4 to 6) and signal oligonucleotide hybridization (steps 7 to 9) can also be combined in two alternative ways as shown in FIG. 4.

Opt. 1: Simultaneous hybridization. Instead of the steps 4 to 9 of FIG. 3, specific hybridization of decoding oligonucleotides and signal oligonucleotides can also be done simultaneously leading to the same result as shown in step 9 of FIG. 3, after eliminating the excess decoding- and signal oligonucleotides.

Opt. 2: Preincubation. Additionally to option 1 of FIG. 3, decoding- and signal oligonucleotides can be preincubated in a separate reaction before being applied to the target nucleic acid with the already bound specific probe set.

Figure 3:
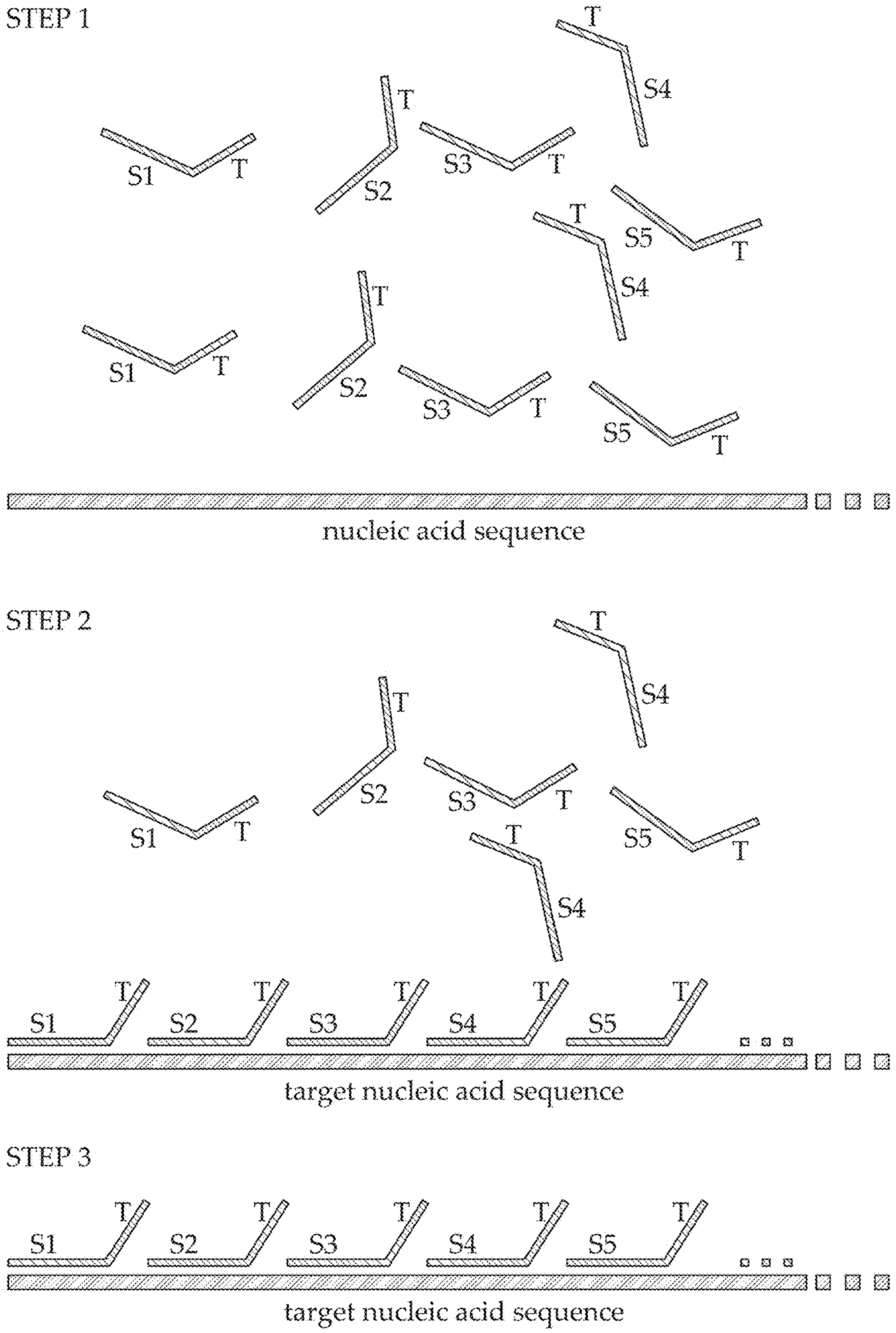
FIG. 3: Flowchart of the method according to the disclosure.
Figure 3:
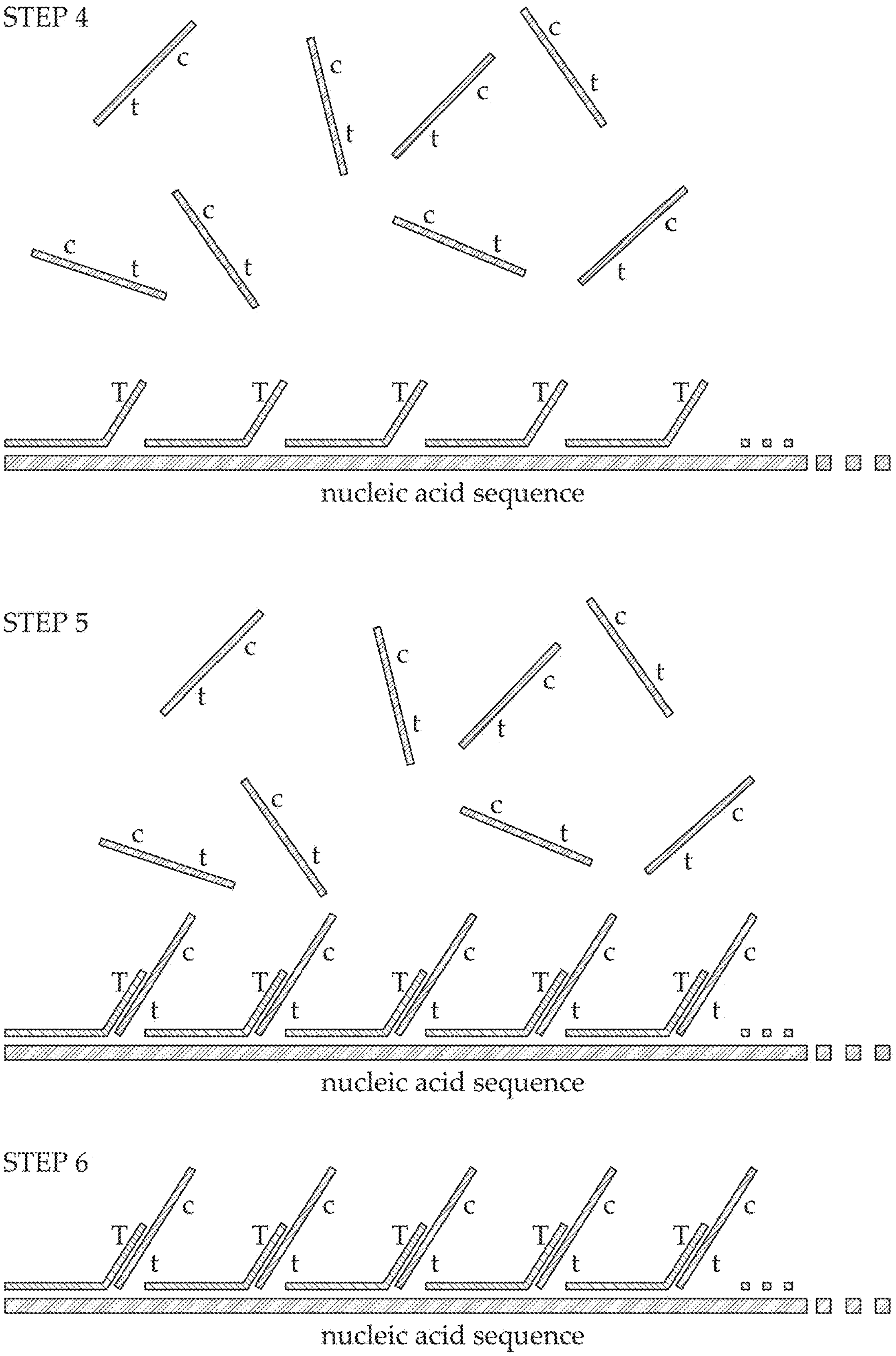
Figure 3:
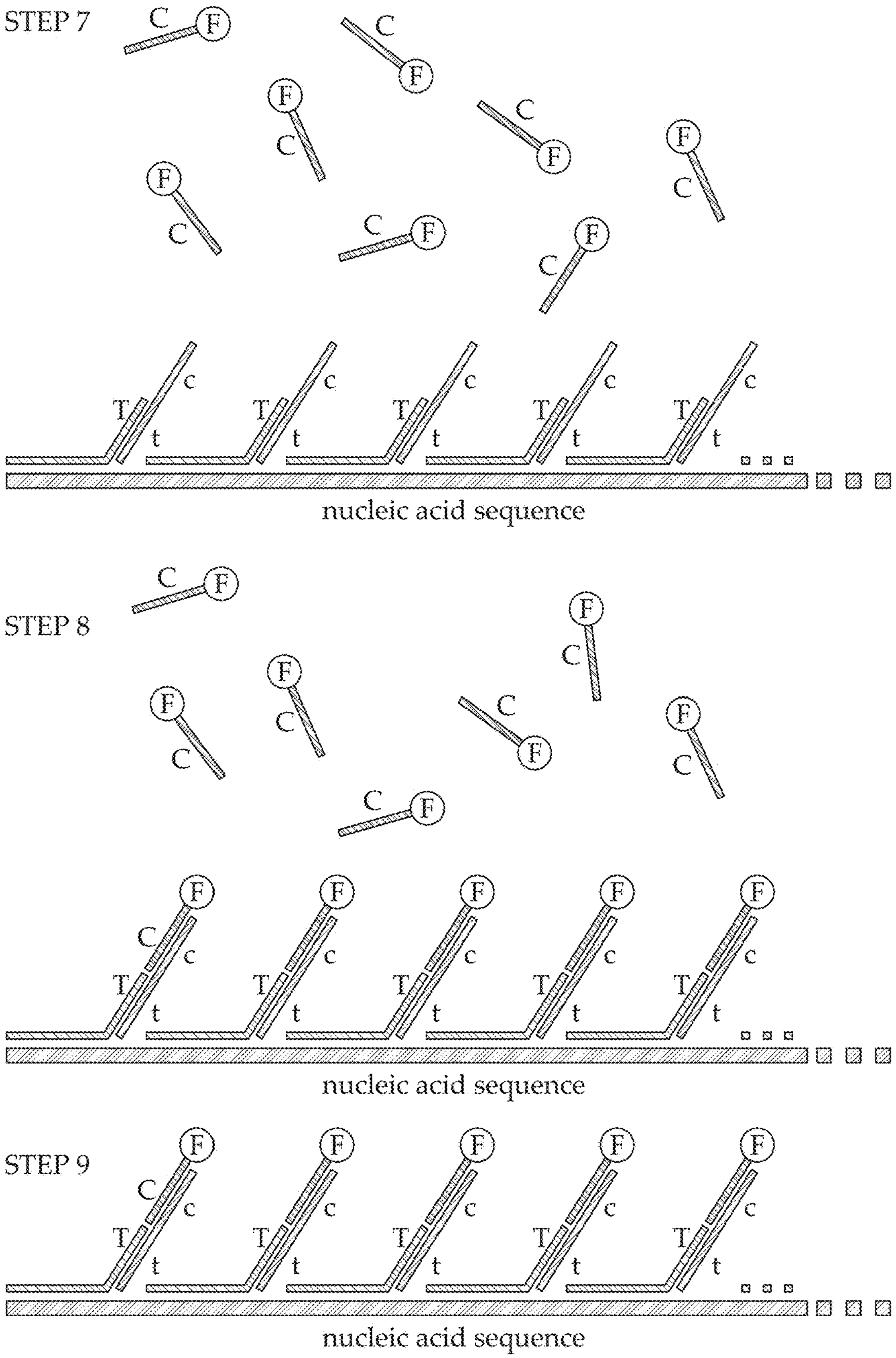
Figure 3:
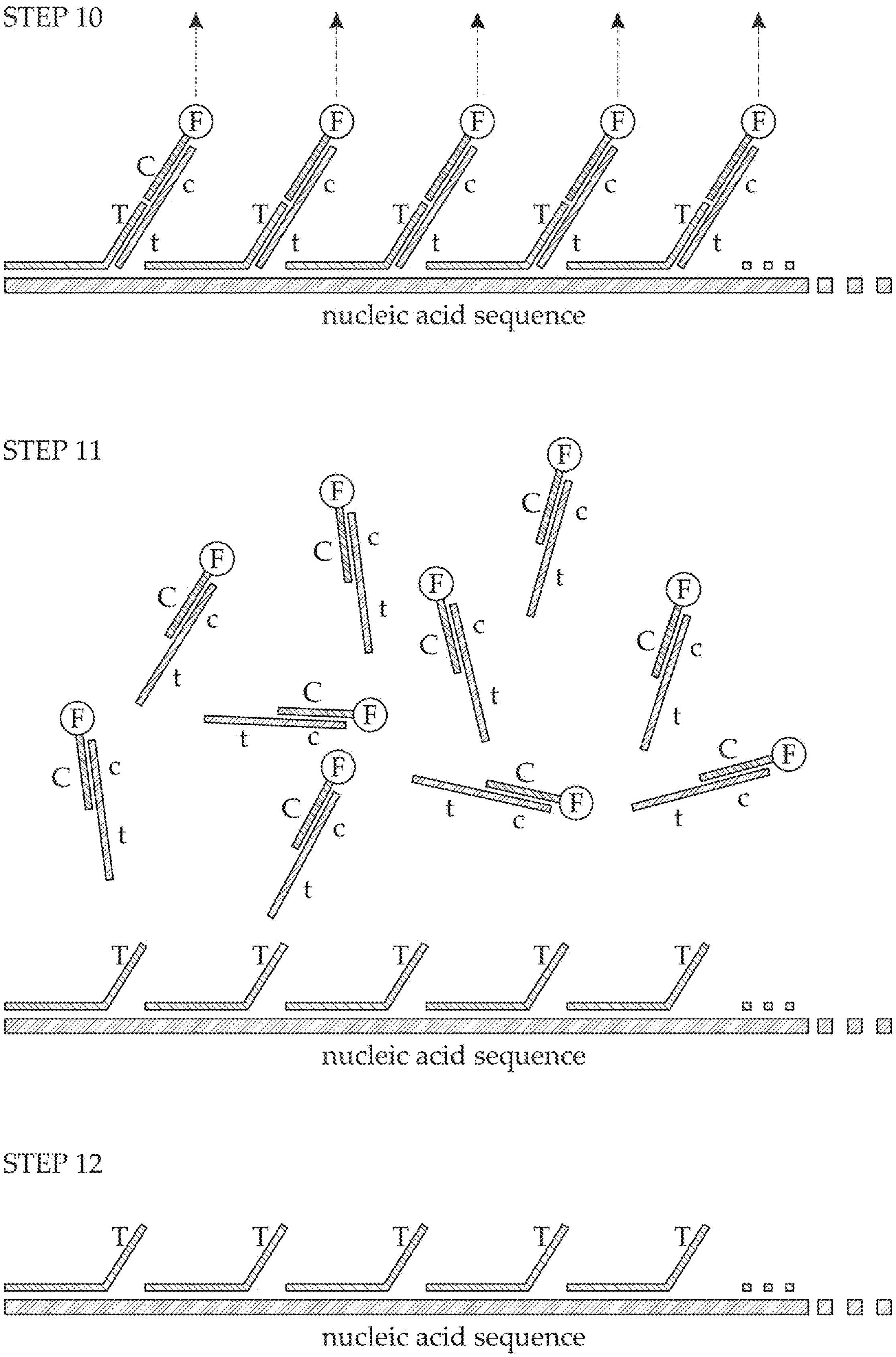
Figure 5:
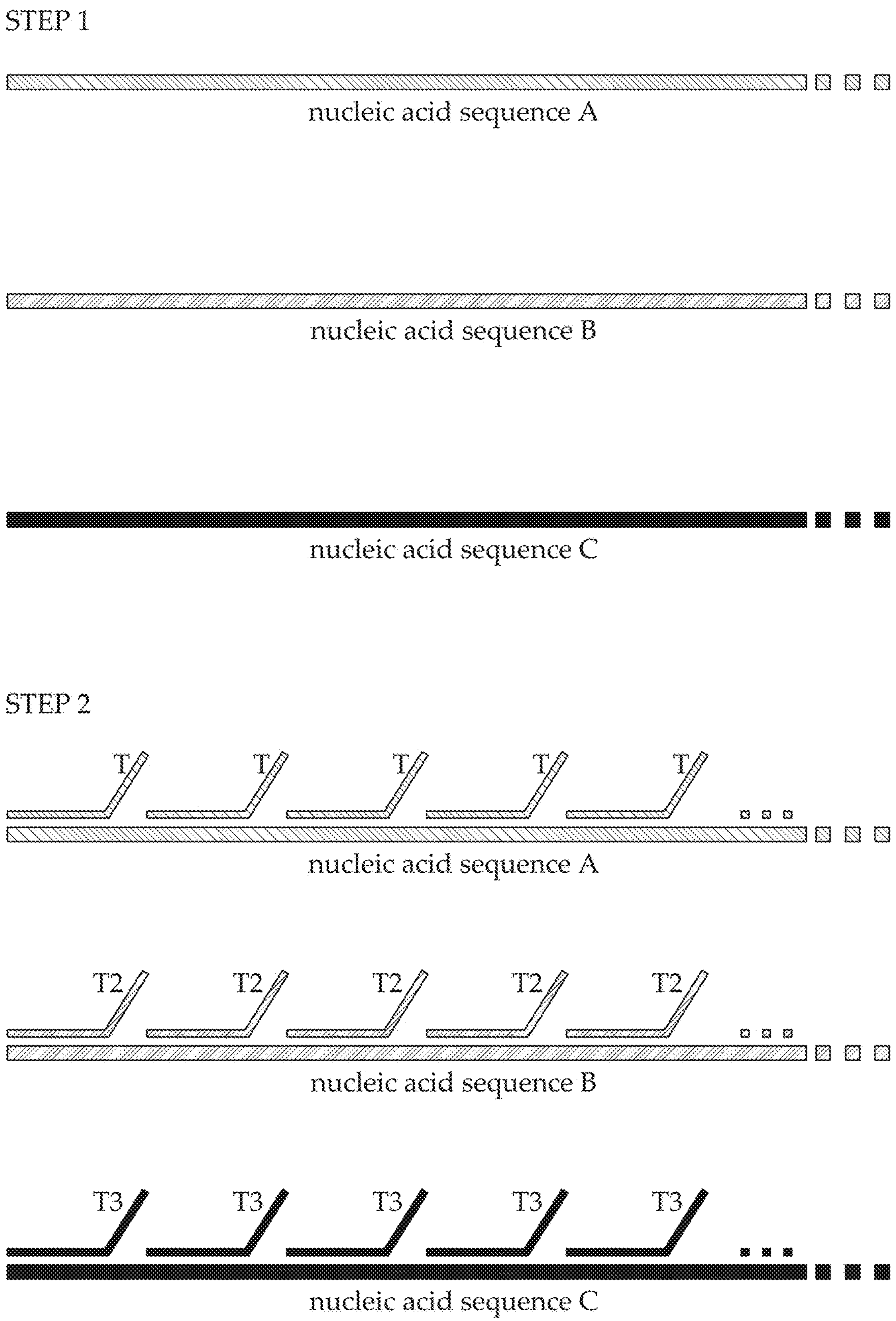
FIG. 5: Example for signal encoding of three different nucleic acid sequences by two different signal types and three detection rounds; in this example, the encoding scheme includes error detection.
Figure 5:
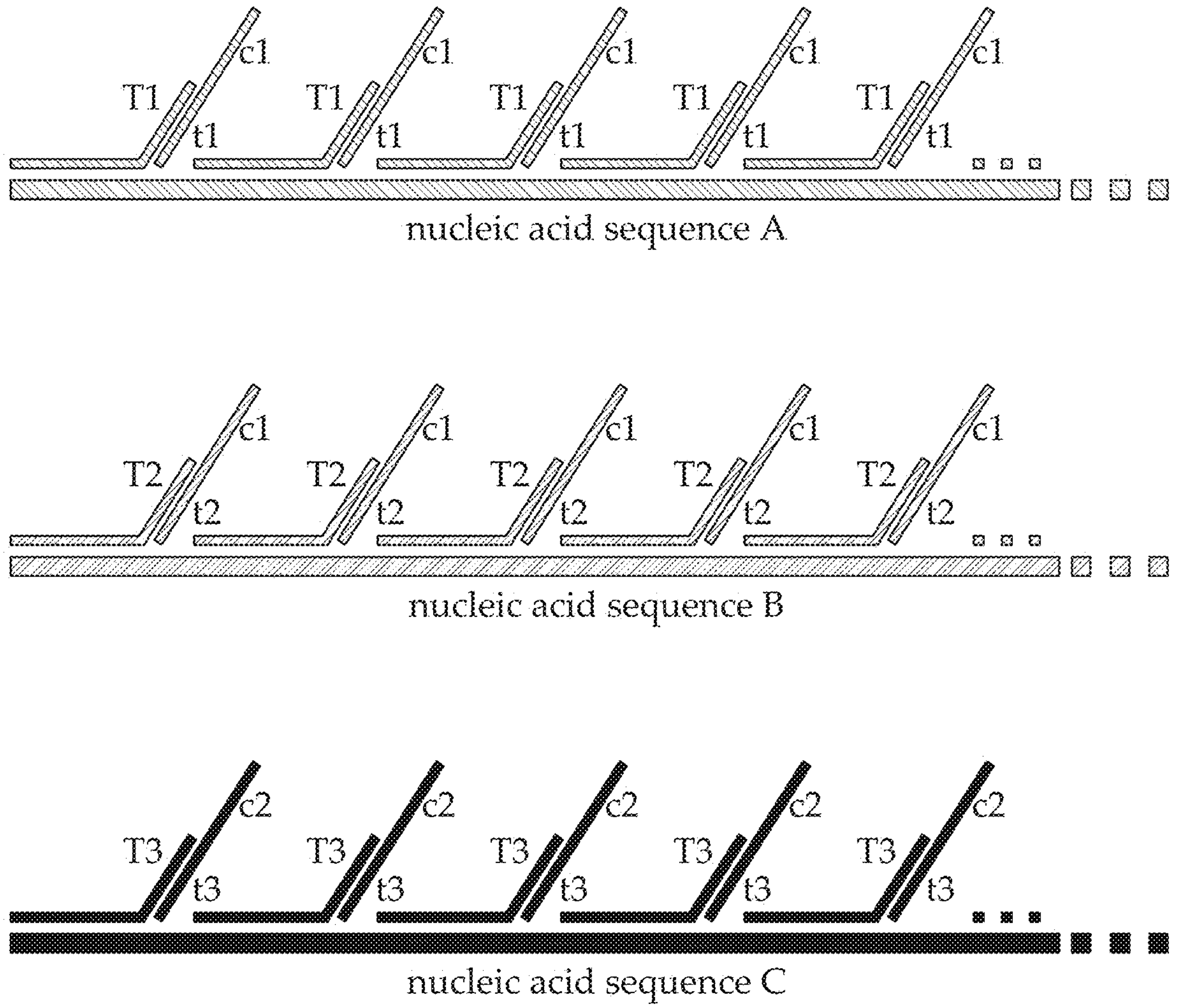
Figure 5:
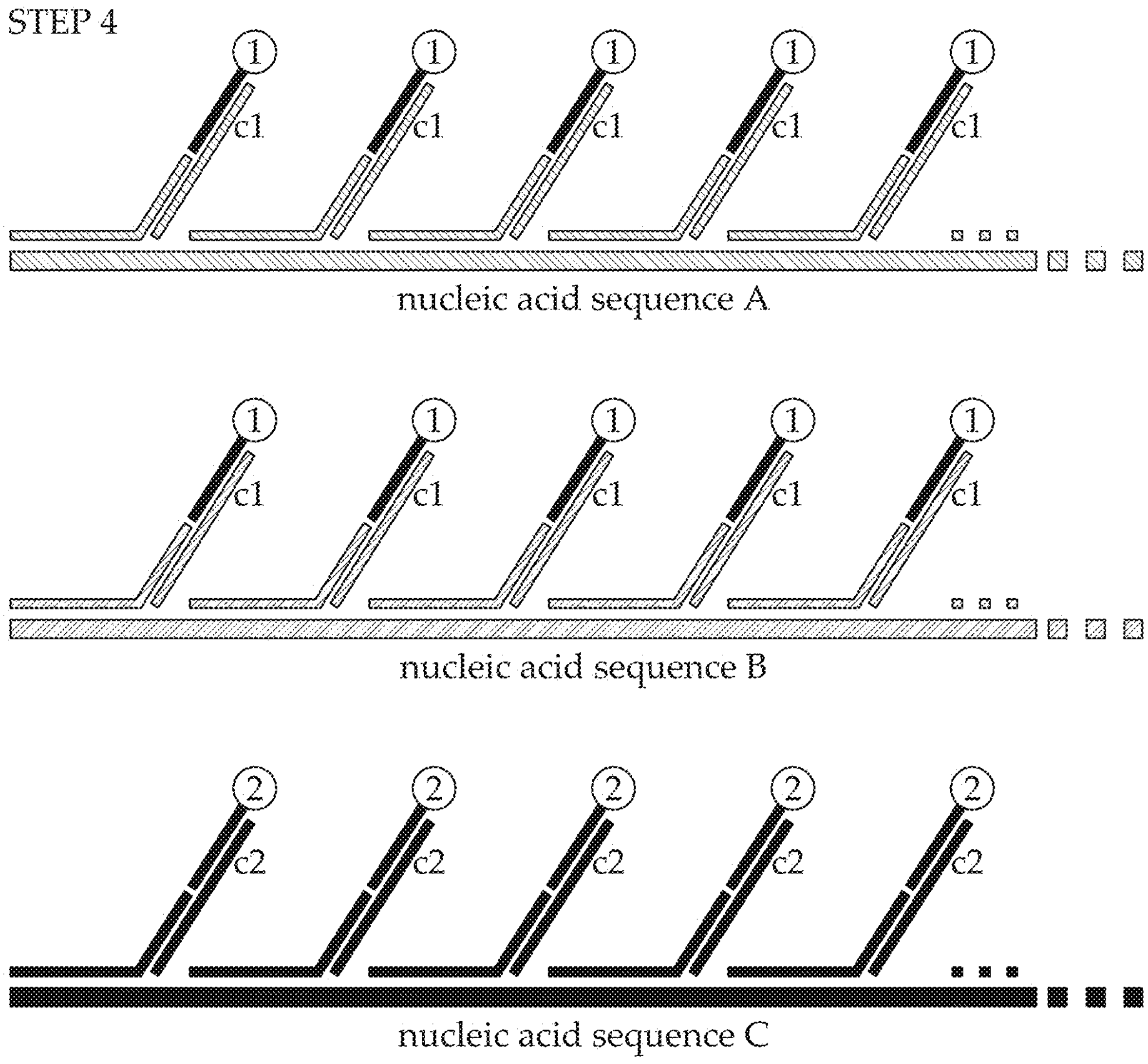
Figure 5:
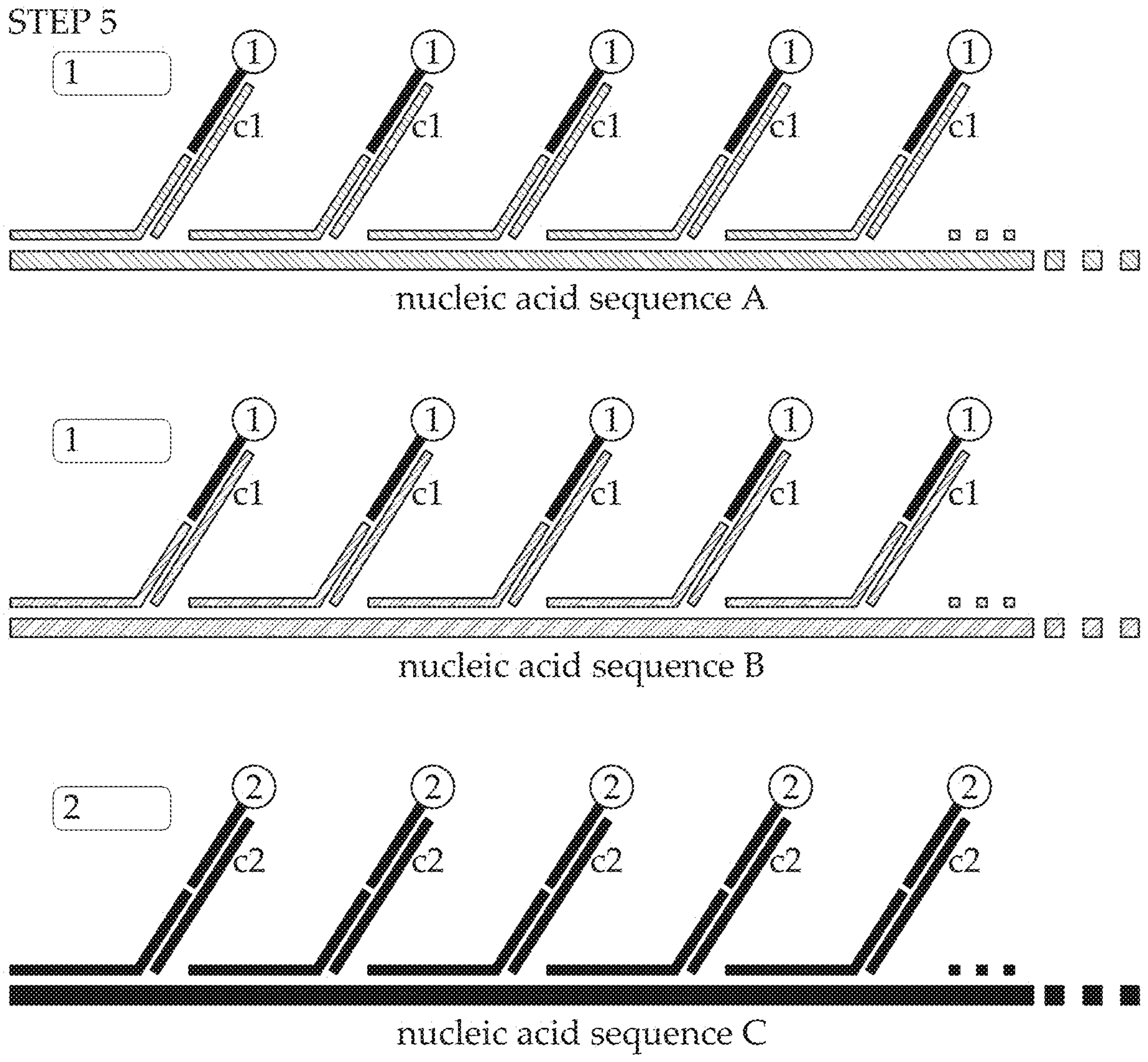
Figure 5:
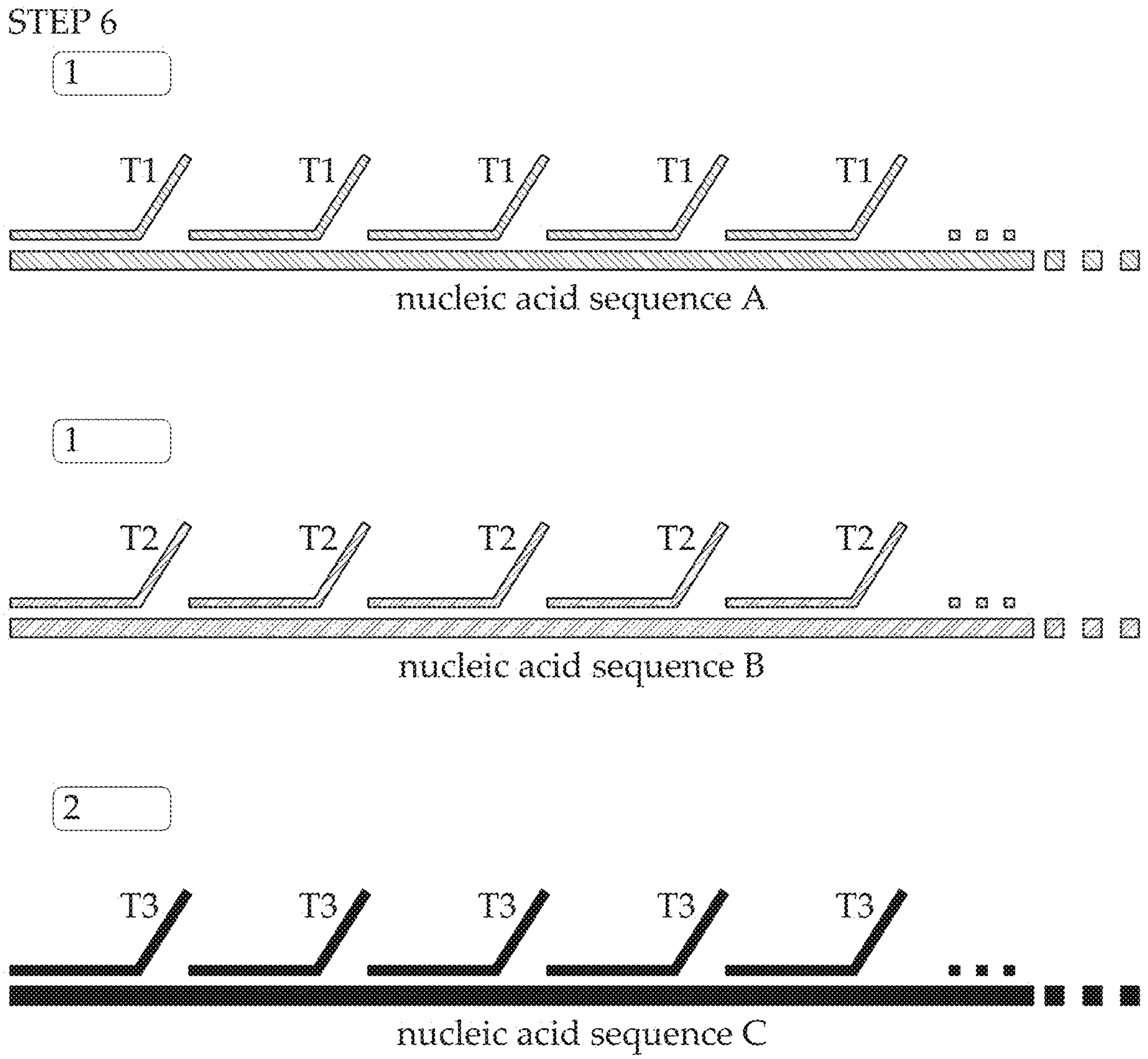
Figure 5:
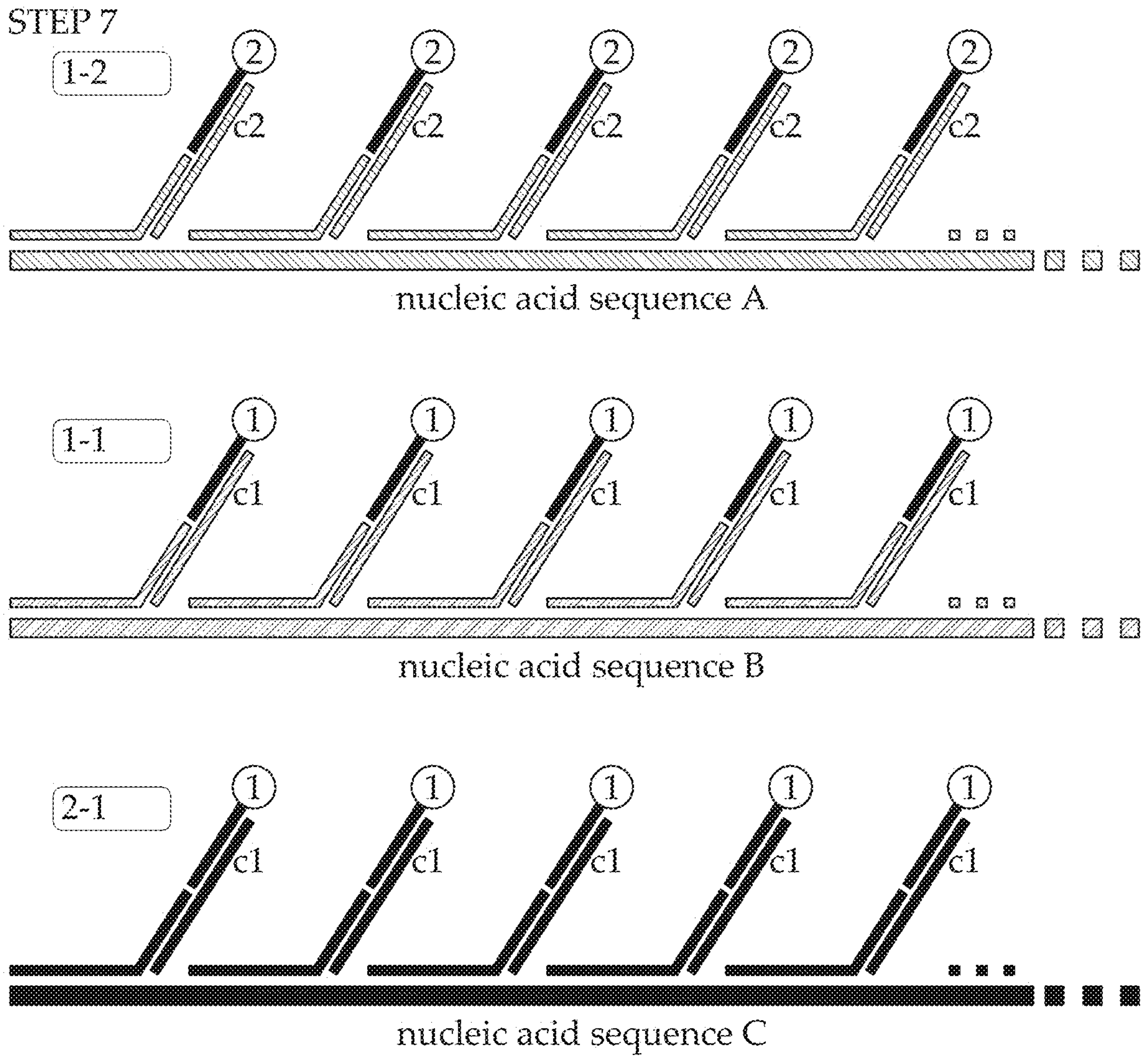
Figure 5:
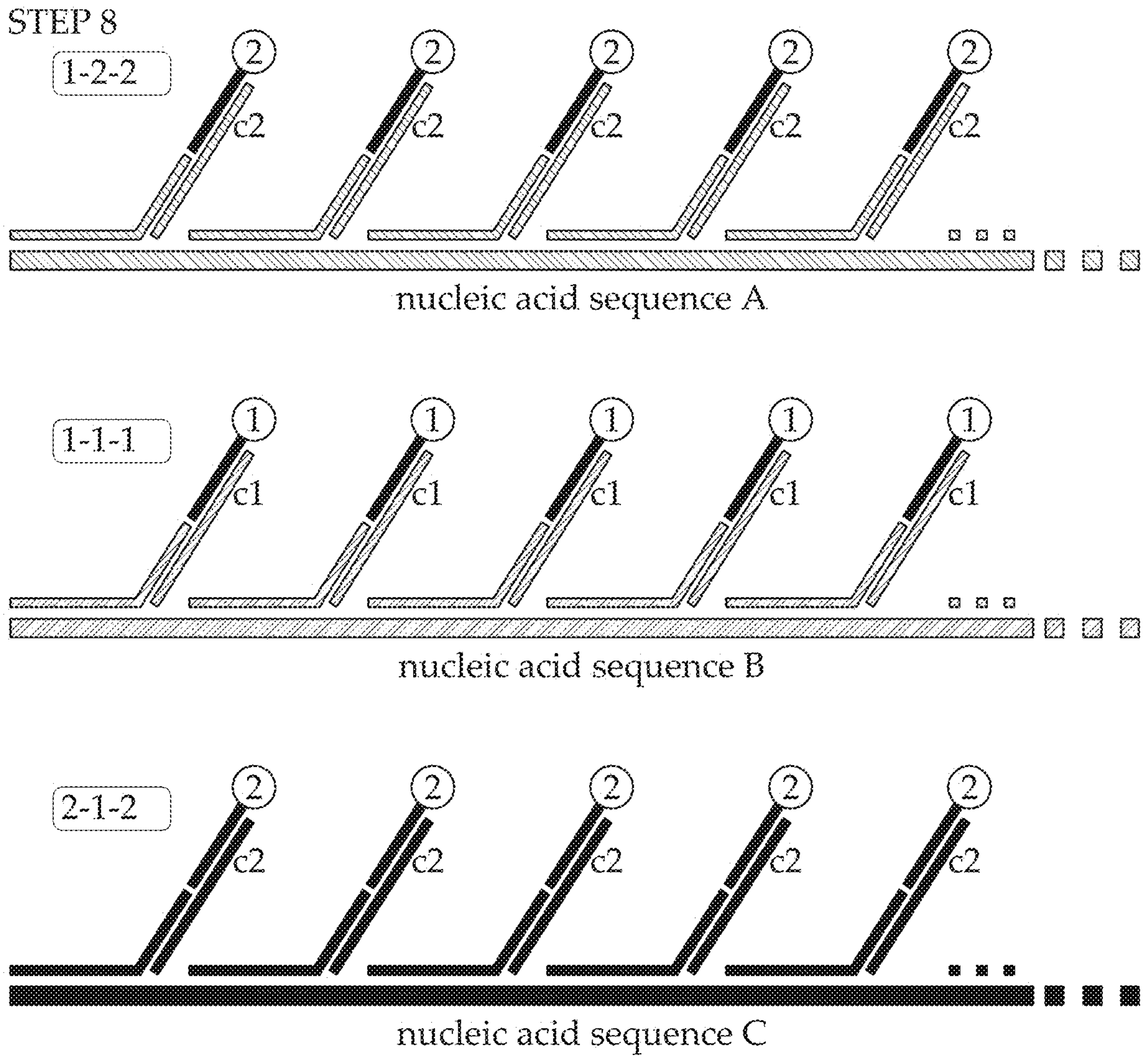

1. Example for Signal Encoding of Three Different Nucleic Acid Sequences by Two Different Signal Types and Three Detection Rounds FIG. 3 shows the general concept of generation and detection of specific signals mediated by decoding oligonucleotides. It does not show the general concept of encoding that can be achieved by this procedure. To illustrate the use of the process shown in FIG. 3 for the generation of an encoding scheme, FIG. 5 shows a general example for a multiple round encoding experiment with three different nucleic acid sequences. In this example, the encoding scheme includes error detection.

Step 1: Target nucleic acids. In this example three different target nucleic acids (A), (B) and (C) have to be detected and differentiated by using only two different types of signal. Before starting the experiment, a certain encoding scheme is set. In this example, the three different nucleic acid sequences are encoded by three rounds of detection with two different signals (1) and (2) and a resulting hamming distance of 2 to allow for error detection. The planed code words are:

sequence A: (1)-(2)-(2);
sequence B: (1)-(1)-(1);
sequence C: (2)-(1)-(2).

Step 2: Hybridization of the probe sets. For each target nucleic acid, an own probe set is applied, specifically hybridizing to the corresponding nucleic acid sequence of interest. Each probe set provides a unique identifier sequence (T1), (T2) or (T3). This way each different target nucleic acid is uniquely labeled. In this example sequence (T) is labeled with (T1), sequence (B) with (T2) and sequence (C) with (T3). The illustration summarizes steps 1 to 3 of FIG. 3.

Step 3: Hybridization of the decoding oligonucleotides. For each unique identifier present, a certain decoding oligonucleotide is applied specifically hybridizing to the corresponding unique identifier sequence by its first sequence element (here (t1) to (T1), (t2) to (T2) and (t3) to (T3)). Each of the decoding oligonucleotides provides a translator element that defines the signal that will be generated after hybridization of signal oligonucleotides. Here nucleic acid sequences (A) and (B) are labeled with the translator element (c1) and sequence (C) is labeled with (c2). The illustration summarizes steps 4 to 6 of FIG. 3.

Step 4: Hybridization of signal oligonucleotides. For each type of translator element, a signal oligonucleotide with a certain signal (2), differentiable from signals of other signal oligonucleotides, is applied. This signal oligonucleotide can specifically hybridize to the corresponding translator element. The illustration summarizes steps 7 to 9 of FIG. 3.

Step 5: Signal detection for the encoding scheme. The different signals are detected. Note that in this example the nucleic acid sequence (C) can be distinguished from the other sequences by the unique signal (2) it provides, while sequences (A) and (B) provide the same kind of signal (1) and cannot be distinguished after the first cycle of detection. This is due to the fact, that the number of different nucleic acid sequences to be detected exceeds the number of different signals available. The illustration corresponds to step 10 of FIG. 3.

Step 6: Selective denaturation. The decoding (and signal) oligonucleotides of all nucleic acid sequences to be detected are selectively denatured and eliminated as described in steps 11 and 12 of FIG. 3. Afterwards the unique identifier sequences of the different probe sets can be used for the next round of hybridization and detection.

Step 7: Second round of detection. A next round of hybridization and detection is done as described in steps 3 to 5. Note that in this new round the mix of different decoding oligonucleotides is changed. For example, decoding oligonucleotide of nucleic acid sequence (A) used in the first round comprised of sequence elements (t1) and (c1) while the new decoding oligonucleotide comprises of the sequence elements (t1) and (c2). Note that now all three sequences can clearly be distinguished due to the unique combination of first and second round signals.

Step 8: Third round of detection. Again, a new combination of decoding oligonucleotides is used leading to new signal combinations. After signal detection, the resulting code words for the three different nucleic acid sequences are not only unique and therefore distinguishable but comprise a hamming distance of 2 to other code words. Due to the hamming distance, an error in the detection of the signals (signal exchange) would not result in a valid code word and therefore could be detected. By this way three different nucleic acids can be distinguished in three detection rounds with two different signals, allowing error detection.

2. Advantages Over Prior Art Technologies

Coding Strategy

Compared to state-of-the-art methods, one particular advantage of the method according to the disclosure is the use of decoding oligonucleotides breaking the dependencies between the target specific probes and the signal oligonucleotides.

Without decoupling target specific probes and signal generation, two different signals can only be generated for a certain target if using two different molecular tags. Each of these molecular tags can only be used once. Multiple readouts of the same molecular tag do not increase the information about the target. In order to create an encoding scheme, a change of the target specific probe set after each round is required (SeqFISH) or multiple molecular tags must be present on the same probe set (like merFISH, intronSeqFISH).

Following the method according to the disclosure, different signals are achieved by using different decoding oligonucleotides reusing the same unique identifier (molecular tag) and a small number of different, mostly cost-intensive signal oligonucleotides. This leads to several advantages in contrast to the other methods.

(1) The encoding scheme is not defined by the target specific probe set as it is the case for all other methods of prior art. Here the encoding scheme is transcribed by the decoding oligonucleotides. This leads to a much higher flexibility concerning the number of rounds and the freedom in signal choice for the code words. Looking on the methods of prior art (e.g. merFISH or intronSeqFISH), the encoding scheme (number, type and sequence of detectable signals) for all target sequences is predefined by the presence of the different tag sequences on the specific probe sets (4 of 16 different tags per probe set in the case of merFISH and 5 of 60 different tags in the case of intron FISH). In order to produce a sufficient number of different tags per probe set, the methods use rather complex oligonucleotide designs with several tags present on one target specific oligonucleotide. In order to change the encoding scheme for a certain target nucleic acid, the specific probe set has to be replaced. The method according to the disclosure describes the use of a single unique tag sequence (unique identifier) per analyte, because it can be reused in every detection round to produce a new information. The encoding scheme is defined by the order of decoding oligonucleotides that are used in the detection rounds. Therefore, the encoding scheme is not predefined by the specific probes (or the unique tag sequence) but can be adjusted to different needs, even during the experiment. This is achieved by simply changing the decoding oligonucleotides used in the detection rounds or adding additional detection rounds.

(2) The number of different signal oligonucleotides must match the number of different tag sequences with methods of prior art (16 in the case of merFISH and 60 in the case of intronSeqFISH). Using the method according to the disclosure, the number of different signal oligonucleotides matches the number of different signals used. Due to this, the number of signal oligonucleotides stays constant for the method described here and never exceeds the number of different signals but increases with the complexity of the encoding scheme in the methods of prior art (more detection rounds more different signal oligonucleotides needed). As a result, the method described here leads to a much lower complexity (unintended interactions of signal oligonucleotides with environment or with each other) and dramatically reduces the cost of the assay since the major cost factor are the signal oligonucleotides.

(3) In the methods of prior art, the number of different signals generated by a target specific probe set is restricted by the number of different tag sequences the probe set can provide. Since each additional tag sequence increases the total size of the target specific probe, there is a limitation to the number of different tags a single probe can provide. This limitation is given by the size dependent increase of several problems (unintended inter- and intramolecular interactions, costs, diffusion rate, stability, errors during synthesis etc.). Additionally, there is a limitation of the total number of target specific probes that can be applied to a certain analyte. In case of nucleic acids, this limitation is given by the length of the target sequence and the proportion of suitable binding sites. These factors lead to severe limitations in the number of different signals a probe set can provide (4 signals in the case of merFISH and 5 signals in the case of intronSeqFISH). This limitation substantially affects the number of different code words that can be produced with a certain number of detection rounds. In the approach of the disclosure only one tag is needed and can be freely reused in every detection round. This leads to a low oligonucleotide complexity/length and at the same time to the maximum encoding efficiency possible (number of colors number of rounds). The vast differences of coding capacity of our method compared to the other methods is shown in FIGS. 1 and 5. Due to this in approach of the disclosure a much lower number of detection rounds is needed to produce the same amount of information. A lower number of detection rounds is connected to lower cost, lower experimental time, lower complexity, higher stability and success rate, lower amount of data to be collected and analyzed and a higher accuracy of the results.

Coding Capacity

All three methods compared in the Table 1 below use specific probe sets that are not denatured between different rounds of detection. For intronSeqFISH there are four detection rounds needed to produce the pseudo colors of one coding round, therefore data is only given for rounds 4, 8,12,16 and 20. The merFISH-method uses a constant number of 4 signals, therefore the data starts with the smallest number of rounds possible. After 8 detection rounds our method exceeds the maximum coding capacity reached with 20 rounds of merFISH (depicted with one asterisk) and after 12 rounds of detection the maximum coding capacity of intron FISH is exceeded (depicted with two asterisks). For the method according to the disclosure usage of 3 different signals is assumed (as is with intronSeqFISH).

TABLE 1

Comparison of coding capacity

| | CODING CAPACITY | | |
|---|---|---|---|
| NUMBER OF ROUNDS: | Method of the present disclosure | intron FISH | merFISH |
| 1 | 3 | — | — |
| 2 | 9 | — | — |
| 3 | 27 | — | — |
| 4 | 81 | 12 | 1 |
| 5 | 243 | — | 5 |
| 6 | 729 | — | 15 |
| 7 | 2187 | — | 35 |
| 8* | 6561 | 144 | 70 |
| 9 | 19683 | — | 126 |
| 10 | 59049 | — | 210 |
| 11 | 177147 | — | 330 |
| 12** | 531441 | 1728 | 495 |
| 13 | 1594323 | — | 715 |
| 14 | 4782969 | — | 1001 |
| 15 | 14348907 | — | 1365 |
| 16 | 43046721 | 20736 | 1820 |
| 17 | 129140163 | — | 2380 |
| 18 | 387420489 | — | 3060 |
| 19 | 1162261467 | — | 3876 |
| 20 | 3486784401 | 248832 | 4845 |

Figure 6:
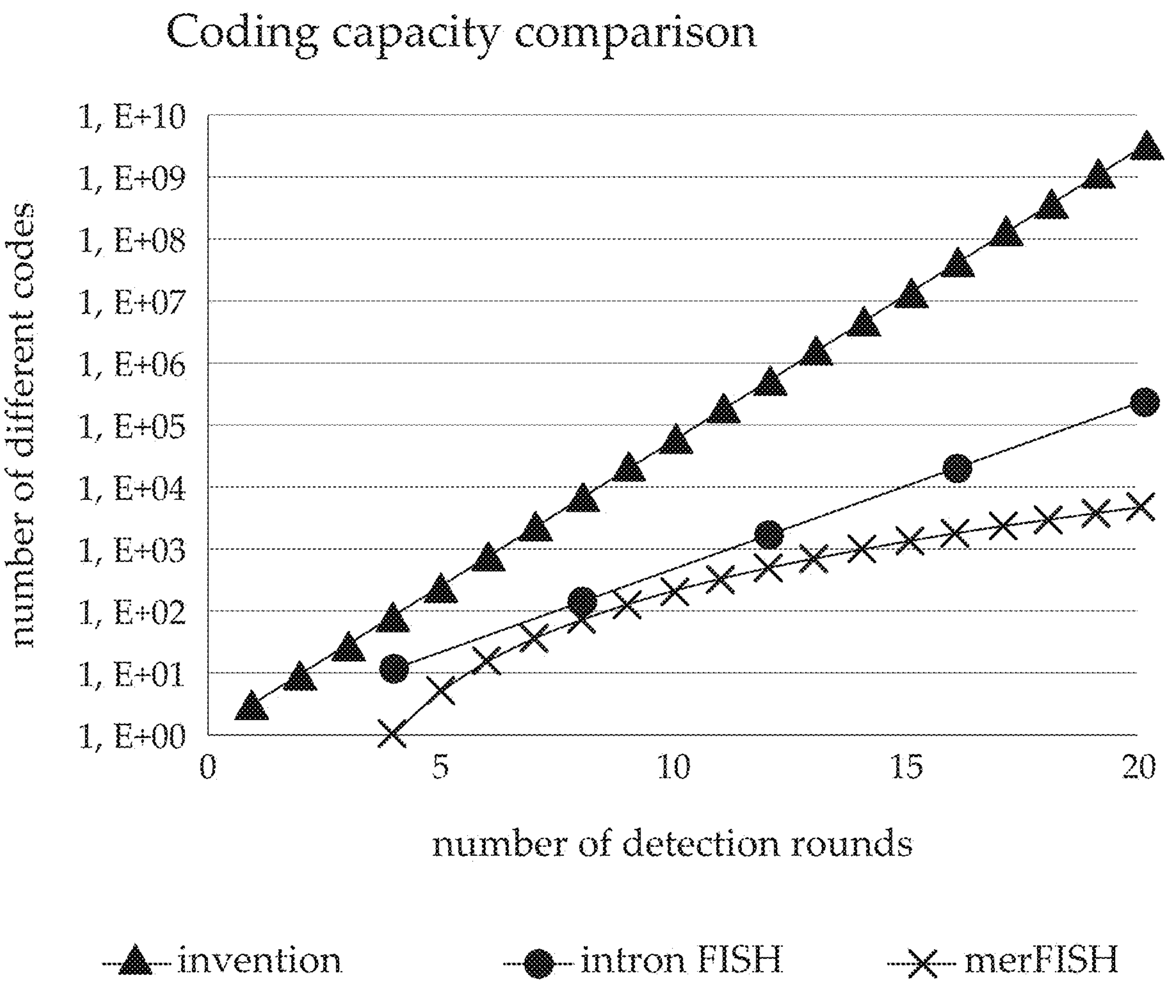
FIG. 6: Number of generated code words (logarithmic scale) against number of detection cycles.

As shown in FIG. 6 the number of code words for merFISH does not exponentially increase with the number of detection cycles but gets less effective with each added round. In contrast, the number of code words for intronSeqFISH in the method according to the disclosure increases exponentially. The slope of the curve for the proposed method is much higher than that of intron FISH, leading to more than 10,000 times more code words usable after 20 rounds of detection.

Note that this maximum efficiency of coding capacity is also reached in case of seqFISH, where specific probes are denatured after every detection round and a new probe set is specifically hybridized to the target sequence for each detection round. However, this method has major downsides to technologies using only one specific hybridization for their encoding scheme (all other methods):

(1) For the efficient denaturation of the specific probes, rather crude conditions must be used (high temperatures, high concentrations of denaturing agent, long incubation times) leading to much higher probability for the loss or the damage of the analyte.

(2) For each round of detection an own probe set has to be used for every target nucleic acid sequence. Therefore, the number of specific probes needed for the experiment scales with the number of different signals needed for the encoding scheme. This dramatically increases the complexity and the cost of the assay.

(3) Because the hybridization efficiency of every target nucleic acid molecule is subject to some probabilistic effects, the fluctuations of signal intensity between the different detection rounds is much higher than in methods using only one specific hybridization event, reducing the proportion of complete codes.

(4) The time needed for the specific hybridization is much longer than for the hybridization of signal oligonucleotides or decoding oligonucleotides (as can be seen in the method parts of the intronSeqFISH, merFISH and seqFISH publications), which dramatically increases the time needed to complete an experiment.

Due to these reasons all other methods use a single specific hybridization event and accept the major downside of lower code complexity and therefore the need of more detection rounds and a higher oligonucleotide design complexity.

The method according to the disclosure combines the advantages of seqFISH (mainly complete freedom concerning the encoding scheme) with all advantages of methods using only one specific hybridization event while eliminating the major problems of such methods.

Note that the high numbers of code words produced after 20 rounds can also be used to introduce higher hamming distances (differences) between different code words, allowing error detection of 1, 2 or even more errors and even error corrections. Therefore, even very high coding capacities are still practically relevant.

Figure 17:
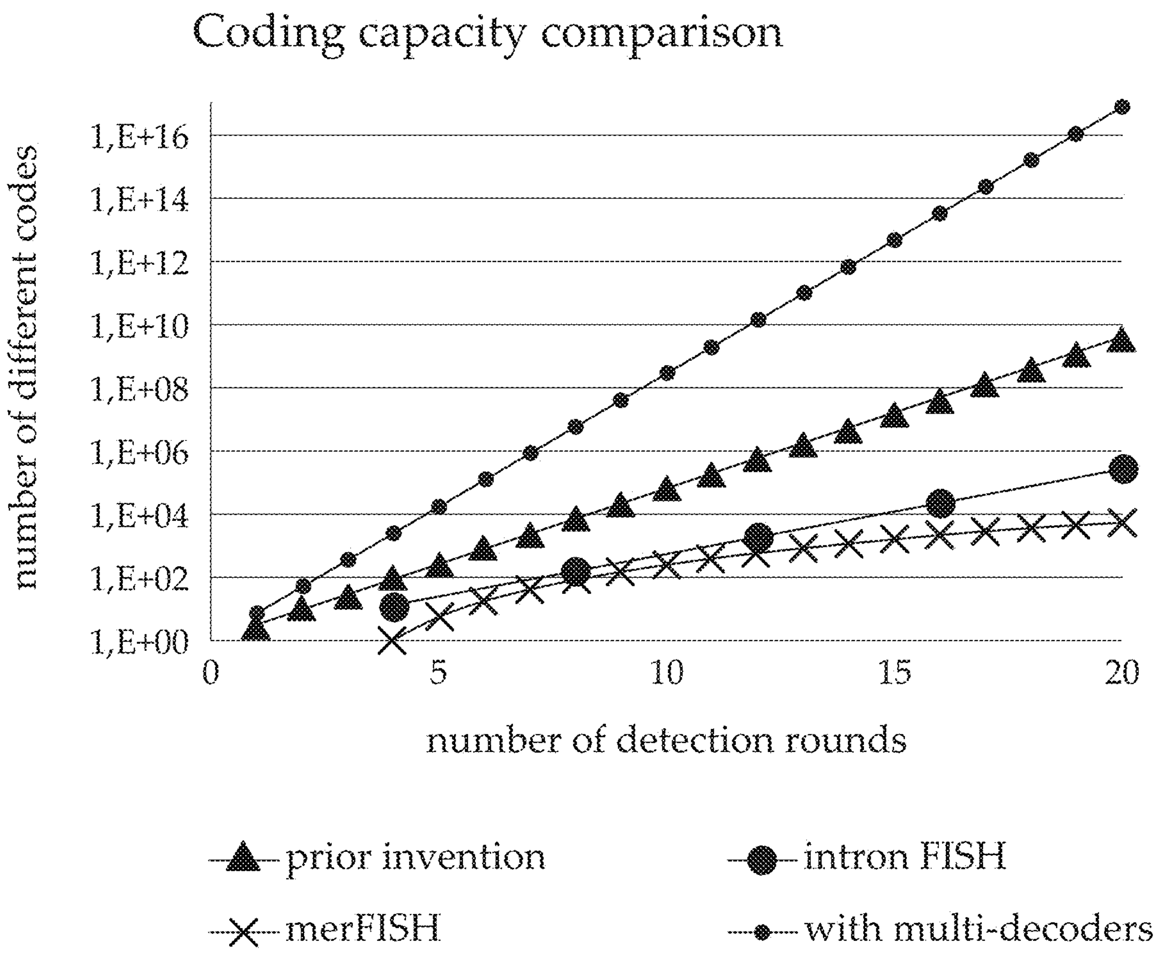
FIG. 17: Number of generated code words (logarithmic scale) against number of detection cycles. The number of code words for merFISH does not exponentially increase with the number of detection cycles but gets less effective with each added round. In contrast, the number of code words for intronSeqFISH, the method of the present disclosure without using multi-decoders, the method with multi-decoders increases exponentially. The slope of the curve for the method using multi-decoders is much higher than that of the prior invention, leading to more than 20 000 000 times more code words usable after 20 rounds of detection.

As mentioned above, the usage of multi-decoders further increases the coding capacity of the encoding scheme. Instead of being limited to the having exactly the same number of different signal types as different signal oligonucleotides and corresponding translator elements, the use of multi-decoders increases the signal types that can be used to: (N×(N+1))/2 (with N being the number of different signal oligonucleotides used). For the code used in table 1 with 3 different signal oligonucleotides this would mean the following 7 different signal types could be used: (S1), (S2), (S3), (S1/S2), (S1/S3), (S2/S3), (S1/S2/S3). The effect to the coding efficiency can be seen in Table 1b and FIG. 17.

| NUMBER OF ROUNDS: | CODING CAPACITY Method of the present disclosure | Method of the present disclosure with multi-decoders | intron FISH | merFISH |
|---|---|---|---|---|
| 1 | 3 | 7 | — | — |
| 2 | 9 | 49 | — | — |
| 3 | 27 | 343 | — | — |
| 4 | 81 | 2401 | 12 | 1 |
| 5* | 243 | 16807 | — | 5 |

-continued

| NUMBER OF ROUNDS: | CODING CAPACITY Method of the present disclosure | Method of the present disclosure with multi-decoders | intron FISH | merFISH |
|---|---|---|---|---|
| 6 | 729 | 117649 | — | 15 |
| 7** | 2187 | 823543 | — | 35 |
| 8 | 6561 | 5764801 | 144 | 70 |
| 9 | 19683 | 40353607 | — | 126 |
| 10 | 59049 | 282475249 | — | 210 |
| 11 | 177147 | 1977326743 | — | 330 |
| 12*** | 531441 | 1,3841 x 10^10 | 1728 | 495 |
| 13 | 1594323 | 9,6889 x 10^10 | — | 715 |
| 14 | 4782969 | 6,7822 x 10^11 | — | 1001 |
| 15 | 14348907 | 4,7476 x 10^12 | — | 1365 |
| 16 | 43046721 | 3,3233 x 10^13 | 20736 | 1820 |
| 17 | 129140163 | 2,3263 x 10^14 | — | 2380 |
| 18 | 387420489 | 1,6284 x 10^15 | — | 3060 |
| 19 | 1162261467 | 1,1399 x 10^16 | — | 3876 |
| 20 | 3486784401 | 7,9792 x 10^16 | 248832 | 4845 |

Table 1b shows the coding capacity of the four methods. All four methods compared in the table use specific probe sets that are not denatured between different rounds of detection. For intronSeqFISH there are four detection rounds needed to produce the pseudo colors of one coding round, therefore data is only given for rounds 4, 8,12,16 and 20. The merFISH-method uses a constant number of 4 signals, therefore the data starts with the smallest number of rounds possible. After 4 detection rounds the method with multi-decoders as described here exceeds the maximum coding capacity reached with 20 rounds of merFISH (depicted with one asterisk), after 7 rounds of detection the maximum coding capacity of intron FISH is exceeded (depicted with two asterisks) and after 12 rounds of detection the maximum coding capacity of the method of the present disclosure is exceeded (depicted with three asterisks). The usage of 3 different signal oligonucleotides is assumed (as is with intronSeqFISH).

3. Selective Denaturation, Oligonucleotide Assembly and Reuse of Unique Identifiers are Surprisingly Efficient A key factor of the method according to the disclosure is the consecutive process of decoding oligonucleotide binding, signal oligonucleotide binding, signal detection and selective denaturation. In order to generate an encoding scheme, this process has to be repeated several times (depending on the length of the code word). Because the same unique identifier is reused in every detection cycle, all events from the first to the last detection cycle are depending on each other. Additionally, the selective denaturation depends on two different events: While the decoding oligonucleotide has to be dissolved from the unique identifier with highest efficiency, specific probes have to stay hybridized with highest efficiency.

Due to this the efficiency E of the whole encoding process can be described by the following equation:

$$E=B_{sp}\times(B_{de}\times B_{si}\times E_{de}\times S_{sp})^{n}$$

E=total efficiency $B_{sp}$=binding of specific probes $B_{de}$=binding of decoding oligonucleotides $B_{si}$=binding of signal oligonucleotides $E_{de}$=elimination of decoding oligonucleotides $S_{sp}$=stability of specific probes during elimination process n=number of detection cycles Based on this equation the efficiency of each single step can be estimated for a given total efficiency of the method. The calculation is hereby based on the assumption, that each process has the same efficiency. The total efficiency describes the portion of successfully decodable signals of the total signals present.

Figure 7:
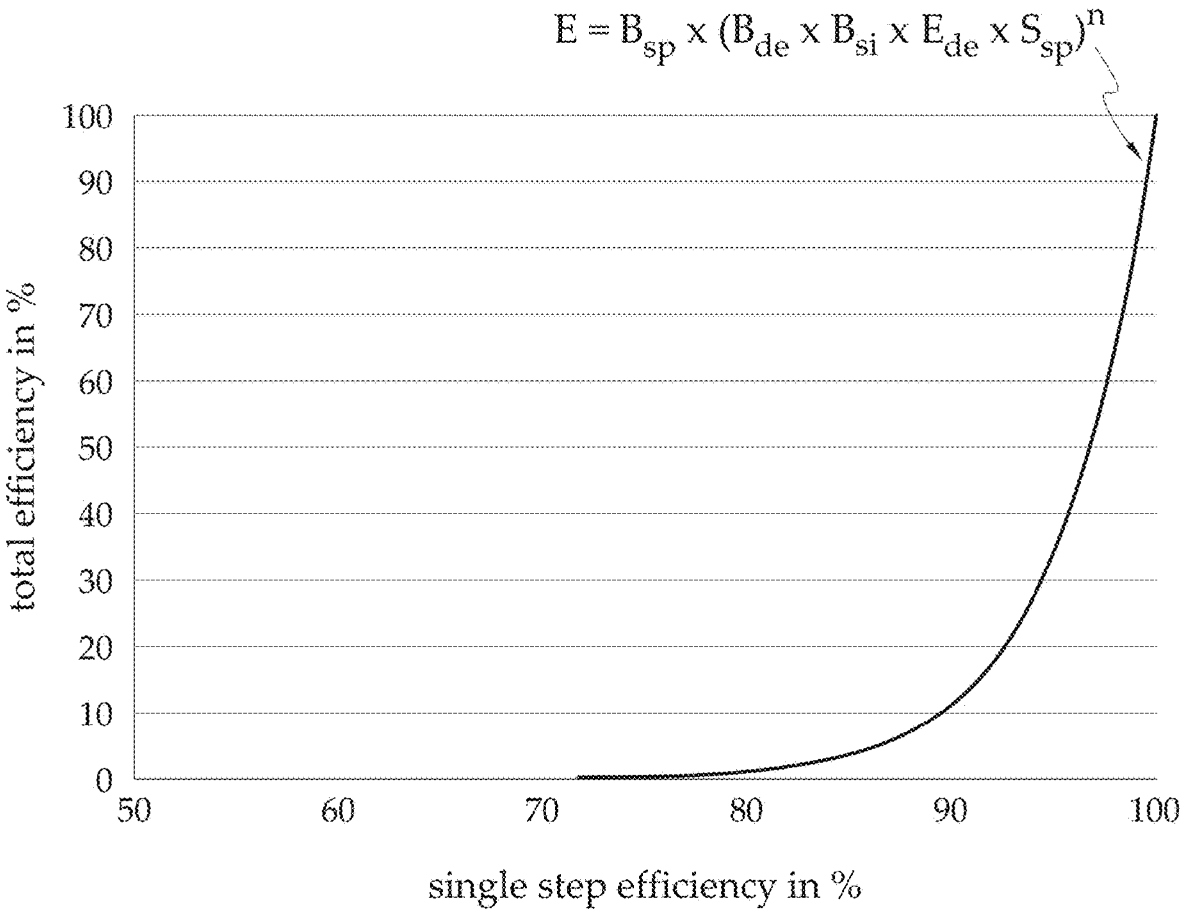
FIG. 7: Calculated total efficiency of a 5-round encoding scheme based on single step efficiencies.

The total efficiency of the method is dependent on the efficiency of each single step of the different factors described by the equation. Under the assumption of an equally distributed efficiency the total efficiency can be plotted against the single step efficiency as shown in FIG. 7. As can be seen, a practically relevant total efficiency for an encoding scheme with 5 detection cycles can only be achieved with single step efficiencies clearly above 90%. For example, to achieve a total efficiency of 50% an average efficiency within each single step of 97.8% is needed. These calculations are even based on the assumption of a 100% signal detection and analysis efficiency. Due to broad DNA melting curves of oligonucleotides of a variety of sequences, the inventors assumed prior to experiments that the selective denaturation would work less efficient for denaturation of decoding oligonucleotides and that sequence specific binding probes are not stable enough. In contrast to this assumption, we found a surprising effectiveness of all steps and a high stability of sequence specific probes during selective denaturation.

Experimentally, the inventors achieved a total decoding efficiency of about 30% to 65% based on 5 detection cycles. A calculation of the efficiency of each single step (Bsp, Bde, Bsi, Ede, Ssp) by the formula given above revealed an average efficiency of about 94.4% to 98%. These high efficiencies are very surprising and cannot easily be anticipated by a well-trained person in this field.

4. Experimental Data

BACKGROUND

The experiment shows the specific detection of 10 to 50 different mRNAs species in parallel with single molecule resolution. It is based on 5 detection cycles, 3 different fluorescent signals and an encoding scheme without signal gaps and a hamming distance of 2 (error detection). The experiment proofs the enablement and functionality of the method according to the disclosure.

Oligonucleotides and their Sequences

All oligonucleotide sequences used in the experiment (target specific probes, decoding oligonucleotides, signal oligonucleotides) are listed in the sequence listing of the appendix. The signal oligonucleotide R: ST05*O_Atto594 was ordered from biomers.net GmbH. All other oligonucleotides were ordered from Integrated DNA Technologies. Oligonucleotides were dissolved in water. The stock solutions (100 μM) were stored at −20° C.

Experimental Overview

The 50 different target specific probe sets are divided into 5 groups. The name of the transcript to be detected and the name of the target specific probe set are the same (transcript variant names of www.ensemble.org). The term "new" indicates a revised probe design. All oligonucleotide sequences of the probe sets can be found in the sequence listing. The table lists the unique identifier name of the probe set as well as the names of the decoding oligonucleotides used in the different detection cycles. The resulting code shows the sequence of fluorescent signals generated during the 5 detection cycles (G(reen)=Alexa Fluor 488, O(range)=Atto 594, Y(ellow)=Alexa Fluor 546).

TABLE 2

Experimental overview

| target transcript | unique identifier | Decoding oligonucleotides in detection cycle: 1 | 2 | 3 | 4 | 5 | resulting code |
|---|---|---|---|---|---|---|---|
| **Group 1** | | | | | | | |
| DDX5-201 | ST21 | ST21-ST07 | ST21-ST05 | ST21-ST07 | ST21-ST05 | ST21-ST06 | GOGOY |
| RAD17-208 | ST02 | ST02-ST06 | ST02-ST07 | ST02-ST06 | ST02-ST06 | ST02-ST07 | YGYYG |
| SPOCK1-202 | ST03 | ST03-ST06 | ST03-ST06 | ST03-ST07 | ST03-ST05 | ST03-ST05 | YYGOO |
| FBXO32-203 | ST04 | ST04-ST07 | ST04-ST06 | ST04-ST06 | ST04-ST06 | ST04-ST05 | GYYYO |
| THRAP3-203 | ST14 | ST14-ST07 | ST14-ST05 | ST14-ST05 | ST14-ST07 | ST14-ST05 | GOOGO |
| GART-203 | ST11 | ST11-ST06 | ST11-ST07 | ST11-ST06 | ST11-ST05 | ST11-ST05 | YGYOO |
| KAT2A-201 | ST13 | ST13-ST06 | ST13-ST06 | ST13-ST07 | ST13-ST06 | ST13-ST07 | YYGYG |
| HPRT1-201 | ST12 | ST12-ST06 | ST12-ST07 | ST12-ST07 | ST12-ST06 | ST12-ST06 | YGGYY |
| CCNA2-201 | ST22 | ST22-ST05 | ST22-ST07 | ST22-ST06 | ST22-ST06 | ST22-ST05 | OGYYO |
| NKRF-201 | ST23 | ST23-ST05 | ST23-ST06 | ST23-ST07 | ST23-ST06 | ST23-ST05 | OYGYO |
| **Group 2** | | | | | | | |
| CCNE1-201-new | NT01 | NT01-ST07 | NT01-ST07 | NT01-ST06 | NT01-ST06 | NT01-ST06 | GGYYY |
| COG5-201 | NT03 | NT03-ST06 | NT03-ST06 | NT03-ST05 | NT03-ST05 | NT03-ST06 | YYOOY |
| FBN1-201 | NT04 | NT04-ST05 | NT04-ST07 | NT04-ST06 | NT04-ST07 | NT04-ST07 | OGYGG |
| DYNC1H1-201 | NT05 | NT05-ST07 | NT05-ST06 | NT05-ST07 | NT05-ST06 | NT05-ST06 | GYGYY |
| CKAP5-202 | NT06 | NT06-ST05 | NT06-ST06 | NT06-ST07 | NT06-ST05 | NT06-ST06 | OYGOY |
| KRAS-202 | NT07 | NT07-ST06 | NT07-ST05 | NT07-ST06 | NT07-ST06 | NT07-ST05 | YOYYO |
| EGFR-207 | NT08 | NT08-ST07 | NT08-ST06 | NT08-ST05 | NT08-ST05 | NT08-ST05 | GYOOO |
| TP53-205 | NT09 | NT09-ST06 | NT09-ST05 | NT09-ST06 | NT09-ST07 | NT09-ST07 | YOYGG |
| NF1-204 | XT01 | XT01-ST06 | XT01-ST06 | XT01-ST07 | XT01-ST07 | XT01-ST06 | YYGGY |
| NF2-204 | XT02 | XT02-ST07 | XT02-ST06 | XT02-ST05 | XT02-ST06 | XT02-ST07 | GYOYG |
| **Group 3** | | | | | | | |
| ACO2-201 | XT03 | XT03-ST06 | XT03-ST06 | XT03-ST06 | XT03-ST07 | XT03-ST05 | YYYGO |
| AKT1-211 | XT04 | XT04-ST07 | XT04-ST06 | XT04-ST07 | XT04-ST07 | XT04-ST05 | GYGGO |
| LYPLAL1-202 | XT05 | XT05-ST07 | XT05-ST05 | XT05-ST06 | XT05-ST05 | XT05-ST05 | GOYOO |
| PKD2-201 | XT06 | XT06-ST06 | XT06-ST07 | XT06-ST05 | XT06-ST05 | XT06-ST07 | YGOOG |
| ENG-204 | XT09 | XT09-ST05 | XT09-ST05 | XT09-ST06 | XT09-ST06 | XT09-ST06 | OOYYY |
| FANCE-201 | XT10 | XT10-ST05 | XT10-ST07 | XT10-ST06 | XT10-ST05 | XT10-ST06 | OGYOY |

TABLE 2-continued

| Experimental overview | | | | | | | |
|---|---|---|---|---|---|---|---|
| target transcript | unique identifier | Decoding oligonucleotides in detection cycle: 1 | 2 | 3 | 4 | 5 | resulting code |
| MET-201 | XT12 | XT12-ST05 | XT12-ST06 | XT12-ST05 | XT12-ST06 | XT12-ST06 | OYOYY |
| NOTCH2-201 | XT13 | XT13-ST05 | XT13-ST05 | XT13-ST06 | XT13-ST07 | XT13-ST05 | OOYGO |
| SPOP-206 | XT14 | XT14-ST05 | XT14-ST07 | XT14-ST05 | XT14-ST07 | XT14-ST06 | OGOGY |
| ABL1-202 | XT16 | XT16-ST05 | XT16-ST06 | XT16-ST06 | XT16-ST05 | XT16-ST05 | OYYOO |
| Group 4 | | | | | | | |
| ATP11C-202 | XT17 | XT17-ST07 | XT17-ST06 | XT17-ST06 | XT17-ST05 | XT17-ST06 | GYYOY |
| BCR-202 | XT18 | XT18-ST05 | XT18-ST06 | XT18-ST06 | XT18-ST07 | XT18-ST06 | OYYGY |
| CAV1-205 | XT19 | XT19-ST07 | XT19-ST05 | XT19-ST06 | XT19-ST07 | XT19-ST06 | GOYGY |
| CDK2-201 | XT20 | XT20-ST05 | XT20-ST05 | XT20-ST07 | XT20-ST07 | XT20-ST06 | OOGGY |
| DCAF1-202 | XT201 | XT201-ST06 | XT201-ST06 | XT201-ST05 | XT201-ST07 | XT201-ST07 | YYOGG |
| FHOD1-201 | XT202 | XT202-ST05 | XT202-ST07 | XT202-ST07 | XT202-ST05 | XT202-ST07 | OGGOG |
| GMDS-202 | XT203 | XT203-ST07 | XT203-ST05 | XT203-ST07 | XT203-ST06 | XT203-ST05 | GOGYO |
| IFNAR1-201 | XT204 | XT204-ST06 | XT204-ST07 | XT204-ST05 | XT204-ST07 | XT204-ST05 | YGOGO |
| NSMF-203 | XT206 | XT206-ST07 | XT206-ST06 | XT206-ST07 | XT206-ST05 | XT206-ST07 | GYGOG |
| POLA2-201 | XT208 | XT208-ST06 | XT208-ST06 | XT208-ST06 | XT208-ST05 | XT208-ST07 | YYYOG |
| Group 5 | | | | | | | |
| BRCA1-210new | NT10 | NT10-ST07 | NT10-ST05 | NT10-ST06 | NT10-ST06 | NT10-ST07 | GOYYG |
| JAK1-201new | XT11 | XT11-ST05 | XT11-ST05 | XT11-ST07 | XT11-ST06 | XT11-ST07 | OOGYG |
| STRAP-202 | XT207 | XT207-ST07 | XT207-ST07 | XT207-ST06 | XT207-ST05 | XT207-ST07 | GGYOG |
| SERPINB5-201 | XT209 | XT209-ST07 | XT209-ST05 | XT209-ST05 | XT209-ST05 | XT209-ST07 | GOOOG |
| SETX-201 | XT210 | XT210-ST06 | XT210-ST07 | XT210-ST06 | XT210-ST07 | XT210-ST06 | YGYGY |
| WDFY1-201 | XT212 | XT212-ST05 | XT212-ST07 | XT212-ST05 | XT212-ST06 | XT212-ST07 | OGOYG |
| TACC1-201 | XT213 | XT213-ST05 | XT213-ST07 | XT213-ST07 | XT213-ST07 | XT213-ST05 | OGGGO |
| KIF2A-203 | XT214 | XT214-ST07 | XT214-ST07 | XT214-ST06 | XT214-ST07 | XT214-ST05 | GGYGO |
| CDT1-201 | XT215 | XT215-ST07 | XT215-ST07 | XT215-ST07 | XT215-ST05 | XT215-ST05 | GGGOO |
| CENPE-202 | XT216 | XT216-ST07 | XT216-ST06 | XT216-ST05 | XT216-ST07 | XT216-ST06 | GYOGY |

Variations of the Experiment

Some variations of the experiment have been performed. Experiments 1 to 4 mainly differ in the number of transcripts detected in parallel. The groups listed as target specific probe sets refer to table 6. Experiments 5 to 8 are single round, single target controls for comparison with the decoded signals.

TABLE 3

| Variations of the experiment | | | |
|---|---|---|---|
| Experiment | Target specific probe sets used | Nr. of detection cylces | Imaging with trolox |
| 1. 50 transcripts_T+ | Groups 1 to 5 of table 6 | 5 | + |
| 2. 50 transcripts_T− | Groups 1 to 5 of table 6 | 5 | − |
| 3. 30 transcripts_T+ | Groups 2 to 4 of table 6 | 5 | + |
| 4. 10 transcripts_T+ | Group 1 of table 6 | 5 | + |
| 5. DDX5 | DDX5-ST21 | 1 | − |
| 6. RAD17 | RAD17-ST02 | 1 | − |
| 7. SPOCK1 | SPOCK1-ST03 | 1 | − |
| 8. THRAP3 | THRAP3-ST14 | 1 | − |

Experimental Details a. Seeding and Cultivation of Cells

Hela cells were grown in Hela cell culture medium to nearly 100% confluency. The Hela cell culture medium comprises DMEM (Thermo Fisher, Cat.: 31885) with 10% FCS (Biochrom, Cat.: S0415), 1% Penicillin-Streptomycin (Sigma-Adrich, Cat.: P0781) and 1% MEM Non-Essential Amino Acids Solution (Thermo Fisher, Cat.: 11140035). After aspiration of cell culture medium, cells were trypsinized by incubation with trypsin EDTA solution (Sigma-Aldrich, Cat.: T3924) for 5 min at 37° C. after a washing step with PBS (1,424 g/l $Na_2HPO_4$*$2H_2O$, 0,276 g/l, $NaH_2PO_4$*$2H_2O$, 8.19 g/l NaCl in water, pH 7,4). Cells were then seeded on the wells of a u-Slide 8 Well ibidiTreat (Ibidi, Cat.: 80826). The number of cells per well was adjusted to reach about 50% confluency after adhesion of the cells. Cells were incubated over night with 200 µl HeLa cell culture medium per well.

B. Fixation of Cells

After aspiration of cell culture medium and two washing steps with 200 µl 37° C. warm PBS per well, cells were fixed with 200 µl precooled methanol (−20° C., Roth, Cat.: 0082.1) for 10 min at −20° C.

C. Counterstaining with Sudan Black

Methanol was aspirated and 150 µl of 0.2% Sudan Black-solution diluted in 70% ethanol were added to each well. Wells were incubated for 5 min in the dark at room temperature. After incubation cells were washed three times with 400 µl 70% ethanol per well to eliminate the excess of Sudan Black-solution.

D. Hybridization of Analyte/Target-Specific Probes

Before hybridization, cells were equilibrated with 200 µl sm-wash-buffer. The sm-wash-buffer comprises 30 mM $Na_3$Citrate, 300 mM NaCl, pH7, 10% formamide (Roth, Cat.: P040.1) and 5 mM Ribonucleoside Vanadyl Complex (NEB, Cat.: S1402S). For each target-specific probe set 1 µl of a 100 µM oligonucleotide stock solution was added to the mixture. The oligonucleotide stock solution comprises equimolar amounts of all target specific oligonucleotides of the corresponding target specific probe set. The total volume of the mixture was adjusted to 100 µl with water and mixed with 100 µl of a 2× concentrated hybridization buffer solution. The 2× concentrated hybridization buffer comprises 120 mM $Na_3$Citrate, 1200 mM NaCl, pH7, 20% formamide and 20 mM Ribonucleoside Vanadyl Complex. The resulting 200 µl hybridization mixture was added to the corresponding well and incubated at 37° C. for 2 h. Afterwards cells were washed three times with 200 µl per well for 10 min with target probe wash buffer at 37° C. The target probe wash buffer comprises 30 mM $Na_3$Citrate, 300 mM NaCl, pH7, 20% formamide and 5 mM Ribonucleoside Vanadyl Complex.

E. Hybridization of Decoding Oligonucleotides

Before hybridization, cells were equilibrated with 200 µl sm-wash-buffer. For each decoding oligonucleotide 1,5 µl of a 5 µM stock solution were added to the mixture. The total volume of the mixture was adjusted to 75 µl with water and mixed with 75 µl of a 2× concentrated hybridization buffer solution. The resulting 150 µl decoding oligonucleotide hybridization mixture was added to the corresponding well and incubated at room temperature for 45 min.

Afterwards cells were washed three times with 200 µl per well for 2 min with sm-wash-buffer at room temperature.

F. Hybridization of Signal Oligonucleotides

Before hybridization, cells were equilibrated with 200 µl sm-wash-buffer. The signal oligonucleotide hybridization mixture was the same for all rounds of experiments 1 to 4 and comprised 0.3 µM of each signal oligonucleotide (see table A3) in 1× concentrated hybridization buffer solution. In each round 150 µl of this solution were added per well and incubated at room temperature for 45 min. The procedure was the same for experiments 5 to 8 with the exception that the final concentration of each signal oligonucleotide was 0.15 µM. Afterwards cells were washed three times with 200 µl per well for 2 min with sm-wash-buffer at room temperature.

G. Fluorescence and White Light Imaging

Cells were washed once with 200 µl of imaging buffer per well at room temperature. In experiments without Trolox (see table 7, last column) imaging buffer comprises 30 mM $Na_3$Citrate, 300 mM NaCl, pH7 and 5 mM Ribonucleoside Vanadyl Complex. In experiments with Trolox, imaging buffer additionally contains 10% VectaCell Trolox Antifade Reagent (Vector laboratories, Cat.: CB-1000), resulting in a final Trolox concentration of 10 mM.

A Zeiss Axiovert 200M microscope with a 63× immersion oil objective (Zeiss, apochromat) with numerical aperture of 1.4, a pco.edge 4.2 CMOS camera (PCO AG) and an LED-light source (Zeiss, colibri 7) was used for imaging of the regions. Filter sets and LED-wavelengths were adjusted to the different optima of the fluorophores used. Illumination times per image were 1000 ms for Alexa Fluor 546 and Atto 594 and 400 ms for Alexa Fluor 488.

In each experiment, three regions were randomly chosen for imaging. For each region, a z-stack of 32 images was detected with a z-step size of 350 nm. Additionally, one white light image was taken from the regions. In experiments with more than one detection cycle, the regions of the first detection round were found back and imaged in every subsequent round.

H. Selective Denaturation

For selective denaturation, every well was incubated with 200 µl of sm-wash-buffer at 42° C. for 6 min. This procedure was repeated six times.

Steps (E) to (H) were repeated 5 times in experiments 1 to 4. Step (H) was omitted for the 5th detection cycle.

1. Analysis

Based on custom ImageJ-plugins a semi-automated analysis of the raw data was performed to distinguish the specific fluorescent signals from the background. The resulting 3D-point clouds of all three fluorescent channels were combined in silico with a custom VBA script. The resulting combined 3D-point clouds of the 5 detection cycles were aligned to each other on the basis of a VBA script. The resulting alignments revealed the code words for each unique signal detected. Successfully decoded signals were used for quantitative and spatial analysis of the experiments based on custom VBA-scripts and ImageJ-plugins.

Results

1. Absolute Numbers of Decoded Signals

The absolute numbers of successfully decoded signals for all transcripts are listed for each region of each experiment in the following Table 4. In summary, the sum of correct codes depicts the total number of decoded signals that were assigned to transcripts detectable in the corresponding experiment, while the sum of incorrect codes it the total number of decoded signals not detectable in the corresponding experiment. The total number of signals comprises successfully decoded as well as unsuccessfully decoded signals.

TABLE 4

Absolute numbers of decoded signals

| | Experiment 1: region | | | Experiment 2: region | | | Experiment 3: region | | | Experiment 4: region | | |
|---|---|---|---|---|---|---|---|---|---|---|---|---|
| | 1 | 2 | 3 | 1 | 2 | 3 | 1 | 2 | 3 | 1 | 2 | 3 |
| Group 1 | | | | | | | | | | | | |
| DDX5-201 | 1214 | 1136 | 927 | 1144 | 1509 | 1176 | 2964 | 2034 | 2141 | 8 | 2 | 2 |
| RAD17-208 | 40 | 126 | 50 | 26 | 55 | 62 | 22 | 30 | 33 | 7 | 9 | 10 |
| SPOCK1-202 | 581 | 655 | 301 | 483 | 875 | 149 | 1349 | 621 | 539 | 2 | 10 | 8 |
| FBXO32-203 | 153 | 175 | 68 | 113 | 106 | 78 | 301 | 160 | 269 | 5 | 13 | 9 |
| THRAP3-203 | 1079 | 2180 | 1035 | 810 | 1179 | 1047 | 2318 | 1609 | 1609 | 6 | 8 | 16 |
| GART-203 | 422 | 397 | 346 | 350 | 333 | 202 | 766 | 658 | 569 | 5 | 3 | 2 |
| KAT2A-201 | 141 | 310 | 166 | 174 | 307 | 186 | 382 | 315 | 340 | 5 | 1 | 3 |
| HPRT1-201 | 63 | 79 | 34 | 44 | 116 | 71 | 85 | 88 | 112 | 1 | 0 | 6 |
| CCNA2-201 | 91 | 248 | 205 | 95 | 134 | 138 | 241 | 151 | 238 | 10 | 20 | 9 |
| NKRF-201 | 162 | 318 | 153 | 101 | 99 | 135 | 313 | 254 | 209 | 7 | 5 | 12 |
| Group 2 | | | | | | | | | | | | |
| CCNE1-201-new | 75 | 180 | 38 | 57 | 110 | 97 | 0 | 0 | 1 | 122 | 104 | 120 |
| COG5-201 | 57 | 21 | 38 | 26 | 45 | 23 | 0 | 0 | 1 | 56 | 86 | 60 |
| FBN1-201 | 202 | 1338 | 499 | 456 | 513 | 571 | 0 | 1 | 3 | 450 | 778 | 895 |
| DYNC1H1-201 | 554 | 892 | 398 | 664 | 1026 | 666 | 4 | 3 | 7 | 823 | 1148 | 1248 |
| CKAP5-202 | 43 | 23 | 77 | 51 | 98 | 74 | 1 | 2 | 1 | 94 | 190 | 212 |
| KRAS-202 | 331 | 417 | 355 | 302 | 333 | 230 | 0 | 0 | 1 | 279 | 637 | 371 |

TABLE 4-continued

Absolute numbers of decoded signals

| | Experiment 1: region | | | Experiment 2: region | | | Experiment 3: region | | | Experiment 4: region | | |
|---|---|---|---|---|---|---|---|---|---|---|---|---|
| | 1 | 2 | 3 | 1 | 2 | 3 | 1 | 2 | 3 | 1 | 2 | 3 |
| EGFR-207 | 527 | 252 | 372 | 293 | 519 | 322 | 0 | 1 | 0 | 411 | 719 | 818 |
| TP53-205 | 116 | 324 | 194 | 138 | 198 | 169 | 0 | 1 | 4 | 182 | 280 | 181 |
| NF1-204 | 381 | 676 | 320 | 347 | 522 | 416 | 3 | 2 | 0 | 507 | 642 | 659 |
| NF2-204 | 434 | 638 | 361 | 336 | 468 | 401 | 0 | 0 | 2 | 508 | 523 | 636 |
| Group 3 | | | | | | | | | | | | |
| ACO2-201 | 456 | 759 | 444 | 333 | 367 | 345 | 0 | 0 | 0 | 556 | 681 | 681 |
| AKT1-211 | 351 | 710 | 301 | 230 | 437 | 297 | 0 | 0 | 3 | 558 | 614 | 690 |
| LYPLAL1-202 | 65 | 62 | 51 | 33 | 58 | 51 | 7 | 6 | 8 | 28 | 34 | 42 |
| PKD2-201 | 72 | 194 | 124 | 95 | 129 | 69 | 1 | 0 | 0 | 122 | 164 | 169 |
| ENG-204 | 472 | 890 | 458 | 446 | 494 | 558 | 0 | 2 | 0 | 1145 | 799 | 1119 |
| FANCE-201 | 24 | 82 | 61 | 56 | 67 | 56 | 0 | 0 | 2 | 119 | 131 | 153 |
| MET-201 | 268 | 744 | 333 | 426 | 275 | 462 | 0 | 0 | 0 | 790 | 662 | 782 |
| NOTCH2-201 | 344 | 823 | 404 | 172 | 256 | 208 | 4 | 0 | 3 | 402 | 779 | 772 |
| SPOP-206 | 43 | 377 | 139 | 68 | 117 | 100 | 0 | 0 | 0 | 215 | 289 | 300 |
| ABL1-202 | 224 | 72 | 218 | 107 | 122 | 153 | 4 | 1 | 1 | 302 | 393 | 480 |
| Group 4 | | | | | | | | | | | | |
| ATP11C-202 | 170 | 116 | 121 | 86 | 165 | 128 | 2 | 1 | 1 | 130 | 206 | 234 |
| BCR-202 | 180 | 401 | 185 | 177 | 149 | 169 | 1 | 0 | 0 | 321 | 372 | 485 |
| CAV1-205 | 728 | 777 | 644 | 328 | 653 | 567 | 2 | 0 | 5 | 613 | 997 | 852 |
| CDK2-201 | 306 | 937 | 367 | 297 | 385 | 358 | 4 | 1 | 3 | 568 | 742 | 888 |
| DCAF1-202 | 119 | 292 | 187 | 59 | 67 | 65 | 0 | 1 | 0 | 108 | 171 | 131 |
| FHOD1-201 | 60 | 233 | 143 | 132 | 185 | 157 | 1 | 0 | 1 | 194 | 294 | 300 |
| GMDS-202 | 67 | 124 | 49 | 56 | 80 | 63 | 7 | 2 | 3 | 59 | 73 | 114 |
| IFNAR1-201 | 81 | 221 | 135 | 99 | 104 | 55 | 1 | 0 | 1 | 159 | 266 | 238 |
| NSMF-203 | 448 | 583 | 386 | 293 | 453 | 331 | 8 | 4 | 11 | 525 | 608 | 616 |
| POLA2-201 | 74 | 111 | 62 | 45 | 72 | 67 | 2 | 4 | 2 | 41 | 75 | 57 |
| Group 5 | | | | | | | | | | | | |
| BRCAl-210new | 230 | 704 | 248 | 324 | 439 | 374 | 2 | 1 | 0 | 2 | 3 | 3 |
| JAK1-201new | 157 | 554 | 223 | 185 | 259 | 263 | 0 | 1 | 0 | 5 | 4 | 2 |
| STRAP-202 | 42 | 75 | 31 | 18 | 52 | 40 | 3 | 1 | 0 | 6 | 4 | 4 |
| SERPINB5-201 | 324 | 598 | 343 | 286 | 344 | 364 | 6 | 13 | 9 | 0 | 1 | 2 |
| SETX-201 | 212 | 540 | 254 | 291 | 439 | 336 | 2 | 2 | 2 | 12 | 9 | 5 |
| WDFY1-201 | 43 | 516 | 218 | 176 | 206 | 147 | 0 | 0 | 0 | 4 | 2 | 8 |
| TACC1-201 | 69 | 373 | 131 | 80 | 156 | 118 | 1 | 0 | 0 | 21 | 29 | 32 |
| KIF2A-203 | 442 | 879 | 445 | 298 | 519 | 430 | 5 | 1 | 2 | 6 | 11 | 9 |
| CDT1-201 | 31 | 27 | 33 | 19 | 61 | 28 | 15 | 8 | 9 | 0 | 8 | 1 |
| CENPE-202 | 192 | 246 | 215 | 94 | 262 | 225 | 0 | 1 | 0 | 8 | 9 | 9 |
| Summary | | | | | | | | | | | | |
| sum of correct codes: | 12960 | 23405 | 12890 | 11319 | 15917 | 12797 | 8741 | 5920 | 6059 | 10387 | 13457 | 14303 |
| sum of incorrect codes: | 0 | 0 | 0 | 0 | 0 | 0 | 86 | 60 | 86 | 120 | 151 | 152 |
| total number of signals: | 42959 | 72157 | 32185 | 32037 | 58793 | 35470 | 13549 | 9182 | 10109 | 26701 | 32966 | 35451 |
| % successfully decoded: | 30.2 | 32.4 | 40.0 | 35.3 | 27.1 | 36.1 | 64.5 | 64.5 | 59.9 | 38.9 | 40.8 | 40.3 |

Table 4 shows a very low number of incorrectly decoded signals compared to the number of correctly decoded signals. The absolute values for decoded signals of a certain transcript are very similar between different regions of one experiment. The fraction of the total number of signals that can be successfully decoded is between 27.1% and 64.5%. This fraction depends on the number of transcripts and/or the total number of signals present in the respective region/experiment.

Conclusion

The method according to the disclosure produces a low amount of incorrectly assigned code words and can therefore be considered specific. The fraction of successfully decodable signals is very high, even with very high numbers of signals per region and very high numbers of transcripts detected in parallel. The high fraction of assignable signals and the high specificity make the method practically useful.

Comparison of Relative Transcript Abundancies Between Different Experiments

Figure 8A:
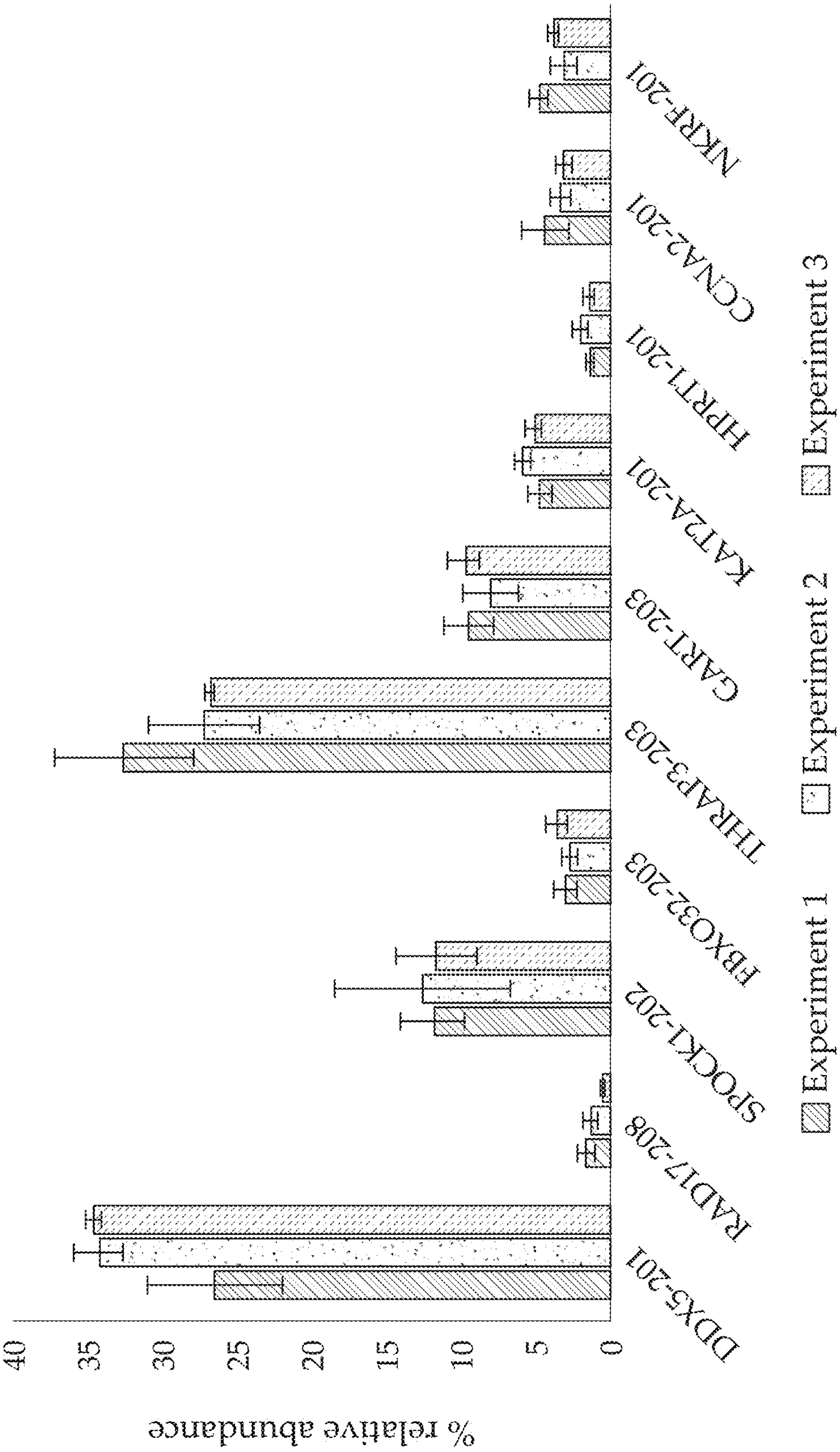
FIG. 8A: Comparison of relative transcript abundances between different experiments.
Figure 8B:
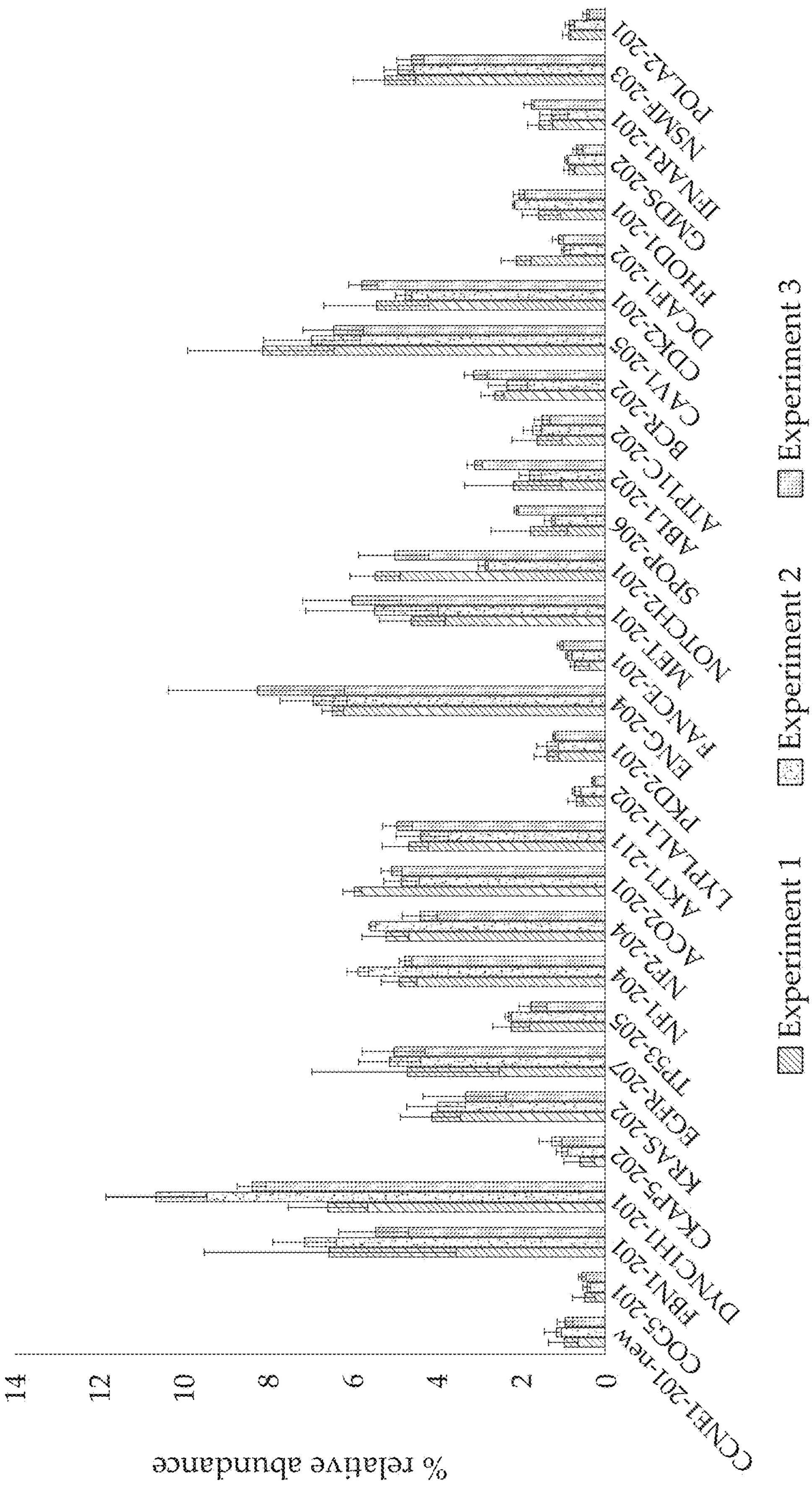
FIG. 8B: Comparison of relative transcript abundances between different experiments.

As shown in FIG. 8A and FIG. 8B for both comparisons the overlap of detected transcripts between the experiments is used for the analysis. Each bar represents the mean abundance of all three regions of an experiment. The standard deviation between these regions is also indicated.

Correlation of Relative Transcript Abundancies Between Different Experiments

Figure 9:
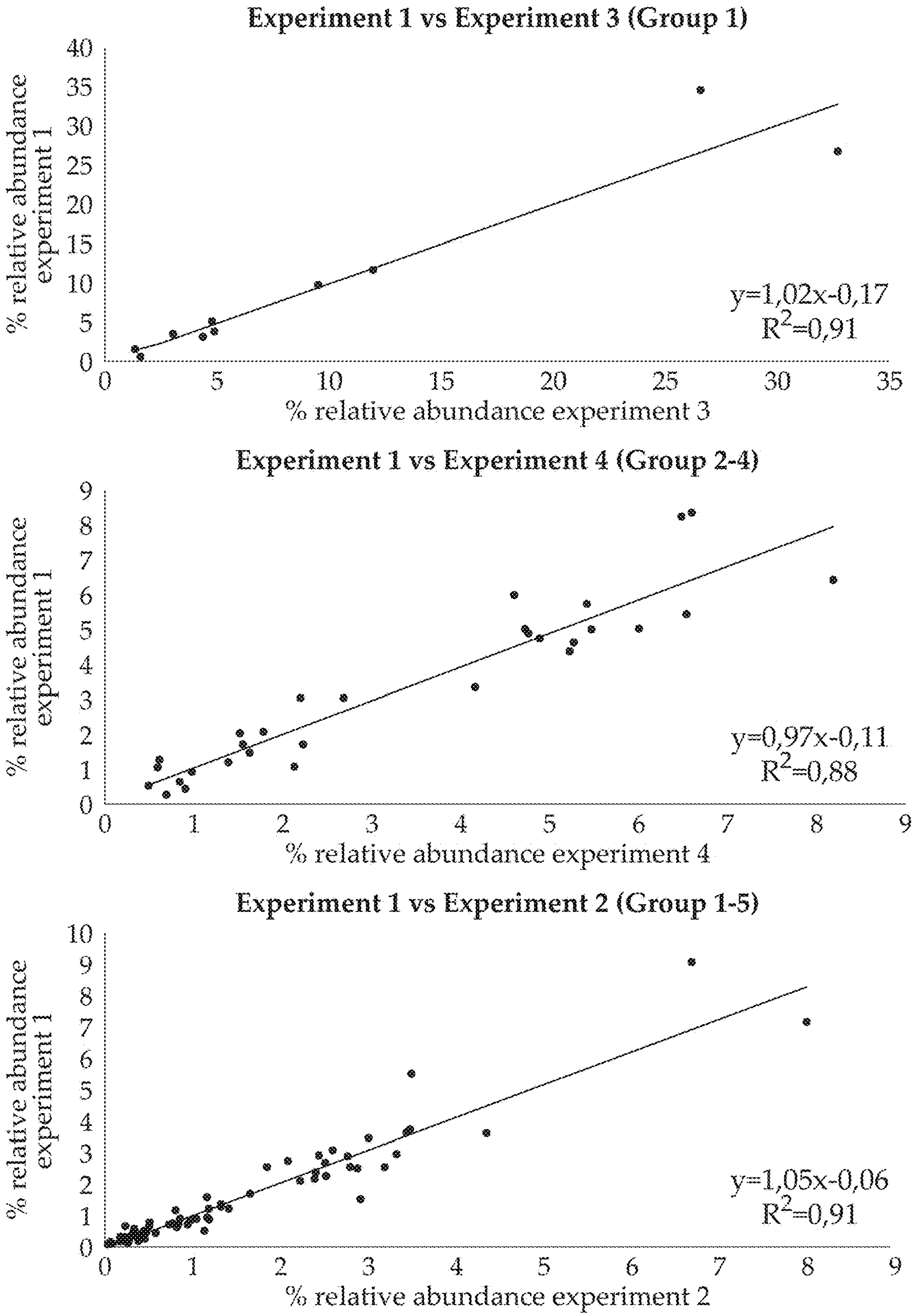
FIG. 9: Correlation of relative transcript abundances between different experiments.

As can be seen in FIG. 9 the mean relative abundances of transcripts from experiment 1 are correlated to the abundances of the overlapping transcripts of experiment 3, 4 and 2. The correlation coefficient as well as the formula for the linear regression are indicated for each correlation.

FIG. 8A and FIG. 8B show low standard deviations, indicating low variations of relative abundances between different regions of one experiment. The differences of relative abundances between transcripts from different experiments are also very low. This is the case for the comparison of transcripts from group 1 (FIG. 8A), that were detected in experiments 1, 2 and 3. It is also the case for the comparison of the transcripts from groups 2, 3 and 4 that were overlapping between experiments 1, 2 and 4. The very high correlation of these abundances can also be seen in FIG. 9. The abundances of transcripts from experiment 1 correlate very well with the abundances of the other multi round experiments. The correlation factors are between 0.88 and 0.91, while the slope of the linear regressions is between 0.97 and 1.05.

Conclusion

The relative abundancies of transcripts correlate very well between different regions of one experiment but also between different experiments. This can be clearly seen by the comparisons of FIGS. 3 and 4. The main difference between the experiments is the number of different targets and hence the total number of signals detected. Therefore, the number of transcripts detected as well as the number and density of signals does not interfere with the ability of the method to accurately quantify the number of transcripts. The very good correlations further support the specificity and stability of the method, even with very high numbers of signals.

Comparison of Intercellular Distribution of Signals

Figure 10:
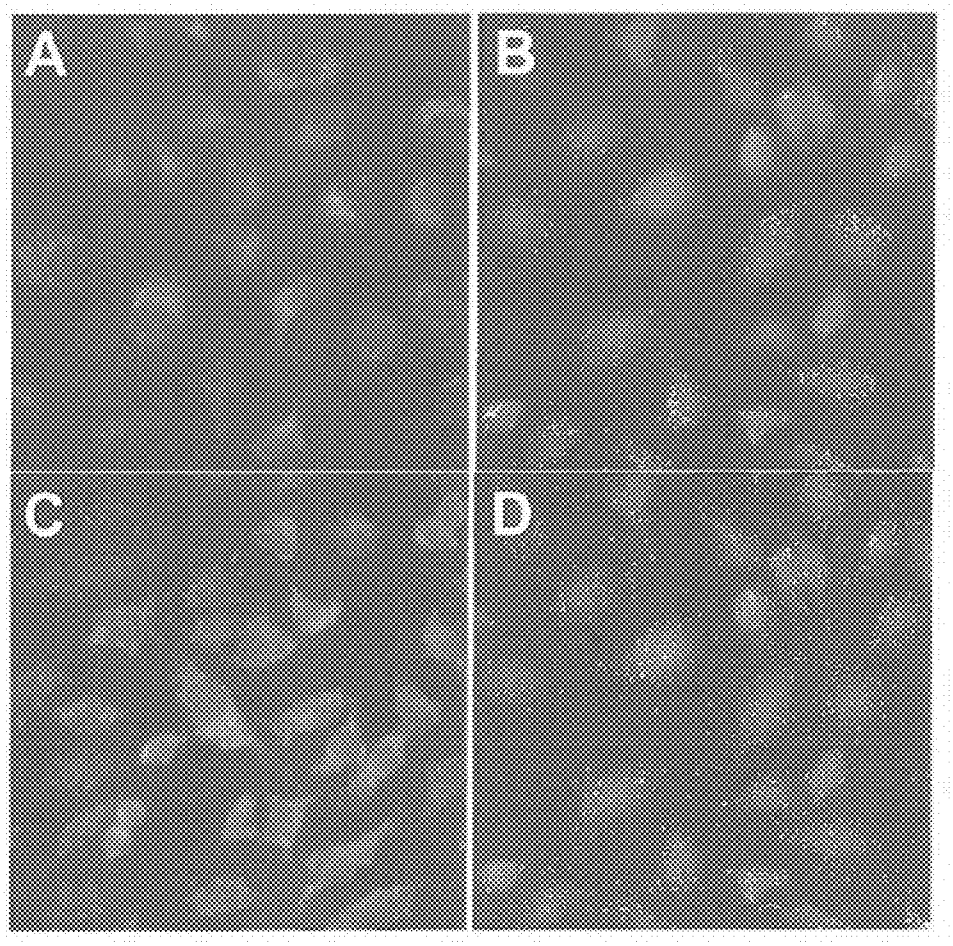
FIG. 10: Comparison of intercellular distribution of signals.

In FIG. 10 the maximum projections of image stacks are shown. A: region 1 of experiment 7 (single round, single transcript experiment detecting SPOCK1), B: 2D-projection of all selected signals from experiment 1, region 1 assigned to SPOCK1, C: region 1 of experiment 8 (single round, single transcript experiment detecting THRAP3), D: 2D-projection of all selected signals from experiment 1, region 1 assigned to THRAP3.

Comparison of Intracellular Distribution of Signals

Figure 11:
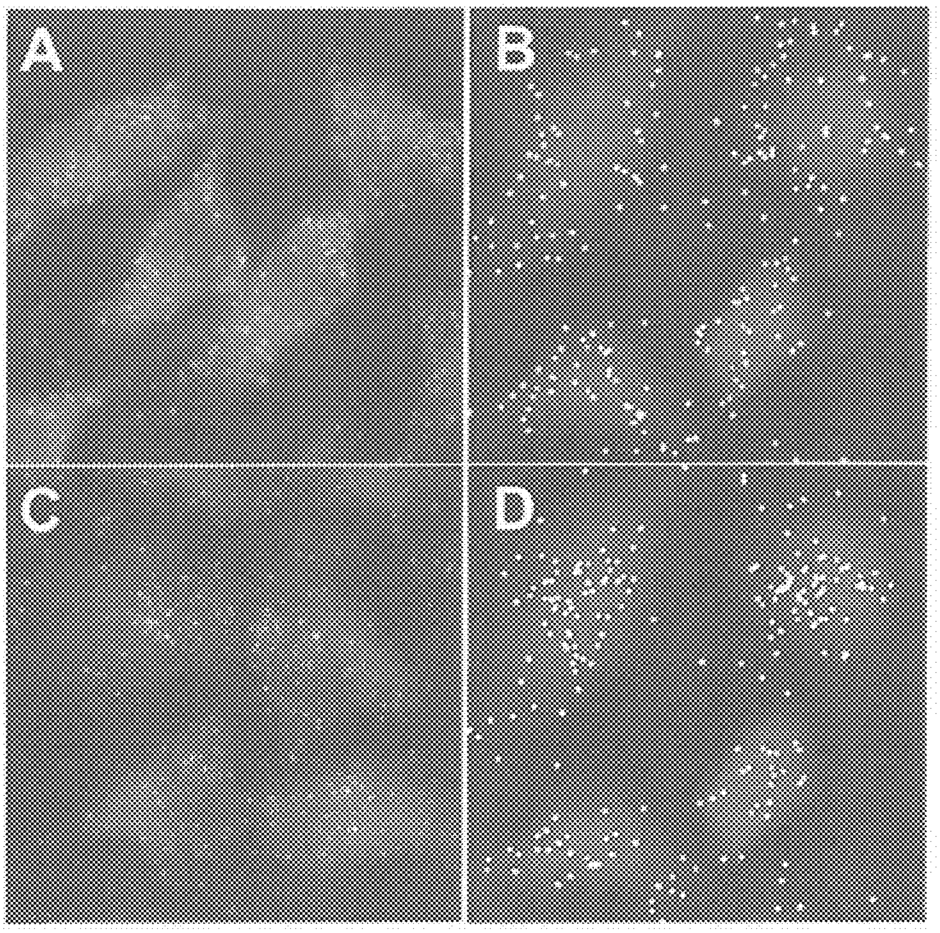
FIG. 11: Comparison of intracellular distribution of signals.

In FIG. 11 the maximum projections of image stacks are shown. Magnified sub regions of the corresponding regions are shown. A: region 1 of experiment 8 (single round, single transcript experiment detecting THRAP3), B: 2D-projection of selected signals from experiment 1, region 1 assigned to THRAP3, C: region 1 of experiment 5 (single round, single transcript experiment detecting DDX5), D: 2D-projection of all selected signals from experiment 1, region 1 assigned to DDX5.

FIG. 10 shows huge differences of intercellular distributions between different transcripts. SPOCK1 seems to be highly abundant in some cells but nearly absent in other cells (FIG. 10A). THRAP3 shows a more uniform distribution over all cells of a region (FIG. 10C). These spatial distribution patterns can also clearly be observed with the point clouds assigned to the corresponding transcripts from experiment 1 (FIG. 10B and D).

FIG. 11 shows huge differences of intracellular distributions between different transcripts. THRAP3 can be mainly observed in the periphery (cytoplasm) of the cells (FIG. 11A), while DDX5 shows a higher abundance in the center (nucleus) of the cells (FIG. 11C). These intracellular distributions can also be observed with the point clouds of experiment 1 assigned to THRAP3 and DDX5 (FIG. 11B and D).

Conclusion

Next to the reliability of quantification, the point clouds of multi round experiments also show the same intracellular and intercellular distribution patterns of transcripts. This is clearly proven by the direct comparison of the assigned point clouds with signals from single round experiments detecting only one characteristic mRNA-species.

Distribution Pattern of Different Cell Cycle Dependent Transcripts

Figure 12:
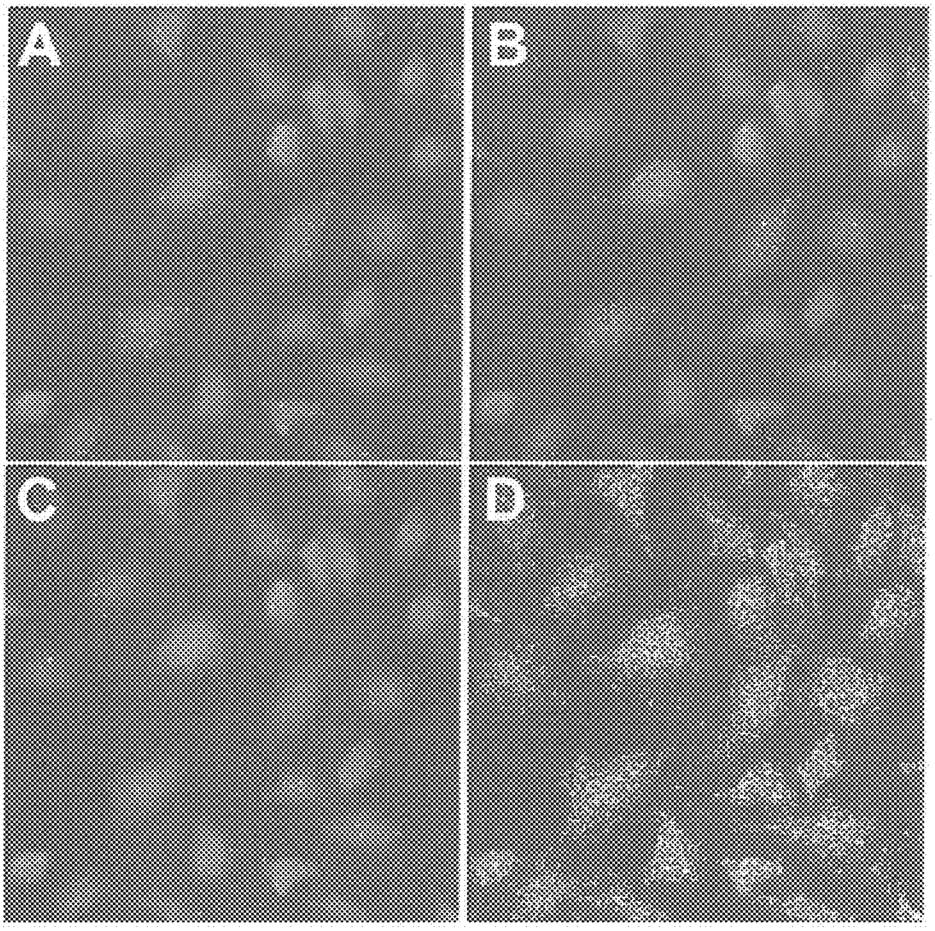
FIG. 12: Distribution pattern of different cell cycle dependent transcripts.

All images of FIG. 12 show region 1 of experiment 1. In each image, a point cloud is shown, that is assigned to a certain transcript, A: CCNA2, B: CENPE, C: CCNE1, D: all transcripts. FIG. 12 shows the transcripts of three different cell cycle dependent proteins. CENPE (FIG. 12B) is also known as Centromere protein E and accumulates during G2 phase. It is proposed to be responsible for spindle elongation and for chromosome movement. It is not present during interphase. CCNA2 (FIG. 12A) is also known as Cyclin A2. It regulates the cell cycle progression by interacting with CDK1 during transition from G2 to M-phase. Interestingly there is an obvious colocalization of both mRNA-species. They are mainly present in the three central cells of region 1. CCNE1 (FIG. 12C) is also known as Cyclin E1. This cyclin interacts with CDK2 and is responsible for the transition from G1 to S-phase. FIG. 12 shows clearly, that the transcripts of this gene are not present in the three central cells, but quite equally distributed over the other cells. It therefore shows an anti-localization to the other two transcripts. The data for the corresponding point-clouds are derived from a point cloud with a very high number of points and a very high point density (FIG. 12D gives an impression).

Conclusion

The three decoded point clouds of cell cycle dependent proteins shown in FIG. 12, show distribution patterns that can be explained by their corresponding function. These data strongly suggest, that our method reliably produces biological relevant data, even with a low number of signals per cell (FIG. 12C) and with very high signal densities (FIG. 12D).

SEQUENCE LISTING

In the accompanying sequence listing SEQ ID Nos. 1-1247 refer to nucleotide sequences of exemplary target-specific oligonucleotides. The oligonucleotides listed consist of a target specific binding site (5'-end) a spacer/linker sequence (gtaac or tagac) and the unique identifier sequence, which is the same for all oligonucleotides of one probe set.

In the accompanying sequence listing SEQ ID Nos. 1248-1397 refer to nucleotide sequences of exemplary decoding oligonucleotides.

In the accompanying sequence listing SEQ ID Nos. 1398-1400 refer to the nucleotide sequences of exemplary signal oligonucleotides. For each signal oligonucleotide the corresponding fluorophore is present twice. One fluorophore is covalently linked to the 5'-end and one fluorophore is covalently linked to the 3'-end. SEQ ID No. 1398 comprises at its 5' terminus "5Alex488N", and at its 3' terminus "3AlexF488N". SEQ ID No. 1399 comprises at its 5' terminus "5Alex546", and at its 3' terminus 3Alex546N. SEQ ID No. 1400 comprises at its 5' terminus and at its 3' terminus "Atto594".

We claim:

1. A method of assigning coded fluorescence patterns to a plurality of target analytes in a sample, comprising: subjecting the sample to a plurality of detection rounds, each detection round comprising: contacting the sample to a decoding oligonucleotide probe population comprising decoding oligonucleotide probes that each recruit, by reverse complementary base pairing, one translator connector element comprising a fluorescence moiety signal element selected from at least two distinct populations of fluorescence moieties to at least some of the plurality of target analytes; wherein the decoding oligonucleotide probes do not directly bind target analytes; and wherein the decoding oligonucleotide probes are recruited to their target analytes by analyte specific probes, each analyte specific probe having an identifier element that is reverse complementary to a portion of at least one decoding oligonucleotide; contacting the sample to the at least two populations of translator connector elements differing in their fluorescence moieties, wherein the at least two populations of translator connector element differ in fluorescence moiety from one another; assaying for fluorescence in the sample; removing the decoding oligonucleotide probe population and the translator connector elements after each round of the assaying without removing the analyte specific probes, by heating the sample until base pairings in the decoding oligonucleotide probe population are destabilized but base pairings between the analyte specific probes and the analytes remain intact; wherein the decoding oligonucleotide probes of the decoding oligonucleotide probe population vary across the plurality of detection rounds causing the translator connector element comprising a fluorescence moiety signal element recruited to a target analyte to vary in fluorescence moiety across the plurality of detection rounds; and wherein the translator connector elements differing in their fluorescence moieties do not vary in composition across the plurality of detection rounds; wherein a fluorescence pattern at an analyte position in the sample is specified by order of decoding oligonucleotide probe addition to the sample.

2. The method of claim 1, wherein a number of patterns detectable increases exponentially with a number of detection rounds.

3. The method of claim 1, wherein the translator connector elements do not comprise nucleic acid tags that are specific to the target analytes.

4. The method of claim 1, wherein separate aliquots of common translator connector elements are used across multiple detection rounds.

5. The method of claim 1, wherein the plurality of detection rounds comprises at least 5 detection rounds.

6. The method of claim 1, wherein the method comprises use of no more than two populations of translator connector elements.

7. The method of claim 1, wherein the analyte specific probes comprise oligo-tagged antibodies.

8. The method of claim 1, wherein the analyte specific probes comprise binding element portions that are reverse complementary to adjacent regions of a nucleotide analyte target, and identifier element portions that identify the target analyte for binding by at least some of the decoding oligonucleotide probes.

9. The method of claim 1, wherein a signal element fluorescence moiety of the translator connector elements is reverse complementary to a portion of a subset of the decoding oligonucleotide probes, causing members of a population of the translator connector elements sharing a common fluorescence moiety to be recruited to a plurality of target analytes tagged by distinct analyte specific probes differing in their identifier elements.

10. The method of claim 9, wherein members of a population of the translator connector elements do not specifically bind an analyte in the absence of a decoding oligonucleotide probe.

11. The method of claim 1, wherein the order of delivery of decoding oligonucleotide probes that bind an analyte specific probe identifier element assigns a coded fluorescence pattern to the target analyte that specifically identifies the analyte.

12. The method of claim 1, wherein the order of delivery decoding oligonucleotide probes that bind an analyte specific probe identifier element assigns a coded fluorescence pattern to the target analyte that uniquely identifies the analyte.

13. The method of claim 1, wherein the coded fluorescence pattern is not determined by a linear series of binding sites on the analyte.

14. The method of claim 1, wherein assigning coded fluorescence patterns to a plurality of target analytes distinguishes at least 1,000 target analytes using no more than two populations of fluorophore labeled translator connector elements.

* * * * *